US011123290B2

(12) United States Patent
Surber et al.

(10) Patent No.: US 11,123,290 B2
(45) Date of Patent: Sep. 21, 2021

(54) SPECIALLY FORMULATED COMPOSITIONS OF INHALED NINTEDANIB AND NINTEDANIB SALTS

(71) Applicant: Avalyn Pharma Inc., Seattle, WA (US)

(72) Inventors: Mark William Surber, San Diego, CA (US); Stephen Pham, San Diego, CA (US)

(73) Assignee: AVALYN PHARMA INC., Seattle, WA (US)

(*) Notice: Subject to any disclaimer, the term of this patent is extended or adjusted under 35 U.S.C. 154(b) by 0 days.

(21) Appl. No.: 16/548,672

(22) Filed: Aug. 22, 2019

(65) Prior Publication Data

US 2020/0060968 A1 Feb. 27, 2020

Related U.S. Application Data

(60) Provisional application No. 62/721,522, filed on Aug. 22, 2018.

(51) Int. Cl.

| | |
|---|---|
| *A61K 9/00* | (2006.01) |
| *A61K 31/4418* | (2006.01) |
| *A61K 31/496* | (2006.01) |

(52) U.S. Cl.

CPC ........ *A61K 9/0078* (2013.01); *A61K 31/4418* (2013.01); *A61K 31/496* (2013.01)

(58) Field of Classification Search

None

See application file for complete search history.

(56) References Cited

U.S. PATENT DOCUMENTS

| | | | | |
|---|---|---|---|---|
| 2004/0266890 | A1* | 12/2004 | Kipp | A61K 9/145 516/20 |
| 2010/0112092 | A1 | 5/2010 | Northey | |
| 2012/0192861 | A1 | 8/2012 | Surber | |
| 2015/0044288 | A1* | 2/2015 | Surber | A61K 9/0075 424/489 |
| 2015/0196543 | A1 | 7/2015 | Surber | |

OTHER PUBLICATIONS

"PCT Search Report and Written Opinion, PCT/US2019/047775", dated Nov. 21, 2019.

* cited by examiner

*Primary Examiner* — Celeste A Roney

(74) *Attorney, Agent, or Firm* — Kurt T. Mulville; VLP Law Group, LLP

(57) ABSTRACT

Disclosed herein are formulations of nintedanib and salts thereof, indolinone derivative compounds and salts thereof for aerosolization and use of such formulations for the prevention or treatment of various fibrotic, carcinogenic, vascular and viral infectious diseases, including diseases associated with the lung, heart, kidney, liver, eye, central nervous system and surgical sites. Formulations and delivery options described herein allow for efficacious local delivery of nintedanib or a indolinone derivative compound or salt thereof. Methods include inhalation procedures, indications and manufacturing processes for production and use of the compositions described. Also included are methods for identifying compounds and indications that benefit by reformulation and inhalation administration.

16 Claims, No Drawings

SPECIALLY FORMULATED COMPOSITIONS OF INHALED NINTEDANIB AND NINTEDANIB SALTS

BACKGROUND OF THE INVENTION

Despite development of a number of promising therapies, a number pulmonary diseases such as interstitial lung disease (ild; and sub-class diseases therein), cancer, vascular and many viral infectious disease remain unmet clinical needs. Additionally, a number of extrapulmonary diseases may also benefit from inhaled delivery of nintedanib. However, development of advanced nintedanib formulations for delivery by inhalation carries a number of challenges that have not been completely overcome.

SUMMARY

Special design considerations for nintedanib impact a number of parameters that are critical for developing an inhaled therapeutic product. By selective manipulation of formulation parameters and aerosol device parameters, the target organ dose, pharmacokinetic profile, and safety profile can be improved to increase efficacy, safety and maximize patient compliance. Described herein are compositions of nintedanib or salt thereof, and indolinone derivatives or salt thereof that are suitable for inhalation delivery to the lungs, central nervous system and/or systemic compartment and methods of use.

Specially formulated nintedanib or nintedanib salt solutions, or indolinone derivatives or salts thereof formulation composition and packaging for oral inhaled or intranasal inhaled delivery for the prevention or treatment of various diseases, including disease associated with the lung, heart, kidney, liver, eye and central nervous system, including fibrosis, cancers, and vascular diseases.

The invention includes an aqueous dosing solution for nebulized inhalation administration comprising water; nintedanib or salt thereof, or a indolinone derivative or salt thereof at a concentration from about 0.005 mg/mL to about 10 mg/mL and optionally one or more osmolality adjusting agents at a concentration of about 0.1% to about 20% to adjust osmolality, inorganic salts at a concentration of 15 mM to about 300 mM to adjust osmolality and provide a permeant ion at a final concentration from about 30 mM to about 150 mM; and optionally one or more buffers to maintain the pH between about pH 3.0 to about pH 7.0, preferably from about pH 3.0 to about pH 6.0, with a final osmolality between 50 mOsmo/kg and 600 mOsmo/kg. The aqueous solution may include one or more osmolality adjusting agents, including co-solvents selected from propylene glycol, ethanol and mannitol and combinations thereof at a concentration from about 0.1% to about 20%. The aqueous solution includes one more inorganic salts selected from sodium chloride, magnesium chloride, calcium chloride, potassium chloride, sodium bromide, potassium bromide, magnesium bromide and calcium bromide and combinations thereof. The inorganic salt content of the aqueous solution is from about 15 mM to about 300 mM. The buffer is selected from one or more of lysinate, acetylcysteine, glycine, glutamate, borate, succinate, tartrate, phosphate or Tris and combinations thereof, the pH of the aqueous solution is from about pH 3.0 to about pH 7.0, preferably pH about 3.0 to about pH 6.0. Described herein are an aqueous solution for nebulized inhalation administration comprising: water; nintedanib or salt thereof, at a concentration from about 0.005 mg/mL to about 10 mg/mL; one or more permeant ions at a concentration from about 30 mM to 150 mM; one or more osmolality adjusting agents; and wherein the osmolality of the aqueous solution is from about 50 mOsmol/kg to about 600 mOsmol/kg. The formulation may be administered as an inhaled aerosol created from a dosing volume ranging from about 0.01 mL to about 10 mL. The formulation may be administered as an inhaled aerosol over a few breaths or by tidal breathing up to 20 minutes.

The invention includes a multi-container system for admixture wherein an aqueous solution of nintedanib or salt thereof, or indolinone derivative is formulated in a container separate from other components of a final solution that is aerosolized in in a liquid nebulizer. The first container comprises nintedanib or salt thereof, or a indolinone derivative or salt thereof at a concentration from about 0.005 mg/mL to about 10 mg/mL; optionally water; optionally more or more buffers at a concentration from about 1 mM to about 1000 mM; optionally, one or more osmolality adjusting agents at a concentration from about 0.1% to about 99%; and optionally one or more taste-masking agents at a concentration from about 0.1% to about 90%. A second container comprises one of more inorganic salts at a concentration from about 15 mM to about 1500 mM, providing a permeant ion concentration from about 30 mM to about 1500 mM; optionally water; optionally one or more buffers at a concentration from about 1 mM to about 1000 mM; optionally, one or more osmolality adjusting agents at a concentration from about 0.1% to about 99%; and optionally one or more taste-masking agents at a concentration from about 0.1% to about 90 mM. Admixture of the containers provides an aqueous dosing solution for nebulized inhalation administration comprising water; nintedanib or salt thereof, or a indolinone derivative or salt thereof at a concentration from about 0.005 mg/mL to about 10 mg/mL, —and optionally one or more osmolality adjusting agents at a concentration of about 0.1% to about 20% to adjust osmolality, inorganic salts at a concentration of about 15 mM to about 300 mM to adjust osmolality and provide a permeant ion at a final concentration from about 30 mM to about 150 mM; and optionally one or more buffers to maintain the pH between about pH 3.0 to about pH 7.0, preferably from about pH 3.0 to about pH 6.0, with a final osmolality between 50 mOsmo/kg and 600 mOsmo/kg. The aqueous solution may include one or more osmolality adjusting agents including co-solvents selected from propylene glycol, ethanol and mannitol and combinations thereof at a concentration from about 0.1% to about 20%. The aqueous solution includes one more inorganic salts selected from sodium chloride, magnesium chloride, calcium chloride, potassium chloride, sodium bromide, potassium bromide, magnesium bromide and calcium bromide and combinations thereof. The inorganic salt content of the aqueous solution is from about 15 mM to about 300 mM and the buffer is selected from one or more of lysinate, acetylcysteine, glycine, glutamate, borate, succinate, tartrate, phosphate or Tris and combinations thereof, the pH of the aqueous solution is from about pH 3.0 to about pH 7.0, preferably pH about 3.0 to about pH 6.0. Described herein is an aqueous solution for nebulized inhalation administration comprising: water; nintedanib or salt thereof, at a concentration from about 0.005 mg/mL to about 10 mg/mL, preferably not exceeding 5.0 mg/mL; one or more permeant ions at a concentration from about 30 mM to about 150 mM; one or more osmolality adjusting agents; and wherein the osmolality of the aqueous solution is from about 50 mOsmol/kg to about 600 mOsmol/kg. Admixed formulation is either mixed prior to and poured into the nebulization device, may be separately poured and mixed within the nebulization device, or admixed within a container serving as the nebulization device medicine reservoir. The admixed formulation may be administered as an inhaled aerosol created from a dosing volume ranging from about 0.01 mL to about 10 mL. The admixed formulation may be administered as an inhaled aerosol over a few breaths or by tidal breathing up to 20 minutes. The rationale for the multi-container system is that the required parameters of the final solution for aerosolization, including specifically the pH, and ion concentration, buffer content, osmolality, or other parameter may require solutes that are incompatible with nintedanib or indolinone composition as the active pharmaceutical ingredient. By maintaining the compositions in separate containers, until prior to admixture and introduction into the nebulizer or administration, the stability of the active ingredient is maintained.

The invention includes a stand-alone, single-container system wherein nintedanib or salt thereof, or an indolinone derivative are stabilized in the presence of pH, and ion concentration, buffer content, osmolality, or other parameters that are otherwise incompatible with nintedanib or indolinone composition as the active pharmaceutical ingredient. The addition of the active ingredient pirfenidone or pyridone analog further increases nintedanib or indolinone composition stability, increases aqueous solubility, and reduces viscosity that otherwise exists at high nintedanib or indolinone composition concentrations greater than about 10 mg/mL to about 50 mg/mL. At these and lower nintedanib or salt thereof, or an indolinone derivative concentrations, the addition of active ingredient pirfenidone or pyridone analog enables formulation of nintedanib or salt thereof, or an indolinone derivative in a stable, single container solution containing ion concentrations, buffer contents, osmolality, pH or other parameters that are otherwise incompatible as a single solution product. For this, the formulation as administered may be prepared as a unit dosage adapted for use in a liquid nebulizer comprising from about 0.01 mL to about 10 mL of an aqueous solution of nintedanib or salt thereof, or a indolinone derivative or salt thereof at a concentration from about 0.005 mg/mL to about 50 mg/mL, and pirfenidone or pyridone analog at a concentration from about 5 mg/mL to about 20 mg/mL, optionally one or more osmolality adjusting agents at a concentration of about 0.1% to about 20% to adjust osmolality, inorganic salts at a concentration of about 15 mM to about 500 mM to adjust osmolality and provide a permeant ion at a final concentration from about 30 mM to about 500 mM; and optionally one or more buffers to maintain the pH between about pH 3.0 to about pH 7.0, preferably from about pH 3.0 to about pH 6.0, with a final osmolality between 50 mOsmo/kg and 1000 mOsmo/kg. The aqueous solution may include one or more osmolality adjusting agents including co-solvents selected from propylene glycol, ethanol, glycerin, and mannitol and combinations thereof at a concentration from about 0.1% to about 20%. The aqueous solution includes one more inorganic salts selected from sodium chloride, magnesium chloride, calcium chloride, potassium chloride, sodium bromide, potassium bromide, magnesium bromide and calcium bromide and combinations thereof. The inorganic salt content of the aqueous solution is from about 15 mM to about 300 mM. The buffer is selected from one or more of lysinate, acetylcysteine, glycine, glutamate, borate, succinate, tartrate, phosphate or Tris and combinations thereof, the pH of the aqueous solution is from about pH 3.0 to about pH 7.0, preferably pH about 3.0 to about pH 6.0. Described herein is an aqueous solution for nebulized inhalation administration comprising: water; nintedanib or salt thereof, at a concentration from about 0.005 mg/mL to about 50 mg/mL; pirfenidone or pyridone analog at a concentration from about 5 mg/mL to about 20 mg/mL; one or more permeant ions; one or more osmolality adjusting agents; and wherein the osmolality of the aqueous solution is from about 50 mOsmol/kg to about 1000 mOsmol/kg. The formulation may be administered as an inhaled aerosol created from a dosing volume ranging from about 0.01 mL to about 10 mL. The formulation may be administered as an inhaled aerosol over a few breaths or by tidal breathing up to 20 minutes.

The special formulation parameters of the invention include the selection of the salt for complexation with the form of nintedanib used for an isolated solution. Preferred salts include esylate, chloride, and bromide. The total delivery dose is from about 0.01 mL to about 10 mL of the aqueous solution described herein.

The invention includes a kit comprising: a unit dosage of an aqueous solution of nintedanib or salt thereof, as described herein in a container that is adapted for use with a liquid nebulizer such that the contents of a single container or multiple containers are combined in anticipation of placing the combined solution in the reservoir of a liquid nebulizer for aerosolization.

Moreover, the physicochemical properties of the resulting aerosol created by the compositions and methods of the present invention are an important part of the therapeutic utility of the present invention because the specially selected formulation design parameters, together with aerosolization by the nebulizer structures as described below, yield an aerosol mist that has uniquely advantageous properties for delivery of the active ingredient to a pulmonary compartment that is tailored to the pharmacodynamic absorption of the active pharmaceutical ingredient in the pulmonary organ. An aerosolized aqueous solution forms a population of nintedanib or indolinone of salt thereof, or nintedanib or indolinone of salt thereof and pirfenidone or pyridone analog wherein the aqueous droplet has a diameter less than about 5.0 μm. The aqueous droplet produced from a final solution placed in a liquid nebulizer, formulated as the specially designed solution containing nintedanib or indolinone or salt thereof has a concentration from about 0.005 mg/mL to about 10 mg/mL and an osmolality from about 50 mOsmol/kg to about 600 mOsmol/kg. Alternatively, the aqueous droplet produced from a final solution placed in a liquid nebulizer, formulated as the specially designed solution containing nintedanib or indolinone or salt thereof has a concentration from about 0.005 mg/mL to about 50 mg/mL and pirfenidone or pyridone analog at a concentration from about 5 mg/mL to about 20 mg/mL and an osmolality from about 50 mOsmol/kg to about 1000 mOsmol/kg.

These and other aspects of the invention will be evident upon reference to the following detailed description. All of the U.S. patents, U.S. patent application publications, U.S. patent applications, foreign patents, foreign patent applications and non-patent publications referred to in this specification, are incorporated herein by reference in their entirety, as if each was incorporated individually.

Certain Terminology

The term "mg" refers to milligram.
The term "mcg" refers to microgram.
The term "microM" refers to micromolar.
As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, which are also effective and safe.

As used herein, the terms "comprising," "including," "such as," and "for example" are used in their open, non-limiting sense.

The terms "administration" or "administering" and "delivery" or "delivery" refer to a method of giving to a human a dosage of a therapeutic or prophylactic formulation, such as an nintedanib or salt thereof formulation described herein, for example as an anti-inflammatory, anti-fibrotic and/or anti-demyelination pharmaceutical composition, or for other purposes. The preferred delivery method or method of administration can vary depending on various factors, e.g., the components of the pharmaceutical composition, the desired site at which the formulation is to be introduced, delivered or administered, the site where therapeutic benefit is sought, or the proximity of the initial delivery site to the downstream diseased organ (e.g., aerosol delivery to the lung for absorption and secondary delivery to the heart, kidney, liver, central nervous system or other diseased destination).

The terms "pulmonary administration" or "inhalation" or "pulmonary delivery" or "oral inhalation" or "intranasal inhalation" and other related terms refer to a method of delivering to a human a dosage of a therapeutic or prophylactic formulation by a route such that the desired therapeutic or prophylactic agent is delivered to the lungs of a human.

The terms "intranasal administration" and "intranasal delivery" refer to a method of giving to a mammal a dosage of a therapeutic or prophylactic formulation, such as an nintedanib or salt thereof formulation described herein, by a route such that the desired therapeutic or prophylactic agent is delivered to the nasal cavity or diseased organs downstream (e.g., aerosol delivery to the nasal cavity for absorption and secondary delivery to the central nervous system or other diseased destination). Such delivery to the nasal cavity may occur by intranasal administration, wherein this route of administration may occur as inhalation of an aerosol of formulations described herein, injection of an aerosol of formulations described herein, gavage of a formulation described herein, or passively delivered by mechanical ventilation.

The term "abnormal liver function" may manifest as abnormalities in levels of biomarkers of liver function, including alanine transaminase, aspartate transaminase, bilirubin, and/or alkaline phosphatase, and is an indicator of drug-induced liver injury. See FDA Draft Guidance for Industry. Drug-Induced Liver Injury: Premarketing Clinical Evaluation, October 2007.

"Grade 2 liver function abnormalities" include elevations in alanine transaminase (ALT), aspartate transaminase (AST), alkaline phosphatase (ALP), or gamma-glutamyl transferase (GGT) greater than 2.5-times and less than or equal to 5-times the upper limit of normal (ULN). Grade 2 liver function abnormalities also include elevations of bilirubin levels greater than 1.5-times and less than or equal to 3-times the ULN.

"Gastrointestinal adverse events" include but are not limited to any one or more of the following: dyspepsia, nausea, diarrhea, gastroesophageal reflux disease (GERD) and vomiting.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

A "diagnostic" as used herein is a compound, method, system, or device that assists in the identification and characterization of a health or disease state. The diagnostic can be used in standard assays as is known in the art.

The term "ex vivo" refers to experimentation or manipulation done in or on living tissue in an artificial environment outside the organism.

The term "pH-reducing acid" refers to acids that retain the biological effectiveness and properties of the compounds of this invention and, which are not biologically or otherwise undesirable. Pharmaceutically acceptable pH-reducing acids include, for example, inorganic acids such as, e.g., hydrochloric acid, hydrobromic acid, sulfuric acid, nitric acid, phosphoric acid, and the like. Also by nonlimiting example, pH-reducing acids may also include organic acids such as acetic acid, propionic acid, napthoic acid, oleic acid, palmitic acid, pamoic (emboic) acid, stearic acid, glycolic acid, pyruvic acid, oxalic acid, malonic acid, succinic acid, tartaric acid, ascorbic acid, glucoheptonic acid, glucuronic acid, lactic acid, lactobioic acid, tartaric acid, benzoic acid, cinnamic acid, mandelic acid, methanesulfonic acid, ethanesulfonic acid, p-toluenesulfonic acid, salicylic acid, and the like. According to certain herein disclosed embodiments an nintedanib or a indolinone derivative compound formulation may comprise an "acidic excipient" that is typically present as an acidic excipient aqueous solution. Examples of may include acid salts such as phosphate, sulphate, nitrate, acetate, formate, tartrate, propionate and sorbate, organic acids such as carboxylic acids, sulfonic acids, phosphonic acids, phosphinic acids, phosphoric monoesters, and phosphoric diesters, and/or other organic acids that contain from 1 to 12 carbon atoms, acetic acid, propionic acid, butyric acid, benzoic acid, mono-, di-, and trichloroacetic acid, salicylic acid, trifluoroacetic acid, benzenesulfonic acid, toluenesulfonic acid, methylphosphonic acid, methylphosphinic acid, dimethylphosphinic acid, and phosphonic acid monobutyl ester.

A "buffer" refers to a compound that functions to regulate pH. In certain related embodiments the pH buffer is present under conditions and in sufficient quantity to maintain a pH that is "about" a recited pH value. "About" such a pH refers to the functional presence of that buffer, which, as is known in the art, is a consequence of a variety of factors including pKa value(s) of the buffer, buffer concentration, working temperature, effects of other components of the composition on pKa (i.e., the pH at which the buffer is at equilibrium between protonated and deprotonated forms, typically the center of the effective buffering range of pH values), and other factors.

Hence, "about" in the context of pH may be understood to represent a quantitative variation in pH that may be more or less than the recited value by no more than 0.5 pH units, more preferably no more than 0.4 pH units, more preferably no more than 0.3 pH units, still more preferably no more than 0.2 pH units, and most preferably no more than 0.1-0.15 pH units. As also noted above, in certain embodiments a substantially constant pH (e.g., a pH that is maintained within the recited range for an extended time period) may be from about pH 4.0 to about pH 7.0, from about pH 4.0 to about pH 7.0, or from about pH 4.0 to about pH 6.8, or any other pH or pH range as described herein, which in preferred embodiments may be from about pH 4.0 to about pH 7.0 for an nintedanib or salt thereof formulation, and greater than about pH 7.0.

Therefore the pH buffer typically may comprise a composition that, when present under appropriate conditions and in sufficient quantity, is capable of maintaining a desired pH level as may be selected by those familiar with the art, for example, buffers comprising, lysinate, acetylcysteine, glycine, glutamate, borate, succinate, tartrate, phosphate or Tris formate, pyridine, piperazine, succinate, histidine, bis-Tris, pyrophosphate, PIPES, ACES, histidine, MES, cacodylic acid, H2CO3/NaHCO3 and N-(2-Acetamido)-2-iminodiacetic acid (ADA) or other buffers for maintaining, preserving, enhancing, protecting or otherwise promoting desired biological or pharmacological activity of an nintedanib or indolinone salt thereof. Suitable buffers may include those listed herein or known to the art (see, e.g., Calbiochem® Biochemicals & Immunochemicals Catalog 2004/2005, pp. 68-69 and catalog pages cited therein, EMD Biosciences, La Jolla, Calif.).

"Solvate" refers to the compound formed by the interaction of a solvent and nintedanib or an indolinone derivative compound, a metabolite, or salt thereof. Suitable solvates are pharmaceutically acceptable solvates including hydrates.

By "therapeutically effective amount" or "pharmaceutically effective amount" is meant nintedanib or a indolinone or salt that are useful in treatment of humans in therapeutically effective amounts and that produce the desired therapeutic effect as judged by clinical trial results and/or model animal pulmonary fibrosis, lung transplant rejection-associated chronic lung allograft dysfunction (CLAD) and restrictive allograft syndrome (RAS), cardiac fibrosis, kidney fibrosis, hepatic fibrosis, heart or kidney toxicity, or disease resulting from active, previous or latent viral infection.

A "therapeutic effect" relieves, to some extent, one or more of the symptoms associated with inflammation, fibrosis and/or demyelination. This includes slowing the progression of, or preventing or reducing additional inflammation, fibrosis and/or demyelination. For IPF and RAS, a "therapeutic effect" is defined as a reduced decline in forced vital capacity (FVC), and/or a patient-reported improvement in quality of life and/or a statistically significant increase in or stabilization of exercise tolerance and associated blood-oxygen saturation, reduced decline in baseline forced vital capacity, decreased incidence in acute exacerbations, increase in progression-free survival, increased time-to-death or disease progression, and/or reduced lung fibrosis. For CLAD, a "therapeutic effect" is defined as a reduced decline in forced expiratory volume in one second (FEV1), For cardiac fibrosis, a "therapeutic effect" is defined as a patient-reported improvement in quality of life and/or a statistically significant improvement in cardiac function, reduced fibrosis, reduced cardiac stiffness, reduced or reversed valvular stenosis, reduced incidence of arrhythmias and/or reduced atrial or ventricular remodeling. For kidney fibrosis, a "therapeutic effect" is defined as a patient-reported improvement in quality of life and/or a statistically significant improvement in glomular filtration rate and associated markers. For hepatic fibrosis, a "therapeutic effect" is defined as a patient-reported improvement in quality of life and/or a statistically significant lowering of elevated aminotransferases (e.g., AST and ALT), alkaline phosphatases, gamma-glutamyl transferase, bilirubin, prothrombin time, globulins, as well as reversal of thrombocytopenia, leukopenia and neutropenia and coagulation defects. Further a potential reversal of imaging, endoscopic or other pathological findings. For disease resulting from active, previous or latent viral infection, a "therapeutic effect" is defined as a patient-reported improvement in quality of life and/or a statistically significant reduction in viral load, improved exercise capacity and associated blood-oxygen saturation, FEV1 and/or FVC, a slowed or halted progression in the same, progression-free survival, increased time-to-death or disease progression, and/or reduced incidence or acute exacerbation or reduction in neurologic symptoms. The term "prophylactic treatment" refers to treating a patient who is not yet diseased but who is susceptible to, or otherwise at risk of, a particular disease, or who is diseased but whose condition does not worsen while being treated with the pharmaceutical compositions described herein. The term "therapeutic treatment" refers to administering treatment to a patient already suffering from a disease. Thus, in preferred embodiments, treating is the administration to a mammal (either for therapeutic or prophylactic purposes) of therapeutically effective amounts of nintedanib or a indolinone derivative compound.

The "respirable delivered dose" is the amount of aerosolized nintedanib or a indolinone derivative compound particles inhaled during the inspiratory phase of the breath simulator that is equal to or less than 5 microns.

"Lung Deposition" as used herein, refers to the fraction of the nominal dose of an active pharmaceutical ingredient (API) that is deposited on the inner surface of the lungs.

"Nominal dose," or "loaded dose" refers to the amount of drug that is placed in the nebulizer prior to administration to a human. The volume of solution containing the nominal dose is referred to as the "fill volume."

"Enhanced pharmacokinetic profile" means an improvement in some pharmacokinetic parameter. Pharmacokinetic parameters that may be improved include, AUC last, AUC (0-∞) Tmax, and optionally a Cmax. The enhanced pharmacokinetic profile may be measured quantitatively by comparing a pharmacokinetic parameter obtained for a nominal dose of an active pharmaceutical ingredient (API) administered with one type of inhalation device with the same pharmacokinetic parameter obtained with oral administration of a composition of the same active pharmaceutical ingredient (API).

"Respiratory condition," as used herein, refers to a disease or condition that is physically manifested in the respiratory tract, including, but not limited to, pulmonary fibrosis, cancer, disease resulting from active, previous or latent viral infection, bronchitis, chronic bronchitis, or emphysema.

"Drug absorption" or simply "absorption" typically refers to the process of movement of drug from site of delivery of a drug across a barrier into a blood vessel or the site of action, e.g., a drug being absorbed in the pulmonary capillary beds of the alveoli.

DETAILED DESCRIPTION

Pulmonary and Regional Diseases

A number of pulmonary diseases such as interstitial lung disease (ILD; and sub-class diseases therein), cancer (lung cancer; and sub-class diseases therein), fibrotic indications of the lungs, kidney, heart and eye, viral infections and diseases of the central nervous system are current areas of unmet clinical need.

In fibrosis, scarring serves a valuable healing role following injury. However, tissue may become progressively scarred following more chronic, repeated and or idiopathic injuries resulting in abnormal function. In the case of idiopathic pulmonary fibrosis (IPF; and other subclasses of ILD), if a sufficient proportion of the lung becomes scarred respiratory failure can occur. In any case, progressive scarring may result from a recurrent series of insults to different regions of the organ or a failure to halt the repair process after the injury has healed. In such cases the scarring process becomes uncontrolled and deregulated. In some forms of fibrosing disease scarring remains localized to a limited region, but in others it can affect a more diffuse and extensive area resulting in direct or associated organ failure.

In epithelial injury, epithelial cells are triggered to release several pro-fibrotic mediators, including the potent fibroblast growth factors transforming growth factor-beta (TGF-beta), tumor necrosis factor (TNF), platelet derived growth factor (PDGF), endothelin, other cytokines, metalloproteinases and the coagulation mediator tissue factor. Importantly, the triggered epithelial cell becomes vulnerable to apoptosis, and together with an apparent inability to restore the epithelial cell layer are the most fundamental abnormalities in fibrotic disease.

In conditions such as diseases, physiological responses characterized by control of pro-fibrotic factors with indolinone derivative, such as nintedanib is beneficial to attenuate and/or reverse fibrosis, treat cancer, or central nervous system disease. Therapeutic strategies exploiting such indolinone derivative and/or nintedanib effects in these and other indications are contemplated herein.

Nintedanib and Indolinone Derivative Compounds—Therapeutic Utility

The indolinone derivative for use in a indolinone derivative formulation as described herein comprises nintedanib (methyl (3Z)-3-[[4-[methyl-[2-(4-methylpiperazin-1-yl)acetyl]amino]anilino]-phenylmethylidene]-2-oxo-1H-indole-6-carboxylate) or a salt thereof.

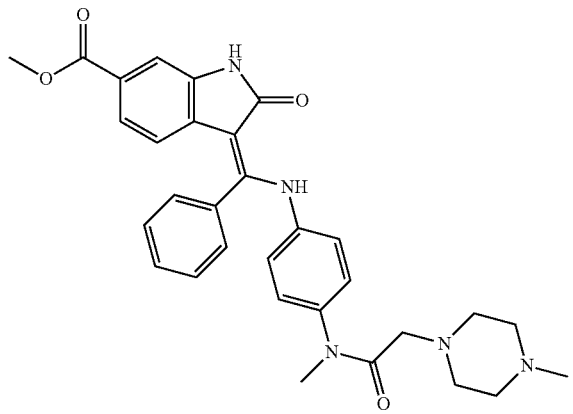

Other indolinone derivative compounds, or salts thereof, may be used in place of nintedanib. Indolinone derivative compounds include, but are not limited to, those compounds that are structurally similar to nintedanib. Indolinone derivative compounds include, but are not limited to, those compounds that are structurally similar to and have the same type of biological activity as nintedanib. Indolinone derivative compounds include modifications to the nintedanib molecule that are foreseeable based on substitution of chemical moieties that preserve the Structure Activity Relationship (SAR) of nintedanib based on the interaction of nintedanib, or the subject derivative as specific and selective inhibitor of certain tyrosine kinases as described below. Indolinone derivative compounds include, but are not limited to, those compounds described in U.S. Pat. Nos. 6,762,180 and 7,119,093.

Nintedanib inhibits a broad range of kinases at pharmacologically relevant concentrations. Examples of targeted kinases include all three VEGFR subtypes (VEGFR-1, IC50 34 nM; VEGFR-2, IC50 21 nM; VEGFR-3, IC50 13 nM), FGFR types (FGFR-1, IC50 69 nM; FGFR-2, IC50 37 nM; FGFR-3, IC50 108 nM; FGFR-4, IC50 610 nM), and PDGFR-α (IC50, 59 nM) and PDGFR-β (IC50, 65 nM). The ability of nintedanib to simultaneously target these three, distinct proangiogenic receptor classes may enhance its antitumor effects and overcome pathways of resistance to VEGF- and VEGFR-2-targeted agents. Nintedanib also inhibited Flt-3 and members of the Src-family (Src, Lyn, and Lck), which may have therapeutic potential for conditions such as hematologic diseases.

The antifibrotic potential of VEGFR, PDGFR, and FGFR inhibition with orally administered nintedanib has also been evaluated in a series of preclinical studies. Nintedanib was shown to inhibit PDGFR-α and PDGFR-β activation and proliferation of normal human lung fibroblasts in vitro and to inhibit PDGF-BB-, FGF-2-, and VEGF-induced proliferation of human lung fibroblasts from patients with IPF and control donors. Nintedanib attenuated PDGF- or FGF-2-stimulated migration of lung fibroblasts from patients with IPF9 and inhibited transforming growth factor (TGF)-β-induced fibroblast to myofibroblast transformation of primary human lung fibroblasts from IPF patients. PDGFR activation and downstream signaling was inhibited by nintedanib in a dose-dependent manner in mouse lung tissue when administered orally in vivo. In two different mouse models of IPF, nintedanib exerted anti-inflammatory effects as shown by significant reductions in lymphocyte and neutrophil counts in the bronchioalveolar lavage fluid, reductions in inflammatory cytokines, and reduced inflammation and granuloma formation in histological analysis of lung tissue. IPF mouse models also revealed nintedanib-associated antifibrotic effects as shown by significant reductions in total lung collagen and by reduced fibrosis identified in histological analyses.

IPF is a chronic and progressive, fibrotic lung disease associated with a short median survival post diagnosis of 2-3 years due to a lack of effective therapies. IPF is characterized by uncontrolled fibroblast/myofibroblast proliferation and differentiation, and excessive collagen deposition within the lung interstitium and alveolar space, leading to symptoms of cough and dyspnea, and ultimately to respiratory failure.

In some embodiments, administration of nintedanib or indolinone or salt thereof, by inhalation has reduced gastrointestinal and liver side-effects when compared to oral administration. Reducing these side-effects increases patient safety, maximizes patient compliance, avoids dose reduction and/or stoppage protocols, and enables local lung dose escalation for additional efficacy otherwise not possible with the oral product.

The specially formulated nintedanib or indolinone aqueous solutions for aerosol administration are used in methods of treatment of lung disease in a human the methods are applied to diseases including, not limited to, pulmonary fibrosis, idiopathic pulmonary fibrosis, radiation induced fibrosis, silicosis, asbestos induced pulmonary or pleural fibrosis, acute lung injury, acute respiratory distress syndrome (ARDS), sarcoidosis, usual interstitial pneumonia (UIP), cystic fibrosis, Chronic lymphocytic leukemia (CLL)-associated fibrosis, Hamman-Rich syndrome, Caplan syndrome, coal worker's pneumoconiosis, cryptogenic fibrosing alveolitis, obliterative bronchiolitis, chronic bronchitis, emphysema, pneumonitis, Wegner's granulamatosis, scleroderma-associated lung fibrosis, systemic sclerosis-associated interstitial lung disease (SSc-ILD), silicosis, interstitial lung disease, asbestos induced pulmonary and/or pleural fibrosis. In some methods the primary, lung disease is lung fibrosis (i.e. pulmonary fibrosis), while in other methodologies the fibrosis is a comorbidity of a separate disease such as cancer or is the result of a prior infection or surgery, including particularly chronic lung allograft dysfunction (CLAD), and including restrictive allograft syndrome (RAS).

Pulmonary Fibrosis

A method for treating or preventing progression of pulmonary disease, comprising administering nintedanib or indolinone or salt thereof or in combination with pirfenidone or pyridone analog to a middle to lower respiratory tract of a patient having or suspected of having pulmonary disease through oral inhalation of an aerosol. A method of treating or preventing progression of interstitial pulmonary fibrosis and includes patients who are being mechanically ventilated.

A method for treating or preventing progression of idiopathic pulmonary fibrosis (IPF), comprising administering nintedanib or indolinone or salt thereof or in combination with pirfenidone or pyridone analog to a middle to lower respiratory tract of a subject having or suspected IPF through oral inhalation of an aerosol comprising nintedanib or salt thereof.

A method for treating or preventing progression of systemic sclerosis associated interstitial lung disease (SSc-ILD), comprising administering nintedanib or indolinone or salt thereof or in combination with pirfenidone or pyridone analog to a middle to lower respiratory tract of a subject having or suspected of having SSc-ILD through oral inhalation of an aerosol comprising nintedanib or indolinone or salt thereof.

A method for treating or preventing progression of bronchiolitis obliterans, comprising administering nintedanib or indolinone or salt thereof or in combination with pirfenidone or pyridone analog to a middle to lower respiratory tract of a patient having or suspected of having bronchiolitis obliterans through oral inhalation of an aerosol comprising nintedanib or indolinone or salt thereof.

A method for treating or preventing progression of chronic lung allograft dysfunction, comprising administering nintedanib or indolinone salt thereof or in combination with pirfenidone or pyridone analog to a middle to lower respiratory tract of a patient having or suspected of having restrictive allograft syndrome through oral inhalation of an aerosol comprising nintedanib or indolinone or salt thereof.

A method for treating or preventing progression of restrictive allograft syndrome, comprising administering nintedanib indolinone salt thereof or in combination with pirfenidone or pyridone analog to a middle to lower respiratory tract of a patient having or suspected of having restrictive allograft syndrome through oral inhalation of an aerosol comprising nintedanib or indolinone or salt thereof.

IPF as described herein refers to "idiopathic pulmonary fibrosis" and is in some embodiments a chronic disease that manifests over several years and is characterized by scar tissue within the lungs, in the absence of known provocation. Exercise-induced breathlessness and chronic dry cough may be the prominent symptoms. IPF belongs to a family of lung disorders known as the interstitial lung diseases (ILD) or, more accurately, the diffuse parenchymal lung diseases. Within this broad category of diffuse lung diseases, IPF belongs to the subgroup known as idiopathic interstitial pneumonia (IIP). There are seven distinct IIPs, differentiated by specific clinical features and pathological patterns. IPF is the most common form of IIP. It is associated with the pathologic pattern known as usual interstitial pneumonia (UIP); for that reason, IPF is often referred to as IPF/UIP. IPF is usually fatal, with an average survival of approximately three years from the time of diagnosis. There is no single test for diagnosing pulmonary fibrosis; several different tests including chest x-ray, pulmonary function test, exercise testing, bronchoscopy and lung biopsy are used in conjunction with the methods described herein.

Idiopathic pulmonary fibrosis (also known as cryptogenic fibrosing alveolitis) is the most common form of interstitial lung disease and may be characterized by chronic progressive pulmonary parenchymal fibrosis. It is a progressive clinical syndrome with unknown etiology; the outcome is frequently fatal as no effective therapy exists. In some embodiments, nintedanib inhibits fibroblast proliferation and differentiation related to collagen synthesis, inhibits the production and activity of TGF-beta, reduces production of fibronectin and connective tissue growth factor, inhibits TNF-alpha and I-CAM, increase production of IL-10, and/or reduces levels of platelet-derived growth factor (PDGF) A and B in bleomycin-induced lung fibrosis. The methods and compositions described herein may provide tolerability and usefulness in patients with advanced idiopathic pulmonary fibrosis and other lung diseases. In some embodiments, nintedanib methods and compositions described herein may provide tolerability and usefulness in patients with mild to moderate idiopathic pulmonary fibrosis. Increased patient survival, enhanced vital capacity, reduced episodes of acute exacerbation (compared to placebo), and/or slowed disease progression are observed following treatment with the compositions of the invention.

Exemplary fibrotic lung diseases for the treatment or prevention using the methods described herein include, but are not limited to, idiopathic pulmonary fibrosis, systemic sclerosis-associated interstitial lung disease, pulmonary fibrosis secondary to transplant rejection such as bronchiolitis obliterans and restrictive allograft syndrome, systemic inflammatory disease such as rheumatoid arthritis, scleroderma, lupus, cryptogenic fibrosing alveolitis, radiation induced fibrosis, sarcoidosis, scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced).

Where the methods of the invention are applied to treatments or preventing progression of pulmonary cancer, the disorder includes lung carcinoid tumors or bronchial cardinoids, primary or secondary lung cancers resulting from metastatic disease, including non-small cell lung cancer, bronchioloalveolar carcinoma, sarcoma, and lymphoma.

Methods of the invention include treatment or prophylaxis of patients identified as having gastrointestinal stromal tumors, relapsed or refractory Ph-positive Acute lymphoblastic leukemia (ALL), myelodysplastic/myeloproliferative diseases associated with platelet-derived growth factor receptor gene re-arrangements, aggressive systemic mastocytosis (ASM) (without or an unknown D816V c-KIT mutation), hypereosinophilic syndrome (HES) and/or chronic eosinophilic leukemia (CEL) who have the FIP1L1-PDGFRα fusion kinase (CHIC2 allele deletion) or FIP1L1-PDGFR-alpha fusion kinase negative or unknown, or unresectable, recurrent and/or metastatic dermatofibrosarcoma protuberans, and combinations thereof.

In one aspect, described herein is a method for treating neurologic disease, comprising administering nintedanib or indolinone or salt thereof, to a patient diagnosed or suspected of having neurologic disease and treated through oral or intranasal inhalation of an aerosol for pulmonary or nasal vascular absorption and delivery to central nervous system, including to treat or alleviate neurofibromatosis, neurofibromatosis type I, Alzheimer's disease, the presence of Lewy Body proteins or precursors thereof, and combinations thereof and wherein the patient may exhibit opioid tolerance.

Lung Transplant Rejection

Lung transplant rejection initially manifests as Chronic Lung Allograft Dysfunction (CLAD) and is the major cause of mortality. The major feature is bronchiolitis obliterans. The rate of decline in lung function when severe averaging about 7-fold higher than seen in a patient with idiopathic pulmonary fibrosis (IPF). Some CLAD patients (approximately 30%) develop Restrictive Allograft Syndrome (RAS) which carries a worse prognosis. In these patients there is loss of both FVC, forced vital capacity creating restrictive pulmonary function. The pathophysiology is similar to IPF with progressive interstitial fibrosis.

A method for treating or preventing progression of pulmonary disease, comprising administering nintedanib or indolinone or salt thereof to a middle to lower respiratory tract of a patient having or suspected of having pulmonary disease through oral inhalation of an aerosol. The method includes treating or preventing progression of Chronic Lung Allograft Dysfunction (CLAD) as a manifestation of lung transplant rejection. The method includes delivery to patients who are being mechanically ventilated. The method also includes administration of nintedanib or indolinone or salt thereof and pirfenidone or pyridone analog in combination.

A method for treating or preventing progression of pulmonary disease, comprising administering nintedanib or indolinone or salt thereof to a middle to lower respiratory tract of a patient having or suspected of having pulmonary disease through oral inhalation of an aerosol. The method includes treating or preventing progression of bronchiolitis obliterans as a manifestation of lung transplant rejection. The method includes delivery to patients who are being mechanically ventilated. The method also includes administration of nintedanib or indolinone or salt thereof and pirfenidone or pyridone analog in combination.

A method for treating or preventing progression of pulmonary disease, comprising administering nintedanib or indolinone or salt thereof to a middle to lower respiratory tract of a patient having or suspected of having pulmonary disease through oral inhalation of an aerosol. The method includes treating or preventing progression of Restrictive Allograft Syndrome (RAS) as a manifestation of lung transplant rejection. The method includes delivery to patients who are being mechanically ventilated. The method also includes administration of nintedanib or indolinone or salt thereof and pirfenidone or pyridone analog in combination.

Kidney Fibrosis

A method for treating or preventing progression of an extrapulmonary disease, comprising administering nintedanib or indolinone or salt thereof, wherein the extrapulmonary disease is kidney fibrosis, and may result or be a co-morbidity chronic infection, obstruction of the ureter by calculi, malignant hypertension, radiation therapy, transplant rejection, severe diabetic conditions, or chronic exposure to heavy metals, and combinations thereof.

The term "kidney fibrosis" by non-limiting example relates to remodeling associated with or resulting chronic infection, obstruction of the ureter by calculi, malignant hypertension, radiation therapy, transplant rejection, severe diabetic conditions or chronic exposure to heavy metals and generally correlates with the overall loss of renal function.

Heart and Kidney Toxicity

A method for treating or preventing progression of an extrapulmonary disease also includes, heart and kidney damage resulting from treatment with other active pharmaceutical ingredients including chemotherapeutic agents that have toxic effects upon multiple organs during therapy. By non-limiting example doxorubicin has a broad spectrum of therapeutic activity against various tumors. However, its clinical use is limited by its undesirable systemic toxicity, especially in the heart and kidney. In some embodiments, because the heart and kidney vasculature are immediately downstream of the lung, inhaled delivery of nintedanib or indolinone or salt thereof, prevents or alleviates chemotherapy-induced cardiac and/or renal inflammation without exposing the systemic compartment to otherwise toxic drug levels associated with oral administration Cardiac Fibrosis A method for treating or preventing progression of an extrapulmonary disease, includes cardiac fibrosis including remodeling of cardiac tissue observed in chronic hypertension and may involve myocyte hypertrophy as well as fibrosis, an increased and non-uniform deposition of extracellular matrix proteins. The extracellular matrix connects myocytes, aligns contractile elements, prevents overextending and disruption of myocytes, transmits force and provides tensile strength to prevent rupture. Fibrosis occurs in many models of hypertension leading to an increased diastolic stiffness, a reduction in cardiac function and an increased risk of arrhythmias. If fibrosis rather than myocyte hypertrophy is the critical factor in impaired cardiovascular function, then reversal of cardiac fibrosis facilitates return of normal cardiac function.

The term "cardiac fibrosis" by non-limiting example relates to remodeling associated with or resulting from viral or bacterial infection, surgery, Duchenne muscular dystrophy, radiation therapy, chemotherapy, transplant rejection and chronic hypertension where myocyte hypertrophy as well as fibrosis is involved and an increased and non-uniform deposition of extracellular matrix proteins occurs. Fibrosis occurs in many models of hypertension leading to an increased diastolic stiffness, a reduction in cardiac function, an increased risk of arrhythmias and impaired cardiovascular function.

Hepatic Fibrosis

A method for treating or preventing progression of an extrapulmonary disease includes hepatic fibrosis caused by chronic liver disease, including disease caused by non-limiting example persistent viral hepatitis, alcohol overload and autoimmune disorders and combinations thereof. Hepatic fibrosis involves an abnormal accumulation of extracellular matrix components, particularly collagens. Hepatic stellate cells are non-parenchymal liver cells residing in the perisinusoidal space. These cells have been shown to be the major cellular source of extracellular matrix in hepatic fibrosis.

The term "hepatic fibrosis" by non-limiting example may be associated with or caused by severe liver damage in patients with chronic liver disease, caused by non-limiting example persistent viral hepatitis, alcohol overload and autoimmune diseases. Hepatic fibrosis involves an abnormal accumulation of extracellular matrix components, particularly collagens. Hepatic stellate cells are non-parenchymal liver cells residing in the perisinusoidal space.

Glaucoma Surgery Post-Operative Fibrosis

A method for treating or preventing progression of an extrapulmonary disease includes postoperative fibrosis following, glaucoma filtration surgery where the success of the surgery is dependent on the degree of post-operative wound healing and the amount of scar tissue formation. Bleb failure occurs as fibroblasts proliferate and migrate toward the wound, eventually causing scarring and closure of the fistula tract. This frequently leads to poor postoperative intraocular pressure control with subsequent progressive optic nerve damage. The use of adjunctive antifibrotic agents such as 5-fluorouracil and mitomycin C has significantly improved the success rate of filtration surgery. However, because of their nonspecific mechanisms of action, these agents can cause widespread cell death and apoptosis, resulting in potentially sight-threatening complications such as severe postoperative hypotony, bleb leaks, and endophthalmitis.

Cancer

Lung cancer mortality is high, and annual lung cancer deaths equal prostate, breast, colon, and rectum cancers combined. Despite the advancement in knowledge on molecular mechanisms and the introduction of multiple new therapeutic lung cancer agents, the dismal 5-year survival rate (11-15%) remains relatively unaltered. This reflects the limited available knowledge on factors promoting oncogenic transformation to and proliferation of malignant cells.

We now know that tumor growth is not determined only by malignant cells, because interactions between cancer cells and the stromal compartment have major impacts on cancer growth and progression. Aggressive malignant cells are clever at exploiting the tumor microenvironment: tumor cells can (1) reside in the stroma and transform it, (2) alter the surrounding connective tissue, and (3) modify the metabolism of resident cells, thus yielding a stroma, which is permissive rather than defensive.

Beyond overcoming the microenvironmental control by the host, key characteristics of cancer cells is their ability to invade the tissue and metastasize distantly. For invasion and metastasis, the concerted interactions between fibroblasts, immune cells, and angiogenic cells and factors are essential.

The tumor stroma basically consists of (1) the nonmalignant cells of the tumor such as CAFs, specialized mesenchymal cell types distinctive to each tissue environment, innate and adaptive immune cells, and vasculature with endothelial cells and pericytes and (2) the extracellular matrix (ECM) consisting of structural proteins (collagen and elastin), specialized proteins (fibrillin, fibronectin, and elastin), and proteoglycans. Angiogenesis is central for cancer cell growth and survival and has hitherto been the most successful among stromal targets in anticancer therapy. Initiation of angiogenesis requires matrix metalloproteinase (MMP) induction leading to degradation of the basement membrane, sprouting of endothelial cells, and regulation of pericyte attachment. However, CAFs play an important role in synchronizing these events through the expression of numerous ECM molecules and growth factors, including transforming growth factor (TGF)-β, vascular endothelial growth factor (VEGF), and fibroblast growth factor (FGF2).

The normal tissue stroma is essential for maintenance and integrity of epithelial tissues and contains a multitude of cells that collaborate to sustain normal tissue homeostasis. There is a continuous and bilateral molecular crosstalk between normal epithelial cells and cells of the stromal compartment, mediated through direct cell-cell contacts or by secreted molecules. Thus, minor changes in one compartment may cause dramatic alterations in the whole system.

A similarity exists between stroma from wounds and tumors, because both entities had active angiogenesis and numerous proliferating fibroblasts secreting a complex ECM, all on a background of fibrin deposition. Consequently, the tumor stroma has been commonly referred to as activated or reactive stroma.

A genetic alteration during cancer development, leading to a malignant cell, will consequently change the stromal host compartment to establish a permissive and supportive environment for the cancer cell. During early stages of tumor development and invasion, the basement membrane is degraded, and the activated stroma, containing fibroblasts, inflammatory infiltrates, and newly formed capillaries, comes into direct contact with the tumor cells. The basement membrane matrix also modifies cytokine interactions between cancer cells and fibroblasts. These cancer-induced alterations in the stroma will contribute to cancer invasion. Animal studies have shown that both wounding and activated stroma provides oncogenic signals to facilitate tumorigenesis. Although normal stroma in most organs contains a minimal number of fibroblasts in association with physiologic ECM, the activated stroma is associated with more ECM-producing fibroblasts, enhanced vascularity, and increased ECM production. This formation of a specific tumor stroma type at sites of active tumor cell invasion is considered an integral part of the tumor invasion and has been termed as tumor stromatogenesis.

The expansion of the tumor stroma with a proliferation of fibroblasts and dense deposition of ECM is termed a desmoplastic reaction. It is secondary to malignant growth and can be separated from alveolar collapse, which do not show neither activated fibroblasts nor the dense collagen/ECM. Morphologically this is termed desmoplasia and was initially conceived as a defense mechanism to prevent tumor growth, but data have shown that in established tumors, this process, quite oppositely, participates in several aspects of tumor progression, such as angiogenesis, migration, invasion, and metastasis. The latter studies show that fibroblasts and tumor cells can enhance local tissue growth and cancer progression through secreting ECM and degrading components of ECM within the tumor stroma. This is in part related to the release of substances sequestered in the ECM, such as VEGF, and cleavage of products from ECM proteins as a response to secretion of carcinoma-associated MMPs.

Profibrotic growth factors, released by cancer cells, such as TGF-β, platelet-derived growth factor (PDGF), and FGF2 govern the volume and composition of the tumor stroma as they are all key mediators of fibroblast activation and tissue fibrosis. PDGF and FGF2 play significant roles in angiogenesis as well.

In tumors, activated fibroblasts are termed as peritumoral fibroblasts or carcinoma-associated fibroblasts (CAFs). CAFs, like activated fibroblasts, are highly heterogeneous and believed to derive from the same sources as activated fibroblasts. The main progenitor seems to be the locally residing fibroblast, but they may also derive from pericytes and smooth muscle cells from the vasculature, from bone marrow-derived mesenchymal cells, or by epithelial or endothelial mesenchymal transition. The term CAF is rather ambiguous because of the various origins from which these cells are derived, as is the difference between activated fibroblasts and CAFs. There are increasing evidence for epigenetic and possibly genetic distinctions between CAFs and normal fibroblasts. CAFs can be recognized by their expression of α-smooth muscle actin, but due to heterogeneity α-smooth muscle actin expression alone will not identify all CAFs. Hence, other used CAF markers are fibroblast-specific protein 1, fibroblast activation protein (FAP), and PDGF receptor (PDGFR) α/β.

In response to tumor growth, fibroblasts are activated mainly by TGF-β, chemokines such as monocyte chemotactic protein 1, and ECM-degrading agents such as MMPs. Although normal fibroblasts in several in vitro studies have demonstrated an inhibitory effect on cancer progression, today, there is solid evidence for a cancer-promoting role of CAFs. In breast carcinomas, as much as 80% of stromal fibroblasts are considered to have this activated phenotype (CAFs).

CAFs promote malignant growth, angiogenesis, invasion, and metastasis. The roles of CAFS and their potential as targets for cancer therapy have been studied in xenografts models, and evidence from translational studies has revealed a prognostic significance of CAFs in several carcinoma types.

In the setting of tumor growth, CAFs are activated and highly synthetic, secreting, for example, collagen type I and IV, extra domain A-fibronectin, heparin sulfate proteoglucans, secreted protein acidic and rich in cysteine, tenascin-C, connective tissue growth factors, MMPs, and plasminogen activators. In addition to secreting growth factors and cytokines, which affect cell motility, CAFs are an important source for ECM-degrading proteases such as MMPs that play several important roles in tumorigenesis. Through degradation of ECM, MMPs can, depending on substrate, promote tumor growth, invasion, angiogenesis, recruitment of inflammatory cells, and metastasis. Besides, a number of proinflammatory cytokines seem to be activated by MMPs.

After injection of B16M melanoma cells in mice, the formation of liver metastases was associated with an early activation of stellate cells (fibroblast-like) in the liver, as these seemed important for creating a metastatic niche and promoting angiogenesis. MMPs have also been linked to tumor angiogenesis in various in vivo models. CAFs, when coinjected into mice, facilitated the invasiveness of otherwise noninvasive cancer cells. Furthermore, xenografts containing CAFs apparently grow faster than xenografts infused with normal fibroblasts.

At CAF recruitment and accumulation in the tumor stroma, these cells will actively communicate with cancer cells, epithelial cells, endothelial cells, pericytes, and inflammatory cells through secretion of several growth factors, cytokines, and chemokines. CAFs provide potent oncogenic molecules such as TGF-β and hepatocyte growth factor (HGF).

TGF-β is a pleiotropic growth factor expressed by both cancer and stromal cells. TGF-β is, in the normal and premalignant cells, a suppressor of tumorigenesis, but as cancer cells progress, the antiproliferative effect is lost, and instead, TGF-β promotes tumorigenesis by inducing differentiation into an invasive phenotype. TGF-β may also instigate cancer progression through escape from immunosurveillance, and increased expression of TGF-β correlate strongly with the accumulation of fibrotic desmoplastic tissue and cancer progression. Recently, a small molecule inhibitor of TGF-β receptor type I was reported to inhibit the production of connective tissue growth factor by hepatocellular carcinoma (HCC) cells, resulting in reduced stromal component of the HCCs. Inhibition of the TGF-β receptor aborted the crosstalk between HCCs and CAFs and consequently avoided tumor proliferation, invasion, and metastasis. HGF belongs to the plasminogen family and is tethered to ECM in a precursor form. It binds to the high-affinity receptor c-met, and overexpression or constant oncogenic c-Met signaling lead to proliferation, invasion, and metastasis.

PDGFs are regulators of fibroblasts and pericytes and play important roles in tumor progression. It is a chemotactic and growth factor for mesenchymal and endothelial cells. It has a limited autocrine role in tumor cell replication, but is a potential player, in a paracrine fashion, and in tumor stroma development. It induces the proliferation of activated fibroblasts and possibly recruits CAFs indirectly by stimulation of TGF-β release from macrophages.

A tumor cannot develop without the parallel expansion of a tumor stroma. Although we still do not comprehend the exact mechanisms regulating fibroblast activation and their accumulation in cancer, the available evidence points to the possibility that the tumor stroma or CAFs are candidate targets for cancer treatment.

CAFs and MMPs have been considered two of the key regulators of epithelial-derived tumors representing potential new targets for integrative therapies, affecting both the transformed and non-transformed components of the tumor environment. As commented earlier, the experience with MMP inhibitors have so far been unsuccessful. Evidence that CAFs are epigenetically and possibly also genetically distinct from normal fibroblasts is beginning to define these cells as potential targets for anticancer therapy. FAP, expressed in more than 90% of epithelial carcinomas, emerged early as a promising candidate for targeting CAFs, and the potential therapeutic benefit of its inhibition was reviewed recently. In preclinical studies, abrogation of FAP attenuates tumor growth and significantly enhance tumor tissue uptake of anticancer drugs. In a phase I study, where patients with FAP-positive advanced carcinomas (colorectal cancer and NSCLC) were treated with FAP-antibody, the antibody bound specifically to tumor sites, but no objective responses were observed.

The consistent and repeated findings of cancer cells that readily undergo invasion and metastasis in response to TGF-β have pointed to the need of novel anticancer agents targeting the oncogenic activities of TGF-β. A large number of anti-TGF-β antibodies and TGF-β-receptor I kinases have been tested preclinically during the past decade. Because of the lack of success, targeting of the TGF-β signaling system still remains elusive. It should be noted that both protumoral and antitumoral effects have been assigned to TGF-β, and the multifunctional nature of TGF-β apparently represents the greatest barrier to effectively target this ligand, its receptor, or downstream effectors.

As a non-limiting example, an indolinone derivative compound as provided herein (e.g., nintedanib) is specially formulated to permit mist or liquid nebulized, or dry powder inhaled aerosol administration to supply effective concentrations or amounts conferring desired anti-inflammatory, anti-fibrotic or tissue-remodeling benefits, for instance, to prevent, manage or treat patients with pulmonary fibrosis.

Because different drug products are known to vary in efficacy depending on the dose, form, concentration and delivery profile, the presently disclosed embodiments provide specific formulation and delivery parameters that produce protection against and treatment for pulmonary fibrosis associated, by non-limiting example with infection, radiation therapy, chemotherapy, inhalation of environmental pollutants (e.g. dust, vapors, fumes, and inorganic and organic fibers), hypersensitivities, silicosis, byssinosis, genetic factors and transplant rejection.

For the applications described herein, liquid nebulized or dry powder aerosol nintedanib or indolinone or salt thereof,) may be co-administered, administered sequentially or prepared in a fixed combination with an antimicrobial (e.g. tobramycin and/or other aminoglycoside such as amikacin, aztreonam and/or other beta or mono-bactam, ciprofloxacin, levofloxacin and/or other, fluoroquinolones, azithromycin and/or other macrolides or ketolides, tetracycline and/or other tetracyclines, quinupristin and/or other streptogramins, linezolid and/or other oxazolidinones, vancomycin and/or other glycopeptides, and chloramphenicol and/or other phenicols, and colistin and/or other polymyxins), bronchodilator (e.g. beta-2 agonists and muscarinic antagonists), corticosteroids (e.g. salmeterol, fluticasone and budesonide), glucocorticoids (e.g. prednisone), Cromolyn, Nedocromil, Leukotriene modifiers (e.g. montelukast, zafirlukast and zileuton) hyperosmolar solution, DNAse or other mucus thinning agent, interferon gamma, cyclophosphamide, colchicine, N-acetylcysteine, azathioprine, bromhexine, endothelin receptor antagonist (e.g. bosentan and ambrisentan), PDE5 inhibitor (e.g. sildenafil, vardenafil and tadalafil), PDE4 inhibitor (e.g. roflumilast, cilomilast, oglemilast, tetomilast and SB256066), prostinoid (e.g. epoprostenol, iloprost and treprostinin), nitric oxide or nitric oxide-donating compound, IL-13 blocker, IL-10 blocker, CTGF-specific antibody, CCN2 inhibitors, angiotensin-converting enzyme inhibitors, angiotensin receptor antagonists, PDGF inhibitors, PPAR antagonist, oral nintedanib, CCL2-specific antibody, CXCR2 antagonist, triple growth factor kinase inhibitor, anticoagulant, TNF blocker, tetracycline or tetracycline derivative, 5-lipoxygenase inhibitor, pituitary hormone inhibitor, TGF-beta-neutralizing antibody, copper chelator, angiotensin II receptor antagonist, chemokine inhibitor, NF-kappaB inhibitor, NF-kappaB antisense oligonucleotide, IKK-1 and -2 inhibitor (e.g. imidazoquinoxaline or derivative, and quinazoline or derivative), JNK2 and/or p38 MAPK inhibitor (e.g. pyridylimidazolbutyn-I-ol, SB856553, SB681323, diaryl urea or derivative, and indole-5-carboxamide), PI3K inhibitor, LTB4 inhibitor, antioxidant (e.g. Mn-pentaazatetracyclohexacosatriene, M40419, N-acetyl-L-cysteine, Mucomyst, Fluimucil, Nacystelyn, Erdosteine, Ebeselen, thioredoxin, glutathione peroxidase memetrics, Curcumin C3 complex, Resveratrol and analogs, Tempol, catalytic antioxidants, and OxSODrol), TNF scavenger (e.g. infliximab, ethercept, adalumimab, PEG-sTNFR 1, afelimomab, and antisense TNF-alpha oligonucleotide), Interferon beta-1a (Avonex, Betaseron, or Rebif), glatiramer acetate (Copaxone), mitoxantrone (Novantrone), natalizumab (Tysabri), Methotrexate, azathioprine (Imuran), intravenous immunoglobulin (IVIg), cyclophosphamide (Cytoxan), lioresal (Baclofen), tizanidine (Zanaflex), benzodiazepine, cholinergic medications, antidepressants and amantadine.

As shown as a promising approach to treat cancer and pulmonary arterial hypertension, to enable "cocktail therapy" or "cocktail prophylaxis" in fibrotic disease, more specifically idiopathic pulmonary fibrosis and other pulmonary fibrotic disease, methods to administer inhaled nintedanib or indolinone or salt thereof, are co-administered, administered sequentially, or co-prescribed (such that medicines are requested by a prescribing physician to be taken in some sequence as combination therapy to treat the same disease) with agents targeting cancer, fibrotic or inflammatory disease. By non-limiting example, nintedanib or indolinone or salt thereof, are administered either in fixed combination, co-administered, administered sequentially, or co-prescribed with the monoclonal GS-6624 (formerly known as AB0024), analog or another antibody targeting LOXL2 protein associated with connective tissue biogenesis to reduce inflammation, tumor stroma and/or fibrosis. By another non-limiting example, nintedanib or indolinone or salt thereof, are administered either in fixed combination, co-administered, administered sequentially, or co-prescribed with IW001 (Type V collagen), analog or other collagen targeting immunogenic tolerance to reduce inflammation, tumor stroma and/or fibrosis. By another non-limiting example, nintedanib or indolinone or salt thereof, are administered either in fixed combination, co-administered, administered sequentially, or co-prescribed with PRM-151 (recombinant pentraxin-2), CC-930 (Jun kinase inhibitor), analog or other Jun kinase inhibitor to reduce the inflammation, tumor stroma and/or fibrosis, oral imatinib (a.k.a. Gleeve or Glivec (tyrosine kinase inhibitor)), analog or other tyrosine to inhibit lung fibroblast-myofibroblast transformation and proliferation as well as extracellular matrix production and tumor stroma formation/maintenance through inhibition of PDFG and transforming growth factor (TGF)-β signaling, STX-100 (monoclonal antibody targeting integrin alpha-v beta-6), analog or other antibody targeting integrin alpha-v beta-6 or other integrin to reduce inflammation, tumor stroma and/or fibrosis, QAX576 (monoclonal antibody targeting interleukin 13 [IL-13]), analog or other antibody targeting IL-13 to reduce inflammation, tumor stroma and/or fibrosis, FG-3019 (monoclonal antibody targeting connective tissue growth factor [CTGF]), analog or other antibody targeting CTGF to reduce inflammation, tumor stroma and/or fibrosis, CNTO-888 (a monoclonal antibody targeting chemokine [C—C motif] ligand 2 [CCL2]), analog or other antibody targeting CCL2 to reduce inflammation, tumor stroma and/or fibrosis, Esbriet®, Pirespa® or Pirfenex® (trade names for pirfenidone), or analog targeting inflammation, tumor stroma and/or fibrosis, SM-04646 (inhaled WNT/MET inhibitor), analog or other chemical targeting WNT/MET to reduce inflammation, tumor stroma and/or fibrosis, N-acetylcysteine (NAC; antioxidant), analog or other chemical targeting oxidation to reduce inflammation, tumor stroma and/or fibrosis, PRM-151 (intravenous recombinant human pentraxin-3; macrophage signal modulator), analog or other chemical targeting macrophage to reduce inflammation, tumor stroma and/or fibrosis, MK-2 (inhaled MK-2 inhibitor), analog or other chemical targeting MK-2 to reduce inflammation, tumor stroma and/or fibrosis, CC-90001 (oral JNK1 inhibitor), analog or other chemical targeting JNK1 to reduce inflammation, tumor stroma and/or fibrosis, GLPG-1690 (oral autotaxin inhibitor), analog or other chemical targeting autotaxin to reduce inflammation, tumor stroma and/or fibrosis, BI1015550 to reduce inflammation, tumor stroma and/or fibrosis, Gefapixant (oral cough inhibitor), analog or other chemical targeting cough to reduce inflammation, tumor stroma and/or fibrosis, cromalin (inhaled cough inhibitor), analog or other chemical targeting cough to reduce inflammation, tumor stroma and/or fibrosis, PBI-4050 (oral endoplasmic reticulum stress (ER stress) inhibitor), analog or other chemical targeting ER stress to reduce inflammation, tumor stroma and/or fibrosis, TD-139 (inhaled galectin-3 inhibitor), analog or other chemical targeting galectin-3 to reduce inflammation, tumor stroma and/or fibrosis, tipelukast (oral leukotriene and PDE inhibitor), analog or other chemical targeting leukotriene and/or PDE to reduce inflammation, tumor stroma and/or fibrosis, or PAT-1251 (oral LoxL2 inhibitor), analog or other chemical targeting LoxL2 to reduce inflammation, tumor stroma and/or fibrosis, and combinations thereof As with administration of nintedanib or indolinone and their salts, oral and parenteral routes of administration (by non-limiting example, intravenous and subcutaneous) of other compounds, molecules and antibodies targeting the reduction of inflammation, tumor stroma and/or fibrosis is often associated with, by non-limiting example, adverse reactions such as gastrointestinal side effects, liver, kidney, skin, cardiovascular or other toxicities. As described herein the benefits of oral or intranasal inhalation directly to the lung or tissues immediately downstream of the nasal and/or pulmonary compartments will also benefit these compounds by avoiding direct delivery to the gastrointestinal tract and/or reducing systemic exposure thereby reducing gastrointestinal symptoms generated in the central nervous system. Therefore, by non-limiting example, the monoclonal GS-6624 (formerly known as AB0024), analog or another antibody targeting LOXL2 protein associated with connective tissue biogenesis to reduce inflammation, tumor stroma and/or fibrosis may be administered by oral or intranasal inhalation for direct delivery to the lung or tissues immediately downstream of the nasal or pulmonary compartments. By another non-limiting example, PRM-151 (recombinant pentraxin-2), analog or other molecule targeting regulation of the injury response to reduce inflammation and/or fibrosis may be administered by oral or intranasal inhalation for direct delivery to the lung or tissues immediately downstream of the nasal or pulmonary compartments, CC-930 (Jun kinase inhibitor), analog or other Jun kinase inhibitor to reduce tumor stroma and/or the inflammatory response may be administered by oral or intranasal inhalation for direct delivery to the lung or tissues immediately downstream of the nasal or pulmonary compartments, oral imatinib (a.k.a. Gleeve or Glivec (tyrosine kinase inhibitor)), transforming growth factor (TGF)-β signaling may be administered by oral or intranasal inhalation for direct delivery to the lung or tissues immediately downstream of the nasal or pulmonary compartments, STX-100 (monoclonal antibody targeting integrin alpha-v beta-6), analog or other antibody targeting integrin alpha-v beta-6 or other integrin to reduce tumor stroma and/or fibrosis, QAX576 (monoclonal antibody targeting interleukin 13 [IL-13]), analog or other antibody targeting IL-13 to reduce tumor stroma and/or inflammation, may be administered by oral or intranasal inhalation for direct delivery to the lung or tissues immediately downstream of the nasal or pulmonary compartments, FG-3019 (monoclonal antibody targeting connective tissue growth factor [CTGF]), analog or other antibody targeting CTGF to reduce tumor stroma and/or fibrosis may be administered by oral or intranasal inhalation for direct delivery to the lung or tissues immediately downstream of the nasal or pulmonary compartments, CNTO-888 (a monoclonal antibody targeting chemokine [C—C motif] ligand 2 [CCL2]), analog or other antibody targeting CCL2 to reduce tumor stroma and/or fibrosis, SM-04646 (inhaled WNT/MET inhibitor), analog or other chemical targeting WNT/MET to reduce tumor stroma and/or fibrosis and/or inflammation, N-acetylcysteine (NAC; anti-oxidant), analog or other chemical targeting oxidation to reduce tumor stroma and/or fibrosis and/or inflammation, PRM-151 (intravenous recombinant human pentraxin-3; macrophage signal modulator), analog or other chemical targeting macrophage to reduce tumor stroma and/or fibrosis and/or inflammation, MK-2 (inhaled MK-2 inhibitor), analog or other chemical targeting MK-2 to reduce tumor stroma and/or fibrosis and/or inflammation, CC-90001 (oral JNK1 inhibitor), analog or other chemical targeting JNK1 to reduce tumor stroma and/or fibrosis and/or inflammation, GLPG-1690 (oral autotaxin inhibitor), analog or other chemical targeting autotaxin to reduce tumor stroma and/or fibrosis and/or inflammation, BI1015550 to reduce tumor stroma and/or fibrosis and/or inflammation, Gefapixant (oral cough inhibitor), analog or other chemical targeting cough to reduce tumor stroma and/or fibrosis and/or inflammation, PBI-4050 (oral endoplasmic reticulum stress (ER stress) inhibitor), analog or other chemical targeting ER stress to reduce tumor stroma and/or fibrosis and/or inflammation, TD-139 (inhaled galectin-3 inhibitor), analog or other chemical targeting galectin-3 to reduce tumor stroma and/or fibrosis and/or inflammation, tipelukast (oral leukotriene and PDE inhibitor), analog or other chemical targeting leukotriene and/or PDE to reduce tumor stroma and/or fibrosis and/or inflammation, PAT-1251 (oral LoxL2 inhibitor), analog or other chemical targeting LoxL2 to reduce tumor stroma and/or fibrosis and/or inflammation, and combinations thereof.

A promising approach to treat cancer and pulmonary arterial hypertension is the administration of "cocktail therapy" or "cocktail prophylaxis" where the method is comprised of co-administering or sequentially administering inhaled nintedanib or indolinone or salt thereof with agents targeting cancer, including but not limited to gefitinib (Iressa, also known as ZD1839), Erlotinib (also known as Tarceva), Bortezomib (originally codenamed PS-341; marketed as Velcade® and Bortecad®), Janus kinase inhibitors, ALK inhibitors, PARP inhibitors (Iniparib; BSI 201); PI3K inhibitors, Apatinib (YN968D1), Selumetinib, Salinomycin, Abitrexate (methotrexate), Abraxane (Paclitaxel Albumin-stabilized Nanoparticle Formulation), Afatinib Dimaleate, Alimta (pemetrexed disodium), Avastin (Bevacizumab), Carboplatin, Cisplatin, Crizotinib, Erlotinib Hydrochloride, Folex (methotrexate), Folex PFS (methotrexate), Gefitinib Gilotrif (afatinib dimaleate), Gemcitabine Hydrochloride, Gemzar (gemcitabine hydrochloride), Iressa (Gefitinib), Methotrexate, Methotrexate LPF (methotrexate), Mexate (methotrexate), Mexate-AQ (methotrexate), Paclitaxel, Paclitaxel Albumin-stabilized Nanoparticle Formulation, Paraplat (carboplatin), Paraplatin (carboplatin), Pemetrexed Disodium, Platinol (cisplatin), Platinol-AQ (Cisplatin), Tarceva (Erlotinib Hydrochloride), Taxol (Paclitaxel), and Xalkori (Crizotinib).

Combinations approved for non-small cell lung cancer may include: Carboplatin-Taxol and Gemcitabine-Cisplatin.

Drugs approved for small cell lung cancer may include: Abitrexate (methotrexate), Etopophos (etoposide phosphate), Etoposide, Etoposide Phosphate, Folex (methotrexate), Folex PFS (methotrexate), Hycamtin (topotecan hydrochloride), Methotrexate, Methotrexate LPF (methotrexate), Mexate (methotrexate), Mexate-AQ (methotrexate), Toposar (etoposide), Topotecan Hydrochloride, and VePesid (etoposide).

Pharmaceutical Formulation and Packaging

Selection of a particular nintedanib composition or indolinone or salt thereof, is accompanied by the selection of a specially designed product packaging and configuration that maximizes the therapeutic utility of the particular composition. Factors to be considered in selecting packaging may include, for example, intrinsic product stability, whether the formulation may be subject to lyophilization, device selection (e.g., liquid nebulizer, dry-powder inhaler, meter-dose inhaler), and/or packaging form (e.g., simple liquid or complex liquid formulation, whether provided in a vial as a liquid or as a lyophilisate to be dissolved prior to or upon insertion into the device; complex suspension formulation whether provided in a vial as a liquid or as a lyophilisate, and with or without a soluble salt/excipient component to be dissolved prior to or upon insertion into the device, or separate packaging of liquid and solid components; dry powder formulations in a vial, capsule or blister pack; and other formulations packaged as readily soluble or low-solubility solid agents in separate containers alone or together with readily soluble or low-solubility solid agents.

In one preferred embodiment, the compositions will take the form of a unit dosage form such as vial containing a liquid, solid to be suspended, dry powder, lyophilisate, or other composition and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like.

Liquid pharmaceutically compositions can, for example, be prepared by dissolving, dispersing, etc. an active compound and optional pharmaceutical adjuvants in a carrier (e.g., water, saline, aqueous dextrose, glycerol, glycols, ethanol or the like). Solutions to be aerosolized can be prepared in conventional forms, either as liquid solutions or suspensions, or in solid forms suitable for dissolution or suspension in liquid prior to aerosol production and inhalation. The percentage of active compound contained in such aerosol compositions is highly dependent on the specific nature thereof, as well as the activity of the compound and the needs of the subject. Typically, 0.25%-50.0% of the active agent in an aqueous solution is acceptable for aerosolization.

Nintedanib or indolinone or salt thereof compound formulations can be separated into two groups; those of simple formulation or complex formulations providing taste-masking for improved tolerability, pH-optimized for stability and tolerability, immediate or sustained-release, and/or area-under-the-curve (AUC) shape-enhancing properties. Simple formulations can be further separated into three groups. 1. Simple formulations may include water-based liquid formulations for nebulization. Water-based liquid formulations include nintedanib or indolinone active ingredient with non-encapsulating water soluble excipients 2) additional organic-based liquid formulations for nebulization or meter-dose inhaler with nintedanib or indolinone non-encapsulating organic soluble excipients; 3) dry powder formulations for administration with a dry powder inhaler nintedanib or indolinone alone or with either water soluble or organic soluble non-encapsulating excipients with or without a carrier agent such as lactose.

Complex formulations containing active ingredient can be further separated into five groups: 1) nintedanib or indolinone formulations with active ingredient encapsulated or complexed with water-soluble excipients such as lipids, liposomes, cyclodextrins, microencapsulations, and emulsions; 2) organic-based liquid formulations for nebulization or meter-dose inhaler with active ingredient nintedanib or indolinone encapsulated or complexed with organic-soluble excipients such as lipids, microencapsulations, and reverse-phase water-based emulsions; 3) formulations including low-solubility, water-based liquid formulations for nebulization comprised of nintedanib or indolinone, stable nanosuspension alone or in co-crystal/co-precipitate excipient complexes, or mixtures with low solubility lipids, such as lipid nanosuspensions; 4) low-solubility, organic-based liquid formulations for nebulization or meter-dose inhaler nintedanib or indolinone as a low-organic soluble, stable nanosuspension alone or in co-crystal/co-precipitate excipient complexes, or mixtures with low solubility lipids, such as lipid nanosuspensions; and 5) dry powder formulations for administration using a dry powder inhaler of nintedanib or indolinone as a co-crystal/co-precipitate/spray dried complex or mixture with low-water soluble excipients/salts in dry powder form with or without a carrier agent such as lactose. Specific methods for simple and complex formulation preparation are described herein.

The aerosol for delivery to the lungs of a human contains a fine particle fraction between 10 and 100% with increment units of 1%. By example, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%. The fine particle dose is between about 0.0001 mg to about 100 mg nintedanib or salt thereof. By example, about 0.0001 mg, about 0.001 mg, about 0.005 mg, about 0.01 mg, and about 0.05 mg in 0.01 mg increments. By further example, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 120 mg, about 140 mg, about 160 mg, about 180 mg, about 200 mg in 0.1 mg increments. By example, about 0.001 mg, about 0.005 mg, about 0.01 mg, about 0.05 mg, about 0.1 mg, and about 0.5 mg, about 1 mg, about 5 mg, about 10 mg, about, about 20 mg, about 30 mg, about 40 mg, about 50 mg, about 100 mg, about 200 mg in 0.01 mg increments.

In some embodiments, nintedanib or indolinone or salt thereof, has a osmolality adjusting agent suitable for pulmonary delivery. The osmolality adjusting agent includes a co-solvent selected from propylene glycol, ethanol, polyethylene glycol 400, mannitol and glycerin. The compositions further comprise a second anti-fibrotic or anti-cancer or anti-infective or anti-infective agent suitable for pulmonary delivery. The compositions further comprise a second anti-inflammatory agent suitable for pulmonary delivery. The composition may be co-administered with a second anti-fibrotic or anti-cancer or anti-infective agent suitable for pulmonary delivery. The composition co-administered a second anti-inflammatory agent suitable for pulmonary delivery.

In another embodiment, a pharmaceutical composition is provided that includes a simple or complex liquid nintedanib or indolinone salt thereof with non-encapsulating water-soluble excipients as described above having an osmolality from about 50 mOsmol/kg to about 600 mOsmol/kg. In other embodiments the osmolality is from about 50, 100, 150, 200, 250, 300, 350, 400, 450, 500 mOsmol/kg to about 1000, 1100, 1200, 1300, 1400, 1500, 1600, 1700, 1800, 1900, 2000 mOsmol/kg and preferably between about 50 mOsmol/kg and about 600 mosmol/kg.

The simple or complex formulation preferably has nintedanib or indolinone a permeant ion concentration between from about 30 mM to about 150 mM. The permeant ions in the composition are preferably selected from the group consisting of chloride and bromide and combinations thereof.

Nintedanib or indolinone nintedanib or indolinone In another embodiment, a pharmaceutical composition is provided that includes a simple or complex liquid nintedanib or indolinone or salt thereof compound formulation as a low water-soluble stable nanosuspension alone or in co-crystal/co-precipitate complexes, or mixtures with low solubility lipids, such as lipid nanosuspensions) as described above having a solution osmolality from about 50 mOsmol/kg to about 600 mOsmol/kg. In one embodiment, the osmolality is from about 100 mOsmol/kg to about 500 mOsmol/kg.

In another embodiment, a pharmaceutical composition is provided that includes a complex suspension of a nintedanib or indolinone or salt thereof compound formulation having a permeant ion concentration from about 30 mM to about 150 mM. In one such embodiment, one or more permeant ions in the composition are selected from the group consisting of chloride and bromide.

In another embodiment, a pharmaceutical composition is provided that includes a complex suspension of a nintedanib or indolinone or salt thereof compound formulation having a permeant ion concentration from about 30 mM to about 150 mM. In one such embodiment, one or more permeant ions in the composition are selected from the group consisting of chloride and bromide.

In other embodiments, nintedanib or indolinone or includes a taste-masking agent including sugar, saccharin (e.g., sodium saccharin), sweetener or other compound or agent that beneficially affects taste, after-taste, perceived unpleasant saltiness, sourness or bitterness, or that reduces the tendency of an oral or inhaled formulation to irritate a recipient (e.g., by causing coughing or sore throat or other undesired side effect, such as may reduce the delivered dose or adversely influence patient compliance with a prescribed therapeutic regimen). Certain taste-masking agents may form complexes with the nintedanib or indolinone or salt thereof.

In another embodiment, a salt form of nintedanib or indolinone counterion of the salt form of nintedanib or indolinone is acetate, acetonide, alanine, aluminum, arginine, ascorbate, asparagine, aspartic acid, benzathine, benzoate, besylate, bisulfate, bisulfite, bitartrate, bromide (including bromide and hydrobromide), calcium, carbonate, camphorsulfonate, cetylpyridinium, chloride (including chloride and hydrochloride), chlortheophyllinate, cholinate, cysteine, deoxycholate, diethanolamine, diethylamine, diphosphate, diproprionate, disalicylate, edetate, edisylate, estolate, ethylamine, ethylenediamine, ethandisulfonate, esylate, esylate hydroxide, gluceptate, gluconate, glucuronate, glutamic acid, glutamine, glycine, hippurate, histidine, hydrobromide, hydrochloride, hydroxide, iodide, isethionate, isoleucine, lactate, lactobionate, laurylsulfate, leucine, lysine, magnesium, mandelate, meglumine, mesylate, metabisulfite, metabisulfite, methionine, methylbromide, methylsulfate, methyl p-hydroxybenzoate, mucate, naphthoate, napsylate, nitrate, nitrite, octadecanoate, oleate, ornithine, oxalate, pamoate, pentetate, phenylalanine, phosphate, piperazine, polygalacturonate, potassium, procaine, proline, propionate, propyl p-hydroxybenzoate, saccharin, salicylate, selenocysteine, serine, silver, sodium, sorbitan, stearate, succinate, sulfate, sulfite, sulfosalicylate, tartrate, threonine, tosylate, triethylamine, triethiodide, trifluoroacetate, trioleate, tromethamine, tryptophan, tyrosine, valerate, valine, xinafoate, or zinc. Included in the above pharmaceutical composition is the maintenance of the buffers described herein, at a pH from about 3.0 to about 7.0, preferably from about pH 3.0 to about pH 6.0, and may include an additional salt form at a level that provides an osmolality of 50 mOsmo/kg and 600 mOsmo/kg. While 300 mOsmo/kg is discussed in the literature as important for acute tolerability upon inhalation of this in a nebulized solution, 600 mOsmo/kg has been shown in unpublished studies to be well tolerated with other drug solutions.

The counterion of the salt form of nintedanib, a indolinone derivative serves as a permeant ion. By non-limiting example, a chloride salt of nintedanib or indolinone derivative may serve or contribute to the pharmaceutical composition permeant ion. By non-limiting example, a bromide salt of nintedanib or indolinone derivative may serve or contribute to the pharmaceutical composition permeant ion. While the nintedanib or indolinone derivative counterion may contribute to permeant ion, additional permeant ion may be added. By non-limiting example, nintedanib or indolinone derivative counterion permeant ion may be supplemented with additional sodium chloride or additional sodium bromide or combinations of chloride and bromide to achieve between about 30 mM to about 150 mM permeant ion. For tolerability, additional solute may be added to the pharmaceutical composition. By non-limiting example, osmolality by be adjusted to within about 50 mOsmo/kg to about 2000 mOsmo/kg by addition of sodium chloride, magnesium chloride or calcium chloride. By non-limiting example, osmolality by be adjusted to within about 50 mOsmo/kg to about 1000 mOsmo/kg by addition of sodium bromide, magnesium bromide or calcium bromide. By non-limiting example, osmolality by be adjusted to within about 50 mOsmo/kg to about 1000 mOsmo/kg by addition of osmolality adjusting agents. By non-limiting example, osmolality adjusting agents include co-solvents selected from ethanol, cetylpyridinium chloride, mannitol glycerin, lecithin, propylene glycol, polysorbate (including polysorbate 20, 40, 60, 80 and 85) and sorbitan triolate.

The nintedanib salt form or indolinone salt form is prepared as a chloride or bromide salt form.

In some embodiments, nintedanib drug product includes nintedanib at a concentration of about 0.01 mg/mL to about 10 mg/mL in water, optionally a buffer (by non-limiting example lysinate, acetylcysteine, glycine, glutamate, borate, succinate, tartrate, phosphate or Tris, optionally an inorganic salts (by non-limiting example sodium chloride, magnesium chloride, calcium chloride, sodium bromide, magnesium bromide, and/or calcium bromide), and optionally a osmolality adjusting agent including co-solvent(s) (by non-limiting example ethanol, propylene glycol, mannitol and glycerin), optionally a surfactant(s) (by non-limiting example Tween 80, Tween 60, lecithin, Cetylpyridinium, and Tween 20), at a pH of about 3.0 to about 7.0, preferably from about pH 3.0 to about pH 6.0. The formulation also includes a taste-masking agent (by non-limiting example sodium saccharin). The pharmaceutical composition includes at least about 0.0001 mg to about 100 mg, including all integral values therein such as 0.0001, 0.00025, 0.0005, 0.001, 0.005, 0.01, 0.05, 0.1, 0.5, 1.0, 1.5, 2.0, 2.5, 3.0, 3.5, 4.0, 4.5, 5.0, 5.5, 6.0, 6.5, 7.0, 7.5, 7.0, 8.5, 9.0, 9.5, 10.0, 15, 20, 30, 40, 50, 100 milligrams. The osmolality of the pharmaceutical composition described herein is between about 50 mOsmo/kg to 600 mOsmo/kg.

In one aspect, provided herein is a kit comprising: a pharmaceutical composition comprising an nintedanib or indolinone or salt thereof is formed in a sealed, sterile container, wherein the solution has an nintedanib or indolinone or salt thereof has a concentration greater than about 0.0001 mg/mL, an osmolality greater than about 100 mOsmol/kg, and a pH greater than about 3.0. The nintedanib or salt thereof or indolinone salt thereof concentration is greater than about 0.01 mg/mL. The nintedanib or salt thereof or indolinone, or salt thereof concentration is greater than about 0.025 mg/mL. The nintedanib or indolinone or salt thereof concentration is greater than about 0.05 mg/mL. The nintedanib or indolinone or concentration is greater than about 0.1 mg/mL. The nintedanib or indolinone or concentration is greater than about 0.25 mg/mL. The nintedanib or indolinone or concentration is greater than about 0.5 mg/mL. The nintedanib or indolinone or concentration is greater than about 0.75 mg/mL. The nintedanib or indolinone or concentration is greater than about 1.0 mg/mL. The nintedanib or indolinone or concentration is greater than about 1.5 mg/mL. The nintedanib or indolinone or salt thereof is greater than about 2.0 mg/mL. The nintedanib or indolinone or salt thereof concentration is greater than about 2.5 mg/mL. The nintedanib or indolinone or salt thereof concentration is greater than about 5.0 mg/mL. The nintedanib or salt thereof or indolinone salt solution has a permeant ion concentration from about 30 mM to about 150 mM. The permeant ion is chloride or bromide. The nintedanib or indolinone nintedanib or indolinone or salt thereof solution has a pH from about 3.0 to about 7.0, preferably from about pH 3.0 to about pH 6.0. The nintedanib or indolinone nintedanib or indolinone or salt thereof solution has an osmolality from about 50 mOsmol/kg to about 600 mOsmol/kg. The nintedanib or indolinone nintedanib or indolinone or salt thereof solution has a taste masking agent selected from the group consisting of lactose, sucrose, dextrose, saccharin, aspartame, sucralose, ascorbate and citrate and combinations thereof. In some embodiments, nintedanib or indolinone or salt thereof, solution has a osmolality adjusting agents suitable for pulmonary delivery. The osmolality adjusting agents includes co-solvents selected from propylene glycol, ethanol, polyethylene glycol 400, and glycerin. The kit further comprises a second anti-fibrotic or anti-cancer or anti-infective agent suitable for pulmonary delivery. The kit further comprises a second anti-inflammatory agent suitable for pulmonary delivery. The composition may be co-administered with a second anti-fibrotic or anti-cancer or anti-infective agent suitable for pulmonary delivery. The composition co-administered a second anti-inflammatory agent suitable for pulmonary delivery.

In one aspect, provided herein is a kit comprising: two containers where upon admixture create a pharmaceutical composition comprising an nintedanib or indolinone or salt thereof solution in a sterile container, wherein the solution has an nintedanib or indolinone or salt thereof concentration greater than about 0.0001 mg/mL, having an osmolality greater than about 50 mOsmol/kg, and having a pH greater than about 3.0. The nintedanib or indolinone or salt thereof concentration is greater than about 0.01 mg/mL. The nintedanib or indolinone or salt thereof concentration is greater than about 0.025 mg/mL. The nintedanib or indolinone or salt thereof concentration is greater than about 0.05 mg/mL. The nintedanib or indolinone or salt thereof concentration is greater than about 0.1 mg/mL. The nintedanib or indolinone or salt thereof concentration is greater than about 0.25 mg/mL. The nintedanib or indolinone or salt thereof concentration is greater than about 0.5 mg/mL. The nintedanib or indolinone or salt thereof concentration is greater than about 0.75 mg/mL. The nintedanib or indolinone or salt thereof concentration is greater than about 1.0 mg/mL. The nintedanib or indolinone or salt thereof concentration is greater than about 1.5 mg/mL. The nintedanib or indolinone or salt thereof concentration is greater than about 2.0 mg/mL. The nintedanib or indolinone or salt thereof concentration is greater than about 2.5 mg/mL. The nintedanib or indolinone or salt thereof concentration is greater than about 5.0 mg/mL.

In one aspect, provided herein is a kit comprising: a unit dose wherein a pharmaceutical composition comprising an nintedanib or indolinone or salt thereof and pirfenidone or pyridone analog solution in a sterile container, wherein the solution has an nintedanib or indolinone or salt thereof concentration greater than about 0.0001 mg/mL and a pirfenidone or pyridone analog concentration greater than about 5 mg/mL, having an osmolality greater than about 50 mOsmol/kg, and having a pH greater than about 3.0. The nintedanib or indolinone or salt thereof concentration is greater than about 0.01 mg/mL. The nintedanib or indolinone or salt thereof concentration is greater than about 0.025 mg/mL. The nintedanib or indolinone or salt thereof concentration is greater than about 0.05 mg/mL. The nintedanib or indolinone or salt thereof concentration is greater than about 0.1 mg/mL. The nintedanib or indolinone or salt thereof concentration is greater than about 0.25 mg/mL. The nintedanib or indolinone or salt thereof concentration is greater than about 0.5 mg/mL. The nintedanib or indolinone or salt thereof concentration is greater than about 0.75 mg/mL. The nintedanib or indolinone or salt thereof concentration is greater than about 1.0 mg/mL. The nintedanib or indolinone or salt thereof concentration is greater than about 1.5 mg/mL. The nintedanib or indolinone or salt thereof concentration is greater than about 2.0 mg/mL. The nintedanib or indolinone or salt thereof concentration is greater than about 2.5 mg/mL. The nintedanib or indolinone or salt thereof concentration is greater than about 5.0 mg/mL. The nintedanib or indolinone or salt thereof concentration is greater than about 10.0 mg/mL. The nintedanib or indolinone or salt thereof concentration is greater than about 15.0 mg/mL. The nintedanib or indolinone or salt thereof concentration is greater than about 20.0 mg/mL. The nintedanib or indolinone or salt thereof concentration is greater than about 25.0 mg/mL. The nintedanib or indolinone or salt thereof concentration is greater than about 30.0 mg/mL. The nintedanib or indolinone or salt thereof concentration is greater than about 35.0 mg/mL. The nintedanib or indolinone or salt thereof concentration is greater than about 40.0 mg/mL. The nintedanib or indolinone or salt thereof concentration is greater than about 45.0 mg/mL. The nintedanib or indolinone or salt thereof concentration is greater than about 50.0 mg/mL. The pirfenidone or pyridone analog concentration is greater than about 5 mg/mL. The pirfenidone or pyridone analog concentration is greater than about 6 mg/mL. The pirfenidone or pyridone analog concentration is greater than about 7 mg/mL. The pirfenidone or pyridone analog concentration is greater than about 8 mg/mL. The pirfenidone or pyridone analog concentration is greater than about 9 mg/mL. The pirfenidone or pyridone analog concentration is greater than about 10 mg/mL. The pirfenidone or pyridone analog concentration is greater than about 11 mg/mL. The pirfenidone or pyridone analog concentration is greater than about 12 mg/mL. The pirfenidone or pyridone analog concentration is greater than about 13 mg/mL. The pirfenidone or pyridone analog concentration is greater than about 14 mg/mL. The pirfenidone or pyridone analog concentration is greater than about 15 mg/mL. The pirfenidone or pyridone analog concentration is greater than about 16 mg/mL. The pirfenidone or pyridone analog concentration is greater than about 17 mg/mL. The pirfenidone or pyridone analog concentration is greater than about 18 mg/mL. The pirfenidone or pyridone analog concentration is greater than about 19 mg/mL. The pirfenidone or pyridone analog concentration is greater than about 20 mg/mL.

The nintedanib or indolinone or salt thereof solution has a permeant ion concentration from about 30 mM to about 150 mM. The permeant ion is chloride or bromide. The nintedanib or indolinone or salt thereof solution has a pH from about 3.0 to about 7.0, preferably from about pH 3.0 to about pH 6.0. The nintedanib or indolinone or salt thereof solution has an osmolality from about 50 mOsmol/kg to about 600 mOsmol/kg. The nintedanib or indolinone or salt thereof solution has a taste masking agent. The taste masking agent is selected from the group consisting of lactose, sucrose, dextrose, saccharin, aspartame, sucralose, and ascorbate. In some embodiments, nintedanib or indolinone or salt thereof, solution has a osmolality adjusting agents suitable for pulmonary delivery, including co-solvents selected from the group consisting of propylene glycol, ethanol, polyethylene glycol 400, and glycerin and combinations thereof. The solution further comprises a second anti-fibrotic or anti-cancer or anti-infective agent suitable for pulmonary delivery. The kit further comprises a second anti-inflammatory agent suitable for pulmonary delivery. The composition may be co-administered with a second anti-fibrotic or anti-cancer or anti-infective agent suitable for pulmonary delivery. The composition co-administered a second anti-inflammatory agent suitable for pulmonary delivery.

The nintedanib or indolinone or salt thereof and pirfenidone or pyridone analog solution has a permeant ion concentration from about 30 mM to about 500 mM. The permeant ion is chloride or bromide. The nintedanib or indolinone or salt thereof solution has a pH from about 3.0 to about 7.0, preferably from about pH 3.0 to about pH 6.0. The nintedanib or indolinone or salt thereof solution has an osmolality from about 50 mOsmol/kg to about 1000 mOsmol/kg. The nintedanib or indolinone or salt thereof solution has a taste masking agent. The taste masking agent is selected from the group consisting of lactose, sucrose, dextrose, saccharin, aspartame, sucralose, and ascorbate. In some embodiments, nintedanib or indolinone or salt thereof, solution has a osmolality adjusting agents suitable for pulmonary delivery, including co-solvents selected from the group consisting of propylene glycol, ethanol, polyethylene glycol 400, and glycerin and combinations thereof. The solution further comprises a second anti-fibrotic or anti-cancer or anti-infective agent suitable for pulmonary delivery. The composition may be co-administered with a second anti-fibrotic or anti-cancer or anti-infective agent suitable for pulmonary delivery. The composition co-administered a second anti-inflammatory agent suitable for pulmonary delivery.

In some embodiments, described herein is a kit comprising: a unit dosage of an aqueous solution of nintedanib or indolinone or salt thereof, as described herein in a container that is adapted for use in a liquid nebulizer.

In some embodiments, described herein is a kit comprising: a unit dosage of an aqueous solution of nintedanib or indolinone or salt thereof and pirfenidone or pyridone analog, as described herein in a container that is adapted for use in a liquid nebulizer.

Nebulized aqueous nintedanib formulation requires at least 30 mM permeant ion for good tolerability. However, aqueous nintedanib is unstable at these permeant ion concentrations. To circumvent this issue, aqueous nintedanib may be formulated as a multi-container system for admixture just prior to use. In one configuration a kit is comprised of two-containers for admixture wherein an aqueous solution of nintedanib or indolinone or salt thereof is dissolved in an aqueous solution in a first container and osmolality adjusting agents, including buffers and permeant and ions are confined to a separate container having no fluid communication between the first and second containers during storage. Just prior to use, the contents of the first and second containers are combined. The first and second containers may be formed as part of the same package specially designed for admixture and for transmitting the contents of the first and second containers once combined into the reservoir of a liquid nebulizer.

In some embodiments, described herein is a unit dosage adapted for use in a liquid nebulizer comprising from about 0.01 mL to about 10 mL of an aqueous solution of nintedanib or salt thereof, wherein the concentration of nintedanib or salt thereof, in the aqueous solution is from about 0.0001 mg/mL to about 10 mg/mL requires admixture prior to administration. For stability purposes the unit dosage form is prepared as a two-container admixture system, wherein container one contains nintedanib or salt thereof is prepared in an aqueous volume from about 0.01 mL to about 10 mL; optionally 0.01 mM to about 1000 mM buffer maintaining a pH from about 3.0 to about 7.0, preferably from about pH 3.0 to about pH 6.0; optionally a osmolality adjusting agent concentration from about 0.1% to about 99%; optionally a taste-masking agent from about 0.01 mM to about 100 mM. Container 2 consists of an aqueous solution from about 0.01 mL to about 10 mL; optionally containing a permeant ion concentration from about 30 mM to about 1500 mM, wherein permeant ions may be selected from chloride ion and bromide ion; optionally 0.01 mM to about 1000 mM buffer maintaining a pH from about 3.0 to about 7.0, preferably from about pH 3.0 to about pH 6.0; optionally a osmolality adjusting agent from about 0.1% to about 99%; optionally a taste-masking agent from about 0.01 mM to about 100 mM. Prior to administration, the two-container admixture system is admixed resulting in a unit dosage form comprising from about 0.01 mL to about 10 mL of an aqueous solution of nintedanib or salt thereof, wherein the concentration of nintedanib or salt thereof, in the aqueous solution is from about 0.0001 mg/mL to about 10 mg/mL; optionally 0.01 to about 100 mM buffer maintaining a pH from about 3.0 to about 7.0, preferably from about pH 3.0 to about pH 6.0; optionally, a osmolality adjusting agent concentration from about 0.1% to about 20%; optionally a taste-masking agent from about 0.01 mM to about 10 mM; optionally containing a permeant ion concentration from about 30 mM to about 150 mM, wherein permeant ions are selected from chloride ion and bromide ion, with a final admixed solution osmolality from about 50 mOsmol/kg to about 600 mOsmol/kg.

In some embodiments, described herein is a unit dosage adapted for use in a liquid nebulizer comprising from about 0.01 mL to about 10 mL of an aqueous solution of nintedanib or salt thereof, wherein the concentration of nintedanib or salt thereof, in the aqueous solution is from about 0.0001 mg/mL to about 10 mg/mL requires admixture prior to administration. For stability purposes the unit dosage form is prepared as a two-container admixture system, wherein container one contains nintedanib or salt thereof is prepared in an aqueous volume from about 0.01 mL to about 10 mL; optionally 0.01 mM to about 1000 mM glycine or glutamate buffer maintaining a pH from about 3.0 to about 7.0, preferably from about pH 3.0 to about pH 6.0; optionally a propylene glycol at a concentration from about 0.1% to about 99%; optionally a taste-masking agent from about 0.01 mM to about 100 mM. Container 2 consists of an aqueous solution from about 0.01 mL to about 10 mL; optionally containing a permeant ion concentration from about 30 mM to about 1500 mM, wherein permeant ions may be selected from chloride ion and bromide ion; optionally 0.01 mM to about 1000 mM glycine or glutamate buffer maintaining a pH from about 3.0 to about 7.0, preferably from about pH 3.0 to about pH 6.0; optionally propylene glycol at a concentration from about 0.1% to about 99%; optionally a taste-masking agent from about 0.01 mM to about 100 mM. Prior to administration, the two-container admixture system is admixed resulting in a unit dosage form comprising from about 0.01 mL to about 10 mL of an aqueous solution of nintedanib or salt thereof, wherein the concentration of nintedanib or salt thereof, in the aqueous solution is from about 0.0001 mg/mL to about 10 mg/mL; optionally 0.01 to about 100 mM glycine or glutamate buffer maintaining a pH from about 3.0 to about 7.0, preferably from about pH 3.0 to about pH 6.0; optionally, propylene glycol at a concentration from about 0.1% to about 20%; optionally a taste-masking agent from about 0.01 mM to about 10 mM; optionally containing a permeant ion concentration from about 30 mM to about 150 mM, wherein permeant ions may be selected from chloride ion and bromide ion, with a final admixed solution osmolality from about 50 mOsmol/kg to about 600 mOsmol/kg.

Described herein is a unit dosage adapted for use in a liquid nebulizer comprising from about 0.01 mL to about 10 mL of an aqueous solution of nintedanib or salt thereof, wherein the concentration of nintedanib hydrobromide salt, in the aqueous solution is from about 0.0001 mg/mL to about 5 mg/mL requires admixture prior to administration. For stability purposes the unit dosage form is prepared as a two-container admixture system, wherein container one contains nintedanib hydrobromide salt is prepared in an aqueous volume from about 0.01 mL to about 10 mL; optionally 0.01 mM to about 1000 mM glycine or glutamate buffer maintaining a pH from about 3.0 to about 7.0, preferably from about pH 3.0 to about pH 6.0; optionally a propylene glycol at a concentration from about 0.1% to about 99%; optionally a taste-masking agent from about 0.01 mM to about 100 mM. Container 2 consists of an aqueous solution from about 0.01 mL to about 10 mL; optionally containing a permeant ion concentration from about 30 mM to about 1500 mM, wherein permeant ions may be selected from chloride ion and bromide ion; optionally 0.01 mM to about 1000 mM glycine or glutamate buffer maintaining a pH from about 3.0 to about 7.0, preferably from about pH 3.0 to about pH 6.0; optionally propylene glycol at a concentration from about 0.1% to about 99%; optionally a taste-masking agent from about 0.01 mM to about 100 mM. Prior to administration, the two-container admixture system is admixed resulting in a unit dosage form comprising from about 0.01 mL to about 10 mL of an aqueous solution of nintedanib hydrobromide salt, wherein the concentration of nintedanib hydrobromide salt, in the aqueous solution is from about 0.0001 mg/mL to about 5 mg/mL; optionally 0.01 to about 50 mM glycine or glutamate buffer maintaining a pH from about 3.0 to about 7.0, preferably from about pH 3.0 to about pH 6.0; optionally, propylene glycol at a concentration from about 0.1% to about 20%; optionally a taste-masking agent from about 0.01 mM to about 10 mM; optionally containing a permeant ion concentration from about 30 mM to about 150 mM, wherein permeant ions may be selected from chloride ion and bromide ion with a final admixed solution osmolality from about 50 mOsmol/kg to about 600 mOsmol/kg.

In some embodiments, described herein is a unit dosage adapted for use in a liquid nebulizer comprising from about 0.01 mL to about 10 mL of an aqueous solution of nintedanib or salt thereof, wherein the concentration of nintedanib hydrochloride salt, in the aqueous solution is from about 0.0001 mg/mL to about 5 mg/mL requires admixture prior to administration. For stability purposes the unit dosage form is prepared as a two-container admixture system, wherein container one contains nintedanib hydrochloride salt is prepared in an aqueous volume from about 0.01 mL to about 10 mL; optionally 0.01 mM to about 1000 mM glycine or glutamate buffer maintaining a pH from about 3.0 to about 7.0, preferably from about pH 3.0 to about pH 6.0; optionally a propylene glycol at a concentration from about 0.1% to about 99%; optionally a taste-masking agent from about 0.01 mM to about 100 mM. Container 2 consists of an aqueous solution from about 0.01 mL to about 10 mL; optionally containing a permeant ion concentration from about 30 mM to about 1500 mM, wherein permeant ions may be selected from chloride ion and bromide ion; optionally 0.01 mM to about 1000 mM glycine or glutamate buffer maintaining a pH from about 3.0 to about 7.0, preferably from about pH 3.0 to about pH 6.0; optionally propylene glycol at a concentration from about 0.1% to about 99%; optionally a taste-masking agent from about 0.01 mM to about 100 mM. Prior to administration, the two-container admixture system is admixed resulting in a unit dosage form comprising from about 0.01 mL to about 10 mL of an aqueous solution of nintedanib hydrochloride salt, wherein the concentration of nintedanib hydrochloride salt, in the aqueous solution is from about 0.0001 mg/mL to about 5 mg/mL; optionally 0.01 to about 50 mM glycine or glutamate buffer maintaining a pH from about 3.0 to about 7.0, preferably from about pH 3.0 to about pH 6.0; optionally, propylene glycol at a concentration from about 0.1% to about 20%; optionally a taste-masking agent from about 0.01 mM to about 10 mM; optionally containing a permeant ion concentration from about 30 mM to about 150 mM, wherein permeant ions may be selected from chloride ion and bromide ion, with a final admixed solution osmolality from about 50 mOsmol/kg to about 600 mOsmol/kg.

In some embodiments, described herein is a unit dosage adapted for use in a liquid nebulizer comprising from about 0.01 mL to about 10 mL of an aqueous solution of nintedanib or salt thereof, wherein the concentration of nintedanib esylate salt, in the aqueous solution is from about 0.0001 mg/mL to about 5 mg/mL requires admixture prior to administration. For stability purposes the unit dosage form is prepared as a two-container admixture system, wherein container one contains nintedanib esylate salt is prepared in an aqueous volume from about 0.01 mL to about 10 mL; optionally 0.01 mM to about 1000 mM glycine or glutamate buffer maintaining a pH from about 3.0 to about 7.0, preferably from about pH 3.0 to about pH 6.0; optionally a propylene glycol at a concentration from about 0.1% to about 99%; optionally a taste-masking agent from about 0.01 mM to about 100 mM. Container 2 consists of an aqueous solution from about 0.01 mL to about 10 mL; optionally containing a permeant ion concentration from about 30 mM to about 1500 mM, wherein permeant ions may be selected from chloride ion and bromide ion; optionally 0.01 mM to about 1000 mM glycine or glutamate buffer maintaining a pH from about 3.0 to about 7.0, preferably from about pH 3.0 to about pH 6.0; optionally propylene glycol at a concentration from about 0.1% to about 99%; optionally a taste-masking agent from about 0.01 mM to about 10 mM. Prior to administration, the two-container admixture system is admixed resulting in a unit dosage form comprising from about 0.01 mL to about 10 mL of an aqueous solution of nintedanib esylate salt, wherein the concentration of nintedanib esylate salt, in the aqueous solution is from about 0.0001 mg/mL to about 5 mg/mL; optionally 0.01 to about 50 mM glycine or glutamate buffer maintaining a pH from about 3.0 to about 7.0, preferably from about pH 3.0 to about pH 6.0; optionally, propylene glycol at a concentration from about 0.1% to about 20%; optionally a taste-masking agent from about 0.01 mM to about 10 mM; optionally containing a permeant ion concentration from about 30 mM to about 150 mM, wherein permeant ions may be selected from chloride ion and bromide ion, with a final admixed solution osmolality from about 50 mOsmol/kg to about 600 mOsmol/kg.

The invention includes a stand-alone, single-container system wherein nintedanib or salt thereof, or an indolinone derivative are stabilized in the presence of pH, and ion concentration, buffer content, osmolality, or other parameters that are otherwise incompatible with nintedanib or indolinone composition as the active pharmaceutical ingredient. The addition of the active ingredient pirfenidone or pyridone analog further increases nintedanib or indolinone composition stability, increases aqueous solubility, and reduces viscosity that otherwise exists at high nintedanib or indolinone composition concentrations greater than about 10 mg/mL to about 50 mg/mL. At these and lower nintedanib or salt thereof, or an indolinone derivative concentrations, the addition of active ingredient pirfenidone or pyridone analog enables formulation of nintedanib or salt thereof, or an indolinone derivative in a stable, single container solution containing ion concentrations, buffer contents, osmolality, pH or other parameters that are otherwise incompatible as a single solution product. For this, the formulation as administered may be prepared as a unit dosage adapted for use in a liquid nebulizer comprising from about 0.01 mL to about 10 mL of an aqueous solution of nintedanib or salt thereof, or a indolinone derivative or salt thereof at a concentration from about 0.0001 mg/mL to about 50 mg/mL, and pirfenidone or pyridone analog at a concentration from about 5 mg/mL to about 20 mg/mL, optionally one or more osmolality adjusting agents at a concentration of about 0.1% to about 20% to adjust osmolality, inorganic salts at a concentration of about 15 mM to about 500 mM to adjust osmolality and provide a permeant ion at a final concentration from about 30 mM to about 500 mM; and optionally one or more buffers to maintain the pH between about pH 3.0 to about pH 7.0, preferably from about pH 3.0 to about pH 6.0, with a final osmolality between 50 mOsmo/kg and 1000 mOsmo/kg. The aqueous solution may include one or more osmolality adjusting agents, including co-solvents selected from propylene glycol, ethanol, glycerin, and mannitol and combinations thereof at a concentration from about 0.1% to about 20%. The aqueous solution includes one more inorganic salts selected from hydrogen chloride, hydrogen bromide, sodium chloride, magnesium chloride, calcium chloride, potassium chloride, sodium bromide, potassium bromide, magnesium bromide and calcium bromide and combinations thereof. The inorganic salt content of the aqueous solution is from about 15 mM to about 300 mM. The buffer is selected from one or more of lysinate, acetylcysteine, glycine, glutamate, borate, succinate, tartrate, phosphate or Tris and combinations thereof, the pH of the aqueous solution is from about pH 3.0 to about pH 7.0, preferably pH about 3.0 to about pH 6.0. In some embodiments, described herein is an aqueous solution for nebulized inhalation administration comprising: water; nintedanib or salt thereof, at a concentration from about 0.005 mg/mL to about 50 mg/mL; pirfenidone or pyridone analog at a concentration from about 5 mg/mL to about 20 mg/mL; one or more permeant ions; one or more osmolality adjusting agents; and wherein the osmolality of the aqueous solution is from about 50 mOsmol/kg to about 1000 mOsmol/kg.

The invention includes a population of aqueous droplets of nintedanib or indolinone or salt thereof wherein the aqueous droplet has a mean diameter less than about 5.0 µm that may collectively be referred to as an aerosol mist. The population of droplets is produced from a liquid nebulizer having an aqueous solution of nintedanib or indolinone or salt thereof disposed in the reservoir of the nebulizer. The aqueous solution of nintedanib or indolinone or salt thereof having a concentration of nintedanib or salt thereof, from about 0.0001 mg/mL to about 10 mg/mL, a permeant ion concentration from about 30 mM to about 150 mM and an osmolality from about 50 mOsmol/kg to about 600 mOsmol/kg.

The invention includes a population of aqueous droplets of nintedanib or indolinone or salt thereof and pirfenidone or pyridone analog wherein the aqueous droplet has a mean diameter less than about 5.0 µm that may collectively be referred to as an aerosol mist. The population of droplets is produced from a liquid nebulizer having an aqueous solution of nintedanib or indolinone or salt thereof and pirfenidone or pyridone analog disposed in the reservoir of the nebulizer. The aqueous solution of nintedanib or indolinone or salt thereof and pirfenidone or pyridone analog having a concentration of nintedanib or salt thereof, from about 0.0001 mg/mL to about 50 mg/mL and pirfenidone or pyridone analog concentration from about 5 mg/mL to about 20 mg/mL, a permeant ion concentration from about 30 mM to about 500 mM and an osmolality from about 50 mOsmol/kg to about 1000 mOsmol/kg.

An aqueous aerosol comprising a plurality of aqueous droplets has a volumetric mean diameter (VMD), mass median aerodynamic diameter (MMAD), and/or mass median diameter (MMD) of less than about 5.0 µm. In some embodiments, at least 20% of the aqueous droplets in the aerosol have a diameter less than about 5 µm.

although as described below, "high efficiency" liquid nebulizers are preferred for production of the aerosol mist, a number of different nebulizer designs exist including a jet nebulizer, an ultrasonic nebulizer, a pulsating membrane nebulizer, a nebulizer comprising a vibrating mesh or plate with multiple apertures, or a nebulizer comprising a vibration generator and an aqueous chamber. A preferred high efficiency nebulizer is comprised of a vibrating mesh or plate with multiple apertures that is in fluid communication with a reservoir for containing the admixture described herein. The liquid nebulizer preferably: (i) achieves lung deposition of at least 7% of the nintedanib or indolinone or salt thereof to the lung of an adult human; (ii) provides a Geometric Standard Deviation (GSD) of emitted droplet size distribution of the aqueous solution of about 1.0 µm to about 2.5 µm; (iii) provides: a) a mass median aerodynamic diameter (MMAD) of droplet size of the aqueous solution emitted with the high efficiency liquid nebulizer of about 1 µm to about 5 µm; b) a volumetric mean diameter (VMD) of about 1 µm to about 5 µm; and/or c) a mass median diameter (MMD) of about 1 µm to about 5 µm; (iv) provides a fine particle fraction (FPF=%≤5 microns) of droplets emitted from the liquid nebulizer of at least about 30%; (v) provides an output rate of at least 0.1 mL/min; and/or (vi) provides at least about 25% of the aqueous solution to the patient.

The liquid nebulizer preferably possesses at least two, at least three, at least four, at least five, or all six of parameters (i), (ii), (iii), (iv), (v), (vi) listed above and preferably achieves lung deposition of (i) at least 5%, at least 6%, at least 7%, at least 8%, at least 9%, at least 10%, at least 12%, at least 14%, at least 16%, at least 18%, at least 20%, at least 25%, at least 30%, at least 35%, at least 40% at least 45%, at least 50%, at least 55%, at least 60%, at least 65%, at least 70%, at least 75%, or at least 80% of the nintedanib or indolinone or salt thereof, or nintedanib or indolinone or salt thereof and pirfenidone or pyridone analog administered to the patient. The liquid nebulizer: (ii) provides a Geometric Standard Deviation (GSD) of emitted droplet size distribution of the aqueous solution of about 1.0 μm to about 2.5 μm, about 1.2 μm to about 2.3 μm, about 1.4 μm to about 2.1 μm, or about 1.5 μm to about 2.0 μm. The liquid nebulizer: (iii) provides a) a mass median aerodynamic diameter (MMAD) of droplet size of the aqueous solution emitted with the high efficiency liquid nebulizer of about less than 5 μm or about 1 μm to about 5 μm; b) a volumetric mean diameter (VMD) of about less than 5 μm or about 1 μm to about 5 μm; and/or c) a mass median diameter (MMD) of about less than 5 μm or about 1 μm to about 5 μm. The liquid nebulizer: (iv) provides a fine particle fraction (FPF=%≤5 microns) of droplets emitted from the liquid nebulizer of at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%. The liquid nebulizer: (v) provides an output rate of at least 0.1 mL/min, of at least 0.2 mL/min, of at least 0.3 mL/min, of at least 0.4 mL/min, of at least 0.5 mL/min, of at least 0.6 mL/min, of at least 0.7 mL/min, of at least 0.8 mL/min, of at least 0.9 mL/min, of at least 1.0 mL/min, or less than about 1.0 mL/min. The liquid nebulizer: (vi) provides at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 95%, of the aqueous solution to the mammal. The liquid nebulizer provides an respirable delivered dose (RDD) of at least 5%, at least 6%, at least 7%, at least 8%, at least 10%, at least 12%, at least 16%, at least 20%, at least 24%, at least 28%, at least 32%, at least 36%, at least 40%, at least 45%, at least 50%, at least 55%, at least 60%, at least 65%, at least 70%, at least 75%, at least 80%, at least 85%, or at least 90%.

The pharmaceutical compositions and methods of the present invention include preparing and administering specific formulations having discrete ranges of concentration, osmolality, and permeant ion concentration in order to generate an aerosol that achieves specific levels of deposition of active ingredient to the lung. The composition comprising nintedanib or indolinone or salt thereof is prepared in an aqueous solution and administered to the patient with a liquid nebulizer; wherein the aqueous solution comprises water; nintedanib or indolinone or salt thereof, at a concentration from about 0.001 mg/mL to about 10 mg/mL; wherein the osmolality of the aqueous solution is from about 50 mOsmol/kg to about 600 mOsmol/kg. The liquid (i) achieves lung deposition of at least 7% of the nintedanib or indolinone or salt thereof administered to the mammal; (ii) provides a Geometric Standard Deviation (GSD) of emitted droplet size distribution of the aqueous solution of about 1.0 μm to about 2.5 μm; (iii) provides: a) a mass median aerodynamic diameter (MMAD) of droplet size of the aqueous solution emitted with the high efficiency liquid nebulizer of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 microns) of droplets emitted from the liquid nebulizer of at least about 30%; (v) provides an output rate of at least 0.1 mL/min; and/or (vi) provides at least about 25% of the aqueous solution to the mammal. The liquid nebulizer delivers from about 0.0001 mg to about 100 mg of nintedanib or indolinone or salt thereof compound to the lungs of the patient in less than about 20 minutes with mass median diameter (MMAD) particles sizes from about 1 to about 5 micron.

The pharmaceutical compositions and methods of the present invention include preparing and administering specific formulations having discrete ranges of concentration, osmolality, and permeant ion concentration in order to generate an aerosol that achieves specific levels of deposition of active ingredient to the lung. The composition comprising nintedanib or indolinone or salt thereof and pirfenidone or pyridone analog is prepared in an aqueous solution and administered to the patient with a liquid nebulizer; wherein the aqueous solution comprises water; nintedanib or indolinone or salt thereof at a concentration from about 0.0001 mg/mL to about 50 mg/mL and pirfenidone or pyridone analog at a concentration from about 5 mg/mL to about 20 mg/mL; wherein the osmolality of the aqueous solution is from about 50 mOsmol/kg to about 1000 mOsmol/kg. The liquid (i) achieves lung deposition of at least 7% of the nintedanib or indolinone or salt thereof administered to the mammal; (ii) provides a Geometric Standard Deviation (GSD) of emitted droplet size distribution of the aqueous solution of about 1.0 μm to about 2.5 μm; (iii) provides: a) a mass median aerodynamic diameter (MMAD) of droplet size of the aqueous solution emitted with the high efficiency liquid nebulizer of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 microns) of droplets emitted from the liquid nebulizer of at least about 30%; (v) provides an output rate of at least 0.1 mL/min; and/or (vi) provides at least about 25% of the aqueous solution to the mammal. The liquid nebulizer delivers from about 0.0001 mg to about 100 mg of nintedanib or indolinone or salt thereof and from about 1 mg to about 20 mg pirfenidone or pyridone analog compounds to the lungs of the patient in less than about 20 minutes with mass median diameter (MMAD) particles sizes from about 1 to about 5 micron.

The methods for the treatment of lung disease in a mammal comprising: administering to mammal in need thereof an aqueous solution comprising nintedanib or indolinone or salt thereof, with a liquid nebulizer. Described herein is a method for the treatment of lung disease in a mammal comprising: administering to mammal in need thereof an aqueous solution comprising nintedanib or salt thereof with a liquid nebulizer; wherein the aqueous solution comprises water; nintedanib or salt thereof at a concentration from about 0.0001 mg/mL to about 10 mg/mL; optionally one or more inorganic salts, wherein the osmolality of the aqueous solution is from about 50 mOsmol/kg to about 600 mOsmol/kg; optionally a permeant ion from about 30 mM to about 150 mM; optionally one or more buffers maintaining the solution pH between about 3.0 and 7.0; optionally a osmolality adjusting agent from about 0.1 to about 20%; optionally a taste-masker from about 0.01 mM to about 10 mM. The nebulizer is a jet nebulizer, an ultrasonic nebulizer, a pulsating membrane nebulizer, a nebulizer comprising a vibrating mesh or plate with multiple apertures, or a nebulizer comprising a vibration generator and an aqueous chamber. In some embodiments, the liquid nebulizer: (i) achieves lung deposition of at least 7% of the nintedanib or indolinone or salt thereof, administered to the mammal; (ii) provides a Geometric Standard Deviation (GSD) of emitted droplet size distribution of the aqueous solution of about 1.0 μm to about 2.5 μm; (iii) provides: a) a mass median aerodynamic diameter (MMAD) of droplet size of the aqueous solution emitted with the high efficiency liquid nebulizer of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 microns) of droplets emitted from the liquid nebulizer of at least about 30%; (v) provides an output rate of at least 0.1 mL/min; and/or (vi) provides at least about 25% of the aqueous solution to the mammal.

The methods for the treatment of lung disease in a mammal comprising: administering to mammal in need thereof an aqueous solution comprising nintedanib or indolinone or salt thereof and pirfenidone or pyridone analog with a liquid nebulizer. Described herein is a method for the treatment of lung disease in a mammal comprising: administering to mammal in need thereof an aqueous solution comprising nintedanib or salt thereof and pirfenidone or pyridone analog with a liquid nebulizer; wherein the aqueous solution comprises water; nintedanib or salt thereof at a concentration from about 0.0001 mg/mL to about 50 mg/mL and pirfenidone or pyridone analog at a concentration from about 5 mg/mL to about 20 mg/mL; optionally one or more inorganic salts, wherein the osmolality of the aqueous solution is from about 50 mOsmol/kg to about 1000 mOsmol/kg; optionally a permeant ion from about 30 mM to about 500 mM; optionally one or more buffers maintaining the solution pH between about 3.0 and 7.0; optionally a osmolality adjusting agent from about 0.1 to about 10%; optionally a taste-masker from about 0.01 mM to about 10 mM. The nebulizer is a jet nebulizer, an ultrasonic nebulizer, a pulsating membrane nebulizer, a nebulizer comprising a vibrating mesh or plate with multiple apertures, or a nebulizer comprising a vibration generator and an aqueous chamber. In some embodiments, the liquid nebulizer: (i) achieves lung deposition of at least 7% of the nintedanib or indolinone or salt thereof, administered to the mammal; (ii) provides a Geometric Standard Deviation (GSD) of emitted droplet size distribution of the aqueous solution of about 1.0 μm to about 2.5 μm; (iii) provides: a) a mass median aerodynamic diameter (MMAD) of droplet size of the aqueous solution emitted with the high efficiency liquid nebulizer of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 microns) of droplets emitted from the liquid nebulizer of at least about 30%; (v) provides an output rate of at least 0.1 mL/min; and/or (vi) provides at least about 25% of the aqueous solution to the mammal.

The liquid nebulizer delivers about 0.0001 mg to about 100 mg of nintedanib or indolinone or salt thereof to the lungs in less than about 20 minutes with mass median diameter (MMAD) particles sizes from about 1 to about 5 micron.

The liquid nebulizer delivers about 0.0001 mg to about 100 mg of nintedanib or indolinone or salt thereof and about 1 mg to about 20 mg pirfenidone or pyridone analog to the lungs in less than about 20 minutes with mass median diameter (MMAD) particles sizes from about 1 to about 5 micron.

The aqueous droplet populations have a median diameter less than about 5.0 μm. The aqueous droplet has a diameter less than about 5.0 μm, less than about 4.5 μm, less than about 3.0 μm, less than about 3.5 μm, less than about 3.0 μm, less than about 2.5 μm, less than about 2.0 μm, less than about 1.5 μm, or less than about 1.0 μm and are further comprised of one or more osmolality adjusting agents including co-solvents selected from ethanol, propylene glycol, mannitol and glycerin and combinations thereof. The aqueous droplet may also be further comprised of a buffer selected from lysinate, acetylcysteine, glycine, glutamate, borate, succinate, tartrate, phosphate or Tris and combinations thereof.

The aqueous droplet populations may exhibit a varying range in the percent of individual droplets above 5 μm such as: and may vary from at least about 15%, 20%, 25%, 30%, 35%, 40%, 45%, 50%, 55%, 60%, 65%, 70%, 75%, 80%, 85%, or 90%.

In some embodiments, administration with the liquid nebulizer does not include an initial dose-escalation period.

In one example, about 0.01 mL to about 10 mL of the aqueous solution is administered to the mammal with a liquid nebulizer, the solution comprising nintedanib or salt thereof, at a concentration from about 0.0001 mg/mL to about 10 mg/mL; optionally one or more inorganic salts, wherein the osmolality of the aqueous solution is from about 50 mOsmol/kg to about 600 mOsmol/kg; optionally a permeant ion from about 30 mM to about 150 mM; optionally one or more buffers maintaining the solution pH between about 3.0 and 7.0; optionally a osmolality adjusting agent from about 0.1 to about 20%; optionally a taste-masker from about 0.01 mM to about 10 mM; and the liquid nebulizer is a nebulizer comprising a vibrating mesh or plate with multiple apertures, the liquid nebulizer delivers about 0.0001 mg to about 100 mg of nintedanib or salt thereof to the lungs in less than about 20 minutes with mass median diameter (MMAD) particles sizes from about 1 to about 5 micron.

In one example, about 0.01 mL to about 10 mL of the aqueous solution is administered to the mammal with a liquid nebulizer, the solution comprising nintedanib or salt thereof, at a concentration from about 0.0001 mg/mL to about 50 mg/mL and pirfenidone or pyridone analog at a concentration from about 5 mg/mL to about 20 mg/mL; optionally one or more inorganic salts, wherein the osmolality of the aqueous solution is from about 50 mOsmol/kg to about 1000 mOsmol/kg; optionally a permeant ion from about 30 mM to about 500 mM; optionally one or more buffers maintaining the solution pH between about 3.0 and 7.0; optionally a osmolality adjusting agent from about 0.1 to about 20%; optionally a taste-masker from about 0.01 mM to about 10 mM; and the liquid nebulizer is a nebulizer comprising a vibrating mesh or plate with multiple apertures, the liquid nebulizer delivers about 0.0001 mg to about 100 mg of nintedanib or salt thereof and from about 1 mg to about 20 mg pirfenidone or pyridone analog to the lungs in less than about 20 minutes with mass median diameter (MMAD) particles sizes from about 1 to about 5 micron.

In the multi-container approach, a first container contains nintedanib or salt thereof dissolved in an aqueous volume from about 0.01 mL to about 10 mL; optionally 0.01 mM to about 1000 mM buffer maintaining a pH from about 3.0 to about 7.0, preferably from about pH 3.0 to about pH 6.0, optionally a osmolality adjusting agent concentration from about 0.1% to about 99% and optionally a taste-masking agent from about 0.01 mM to about 100 mM. Because nintedanib lacks long-term stability in the presence of permeant ion, permeant ion is prepared in a separate, second container. The second container contains an aqueous solution from about 0.01 mL to about 10 mL; optionally containing a concentration from about 15 mM to about 1500 mM inorganic salt; optionally 0.01 mM to about 1000 mM buffer maintaining a pH from about 3.0 to about 7.0, preferably from about pH 3.0 to about pH 6.0; optionally a osmolality adjusting agent from about 0.1% to about 99%;

optionally a taste-masking agent from about 0.01 mM to about 100 mM. Just prior to administration, the two-container system is admixed resulting in a unit dosage form comprising from about 0.01 mL to about 10 mL of an aqueous solution of nintedanib or salt thereof, wherein the concentration of nintedanib or salt thereof in the aqueous solution is from about 0.01 mg/mL to about 10 mg/mL; optionally 0.01 to about 100 mM buffer maintaining a pH from about 3.0 to about 7.0, preferably from about pH 3.0 to about pH 6.0; optionally, a osmolality adjusting agent concentration from about 0.1% to about 20%; optionally a taste-masking agent from about 0.01 mM to about 10 mM; optionally an inorganic salt from about 15 mM to about 300 mM, creating a permeant ion concentration from about 30 mM to about 150 mM, with a final admixed solution osmolality from about 50 mOsmol/kg to about 600 mOsmol/kg.

In the unit dose approach, the container contains nintedanib or salt thereof and pirfenidone or pyridone analogy dissolved in an aqueous volume from about 0.01 mL to about 10 mL; optionally 0.01 mM to about 100 mM buffer maintaining a pH from about 3.0 to about 7.0, preferably from about pH 3.0 to about pH 6.0, optionally a osmolality adjusting agent concentration from about 0.1% to about 20%, an inorganic salt from about 15 mM to about 500 mM, providing a permeant ion concentration from about 30 mM to about 500 mM, and optionally a taste-masking agent from about 0.01 mM to about 100 mM. Because pirfenidone stabilizes nintedanib in the presence of permeant ion, this approach permits a stable single container, unit dose configuration. This single container system provides a unit dosage form comprising from about 0.01 mL to about 10 mL of an aqueous solution of nintedanib or salt thereof and pirfenidone or pyridone analog, wherein the concentration of nintedanib or salt thereof in the aqueous solution is from about 0.01 mg/mL to about 50 mg/mL and the concentration of pirfenidone or pyridone analog is from about 5 mg/ml to about 20 mg/mL; optionally 0.01 to about 100 mM buffer maintaining a pH from about 3.0 to about 7.0, preferably from about pH 3.0 to about pH 6.0; optionally, a osmolality adjusting agent concentration from about 0.1% to about 20%; optionally a taste-masking agent from about 0.01 mM to about 10 mM; optionally an inorganic salt from about 15 mM to about 500 mM, creating a permeant ion concentration from about 30 mM to about 500 mM, with a final admixed solution osmolality from about 50 mOsmol/kg to about 1000 mOsmol/kg.

In the unit dose approach, the container contains nintedanib hydrobromide and pirfenidone dissolved in an aqueous volume from about 0.01 mL to about 10 mL; optionally 0.01 mM to about 100 mM buffer maintaining a pH from about 3.0 to about 7.0, preferably from about pH 3.0 to about pH 6.0, optionally a osmolality adjusting agent concentration from about 0.1% to about 20%, an inorganic salt from about 15 mM to about 500 mM, providing a permeant ion concentration from about 30 mM to about 500 mM, and optionally a taste-masking agent from about 0.01 mM to about 100 mM. Because pirfenidone stabilizes nintedanib in the presence of permeant ion, this approach permits a stable single container, unit dose configuration. This single container system provides a unit dosage form comprising from about 0.01 mL to about 10 mL of an aqueous solution of nintedanib hydrobromide and pirfenidone, wherein the concentration of nintedanib hydrobromide in the aqueous solution is from about 0.01 mg/mL to about 50 mg/mL and the concentration of pirfenidone is from about 5 mg/ml to about 20 mg/mL; optionally 0.01 mM to about 100 mM buffer maintaining a pH from about 3.0 to about 7.0, preferably from about pH 3.0 to about pH 6.0; optionally, a osmolality adjusting agent concentration from about 0.1% to about 20%; optionally a taste-masking agent from about 0.01 mM to about 10 mM; optionally an inorganic salt from about 15 mM to about 500 mM, creating a permeant ion concentration from about 30 mM to about 500 mM, with a final admixed solution osmolality from about 50 mOsmol/kg to about 1000 mOsmol/kg.

The invention includes a dry powder formulation for oral comprising nintedanib or salt thereof, or a indolinone derivative or salt thereof, at concentrations of 0.1% w/w to about 100% w/w in a finely divided form having mass median diameters of 0.5 micrometers to 10 micrometers. The nintedanib or salts thereof, or a indolinone or salt thereof and optionally one or more carrier excipients (e.g. lactose, mannitol, sucrose, glucose, trehalose) at about 10% to about 99.99% to improve handling, dispensing, metering and dispersion of the drug. The formulation may optionally contain one or more slipping agents (e.g., L-leucine, magnesium stearate) at a concentration of about 0.1% w/w to about 10% w/w to reduce inter-particulate adhesion, improve powder flowability and reduce moisture effects. The formulations may be prepared by physical blending of nintedanib or salt thereof, with the aforementioned excipients. Alternatively, the dry powder formulation may form by precipitation techniques that include spray drying, vacuum drying, solvent extraction, controlled precipitation, emulsification or lyophilization. For these formulations, in addition to the excipients mentioned above for blended dry powder formulations, these may contain phospholipids (e.g., dipalmitoylphosphatidylcholine, disteroylphosphatidylcholine, diarachidoylphosphatidylcholine dibehenoylphosphatidylcholine, diphosphatidyl glycerol) at 10% w/w to about 99.9% w/w to act as emulsifying agent and bulking agent. Optionally the formulation of the present invention may also include a biocompatible, preferably biodegradable polymer, copolymer, or blend or other combination thereof at about 0.1% w/w 99.9% w/w. Examples of polymers include but not limited to polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). The dry powder can be packaged as unit dose in blister pack or capsules at fill weights of 1 mg to 100 mg. Alternatively, the dry powder formulation can be packaged in a device reservoir that meters 1 mg to 100 mg at the point of use.

A vial contains a dry powder comprising of nintedanib or salt thereof, or a indolinone derivative or salt thereof at a concentration, optionally an inorganic salt containing permeant ion(s), optionally a buffer, optionally a non-ionic osmolality adjusting agent and optionally a taste masking agent, and optionally a bulking agent. These components may be prepared by mechanical blending, or by precipitation techniques known in the art that include spray drying, vacuum drying, solvent extraction, controlled precipitation, emulsification or lyophilization. The weight of the contents in the dry powder vial is about 0.05 gram to 1 gram. A second vial contains a diluent comprising of water, optionally one or more solvents, optionally one or more an inorganic salt containing permeant ion(s), optionally a buffer, optionally an osmolality adjusting agent and optionally a taste masking agent. The volume of the contents in the diluent vial is about 0.5 mL to 10 mL. A lyophilized vial contains nintedanib or its derivative, optionally an inorganic salt containing permeant ion(s) (e.g., NaCl, NaBr, MgCl2), optionally a buffer (e.g., glycinate, glutamate, maleate, malate), optionally a non-ionic osmolality adjusting agent (e.g., lactose, mannitol, sucrose), and optionally a taste masking agent, and optionally a bulking agent (e.g. lactose, mannitol, sucrose). A diluent vial contains sterile water, optionally an inorganic salt containing permeant ion(s) (e.g., NaCl, NaBr, MgCl2, CaCl2, CaBr, MgBr2, HCl, HBr), optionally a buffer (e.g., glycinate, glutamate, maleate, malate), optionally an osmolality adjusting agent (e.g., lactose, mannitol, glucose, sucrose), and optionally a taste masking agent. The lyophilized solution would be reconstituted with the diluent solution at the point of use.

Osmolality adjusting agents are comprised of consists of one or more classes of excipients from the following groups: sugars, alcohols, inorganic salts, amino acids, and acids/bases and combinations thereof. Individually, sugars can be selected from, but not limited to: glucose, fructose, lactose, sucrose, maltose, mannose, trehalose and xylose. Alcohols include but not limited to: erythritol, glycerol, inositol, maltitol, mannitol, menthol, propylene glycol, sorbitol, xylitol, threitol, propylene glycol. Inorganic salts may include but not limited to: sodium acetate, sodium bromide, sodium chloride, sodium sulfate, sodium phosphate, sodium carbonate, sodium bicarbonate, potassium carbonate, potassium iodide, potassium chloride, potassium bromide, magnesium chloride, calcium chloride Amino acids include, but not limited to: arginine, asparagine, aspartic acid, glutamic acid, glutamine, glycine, histidine, lysine and proline. Finally, acids and bases may include, but not limited to: boric acid, acetic acid, hydrogen bromide, hydrogen chloride, sulfuric acid, nitric acid, phosphoric acid, sodium hydroxide, sodium hydroxide, potassium hydroxide and calcium hydroxide At the point of use, the contents in the diluent vial is added to the contents in the dry powder vial to make a reconstituted solution for nebulization comprising water; nintedanib or salt thereof, or a indolinone derivative or salt thereof at a concentration from about 0.005 mg/mL to about 10 mg/mL; optional osmolality adjusting agent at a concentration of about 0.1% to about 20% to adjust osmolality, optional inorganic salts at a concentration of about 15 mM to about 300 mM to adjust osmolality and provide a permeant ion at a final concentration from about 30 mM to about 150 mM; and optional buffers from about 0.01 mM to 100 mM to maintain the pH between about pH 3.0 to about pH 7.0, preferably from about pH 3.0 to about pH 6.0, with a final osmolality between 50 mOsmo/kg and 600 mOsmo/kg. The osmolality adjusting agents used in the diluent solution may include one or more co-solvents selected from propylene glycol, ethanol, glycerin and mannitol and combinations thereof to produce a final concentration from about 0.1% to about 20% in the reconstituted solution. The inorganic salts used in either the dry powder vial or the diluent vial are selected from sodium chloride, magnesium chloride, calcium chloride, potassium chloride, sodium bromide, potassium bromide, magnesium bromide and calcium bromide and combinations thereof. The inorganic salt content in the reconstituted aqueous solution is from about 15 mM to about 300 mM. The buffer is selected from one or more of lysinate, acetylcysteine, glycine, glutamate, borate, succinate, tartrate, phosphate or Tris and combinations thereof, the pH of the reconstituted aqueous solution is from about pH 3.0 to about pH 7.0, preferably pH about 3.0 to about pH 6.0. Described herein is a reconstituted aqueous solution for nebulized inhalation administration comprising: water; nintedanib or salt thereof, at a concentration from about 0.005 mg/mL to about 10 mg/mL, preferably not exceeding 5.0 mg/mL; one or more permeant ions at a concentration from about 30 mM to 150 mM; one or more osmolality adjusting agents; and wherein the osmolality of the aqueous solution is from about 50 mOsmol/kg to about 600 mOsmol/kg. The formulation may be administered as an inhaled aerosol created from a dosing volume ranging from about 0.01 mL to about 10 mL. The formulation may be administered as an inhaled aerosol over a few breaths or by tidal breathing up to 20 minutes.

Methods to Treat or Prevent Disease

For purposes of the methods described herein, a indolinone, salt or derivative thereof compound, most preferably nintedanib salt is administered using a liquid nebulizer having a vibrating mesh screen that produces an aerosol mist having a particle size distribution optimized for delivery of the aerosol to the pulmonary compartment. In some embodiments, nintedanib or an indolinone derivative compound or salt thereof is formulated as a pharmaceutical composition suitable for aerosol formation, dose for indication, deposition location, pulmonary or intra-nasal delivery for pulmonary, intranasal/sinus, or extra-respiratory therapeutic action, good taste, manufacturing and storage stability, and patient safety and tolerability. The methods include steps for performing an admixture of solutions contained in a multi-container system that separates the active pharmaceutical ingredient (API) from other solutions prior to or immediately following placement into a nebulizer for aerosol administration.

The methods include administering a second anti-fibrotic, anti-cancer, anti-infective anti-inflammatory, or anti-pulmonary hypertension agent. The pulmonary diseases subject to treatment under the present invention include interstitial lung disease, such as idiopathic pulmonary fibrosis, and radiation-therapy-induced pulmonary fibrosis, chronic lung allograft dysfunction, bronchiolitis obliterans, restrictive allograft syndrome, and systemic sclerosis associated interstitial lung disease (SSc-ILD). The pulmonary diseases also include chronic obstructive pulmonary disease, chronic bronchitis, and cancer, including small cell lung cancer, large cell carcinoma, mesothelioma, lung carcinoid tumors or bronchial cardinoids, secondary lung cancer resulting from metastatic disease, non-small cell lung cancer, bronchioloalveolar carcinoma, sarcoma, and lymphoma.

The inhaling step is performed in less than about 10 minutes, less than about 7.5 minutes, less than about 5 minutes, less than about 2.5 minutes, less than about 1.5 minutes, and less than about 30 seconds. The inhaling step may be performed in less than 5 breaths, less than 3 breaths, or less than bout 2 breaths.

The methods include to treat a neurologic disease comprising intranasal inhalation of the aerosol described herein.

Intranasal delivery includes the method of administering an anti-demyelination agent to nasal cavity of a patient, comprising:

In the methods described herein involving admixture of separate containers, the methods include the affirmative steps of opening and admixing the contents of at least two sterile single-use containers whose final admixed solution contains between about 0.01 mL to about 10 mL of a solution of nintedanib or indolinone or salt thereof for introduction into a nebulizer immediately prior to administration to a patient.

In the methods described herein, the aerosol comprises particles having a mean aerodynamic diameter from about 1 micron to about 5 microns. The aerosol has a mean particle size from about 1 microns to about 20 µm and preferably from about 1 5 microns volumetric mean diameter and a particle size geometric standard deviation of less than or equal to 3 microns. The inhaling step delivers a dose of a least 0.0001 mg nintedanib or indolinone or salt thereof, at least 0.001 mg, at least 0.01 mg, at least 0.1 mg, at least 1.0 mg, at least 10 mg, at least 50 mg, at least 100 mg nintedanib or indolinone or salt thereof.

In the methods described herein, the aerosol comprises particles having a mean aerodynamic diameter from about 1 micron to about 5 microns. The aerosol has a mean particle size from about 1 microns to about 20 µm and preferably from about 1 5 microns volumetric mean diameter and a particle size geometric standard deviation of less than or equal to 3 microns. The inhaling step delivers a dose of a least 0.0001 mg, at least 0.001 mg, at least 0.01 mg, at least 0.1 mg, at least 1.0 mg, at least 10 mg, at least 50 mg, at least 100 mg nintedanib or indolinone or salt thereof and at least 1 mg, at least 2 mg, at least 3 mg, at least 4 mg, at least 5 mg, at least 10 mg, at least 50 mg, at least 100 mg pirfenidone or pyridone analog.

In one aspect, described herein is a method for the treatment methods include of administering nintedanib or indolinone or salt thereof, to treat a patient, wherein the patient avoids abnormal liver function exhibited by a grade 2 or higher abnormality following oral administration in one or more biomarkers of liver function after nintedanib or indolinone or salt thereof, administration, comprising administering to said patient nintedanib or indolinone or salt thereof, at doses less than 1056 mg per day. "Grade 2 liver function abnormalities" include elevations in alanine transaminase (ALT), aspartate transaminase (AST), alkaline phosphatase (ALP), or gamma-glutamyl transferase (GGT) greater than 2.5-times and less than or equal to 5-times the upper limit of normal (ULN). Grade 2 liver function abnormalities also include elevations of bilirubin levels greater than 1.5-times and less than or equal to 3-times the ULN. The nintedanib or indolinone or salt thereof, is delivered to the patient by oral inhalation or intranasal inhalation. One or more biomarkers of liver function is selected from the group consisting of alanine transaminase, aspartate transaminase, bilirubin, and alkaline phosphatase. The method further comprises the step of measuring one or more biomarkers of liver function. The blood Cmax following inhaled administration of nintedanib or indolinone or salt thereof, is less than 100.0 ng/mL. The blood Cmax following administration of nintedanib or indolinone or salt thereof, is less than 10.0 ng/mL, less than 1.0 ng/mL, less than 0.1 ng/mL, less than 0.01 ng/mL.

The methods of administering nintedanib or indolinone or salt thereof, include the avoidance of nausea, diarrhea, headaches, leg aches/cramps, fluid retention, visual disturbances, itchy rash, lowered resistance to infection, bruising or bleeding, loss of appetite, weight gain, reduced number of blood cells (neutropenia, thrombocytopenia, anemia), headache, edema, congestive cardiac failure observed following oral administration, comprising administering to said patient inhaled nintedanib or indolinone or salt thereof at doses less than 100 mg per day. The nintedanib or indolinone or salt thereof is delivered to the patient by oral inhalation or intranasal inhalation.

The methods of the invention include daily maximum dosages of less than 100 mg per day of nintedanib or salt thereof is delivered to the patient by inhalation. In some embodiments, less than 50 mg, less than 25 mg, less than 10 mg, less than 5 mg, less than 2.5 mg, less than 1 mg, less than 0.1 mg, less than 0.05 mg or less than 0.01, less than 0.005, less than 0.001 mg per day of nintedanib or indolinone or salt thereof is delivered to the patient by inhalation once per day, twice per day, three times a day, four times a day, five times a day, six times a day or greater than six times per day, and may be administered daily, every other day, every third day, every fourth day, every fifth day, every sixth day or weekly, every other week, every third week or monthly.

The methods of the invention include daily maximum dosages of less than 100 mg per day of nintedanib or salt thereof and pirfenidone less than 100 mg per day is delivered to the patient by inhalation. In some embodiments, nintedanib or salt thereof is less than 100 mg, less than 50 mg, less than 25 mg, less than 10 mg, less than 5 mg, less than 2.5 mg, less than 1 mg, less than 0.1 mg, less than 0.05 mg or less than 0.01, less than 0.005, less than 0.001 mg per day and pirfenidone is less than 100 mg, less than 50 mg, less than 25 mg, less than 10 mg, less than 5 mg, less than 2.5 mg, less than 1 mg is delivered to the patient by inhalation once per day, twice per day, three times a day, four times a day, five times a day, six times a day or greater than six times per day, and may be administered daily, every other day, every third day, every fourth day, every fifth day, every sixth day or weekly, every other week, every third week or monthly.

Methods of treatment include as prophylaxis against interstitial lung disease (ILD) by administering nintedanib or indolinone or salt thereof to a subject having or suspected to have interstitial lung disease. Interstitial lung disease includes those described above and all conditions of idiopathic interstitial pneumonias as defined by American Thoracic Society/European Respiratory Society international multidisciplinary consensus classification of the idiopathic interstitial pneumonias, AM. J. Respir. Crit. Care Med. 165, 277-304 (2002) (incorporated herein by reference).

The therapeutic method may also include a diagnostic step, such as identifying a subject with or suspected of having ILD. The method further sub-classifies into idiopathic pulmonary fibrosis based on extent of disease, progression of disease, rate of advancement, or response to any existing therapy. The delivered amount of aerosol nintedanib or indolinone or salt thereof compound (or salt thereof) formulation is sufficient to provide acute, sub-acute, or chronic symptomatic relief, slowing of fibrosis progression, halting fibrosis progression, reversing fibrotic damage, and/or subsequent increase in survival and/or improved quality of life.

The therapeutic method may also include a diagnostic step of identifying a subject with or suspected of having fibrosis in other tissues, by non-limiting example in the heart, liver, kidney or skin and the therapeutic amount of liquid nebulized, dry powder or metered-dose aerosol nintedanib or indolinone or salt thereof compound is sufficient to provide acute, sub-acute, or chronic symptomatic relief, slowing of fibrosis progression, halting fibrosis progression, reversing fibrotic damage, and/or subsequent increase in survival and/or improved quality of life.

The therapeutic method may also include a diagnostic step identifying a subject with or suspected of having multiple sclerosis and the therapeutic method comprises administering liquid nebulized, dry powder or metered-dose aerosol nintedanib or indolinone or salt thereof sufficient to provide acute, sub-acute, or chronic symptomatic relief, slowing of demyelination progression, halting demyelination progression, reversing demyelinated damage, and/or subsequent increase in survival and/or improved quality of life.

Therapeutic treatment methods include administering a therapeutically effective aerosol doses to a patient wherein the dosage is calculated, titrated, or measured to establish or maintain therapeutically effective threshold drug concentrations in the lung and/or targeted downstream tissue, which may be measured as drug levels in epithelial lining fluid (ELF), sputum, lung tissue, bronchial lavage fluid (BAL), or by deconvolution of blood concentrations through pharmacokinetic analysis. One embodiment includes the use of aerosol administration, delivering high or titrated concentration drug exposure directly to the affected tissue for treatment of pulmonary fibrosis and inflammation associated with ILD (including idiopathic pulmonary fibrosis) in animals and humans. Peak lung ELF levels achieved following aerosol administration to the lung will be between 0.01 mg/mL and about 100 mg/mL nintedanib or indolinone or salt thereof or between 0.1 ng/gram lung tissue and about 500 mcg/gram lung tissue nintedanib or indolinone or salt thereof.

As a non-limiting example, in a preferred embodiment, a indolinone derivative compound as provided herein (e.g., nintedanib) formulated to permit mist, gas-liquid suspension or liquid nebulized, dry powder and/or metered-dose inhaled aerosol administration to supply effective concentrations or amounts to produce and maintain threshold drug concentrations in the blood and/or lung, which may be measured as drug levels in epithelial lining fluid (ELF), sputum, lung tissue, bronchial lavage fluid (BAL), or by deconvolution of blood concentrations through pharmacokinetic analysis that absorb to the pulmonary vasculature producing drug levels sufficient for extra-pulmonary therapeutics, maintenance or prophylaxis. Therapeutic treatment methods include the use of aerosol administration, delivering high concentration drug exposure in the pulmonary vasculature and subsequent tissues and associated vasculature for treatment, maintenance and/or prophylaxis of, but not limited to cardiac fibrosis, kidney fibrosis, hepatic fibrosis, heart or kidney toxicity, or multiple sclerosis. Peak tissue-specific plasma levels (e.g., heart, kidney and liver) or cerebral spinal fluid levels (e.g. central nervous system) achieved following aerosol administration to the lung following oral inhalation or to the lung or nasal cavity following intra-nasal administration will be between 0.0001 mcg/mL and about 50 mcg/mL nintedanib or indolinone or salt thereof. Peak lung wet tissue or epithelial lining fluid levels achieved following aerosol administration to the lung are between 0.004 mcg/gram lung tissue or epithelial lining fluid and about 500 mcg/gram lung tissue or epithelial lining fluid nintedanib or indolinone or salt thereof.

Therapeutic methods include acute or prophylactic treatment of a patient through non-oral or non-nasal topical administration of nintedanib or indolinone or salt thereof (or a salt thereof) compound formulation to produce and maintain threshold drug concentrations at a burn site, including the use of aerosol administration, delivering high concentration drug exposure directly to the affected tissue for treatment or prevention of scarring in skin.

Therapeutic methods include acute or prophylactic treatment of a patient through non-oral or non-nasal topical administration of nintedanib or indolinone or salt thereof compound formulation to produce and maintain threshold drug concentrations in the eye. One embodiment includes the use of aerosol administration or formulation drops to deliver high concentration drug exposure directly to the affected tissue for treatment or prevention of scarring following surgical glaucoma surgery (e.g., bleb fibrosis). For example according to these and related embodiments, the term aerosol may include a spray, mist, or other nucleated liquid or dry powder form. A drop may be simple liquid or suspension formulation.

As a non-limiting example, an indolinone derivative compound remains at the therapeutically effective concentration at the site of pulmonary pathology, suspected pulmonary pathology, and/or site of pulmonary absorption into the pulmonary vasculature for at least about 10 seconds, at least 1 minute, at least about a 5 minute period, at least about a 10 min period, at least about a 20 min period, at least about a 30 min period, at least about a 1 hour period, at least a 2 hour period, at least about a 4 hour period, at least an 8 hour period, at least a 12 hour period, at least a 24 hour period, at least a 48 hour period, at least a 72 hour period, or at least one week. The effective nintedanib or indolinone or salt thereof concentration is sufficient to cause a therapeutic effect and the effect may be localized or broad-acting to or from the site of pulmonary pathology.

Delivery sites such as a pulmonary site, nasal cavity or sinus, the an nintedanib or indolinone or salt thereof compound formulation as provided herein is administered in one or more administrations so as to achieve a respirable delivered dose daily of nintedanib or indolinone or salt thereof of at least about 0.0001 mg to about 100 mg, including all integral values therein such as 0.0001, 0.001, 0.006, 0.01, 0.02, 0.4, 0.6, 0.8, 1, 1.2, 1.4, 1.6, 1.8, 2, 3, 4, 5, 6, 10, 15, 20, 25, 30, 35, 40, 45, 50, 60, 70, 80, 90, 100 milligrams.

Delivery sites such as a pulmonary site, nasal cavity or sinus, the an nintedanib or indolinone or salt thereof compound formulation as provided herein is administered in one or more administrations so as to achieve a respirable delivered dose daily of nintedanib or indolinone or salt thereof of at least about 0.0001 mg to about 100 mg, including all integral values therein such as 0.0001, 0.001, 0.006, 0.01, 0.02, 0.4, 0.6, 0.8, 1, 1.2, 1.4, 1.6, 1.8, 2, 3, 4, 5, 6, 10, 15, 20, 25, 30, 35, 40, 45, 50, 60, 70, 80, 90 or 100 milligrams, and pirfenidone or pyridone analog as provided herein is administered in one or more administrations so as to achieve a respirable delivered dose daily of pirfenidone or pyridone analog of at least about 0.0001 mg to about 100 mg, including all integral values therein such as 0.0001, 0.001, 0.006, 0.01, 0.02, 0.4, 0.6, 0.8, 1, 1.2, 1.4, 1.6, 1.8, 2, 3, 4, 5, 6, 10, 15, 20, 25, 30, 35, 40, 45, 50, 60, 70, 80, 90, 100, 200 or 300 milligrams.

In embodiments where a human is mechanically ventilated, aerosol administration would be performed using an in-line device (by non-limiting example, the Nektar Aeroneb Pro or PARI eFlow in-line system) or similar adaptor with device for liquid nebulization. Aerosol administration could also be performed using an in-line adaptor for dry powder or metered-dose aerosol generation and delivery.

The methods and the combination of the invention include the administration of a nintedanib or indolinone salt using a mechanical ventilator wherein an in-line nebulizer is operably connected with the forced air circulation of the ventilator such that an aerosol is generated by the nebulizer and administered to a patient connected to the ventilator such that the breathing support function of the ventilator also administers the formulation of the invention described herein. In in-line nebulizer suitable for use with the invention is compatible with all ventilator models and is capable of matching the performance parameters described herein for generating an aerosol mist having particle size and particle distribution parameters substantially similar to the nebulizers described herein. The in-line nebulizer is typically operated continuously until the equivalent dose as described herein for a portable nebulizer is delivered.

Alternatively, the admixture of the first solution and the second solution, or a suitably formulated dry powder is introduced at a point in the ventilator air circuitry wherein inspiration by the patient or movement of air in the ventilator airway advances the admixture into the lungs of the patient. Preferably, the nebulizer is sealed in the airway to prevent additional airflow from being introduced and to permit a combination of the aerosol mist of the admixture with humidified air generated by the ventilator system. In the system described herein, movement of air through the pathway of the ventilator combines humidified air and the aerosol mist containing the admixture and may be triggered by patient inspiration or as part of a continuous or programmed delivery protocol such that the nebulizer is in intermittent or continuous operation during the administration of the admixture. In each case, the formation of the aerosol is maintained for a duration adequate to deliver therapeutically effective amounts of the admixture combination to the lungs of the patient.

Manufacture

The isoform content of the manufactured indolinone derivative compound, most preferably nintedanib may be optimized for drug substance and drug product stability, dissolution (in the case of dry powder or suspension formulations) in the nose and/or lung, tolerability, and site of action (be that lung, nasal/sinus, or regional tissue).

A pharmaceutical composition comprising a therapeutically effective amount of an inhaled agent, wherein the agent is nintedanib or salt thereof, wherein the agent is in a particle less than 5 microns in mass mean aerodynamic diameter or less than 10 microns volumetric mean diameter wherein the composition, upon inhalation, delivers a dose to the lung greater than about 0.0001 mg nintedanib or salt thereof compound per gram of adult human lung tissue, or about 0.0001 mg nintedanib or salt thereof and 0.001 mg pirfenidone or pyridone analog compound per gram of adult human lung tissue.

The compositions described herein are formulated under or to result in conditions of reduced oxygen. In some embodiments, oxygen is reduced by sparging the formulation diluent prior to addition of the active pharmaceutical ingredient. Sparging gases may be selected from the group consisting of carbon dioxide, argon or nitrogen. Oxygen is reduced by sparging the formulation diluent after addition of the active pharmaceutical ingredient. Sparging gases may be selected from the group consisting of carbon dioxide, argon or nitrogen. Oxygen exposure is reduced by replacing the ambient gas headspace of the formulation container with an inert gas. Inert gases may be selected from the group consisting of argon or nitrogen.

Oxygen exposure is reduced by replacing the ambient gas headspace of the primary packaging container with an inert gas for example selected from the group consisting of argon or nitrogen and combinations thereof, inserting the primary packaging into a gas-impermeable secondary packaging container, replacing the ambient gas headspace of the secondary packaging with an inert gas, for example selected from the group consisting of argon or nitrogen and combinations thereof.

To achieve desired nintedanib aqueous concentrations, manufacturing process are controlled to enable synthesis of a compound suitable for use in an aqueous solution for inhalation. The manufacturing process includes high temperature nintedanib aqueous dissolution, followed by osmolality adjusting agents and/or co-solvent and/or surfactant and/or salt addition, and subsequent cooling to ambient temperature. In this process, added osmolality adjusting agents and/or co-solvent and/or surfactant and/or salt stabilize the high-temperature-dissolved nintedanib during the cooling process and provide a stable, high-concentration, ambient-temperature formulation of nintedanib. The processing temperature is 30° C., 35° C., 40° C., 45° C., 50° C., 55° C., 60° C., 65° C., 70° C., 75° C., 80° C., 85° C., 90° C., 95° C., 100° C. or other pressure-enabled increased temperature. The process includes addition of surfactant and/or osmolality adjusting agents and/or co-solvent and/or salt at the highest temperature or incrementally-lower temperature as the solution is cooled. Addition of surfactant and/or osmolality adjusting agents and/or co-solvent and/or salt occurs all at once or incrementally during a maintained temperature or as the solution is cooled. The time by which the solution is maintained at the highest temperature is from 0 minutes to 24 hours. The time by which the solution is cooled from the highest temperature is from 0 minutes to 24 hours. The manufacturing process may be shielded from light and the reaction vessel headspace purged with an inert gas such as nitrogen or argon or combinations thereof.

In another embodiment, a kit is provided that includes two containers, each comprising a portion of the pharmaceutical formulation to be admixed to a final dosing solution comprising an nintedanib or indolinone or salt thereof compound and a nebulizer to generate an aerosol of the pharmaceutical formulation.

Aerosol Dosing

The indolinone derivative compound, most preferably nintedanib as disclosed herein can be administered at a therapeutically effective dosage, e.g., a dosage sufficient to provide treatment for the disease states previously described. For example, a daily aerosol dose of nintedanib in a nintedanib compound formulation to a 70 kg human.

The indolinone derivative compound, most preferably nintedanib as disclosed herein can be administered at a therapeutically effective dosage, e.g., a dosage sufficient to provide treatment for the disease states previously described. In some embodiments, for example, a daily aerosol dose of nintedanib in an nintedanib compound formulation to a 70 kg human may be from about 0.000001 mg to about 4.5 mg nintedanib per kg of body weigh per dose. The amount of active compound administered will, of course, be dependent on the subject and disease state being treated, the severity of the affliction, the manner and schedule of administration, the location of the disease (e.g., whether it is desired to effect intra-nasal or upper airway delivery, pharyngeal or laryngeal delivery, bronchial delivery, pulmonary delivery and/or pulmonary delivery with subsequent systemic or central nervous system absorption), and the judgment of the prescribing physician; for example, a likely dose range for aerosol administration of nintedanib in preferred embodiments, or in other embodiments of indolinone derivative compound would be about 0.0001 mg to 10 mg per dose to about 0.0001 mg to about 100 mg per day. Similarly, if pirfenidone or pyridone analog is included in the formulation, a daily aerosol dose to a 70 kg human may be from about 0.01 mg to about 4.5 mg nintedanib per kg of body weigh per dose. A likely dose range for aerosol administration of pirfenidone in combination with nintedanib in preferred embodiments would be about 2.5 mg to 50 mg per dose to about 2.5 mg to about 300 mg per day.

Liquid Nebulizer

Previously, two types of nebulizers, jet and ultrasonic, have been shown to be able to produce and deliver aerosol particles having sizes between 1 and 5 microns. These particle sizes have been shown as being optimal for middle airway deposition. However, unless a specially formulated solution is used, these nebulizers typically need larger volumes to administer sufficient amount of drug to obtain a therapeutic effect. A jet nebulizer utilizes air pressure breakage of an aqueous solution into aerosol droplets. An ultrasonic nebulizer utilizes shearing of the aqueous solution by a piezoelectric crystal. Typically, however, the jet nebulizers are only about 10% efficient under clinical conditions, while the ultrasonic nebulizer is only about 5% efficient. The amount of pharmaceutical deposited and absorbed in the lungs is thus a fraction of the 10% in spite of the large amounts of the drug placed in the nebulizer. The amount of drug that is placed in the nebulizer prior to administration to the mammal is generally referred to the "nominal dose," or "loaded dose." The volume of solution containing the nominal dose is referred to as the "fill volume." Smaller particle sizes or slow inhalation rates permit deep lung deposition. Both middle-lung and alveolar deposition may be desired for this invention depending on the indication, e.g., middle and/or alveolar deposition for pulmonary fibrosis and systemic delivery. Exemplary disclosure of compositions and methods for formulation delivery using nebulizers can be found in, e.g., US 2006/0276483, including descriptions of techniques, protocols and characterization of aerosolized mist delivery using a vibrating mesh nebulizer.

Accordingly, a vibrating mesh nebulizer comprising a liquid storage container in fluid contact with a diaphragm and inhalation and exhalation valves is preferably used. In one embodiment, about 0.01 to about 10 mL of the nintedanib compound formulation (or in another related embodiment, of a indolinone derivative is placed in the reservoir and the aerosol generator is engaged producing atomized aerosol of particle sizes selectively between about 1 and about 5 micron. In another embodiment, pirfenidone or pyridone analog is included.

In some embodiments an nintedanib or indolinone or salt thereof compound formulation as disclosed herein, is placed in a liquid nebulization inhaler and prepared in dosages to deliver from about 0.0001 mg to 100 mg nintedanib, indolinone derivative compound from a dosing solution of about 0.01 mL to about 10 mL with MMAD particles sizes between about 1 to about 5 micron being produced. In another embodiment, pirfenidone or pyridone analog is included and delivered from about 2.5 mg to about 100 mg pirfenidone or pyridone analog.

The manner in which the first solution and the second solution are combined to yield an admixture requires only that the solutions are thoroughly mixed. Similarly, where dissolution of a solid in an aqueous solution is provided, the solution is thoroughly combined with the solid and agitated until no solid precipitate remains. Similarly, the combination of any two solutions is agitated until no solid precipitate remains. The individual concentrations of the nintedanib or indolinone salt have been specifically formulated as described herein for solubility, even though the discovery has been made that many permeant ion species that are suitable for enabling tolerability of an inhaled aerosol are incompatible with the active ingredient.

The capability to physically combine the first and the second solution may be provided by providing additional space or volume in either of the container holding the first solution or the container holding the second solution such that the volume of either solution can be accommodated by the available volume or headspace of the other container. An additional container can be used to permit admixture of the first and the second solutions, or the two solutions can simply be added directly into the reservoir of the nebulizer and the admixture created by mixing within the reservoir. Reference to the containing the admixture in the reservoir of the nebulizer includes the process of forming admixture of the first and the second solutions in any container, either inside or outside of the reservoir of the nebulizer.

In one embodiment of a multi-compartment combination, a container having sealed compartments such as a blister pack it is used that have segregated compartments or chambers that contain the first and the second solution in a separate, sterile, sealed configurations for individual placement into the reservoir of a nebulizer or for combination into an admixture immediately before having the combined solutions for containing the admixture within the reservoir of the nebulizer. The individual or multiunit containers may have a pouring fixture, such as of spout or other outflow design that either mates with the input of the nebulizer reservoir or is conveniently sized so that the outflow of the container enables ready insertion of the individual solutions or the admixture into the nebulizer reservoir. Accordingly, in either individual or combined format, the containers are shaped to allow easy dispensing of the individual contents or the admixture. For instance, one side of the container may be tapered or have a tapered portion or region through which the content is dispensable into another vessel upon opening the sealed solution container at a tip or tapered end. Two or more chambers of a container are connected by a channel, the channel being adapted to direct fluid from the one container having the first solution contained therein to the second container, or vice versa, having the other solution and having adequate internal headspace volume to permit thorough mixing of the two solutions. During storage, the individual compartments are sealed and closed, but may feature a removable barrier that is literally removed or broken to permit mixture of the liquid solutions. A similar configuration is usable where one component is a solid powder or crystalline form and is segregated from an aqueous solution, particularly including dissolved permeant ions. Typically, a channel is closed with a seal that prevents the two solutions from being combined prior to action by the user. As described herein, this is an ideal arrangement where individual components of the admixture are unstable when combined, but may be combined in the admixture just prior to being contained within the nebulizer.

In another embodiment for multiple-dose separated-compartment nebulizers, both the solid composition and the liquid solvent are provided as matched unit doses within multiple containers or within multiple chambers of a container. For instance, two-chambered containers can be used to hold one unit of the solid composition in one of the chambers and one unit of liquid in the other. As used herein, one unit is defined by the amount of drug present in the solid composition, which is one unit dose. Such two-chambered containers may, however, also be used advantageously for nebulizers containing only one single drug dose.

In one embodiment of a separated-compartment nebulizer, a blister pack having two blister-type containers may be used, the blisters representing the containers for separating an aqueous solution containing the active ingredient from other osmolality adjusting agents that cause instability of the chemical structure of nintedanib or indolinone or salt thereof. The blister pack may be shaped to allow easy dispensing of the admixture into the reservoir of the nebulizer. For instance, one side of the pack may be tapered or have a tapered portion or region through which the content is dispensable into another vessel upon opening the blister pack at the tapered end. The tapered end may represent a tip.

In one embodiment, a vial or container having two compartments is used, the compartment representing the chambers for containing the solution containing the active ingredient and solution containing osmolality adjusting agents admixed to prepare a unit dosage of the final liquid composition for aerosolization. The first and second liquid compositions respectively are preferably contained in matched quantities for preparing a single unit dosage of the final liquid composition (by non-limiting example in cases where soluble of the nintedanib or indolinone or salt thereof compound and a osmolality adjusting agent required for formulating the desired concentrations of buffer, permeant anion, or other osmolality adjusting agents are unstable for storage, yet all components are desired in the same admixture for administration.

The two compartments are physically separated but in fluid communication such as when the vial or container are connected by a channel or breakable barrier, the channel or breakable barrier being adapted to direct fluid between the two compartments to enable mixing prior to administration. During storage, the channel is closed with a seal or the breakable barrier intact. In this sense, a seal is any structure that prevents mixing of contents in the two compartments. The seal is preferably breakable or removable; breaking or removing the seal when the nebulizer is to be used will allow the liquid solvent to enter the other chamber and dissolve the solid composition or in the case of two liquids permit mixing of the two solutions. The dissolution or mixing process may be improved by shaking the container.

High Efficiency Liquid Nebulizers

High efficiency liquid nebulizers are inhalation devices that are adapted to deliver a large fraction of a loaded dose to a patient. Some high efficiency liquid nebulizers utilize microperforated membranes. High efficiency liquid nebulizers also utilize one or more actively or passively vibrating microperforated membranes. The high efficiency liquid nebulizer contains one or more oscillating membranes. The high efficiency liquid nebulizer contains a vibrating mesh or plate with multiple apertures and optionally a vibration generator with an aerosol mixing chamber. The mixing chamber functions to collect (or stage) the aerosol from the aerosol generator. An inhalation valve is also used to allow an inflow of ambient air into the mixing chamber during an inhalation phase and is closed to prevent escape of the aerosol from the mixing chamber during an exhalation phase. The exhalation valve is arranged at a mouthpiece which is removably mounted at the mixing chamber and through which the patient inhales the aerosol from the mixing chamber which may operate continuously.

The high efficiency liquid nebulizer may contain a vibrating microperforated membrane of tapered nozzles against a bulk liquid that generates a plume of droplets without the need for compressed gas. In these designs, a solution in the microperforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Some high efficiency liquid nebulizers use passive nozzle membranes and a separate piezoelectric transducer that are in contact with the solution. In contrast, some high efficiency liquid nebulizers employ an active nozzle membrane, which uses the acoustic pressure in the nebulizer to generate very fine droplets of solution via the high frequency vibration of the nozzle membrane.

Some high efficiency liquid nebulizers contain a resonant system. In some such high efficiency liquid nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. Additional features of a high efficiency liquid nebulizer with perforated membranes are disclosed in U.S. Pat. Nos. 6,962,151, 5,152,456, 5,261,601, and 5,518,179, 6,983,747, each of which is hereby incorporated by reference in its entirety. Other embodiments of the high efficiency liquid nebulizers contain oscillatable membranes. Features of these high efficiency liquid nebulizers are disclosed in U.S. Pat. Nos. 7,252,085; 7,059,320; 6,983,747, each of which is hereby incorporated by reference in its entirety.

Commercial high efficiency liquid nebulizers are available from: PARI (Germany) under the trade name eFlow®; Nektar Therapeutics (San Carlos, Calif.) under the trade names AeroNeb® Go and AeroNeb® Pro, and AeroNeb® Solo, Philips (Amsterdam, Netherlands) under the trade names I-Neb®, Omron (Bannockburn, Ill.) under the trade name Micro-Air®, and Activaero (Germany) under the trade name Akita®. Commercial High Efficiency Nebulizers are also available from Aerogen (Galaway, Ireland) utilizing the OnQ® nebulizer technology, and Pocket Neb from MicroVapor® devices.

Dry Powder Inhaler (DPI)

Based upon allometric scaling of animal efficacy data and human modeling, it is observed that the human nintedanib or salt thereof dose may be as low as a range between about 0.04 mg and about 2.4 mg. If clinical observations support these low levels, a dry powder inhaled product may be a selected alternative to an aqueous nebulized product.

There are two major designs of dry powder inhalers. One design is the metering device in which a reservoir for the drug is placed within the device and the patient adds a dose of the drug into the inhalation chamber. The second is a factory-metered device in which each individual dose has been manufactured in a separate container. Both systems depend upon the formulation of drug into small particles of mass median diameters from about 1 to about 5 micron, and usually involve co-formulation with larger excipient particles (typically 100 micron diameter lactose particles). Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to disperse, and the mass of the large excipient particles causes their impaction at the back of the throat, while the smaller drug particles are deposited deep in the lungs.

As with liquid nebulization and MDIs, particle size of the nintedanib or salt thereof, or indolinone derivative or salt thereof may be optimized for aerosol administration for aerosol administration. If the particle size is larger than about 5 micron MMAD then the particles are deposited in upper airways. If the aerodynamic particle size of the aerosol is smaller than about 1 micron then it is delivered into the alveoli and may get transferred into the systemic blood circulation.

By non-limiting example, in dry powder inhalers, the nintedanib or salt thereof, or indolinone derivative or salt thereof disclosed herein are prepared in dosages to disperse and deliver from about 34 mcg to about 463 mg from a dry powder formulation.

By non-limiting example, a dry powder nintedanib or salt thereof, or indolinone derivative or salt thereof may be administered in the described respirable delivered dose in 10 or fewer inhalation breaths, or in 8 or fewer inhalation breaths, or in 6 or fewer inhalation breaths, or in 4 or fewer inhalation breaths, or in 2 or fewer inhalation breaths.

In some embodiments, a dry powder inhaler (DPI) is used to dispense the nintedanib or salt thereof, or indolinone derivative or salt thereof described herein. DPIs contain the drug substance in fine dry particle form. Typically, inhalation by a patient causes the dry particles to form an aerosol cloud that is drawn into the patient's lungs. The fine dry drug particles may be produced by any technique known in the art. Some well-known techniques include use of a jet mill or other comminution equipment, precipitation from saturated or super saturated solutions, spray drying, in situ micronization (Hovione), particle engineering (Pulmosphere™, Technosphere®, PRINT®) or supercritical fluid methods. Typical powder formulations include production of spherical pellets or adhesive mixtures. In adhesive mixtures, the drug particles are attached to larger carrier particles, such as lactose monohydrate of size about 50 to about 100 microns in diameter. The larger carrier particles decrease the adhesive forces on the carrier/drug agglomerates to improve drug dispersion. Turbulence and/or mechanical devices break the agglomerates into their constituent parts. The smaller drug particles are then drawn into the lungs while the larger carrier particles deposit in the mouth or throat. Some examples of adhesive mixtures are described in U.S. Pat. No. 5,478,578 and PCT Publication Nos. WO 95/11666, WO 87/05213, WO 96/23485, and WO 97/03649, all of which are incorporated by reference in their entirety. Additional excipients may also be included with the drug substance. Alternatively, porous particles may be used to deliver the drug without the need of the larger carrier particles. Such porous particles can be manufactured using the Pulmosphere™ or Technosphere® technologies produce particles that are large in size but small in density and in aerodynamic diameter. Additionally, making drug particles having a specific shape and size using the PRINT® technology can reduce the dispersion force and enable the drug particles to be delivered without the use of a carrier excipient.

There are three common types of DPIs, all of which may be used with the nintedanib or salt thereof, or indolinone derivative or salt thereof compounds described herein. In a single-dose DPI, a capsule containing one dose of dry drug substance/excipients is loaded into the inhaler. Upon activation, the capsule is breached, allowing the dry powder to be dispersed and inhaled using a dry powder inhaler. To dispense additional doses, the old capsule must be removed and an additional capsule loaded. Examples of single-dose DPIs are described in U.S. Pat. Nos. 3,807,400; 3,906,950; 3,991,761; and 4,013,075, all of which are hereby incorporated by reference in their entirety. In a multiple unit dose DPI, a package containing multiple single dose compartments is provided. For example, the package may comprise a blister pack, where each blister compartment contains one dose. Each dose can be dispensed upon breach of a blister compartment. Any of several arrangements of compartments in the package can be used. For example, rotary or strip arrangements are common. Examples of multiple unit does DPIs are described in EPO Patent Application Publication Nos. 0211595A2, 0455463A1, and 0467172A1, all of which are hereby incorporated by reference in their entirety. In a multi-dose DPI, a single reservoir of dry powder is used. Mechanisms are provided that measure out single dose amounts from the reservoir to be aerosolized and inhaled, such as described in U.S. Pat. Nos. 5,829,434; 5,437,270; 2,587,215; 5,113,855; 5,840,279; 4,688,218; 4,667,668; 5,033,463; and 4,805,811 and PCT Publication No. WO 92/09322, all of which are hereby incorporated by reference in their entirety.

In some embodiments, auxiliary energy in addition to or other than a patient's inhalation may be provided to facilitate operation of a DPI. For example, pressurized air may be provided to aid in powder de-agglomeration, such as described in U.S. Pat. Nos. 3,906,950; 5,113,855; 5,388,572; 6,029,662 and PCT Publication Nos. WO 93/12831, WO 90/07351, and WO 99/62495, all of which are hereby incorporated by reference in their entirety. Electrically driven impellers may also be provided, such as described in U.S. Pat. Nos. 3,948,264; 3,971,377; 4,147,166; 6,006,747 and PCT Publication No. WO 98/03217, all of which are hereby incorporated by reference in their entirety. Another mechanism is an electrically powered tapping piston, such as described in PCT Publication No. WO 90/13327, which is hereby incorporated by reference in its entirety. Other DPIs use a vibrator, such as described in U.S. Pat. Nos. 5,694,920 and 6,026,809, both of which are hereby incorporated by reference in their entirety. Finally, a scraper system may be employed, such as described in PCT Publication No. WO 93/24165, which is hereby incorporated by reference in its entirety.

Additional examples of DPIs for use herein are described in U.S. Pat. Nos. 4,811,731; 5,113,855; 5,840,279; 3,507,277; 3,669,113; 3,635,219; 3,991,761; 4,353,365; 4,889,144, 4,907,538; 5,829,434; 6,681,768; 6,561,186; 5,918,594; 6,003,512; 5,775,320; 5,740,794; and 6,626,173, all of which are hereby incorporated by reference in their entirety.

In some embodiments, a spacer or chamber may be used with any of the inhalers described herein to increase the amount of drug substance that gets absorbed by the patient, such as is described in U.S. Pat. Nos. 4,470,412; 4,790,305; 4,926,852; 5,012,803; 5,040,527; 5,024,467; 5,816,240; 5,027,806; and 6,026,807, all of which are hereby incorporated by reference in their entirety. For example, a spacer may delay the time from aerosol production to the time when the aerosol enters a patient's mouth. Such a delay may improve synchronization between the patient's inhalation and the aerosol production. A mask may also be incorporated for infants or other patients that have difficulty using the traditional mouthpiece, such as is described in U.S. Pat. Nos. 4,809,692; 4,832,015; 5,012,804; 5,427,089; 5,645,049; and 5,988,160, all of which are hereby incorporated by reference in their entirety.

Dry powder inhalers (DPIs), which involve deaggregation and aerosolization of dry powder particles, normally rely upon a burst of inspired air that is drawn through the unit to deliver a drug dosage. Such devices are described in, for example, U.S. Pat. No. 4,807,814, which is directed to a pneumatic powder ejector having a suction stage and an injection stage; SU 628930 (Abstract), describing a hand-held powder disperser having an axial air flow tube; Fox et al., Powder and Bulk Engineering, pages 33-36 (March 1988), describing a venturi eductor having an axial air inlet tube upstream of a venturi restriction; EP 347 779, describing a hand-held powder disperser having a collapsible expansion chamber, and U.S. Pat. No. 5,785,049, directed to dry powder delivery devices for drugs.

Commercial examples of capsule-based or blister pack-based dry powder inhalers that can be used with the nintedanib or salt thereof, or indolinone derivative or salt thereof formulations described herein include the Aerohaler, Aerolizer, Aspirair, Breezehaler, Diskhaler Forspiro, Gyrohaler, Plastiaphe Monodose, Podhaler, Prohaler, Redihaler, Rotahaler, Turbohaler, Handihalerand Discus. Multi dose reservoir devices include E Flex, Jethaler, NEXThaler, Novolizer, PADD, Pulmojet, Spiromax, Swinghaler, Turbuhaler and Ultrahaler.

Pharmacokinetics

Inhalation therapy of aerosolized nintedanib or a indolinone derivative compound enables direct deposition of the sustained-release or active substance in the respiratory tract (be that intra-nasal or pulmonary) for therapeutic action at that site of deposition or systemic absorption to regions immediately down stream of the vascular absorption site. In the case of central nervous system (CNS) deposition, intranasal inhalation aerosol delivery deposits nintedanib or a indolinone derivative compound directly upstream of the CNS compartment.

Similar to the intra-nasal and pulmonary applications described above, treatment or prevention of organs outside the respiratory tract requires absorption to the systemic vascular department for transport to these extra-respiratory sites. In the case of treating or preventing fibrotic or inflammatory diseases associated with the heart, liver and kidney, deposition of drug in the respiratory tract, more specifically the deep lung will enable direct access to these organs through the left atrium to either the carotid arteries or coronary arteries. Similarly, in the case of treating CNS disorder (e.g., multiple sclerosis), deposition of drug in the respiratory tract (as defined above) or nasal cavity, more specifically the absorption from the nasal cavity to the nasal capillary beds for immediate access to the brain and CNS. This direct delivery will permit direct dosing of high concentration nintedanib or a indolinone derivative compound in the absence of unnecessary systemic exposure. Similarly, this route permits titration of the dose to a level for these indications.

Pharmacokinetics is concerned with the uptake, distribution, metabolism and excretion of a drug substance. A pharmacokinetic profile comprises one or more biological measurements designed to measure the absorption, distribution, metabolism and excretion of a drug substance. One way of visualizing a pharmacokinetic profile is by means of a blood plasma concentration curve, which is a graph depicting mean active ingredient blood plasma concentration on the Y-axis and time (usually in hours) on the X-axis. Some pharmacokinetic parameters that may be visualized by means of a blood plasma concentration curve include:

1) Cmax: The maximum plasma concentration in a patient;

2) AUC: area under the curve

3) TOE: time of exposure

4) T½: period of time it takes for the amount in a patient of drug to decrease by half 5) Tmax: The time to reach maximum plasma concentration in a patient Pharmacokinetics (PK) is concerned with the time course of a therapeutic agent, such as nintedanib or a indolinone derivative compound concentration in the body. Pharmacodynamics (PD) is concerned with the relationship between pharmacokinetics and efficacy in vivo. PK/PD parameters correlate the therapeutic agent, such as exposure with efficacious activity. Accordingly, to predict the therapeutic efficacy of a therapeutic agent, such as with diverse mechanisms of action different PK/PD parameters may be used.

As used herein, the "peak period" of a pharmaceutical's in vivo concentration is defined as that time of the pharmaceutical dosing interval when the pharmaceutical concentration is not less than 50% of its maximum plasma or site-of-disease concentration. "Peak period" is used to describe an interval of nintedanib or a indolinone derivative compound dosing. When considering treatment of lung diseases, a method or system described herein provides at least a two-fold enhancement in pharmacokinetic profile for treatment of the lung disease. The methods and systems described herein provide at least a two-fold enhancement in the lung tissue pharmacokinetic profile of nintedanib or indolinone or salt thereof compound as compared to oral administration.

The amount of nintedanib or indolinone or salt thereof compound that is administered to a human by inhalation may be calculated by measuring the amount of nintedanib or indolinone or salt thereof compound and associated metabolites that are found in the urine. About 80% of administered nintedanib is excreted in the urine. The calculation based on compound and metabolites in urine may be done through a 48 hour urine collection (following a single administration), whereby the total amount of nintedanib or indolinone or salt thereof compound delivered to the human is the sum of measured nintedanib and its metabolites. By non-limiting example, knowing that 80% of nintedanib is excreted, a 50 mg sum urinary measurement of nintedanib and its metabolites would translate to a delivered dose of about 63 mg (50 mg divided by 80%). If the inhaled aerosol fine-particle fraction (FPF) is 75%, one may assume that about 75% of the drug deposited in the lung (and about 25% was swallowed, and subsequently absorbed from the gut with 80% excreted in the urine). Integrating these two calculations, of a 63 mg delivered dose (as measured by urinary excretion), about 47 mg would be the amount of inhaled aerosol nintedanib delivered to the lung (the actual RDD; calculated as the product of 63 mg and a 75% FPF). This RDD can then be used in a variety of calculations, including lung tissue concentration.

The lung tissue Cmax and/or AUC of nintedanib or indolinone or salt thereof, that is obtained after administration of a single inhaled dose to the mammal is about the same or greater than the lung tissue Cmax and/or AUC of nintedanib or indolinone or salt thereof, that is obtained after a single dose of orally administered dose that is from about 80% to about 120% of the inhaled dose; and/or the plasma Cmax and/or AUC that is obtained after administration of a single inhaled dose to the mammal is less than the plasma Cmax and/or AUC of obtained after a single dose of orally administered nintedanib or indolinone or salt thereof, at a dose that is from about 80% to about 120% of the inhaled dose. The lung tissue Cmax that is obtained after administration of a single inhaled dose to the mammal is greater than the lung tissue obtained after a single dose of orally administered nintedanib or indolinone or salt thereof, at a dose that is from about 80% to about 120% of the inhaled dose. The lung tissue AUC of nintedanib or indolinone or salt thereof, that is obtained after administration of a single inhaled dose to the mammal is greater than the lung tissue AUC obtained after a single dose of orally administered nintedanib or indolinone or salt thereof, at a dose that is from about 80% to about 120% of the inhaled dose. The plasma Cmax of nintedanib or indolinone or salt thereof, that is obtained after administration of a single inhaled dose to the mammal is less than the plasma Cmax obtained after a single dose of orally administered nintedanib or indolinone or salt thereof, at a dose that is from about 80% to about 120% of the inhaled dose. The plasma AUC of nintedanib or indolinone or salt thereof, that is obtained after administration a single inhaled dose to the mammal is less than the plasma AUC obtained after a single dose of orally administered nintedanib or indolinone or salt thereof, compound at a dose that is from about 80% to about 120% of the inhaled dose.

In one aspect, described herein is a method of achieving a lung tissue Cmax of nintedanib or indolinone or salt thereof compound that is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 20 times a Cmax of up to 200 mg of an orally administered dosage of nintedanib or indolinone or salt thereof, the method comprising nebulizing an aqueous solution comprising nintedanib or indolinone or salt thereof, and administering the nebulized aqueous solution to a human Described herein is a method of achieving a lung tissue Cmax of nintedanib or indolinone or salt thereof compound that is at least equivalent to or greater than a Cmax of up to 200 mg of an orally administered dosage of nintedanib or indolinone or salt thereof, the method comprising nebulizing an aqueous solution comprising nintedanib or indolinone or salt thereof, and administering the nebulized aqueous solution to a human In one aspect, described herein is a method of achieving a lung tissue $AUC_{0-24}$ of nintedanib or indolinone or salt thereof, that is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 1.5-20 times, at least 1.5-15 times, at least 1.5-10 times, at least 1.5-5 times, or at least 1.5-3 times $AUC_{0-24}$ of up to 200 mg of an orally administered dosage, the method comprising nebulizing an aqueous solution comprising nintedanib or indolinone or salt thereof compound and administering the nebulized aqueous solution to a human. A method of achieving a lung tissue $AUC_{0-24}$ of nintedanib or indolinone or salt thereof compound that is at least equivalent to or greater than $AUC_{0-24}$ of up to 600 mg of an orally administered dosage of nintedanib or indolinone or salt thereof, the method comprising nebulizing an aqueous solution comprising nintedanib or indolinone or salt thereof and administering the nebulized aqueous solution to a human.

The methods include a method of administering nintedanib or indolinone or salt thereof, to a human, comprising administering a nebulized aqueous solution containing the nintedanib or indolinone or salt thereof, wherein the lung tissue Cmax achieved with the nebulized solution is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 20 times the lung tissue Cmax achieved with an orally administered nintedanib or indolinone or salt thereof, dosage that is from 80% to 120% of the dose amount of nintedanib that is administered by nebulization.

The methods include a method of administering nintedanib or indolinone or salt thereof, to a human, comprising administering a nebulized aqueous solution containing the nintedanib or indolinone or salt thereof, wherein the lung tissue Cmax achieved with the nebulized solution is at least equivalent to or greater than the lung tissue Cmax achieved with an orally administered nintedanib or indolinone or salt thereof, dosage that is from 80% to 120% of the dosage of nintedanib or indolinone or salt thereof, in the nebulized aqueous solution of nintedanib or indolinone or salt thereof that is administered.

The methods include a method of administering nintedanib or indolinone or salt thereof, to a human, comprising administering a nebulized aqueous solution containing the nintedanib or indolinone or salt thereof, wherein the plasma $AUC_{0-24}$ achieved with the nebulized solution is less than the plasma $AUC_{0-24}$ achieved with an orally administered nintedanib or indolinone or salt thereof, dosage that is from 80% to 120% of the dosage of nintedanib or indolinone or salt thereof, in the nebulized aqueous solution of nintedanib or indolinone or salt thereof, that is administered.

The methods include a method of administering nintedanib or indolinone or salt thereof comprising administering a nebulized aqueous solution containing the nintedanib or indolinone or salt thereof, wherein the lung tissue $AUC_{0-24}$ achieved with the nebulized solution is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 1.5-20 times, at least 1.5-15 times, at least 1.5-10 times, at least 1.5-5 times, or at least 1.5-3 times the lung tissue $AUC_{0-24}$ achieved with an orally administered nintedanib or indolinone or salt thereof compound dosage that is from 80% to 120% of the dosage of nintedanib or indolinone or salt thereof, in the nebulized aqueous solution of nintedanib or indolinone or salt thereof. The methods include a method of administering nintedanib or indolinone or salt thereof, to a human, comprising administering a nebulized aqueous solution containing the nintedanib or indolinone or salt thereof, wherein the lung tissue $AUC_{0-24}$ achieved with the nebulized solution is at least 1.5 times the lung tissue $AUC_{0-24}$ achieved with an orally administered nintedanib or indolinone or salt thereof, dosage that is from 80% to 120% of the dosage of nintedanib or indolinone or salt thereof, in the nebulized aqueous solution of nintedanib or indolinone or salt thereof compound.

The methods include a method of improving the pharmacokinetic profile obtained in a human following a single oral dose administration of nintedanib or indolinone or salt thereof. The single oral dose comprises up to about 200 mg of nintedanib or indolinone or salt thereof. The method of improving the pharmacokinetic profile further comprises a comparison of the pharmacokinetic parameters following inhalation administration to the same parameters obtained following oral administration and may require multiple measurements of a single patient over time comparing the pharmacokinetic parameters in a single patient varying by dosage, route of administration, form of active pharmaceutical ingredient and other parameters as described herein. A prolonged improvement in pharmacokinetic profile is obtained by repeated and frequent administrations of the aqueous solution of nintedanib or indolinone or salt thereof, as described herein by inhalation. Repeated administration of nintedanib or indolinone or salt thereof, by inhalation provides more frequent direct lung exposure benefitting the human through repeat high Cmax levels. The inhaled nintedanib or indolinone or salt thereof, doses are administered once a day, twice a day, three times a day, four time a day, every other day, twice a week, three times a week, four times a week, five times a week, six times a week, seven times a week, or any combination thereof.

Small intratracheal aerosol doses deliver a rapidly-eliminated high lung Cmax and low AUC. Human, animal and in vitro studies all indicate that nintedanib efficacy is dose responsive (i.e. larger doses correlate with improved efficacy) and suggest Cmax is a key driver in nintedanib efficacy. While lung Cmax appears important for efficacy, more regular nintedanib exposure is important to enhance this effect. In the context of treating lung diseases in a human, more frequent direct-lung administration of nintedanib or indolinone or salt thereof compound may provide benefit through both repeat high Cmax dosing and providing more regular exposure of the active therapeutic agent.

Methods of treatment include a method for the treatment of lung disease in a mammal comprising administering directly to the lungs of the mammal in need thereof nintedanib or salt thereof, or a indolinone derivative compound or salt thereof, on a continuous dosing schedule, wherein the observed lung tissue Cmax of a dose of nintedanib or indolinone derivative or salt thereof greater than 0.1, 1.0, 10, 100, or 1000, ng/mL lung epithelial lining fluid. The observed lung tissue Cmax from a dose of nintedanib or salt thereof, or a indolinone derivative compound or salt thereof, is greater than 10, 50, 100, 150, 200, 250, 300, 350, 400, 450, 500, 750, or 1000 mcg/mL lung epithelial lining fluid. Methods of Dosing and Treatment Regimens The term "continuous dosing schedule" refers to the administration of a particular therapeutic agent at regular intervals. Continuous dosing schedule refers to the administration of a particular therapeutic agent at regular intervals without any drug holidays from the particular therapeutic agent. Continuous dosing schedule refers to the administration of a particular therapeutic agent in alternating cycles of drug administration followed by a drug holiday (e.g. wash out period) from the particular therapeutic agent. For example, in some embodiments the therapeutic agent is administered once a day, twice a day, three times a day, once a week, twice a week, three times a week, four times a week, five times a week, six times a week, seven times a week, every other day, every third day, every fourth day, daily for a week followed by a week of no administration of the therapeutic agent, daily for a two weeks followed by one or two weeks of no administration of the therapeutic agent, daily for three weeks followed by one, two or three weeks of no administration of the therapeutic agent, daily for four weeks followed by one, two, three or four weeks of no administration of the therapeutic agent, weekly administration of the therapeutic agent followed by a week of no administration of the therapeutic agent, or biweekly administration of the therapeutic agent followed by two weeks of no administration of the therapeutic agent. [Is this still a "continuous dosing schedule" if there are weekly breaks?]

The amount of nintedanib or a indolinone derivative compound is administered once-a-day. In some other embodiments, the amount of nintedanib or a indolinone derivative compound is administered twice-a-day. In some other embodiments, the amount of nintedanib or a indolinone derivative compound is administered three times a day.

Where improvement in the status of the disease or condition in the human is not observed, the daily dose of nintedanib or a indolinone derivative compound is increased for example, a once-a-day dosing schedule is changed to a twice-a-day dosing schedule. a three times a day dosing schedule is employed to increase the amount of nintedanib or a indolinone derivative compound that is administered. Frequency of administration by inhalation is increased in order to provide repeat high Cmax levels on a more regular basis. The frequency of administration by inhalation is increased in order to provide maintained or more regular exposure to Nintedanib The frequency of administration by inhalation is increased in order to provide repeat high Cmax levels on a more regular basis and provide maintained or more regular exposure to nintedanib.

The amount of repeat high Cmax dosing providing more regular exposure of the active therapeutic agent that is given to the human varies depending upon factors such as, but not limited to, condition and severity of the disease or condition, and the identity (e.g., weight) of the human, and the particular additional therapeutic agents that are administered (if applicable).

EXAMPLES

Example 1. Compound Screening Platform

Each of the active ingredients described herein are susceptible of minor chemical structural modifications or alternative molecular compounding that do not affect the utility for the purposes described herein. Although the following description is exemplified by nintedanib salts, alternative forms of nintedanib or other indolinones can be screened for efficacy as follows.

Rat and human derived pulmonary tissue were cut in pieces and placed on a polystyrene petri dish containing antibiotics/antimycotics and LG DMEM 10% FBS 1% P/S media. Cells are expanded in LG DMEM 10% FBS 1% P/S media until an appropriate number of cells are available. All experiments will be performed before passage 10. Expanded rat and human pulmonary fibroblasts are trypsinized and plated in 6-well plates containing a coverslip, attachment factor and media followed by overnight incubation. After incubation, media is changed to 1% FBS LG DMEM. Fibroblast to myofibroblast diffe review for your review small rentiation and or proliferation is induced with 2.5 to 10 ng/mL active tumor growth factor beta 1 (TGF-beta1). The kinetics of differentiated myofibroblast appearance is measured by assessing incubated cells at 12, 24, 36, 48 and 72 hours post-TGF-beta1 induction. Each cell condition is performed in triplicate. At each time point, cells are fixed using paraformaldehyde and stained for F-actin, DAPI, and alpha-SMA (for myofibroblast formation). Proliferation is quantified microscopically. This method may employ difference cell lines such as pulmonary arterial smooth muscle cells and/or may be induced by other cytokines, such as platelet-derived growth factor (PDGF). After processing cells for immunohistochemistry, cells will be imaged using an Olympus 1X-81 fluorescent microscope and analyzed using Metamorph Premier software.

To assess the effect of a target compound on fibroblast proliferation, differentiation and/or collagen production, potential therapeutics may be added at the same time, prior to or after addition of TGFβ, PDGF or other inducing cytokine. Non-limiting examples of potential therapeutic agents include all those listed herein. Moreover, addition of potential therapeutic may be done to mimic a drugs in vivo pharmacokinetic profile. By example, an orally-administered drug for a pulmonary indication would have a characteristic vascular and pulmonary absorption phase, Cmax, Tmax, AUC and elimination half-life. By comparison, an inhaled drug may exhibit pharmacokinetic characteristics that differ from the oral route. By example, inhalation may deliver a higher lung Cmax, more rapid lung Tmax, higher lung AUC, be rapidly eliminated from the lung and/or may result in less residual drug. By non-limiting example, to employ the assay described herein, an oral drug under consideration for inhaled aerosol delivery may be exposed to fibroblasts or other cell type in the presence of TGF-beta (or other cytokine) using that drug's real or estimated oral pharmacokinetic profile. Separately or in parallel, in a separate set of wells expose the same cell type in the presence of TGF-beta (or other cytokine) using that drugs real or estimated inhaled pharmacokinetic profile. This may be accomplished by time-course dilution or addition of the potential therapeutic. Moreover, this assay may be used to mimic repetitive TGF-beta or other cytokine exposure and/or therapeutic regimen (by example once a day, twice a day or three times a day) to assess the effect this may have on the drugs anti-proliferative, anti-differentiation, anti-collagen production and/or other measurable endpoint. By non-limiting example, markers of fibroblast activation, proliferation and/or myofibroblast differentiation and collagen production may include alpha-SMA, SMAD, GAPDH, HSP47, procollagen, markers of endoplasmic reticulum un-folded protein response (UPR, e.g., GRP78) and many others. Detection of these components may be by Western and Northern blot analysis, microscopy, phosphorylation signaling, gene and protein array technology, and metagenomic analysis.

In addition to identifying individual forms of an active ingredient that interfere with fibroblast proliferation, differentiation and myofibroblast collage production, this assay may also be employed to assess the effect of combinations of active ingredient and differing salt forms. Further, through some active ingredient formulations have different targets, this and variations of this assay may be used to dissect the role of different targets in fibrosis formation and the fibrotic disease, stroma formation and/or stroma-associated metastatic processes.

Example 2. PDGF-Induced Fibroblast Proliferation

The impact of nintedanib on inhibiting PDGF-induced fibroblast proliferation was determined in primary human fibroblasts. Briefly, fibroblasts were seeded at 2,500 cells/well in 96-well flat clear bottom Falcon plates in 10% FBS F12/DMEM Media with 1% Pen/Strep. These cells were left in a 37 degree incubator (5% $CO_2$) for 24 hours to allow the cells to adhere to the plate. The media was then removed, washed with PBS and replaced the media with 0.5% FBS F12/DMEM Media with 1% Pen/Strep for another 24 hours. To characterize the impact exposure duration of each drug on inhibiting proliferation, cells were pretreated with or without drug (0.5 to 50 nM) for 30 minutes, washed and either replaced with 0.5% FBS F12/DMEM media with 1% Pen/Strep+/−20 ng/mL PDGF-BB (short-duration drug exposure mimicking pulmonary inhalation pharmacokinetics) or 0.5% FBS F12/DMEM media with 1% Pen/Strep+/−20 ng/mL PDGF-BB and the initial drug concentration (long duration drug exposure mimicking oral pharmacokinetics). After 72 hours of viable cells was assessed using the MTS assay. Drug concentrations tested were not cytotoxic (data not shown).

TABLE 1

Impact of nintedanib and exposure duration on PDGF-induced fibroblast differentiation.

| Nintedanib | Nintedanib Exposure | | | |
|---|---|---|---|---|
| | Short Duration | | Long Duration | |
| nM | Proliferation* | SEM | Proliferation* | SEM |
| 0 | 0.160 | 0.080 | 0.160 | 0.065 |
| 0.5 | 0.115 | 0.070 | 0.003 | 0.095 |
| 5.0 | 0.011 | 0.185 | −0.359 | 0.120 |
| 50.0 | −0.175 | 0.047 | −0.642 | 0.068 |

*Relative proliferation

Results from Table 1 show that nintedanib is dose-responsive in inhibiting PDGF-induced fibroblast proliferation. The data also show that only short-term nintedanib exposure is required for this activity with a fifty-percent inhibitory concentration (IC50) of about 3 nM (about 1.6 ng/mL).

Example 3. Salt Screen Determination for Nintedanib

XRPD analysis was carried out on a PANalytical X'pert pro, scanning the samples between 3 and 35° 2θ. The material was gently compressed and loaded onto a multi-well plate with Kapton or Mylar polymer film to support the sample. The multi-well plate was then placed into the diffractometer and analyzed using Cu K radiation (α1 λ=1.54060 Å; α2=1.54443 Å; β=1.39225 Å; α1:α2 ratio=0.5) running in transmission mode (step size 0.0130° 2θ) using 40 kV/40 mA generator settings.

Polarized Light Microscopy (PLM). The presence of crystallinity (birefringence) was determined using an Olympus BX50 polarizing microscope, equipped with a Motic camera and image capture software (Motic Images Plus 2.0). All images were recorded using the 20× objective, unless otherwise stated.

Thermogravimetric Analysis (TGA). Approximately, 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm3/min Differential Scanning calorimetry (DSC). Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 275° C. at scan rate of 10° C./min and the resulting heat flow response monitored. Nitrogen was used as the purge gas, at a flow rate of 50 cm3/min.

Infrared spectroscopy (IR) was carried out on a Bruker ALPHA P spectrometer. Sufficient material was placed onto the center of the plate of the spectrometer and the spectra were obtained using the following parameters: Resolution: 4 cm-1; Background Scan Time: 16 scans; Sample Scan Time: 16 scans; Data Collection: 4000 to 400 cm-1; Result Spectrum: Transmittance Software: OPUS version 6

Nuclear Magnetic Resonance (NMR). NMR experiments were performed on a Bruker AVIIIHD spectrometer equipped with a DCH cryoprobe operating at 500.12 MHz for protons. Experiments were performed in deuterated DMSO and each sample was prepared to ca. 10 mM concentration.

Dynamic Vapour Sorption (DVS). Approximately, 10 mg of sample was placed into a mesh vapour sorption balance pan and loaded into a DVS-1 or DVS Advantage dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

High Performance Liquid Chromatography-Ultraviolet Detection (HPLC-UV): Instrument: Dionex Ultimate 3000; Column: Acquity CSH C18 100 mm×2.1 mm 1.7 µm; Column Temperature: 50° C.; Autosampler Temperature: Ambient; UV wavelength: 210 nm; Injection Volume: 4 µL; Flow Rate: 0.6 mL/min; Mobile Phase A: 0.1% formic acid in water; Mobile Phase B: 0.1% formic acid in acetonitrile. The HPLC method used the gradient in Table 2.

TABLE 2

Gradient program:

| Time (minutes) | Solvent B [%] |
|---|---|
| 0 | 10 |
| 1 | 10 |
| 15 | 60 |
| 16 | 60 |
| 16.1 | 10 |
| 20 | 10 |

Mass Spectrometry: Instrument: LCQ Ion Trap Mass Spectrometer using Agilent 1100; Column: ACE Excel 3 C18, 3.0 µm, 75 mm×4.6 mm; Mobile Phase A: 0.1% formic acid in deionized water; Mobile Phase B: 0.1% formic acid in acetonitrile; Diluent: Acetonitrile:water 50:50; Flow Rate: 1.0 mL/min; Runtime: 20 mins; Column Temperature: 30° C.; Injection Volume: 10 µL; PDA Range: 190-400 nm; Scan: +ve 100.0-2000.0 m/z, −ve 100.0-2000.0 m/z. The MS method used the gradient in Table 3.

TABLE 3

Gradient program:

| Time (minutes) | Solvent B [%] |
|---|---|
| 0.00 | 5 |
| 12.00 | 95 |
| 15.00 | 95 |
| 15.10 | 5 |
| 20.00 | 5 |

Initial Characterization: Nintedanib was characterized by XRPD, PLM, TG/DTA, DSC, DVS, NMR, UPLC and HPLC-MS.

pka measurement was carried out using UV-metric triple titration using methanol as co-solvent and pH-metric techniques also by triple titration using methanol as co-solvent.

Solvent Solubility: Approximately 10 mg of Nintedanib was weighed into 24 vials and a known volume aliquot (50 µL) of the appropriate solvent was added until dissolution was observed or 100 volumes of solvent had been added. Between each addition, the mixture was checked for dissolution and where no dissolution was apparent, the mixture was heated to ca. 40° C. and checked again. Samples where the material dissolved, were left to evaporate. Any solids produced from evaporation samples were analyzed by XRPD in order to assess the polymorphic form.

The solvent systems used during the solvent solubility screen, together with the corresponding ICH Class, are detailed in Table 4.

TABLE 4

Solvents selected for solubility screen

| Number | Solvent | ICH Class |
|---|---|---|
| 1 | 1-Butanol | 3 |
| 2 | 1-Propanol | 3 |
| 3 | 2-Propanol | 3 |
| 4 | 40% Methanol: 60% Water (% v/v) (calc. $a_w$ 0.8) | N/A |
| 5 | 50% 2-Propanol: 50% Water (% v/v) (calc. $a_w$ 0.8) | N/A |
| 6 | Acetone | 3 |
| 7 | Acetonitrile | 2 |
| 8 | Anisole | 3 |
| 9 | Dichloromethane | 2 |
| 10 | Dimethylsulfoxide | 3 |
| 11 | Ethanol | 3 |
| 12 | Ethyl Acetate | 3 |
| 13 | Ethyl Ether | 3 |
| 14 | Heptane | 3 |
| 15 | Isopropyl Acetate | 3 |
| 16 | Methanol | 2 |
| 17 | Methylethyl Ketone | 3 |
| 18 | Methylisobutyl Ketone | 2 |
| 19 | N,N'-Dimethylacetamide | 2 |
| 20 | n-Hexane | 3 |
| 21 | tert-Butylmethyl Ether | 3 |
| 22 | THF | 2 |
| 23 | Toluene | 2 |
| 24 | Water | N/A |

Primary Salt Screening. The 17 counterions shown in Table were selected for salt screening, pirfenidone was also screened and a control experiment with Nintedanib only. The solvent systems shown in Table were selected for salt screening. For sulfonic acids MEK was used instead of methanol and acetone:water 50:50 (v/v) was used instead of IPA:water to avoid any potential genotoxic impurities. Ca. 40 mg of Nintedanib was slurried in 300 µL of solvent and mixed with 1.05 equivalent of acid, dissolved/slurried in 200-300 µL of the allocated solvent. If the acid was insoluble in the selected solvent, a slurry was used. If the acid was a liquid it was added to the API slurry from a stock solution in the allocated solvent. The mixtures of API/counterion/solvent were temperature cycled between ambient and 40° C. in 4 hour cycles for ca. 3 days. Any solids present were isolated and allowed to dry at ambient conditions, for ca. 30 minutes prior to analysis by XRPD. Where solutions were obtained they were evaporated to obtain solid material. Every potential salt that yielded sufficient material was analyzed by XRPD, TG/DTA, NMR and stored at 40° C./75% RH for ca. 72h then re-analyzed by XRPD.

TABLE 5

Counterions selected for salt screening

| Acid | pKa1 | pKa2 | pKa3 |
|---|---|---|---|
| HBr | −9.00 | | |

TABLE 5-continued

Counterions selected for salt screening

| Acid | pKa1 | pKa2 | pKa3 |
|---|---|---|---|
| HCl | −6.10 | | |
| Sulfuric acid | −3.00 | 1.92 | |
| Methanesulfonic acid | −1.20 | | |
| Saccharin | 1.6 | | |
| Hydroxyethanesulfonic acid | 1.66 | | |
| L-Aspartic acid | 1.88 | 3.65 | |
| Maleic acid | 1.92 | 6.23 | |
| Phosphoric acid | 1.96 | 7.12 | 12.32 |
| EDTA | 2 | 2.7 | 6.2 |
| L-Glutamic acid | 2.19 | 4.25 | |
| L-Tartaric acid | 3.02 | 4.36 | |
| Fumaric acid | 3.03 | 4.38 | |
| Citric acid | 3.13 | 4.76 | 6.40 |
| DL-Lactic acid | 3.86 | | |
| L-Ascorbic acid | 4.17 | 11.57 | |
| Acetic acid | 4.76 | | |

TABLE 6

Solvent systems selected for salt screening

| | Solvent | ICH Class | Approximate Solubility (mg/mL) | Color of Solution/Slurry | Pattern |
|---|---|---|---|---|---|
| 1 | Dichloromethane | 2 | 17 | yellow | 2 |
| 2 | THF | 2 | <10 | yellow | 2 |
| 3 | N,N'-Dimethylacetamide | 2 | 26 | yellow | 3 |
| 4 | Methanol | 2 | <11* | yellow | 1 (input) |
| 5 | Acetone | 3 | <10 | yellow | 1 (input) |
| 6 | 50% 2-Propanol: 50% Water (% v/v) (calc. aw 0.8) | N/A | <10 | yellow | 1 (input) |

Initial Characterization. The received material (batch: FM341441402 5 g) was characterized, with the following results observed: XRPD analysis showed Nintedanib to be crystalline and will be referred to as Pattern 1; PLM analysis showed birefringent plate-like particles of various sizes; TGA showed a loss of 1.41% between ca. 25-120° C. This loss in mass is likely a result of unbound solvent loss. The DTA trace showed a single endotherm with onset ca. 254° C., likely due to melting; DSC analysis showed a single endotherm with onset ca. 253° C., indicating that pattern 1 is a pure form with a single melting event observed; DVS analysis showed Nintedanib to be slightly hygroscopic with ca. 1.7% mass uptake at 90% RH. The kinetics showed no evidence of recrystallization, but in the second cycle it was noted that the balance was noisier. Post DVS the material was found to remain Pattern 1, with an additional peak observed ca. 12.7° 2θ, the peaks were generally also observed to be sharper; 1H NMR spectroscopy corresponded with the structure of Nintedanib; HPLC average purity was measured to be 99.9%; and LC-MS analysis measured 540.3 m/z ([M+H]+) using positive ionization mode which corresponds with the expected mass of 539.636 Da.

Solvent Solubility Screen. The results from the solvent solubility screen are shown in Table 7. Solubility of ≥17 mg/mL was observed for 2 of the 24 solvent systems. The majority of the experiments showed solubility less than 10 mg/mL and most isolated solids produced Pattern 1 of the free base. Two new patterns of the free base were also produced. Pattern 2 was observed from DCM and THF and Pattern 3 was observed from DMA.

TABLE 7

Solubility Screen Results.

| | Solvent | ICH Class | Approximate Solubility (mg/mL) | Color of Solution/Slurry Liquid | Pattern |
|---|---|---|---|---|---|
| 1 | 1-Butanol | 3 | <10 | yellow | 1 |
| 2 | 1-Propanol | 3 | <10 | yellow | 1 |
| 3 | 2-Propanol | 3 | <11 | yellow | 1 |
| 4 | 40% Methanol:60% Water (% v/v) (calc. aw 0.8) | N/A | <10 | pale yellow | 1 |
| 5 | 50% 2-Propanol: 50% Water (% v/v) (calc. aw 0.8) | N/A | <10 | yellow | 1 |
| 6 | Acetone | 3 | <10 | yellow | 1 |
| 7 | Acetonitrile | 2 | <10 | yellow | 1 |
| 8 | Anisole | 3 | <10 | yellow | 1 |
| 9 | Dichloromethane | 2 | 17 | yellow | 2 |
| 10 | Dimethylsulfoxide | 3 | <10* | yellow | Solution |
| 11 | Ethanol | 3 | <10 | yellow | 1 |
| 12 | Ethyl Acetate | 3 | <10 | yellow | 1 |
| 13 | Ethyl Ether | 3 | <10 | pale yellow | 1 |
| 14 | Heptane | 3 | <10 | colorless | 1 |
| 15 | Isopropyl Acetate | 3 | <10 | yellow | 1 |
| 16 | Methanol | 2 | <11* | yellow | 1 |
| 17 | Methylethyl Ketone | 3 | <10 | yellow | 1 |
| 18 | Methylisobutyl Ketone | 2 | <10 | yellow | 1 |
| 19 | N,N'-Dimethylacetamide | 2 | 26 | yellow | 3 |
| 20 | n-Hexane | 3 | <10 | colorless | 1 |
| 21 | tert-Butylmethyl Ether | 3 | <11 | yellow | 1 |
| 22 | THF | 2 | <10 | yellow | 3 |
| 23 | Toluene | 2 | <10 | yellow | 1 |
| 24 | Water | N/A | <10 | colorless | 1 |

Primary Salt Screening. The results from the primary salt screen are shown in Table 8. Potential salts were observed for 15 of the 17 counterions tested. Nintedanib freebase patterns were obtained for pirfenidone experiments which indicated that no salt or co-crystal formation was successful.

TABLE 8

Primary Salt Screen Results

| | Solvent | | | | | |
|---|---|---|---|---|---|---|
| Counterion | DCM | THF | DMA | Methanol (MEK for sulfonic acids) Pattern (notes) | Acetone | IPA:water 50:50 (acetone:water 50:50 for sulfonic acids) |
| HBr | 5 | 4 | 3 | 2 | 1 | 5 |
| HCl | 2(FB) | 1 | 3 | 2 | 1 | 1 |

TABLE 8-continued

Primary Salt Screen Results

| | Solvent | | | | | |
|---|---|---|---|---|---|---|
| Counterion | DCM | THF | DMA | Methanol (MEK for sulfonic acids) Pattern (notes) | Acetone | IPA:water 50:50 (acetone:water 50:50 for sulfonic acids) |
| Sulfuric acid | 4 | 1 | 3 | 2 | 1 | 3 |
| Methanesulfonic acid | 1 | 1 | 2 | 1 | 1 | (GL) |
| Hydroxyethanesulfonic acid | 2(FB) | 2 | 1 | 2 | 2 | 2 |
| L-Aspartic acid | 2(FB) | 3(FB) | 3(FB) | 1(FB) | 1(FB) | 1 |
| Maleic acid | 1 | 1 | 2 | 1 | 1 | 1(FB) |
| Phosphoric acid | 2(FB) | 3(FB) | 2 | 2(+Ukn) | 2 | 1 |
| L-Glutamic acid | 3(FB) | 3(FB) | 3(FB) | 1(FB) | 1(FB) | 1(FB) |
| L-Tartaric acid | 1, 2(FB) | 1 | 3(FB) | 1 | 1, 2(FB) | 1(+Ukn) |
| Fumaric acid | 2 | 2 | 2 | 2(+Ukn) | 2 | 1 |
| Citric acid | 2(FB, AC) | 1(3; FB) | 3(FB) | 1(+Ukn) | 1 | 2 |
| DL-Lactic acid | 2, 3(FB) | 1(3; FB) | 3(FB) | 2 | 1 | 2 |
| L-Ascorbic acid | 3(FB) | 2, 3(FB) | 3(FB) | 1(FB) | 1(FB) | 1(FB) |
| Acetic acid | 2 | 3(FB) | 3(FB) | 1(FB) | 1 | 2 |
| Saccharin | 1 | 1 | NS | 2 | 1 | 2 |
| EDTA | 2(FB) | 2(FB) | 3(FB) | 1(FB) | 1(FB) | 1 |
| Pirfenidone | 2(FB) | 3(FB) | 3(FB) | 1(FB) | 1(FB) | 1(FB) |

Potential Salt
FB: Freebase
AC: Acid counterion
NS: No solid obtained
Ukn: Unknown
GL: Gel-like material, solution at 40° C.

Potential salts were stored at 40° C./75% RH for ca. 3 days and analyzed by XRPD, the results are summarized Table 9.

cycling for 72 h and re-slurrying in acetone with additional temperature cycling for 24 h. The pattern produced contained less peaks than the Pattern 1 material produced in the

TABLE 9

Pattern Stability Screen

| Counterion | Initial | 72 hrs 40° C./ 75% RH | Initial | 72 hrs 40° C./ 75% RH | Initial | 72 hrs 40° C./ 75% RH | Initial | 72 hrs 40° C./ 75% RH | Initial | 72 hrs 40° C./ 75% RH |
|---|---|---|---|---|---|---|---|---|---|---|
| HBr | 1 | 1 | 2 | 2 | 3 | 3 | 4 | 4 | 5 | 5 |
| HCl | 1 | 1 | 2 | 2 | 3 | 1 | | | | |
| Sulfuric acid | 1 | 1 | 2 | 1 | 3 | 3 | 4 | 3 | | |
| MSA | 1 | 1 | 2 | 1 | | | | | | |
| HESA | 1 | 2 | 2 | 2 | | | | | | |
| L-Aspartic acid | 1 | 1 | | | | | | | | |
| Maleic acid | 1 | 1 | 2 | 2 | | | | | | |
| Phosphoric acid | 1 | 1 | 2 | 2 | | | | | | |
| L-Tartaric acid | 1 | 1 | | | | | | | | |
| Fumaric acid | 1 | 1 | 2 | 2(MU) | | | | | | |
| Citric acid | 1 | 1 | 2 | 2(MU) | | | | | | |
| DL-Lactic acid | 1 | 1 | 2 | 2 | | | | | | |
| Acetic acid | 1 | 1(FB) | 2 | 1 | | | | | | |
| Saccharin | 1 | 2 | 2 | 2 | | | | | | |
| EDTA | 1 | 1(MU) | | | | | | | | |

MSA: Methanesulfonic acid
HESA: Hydroxyethanesulfonic acid
Unchanged pattern
FB: Freebase
MR: Mainly unchanged pattern Secondary HCl Salt Screen:

XRPD analysis showed that Pattern 1 of the HCl salt appeared to be successfully scaled-up after temperature cycling for 72 h and re-slurrying in acetone with additional temperature cycling for 24 h. The pattern produced contained less peaks than the Pattern 1 material produced in the primary salt screen. [is a conclusion possible here?] The other form in the mixture from the primary screen appears to be that produced when the HCl salt was prepared on a 5 g scale.

The first post-slurry diffractogram showed the presence of free base. The material was re-slurried after 72 h due to solvent evaporation occurring during cycling and to therefore ensure that salt formation was completed. PLM analysis particles with no clearly defined morphology with birefringence observed under polarized light. TGA showed a weight loss of 4.41% between ca. 25-60° C. (likely due to loss of water from a monohydrate plus some possible surface-bound moisture loss) and a further loss of 4.03% between ca. 175-250° C. (likely associated with degradation). DTA showed endotherms with onsets ca. 50° C., 183° C. and 273° C. associated with these losses in mass and degradation, respectively. Material likely a monohydrate. In the primary screen the initial weight loss was only 2.3% and the further loss was 0.7%, endotherm ca. 183° C. not observed in primary screen.

DVS analysis showed the input material to contain ca. 5.4% (likely water) showing ca. 2.2% uptake from the input material at 90% RH on the first cycle, showing the HCl salt to be hygroscopic—loss of ca. 4% water below 10% RH supports the idea that the material is a monohydrate. The sample re-hydrated on the second sorption step whilst also uptaking what appeared to be further surface bound water. No evidence of re-crystallization was observed during the analysis. Post-DVS XRPD analysis showed the HCl salt to remain unchanged.

NMR analysis showed the salt to be consistent with the primary screen, 0.04 eq. of acetone observed and peak shifting was observed compared with the free base and a broad water peak, indicating salt formation.

CAD analysis for counterion content measured 1.35 eq. of chloride. This indicates that the material is a monosalt. A hydrated form slightly increases the % recovery of chloride detected.

FT-IR appeared to be consistent with the structure. 7 day stability testing at 40° C./75% RH, 80° C. and ambient light showed the salt to remain pattern 1. The material was physically stable to changes in temperature and humidity when stored for one week. Purity of these materials remained unchanged as shown in Table 10.

TABLE 10

Purity results for stability testing for HCl salt
Purity (%)

| Input | Ambient | 80° C. | 40° C./75% RH |
|---|---|---|---|
| 99.9 | 99.9 | 99.9 | 99.9 |

Table 11 shows the measured pH values for disproportionation/hydration experiments. The acetone:water samples were observed to be solutions after 24h, the disproportionation sample in water was observed to be mostly dissolved resulting in a slightly turbid solution. No XRPD data could be compiled on the hydration or disproportionation of the salt due to the high solubility in water and acetone/water mixtures.

TABLE 11

Measured pH values for disproportionation/hydration studies

| Water Activity | Volume of water (μL) in 5 mL of Acetone | pH Pre-Agitation | pH Post-Agitation |
|---|---|---|---|
| 0.3 | 30 | 1.94 | 2.45 |
| 0.6 | 205 | 2.32 | 2.33 |
| 0.9 | 2900 | 1.89 | 2.24 |
| 1.0 | 5000 | 2.05 | 2.33 |

Secondary Phosphate Salt Screen:

The phosphate scale-up attempt appeared to produce mostly free base material after 24 h thermal cycling. Slurrying for 72 h produced a pattern containing free base and an unknown pattern. Some solvent evaporation was observed post-thermal cycle. The material was re-slurried in more solvent for a further 24 h as the lack of Pattern 2 reproduction may have been a solubility issue. Pattern 2 was not produced and some peaks of the free base were still visible in the diffractogram produced. A further 0.5 equiv. of acid was added to ensure complete salt formation and therefore eliminate the presence of freebase. Pattern 2 was not reproduced. Additional peaks were observed at 4, 5 and 6° 2θ, which could not be attributed to freebase. The material obtained was assigned as Pattern 3.

Small agglomerated particles were observed by PLM with birefringence observed under polarized light.

TGA showed a loss of 1.26% between ca. 25-60° C., likely unbound solvent, with a loss of 2.70% between ca. 60-200° C., likely due to bound solvent. Pattern 3 is possibly a hydrated form. An endotherm was observed with onset ca. 32° C. (associated with the first weight loss), multiple events observed upon degradation.

DVS analysis showed the input material to contain ca. 4.1% likely water showing a further ca. 10.6% uptake from input material at 90% RH, showing the phosphate salt to be hygroscopic. No evidence of re-crystallization was observed during the analysis. Post-DVS XRPD analysis showed the phosphate salt to produce a similar pattern but decrease in crystallinity.

1H NMR analysis showed the salt to be consistent with the primary screen, 0.7 eq. of acetone observed, salt formation was shown by peak shifting compared to the freebase. 31P NMR analysis showed the salt to be a bis-phosphate salt.

FT-IR appeared to be consistent with the structure.

XRPD analysis showed the phosphate salt to remain Pattern 3 after storage at 80° C. and ambient conditions. A new, poorly crystalline pattern was produced when stored at 40° C./75% RH—Pattern 4. Purity analysis of these materials (Table showed a slight decrease at 40° C./75% RH and ambient and a slightly larger decrease at 80° C. but not any significant reduction in purity was noted.

TABLE 12

Purity results for stability testing for phosphate salt
Purity (%)

| Input | Ambient | 80° C. | 40° C./75% RH |
|---|---|---|---|
| 99.9 | 99.6 | 99.2 | 99.8 |

Table shows the measured pH values for disproportionation/hydration experiments. The 0.3 and 0.6 aw samples were observed to be mostly dissolved resulting in slightly turbid solutions after 24h, 0.9 and 1 aw were observed to be thin slurries.

TABLE 13

Measured pH values for disproportionation/hydration studies

| Water Activity | Volume of water (μL) in 5 mL of Acetone | pH Pre-Agitation | pH Post-Agitation |
|---|---|---|---|
| 0.3 | 30 | 3.08 | 2.68 |
| 0.6 | 205 | 2.60 | 2.52 |
| 0.9 | 2900 | 2.34 | 2.35 |
| 1.0 | 5000 | 2.75 | 1.78 |

Secondary HBr Salt Screen:

XRPD analysis showed that Pattern 1 of the HBr salt appeared to be successfully scaled-up after temperature cycling for 72 h.

PLM analysis showed particles with no clearly defined morphology with birefringence observed under polarized light.

TGA showed a weight loss of 0.1% between ca. 25-180° C., likely due to the loss of unbound acetone. DTA showed an endotherm with onset ca. 263° C., due to melting. In the primary screen an initial weight loss of 0.81% was observed, the primary screen sample was not dried under vacuum.

DSC analysis showed an endotherm with onset ca. 260° C., due to melting.

DVS analysis showed the input material to contain ca. 1.0% (likely water) with a ca. 4.5% uptake from the input material at 90% RH observed on the first cycle, showing the HCl salt to be hygroscopic. No evidence of re-crystallization was observed during the analysis. Post-DVS XRPD analysis showed the HBr salt to remain unchanged.

NMR analysis showed the salt to be consistent with the primary screen. Around 0.04 eq. of acetone was observed in the sample. Peak shifting was observed compared with the free base along with a broad water peak, both indicating salt formation.

CAD analysis for counterion content measured eq. of bromide

FT-IR appeared to be consistent with the structure.

7 day stability testing showed the salt to remain Pattern 1 at 80° C. and ambient light and to be a mixture of Pattern 1 and 4 at 40° C./75% RH. Purity of these materials remained unchanged (as shown in Table) apart from the sample stored at ambient light, where a 0.5% drop in purity was observed.

TABLE 14

Purity results for stability testing for HBr salt
Purity (%)

| Input | Ambient | 80° C. | 40° C./75% RH |
|---|---|---|---|
| 99.7 | 99.2 | 99.6 | 99.7 |

Table shows the measured pH values for disproportionation/hydration experiments. The salt only remained Pattern 1 at 0.3 aw. New patterns 6 and 7 are likely hydrated due to the high water activity conditions for production.

TABLE 15

Measured pH values for disproportionation/hydration studies

| Water Activity | pH Pre-Agitation | Pattern |
|---|---|---|
| 0.3 | 4.84 | 1 |
| 0.6 | 5.38 | 4 |

TABLE 15-continued

Measured pH values for disproportionation/hydration studies

| Water Activity | pH Pre-Agitation | Pattern |
|---|---|---|
| 0.9 | 5.56 | New pattern (Pattern 6) |
| 1 | 2.27 | New pattern (Pattern 7) |

Solubility Assessment of HCl and Phosphate Salt in Water. Dissolution was observed for the HCl salt after 1.8 mL of deionized water was added to 20 mg of salt; giving ca. 11 mg/mL solubility. See Table for pH measurements, over time the pH values were observed to remain fairly constant. Dissolution was not observed for the phosphate salt after 2 mL of water was added; giving solubility <10 mg/mL. After ca. 6 h and 18 h of agitation the pH was re-measured. The HCl sample remained a solution and the phosphate salt a slurry.

TABLE 16 pH measurements for HCl salt solubility assessment

| Salt | Initial pH | pH at 6 h | pH at 18 h |
|---|---|---|---|
| HCl | 2.22 | 2.26 | 2.08 |
| Phosphate | 3.43 | 3.00 | 2.11 |

Aqueous Solubility Measurement for Primary Screen Samples. The aqueous solubility measurement results are shown in Table 17.

TABLE 17

Aqueous solubility measurement

| Salt | Pattern | Solubility | pH |
|---|---|---|---|
| HBr | 1 | ~5 mg/mL (heated to 40° C.), precipitation observed after 24 h | 3.95 |
| Fumarate | 1 | <0.625 mg/mL | 6.41 |
| Citrate | 1 | <0.625 mg/mL | 3.74 |
| Tartrate | 1 | <0.625 mg/mL | 5.22 |
| Lactate | 1 | 0.625 mg/mL | 4.74 |
| Acetate | 1 | <0.625 mg/mL | 5.24 |
| Saccharin | 2 | <0.625 | 5.51 |
| Edetate | 1 | ~5 mg/mL, viscous solution, gel formed on standing for ~72 h | 3.31 |

Water pH Titration. The pH upon cooling for 2 mg/mL Nintedanib slurry HCl sample was measured to be 4.76, the concentration of the filtered sample was measured to be 1.7 mg/mL by HPLC.

For the HCl salt solution prepared at 1.7 mg/mL Nintedanib the pH prior to filtration was 4.75 and 4.88 post filtration.

The results from adjusting the pH are shown in Table. After 1 week the sample was observed to remain clear.

TABLE 18

Water pH titration results

| Acid/Base Added | Volume Added (μL) | pH | Observations |
|---|---|---|---|
| N/A | N/A | 4.75 | Initial pH |
| N/A | N/A | 4.88 | Post-filtration |
| NaOH | 10 | 5.12 | Slightly turbid solution |

TABLE 18-continued

Water pH titration results

| Acid/Base Added | Volume Added (μL) | pH | Observations |
|---|---|---|---|
| HCl | 5 | 4.38 | Transparent solution |
| NaOH | 5 | 4.85 | Initial increase in turbidity which cleared |
| NaOH | 5 | 5.72 | Initial increase in turbidity which cleared |
| N/A | N/A | 5.30 | Slightly turbid solution after 1 h |
| HCl | 5 | 4.74 | Transparent solution |
| N/A | N/A | 4.78 | Transparent solution after 1 h |
| N/A | N/A | 4.88 | Clear, 1 week at ambient temperature |

Table shows the 0.5 mg/mL results for HBr water titration and Table for HCl water titration using 5 g batch. Both samples were observed to remain in solution after 1 week.

TABLE 19

Water pH titration results for HBr salt

| Acid/Base Added | Volume Added (μL) | pH | Observations |
|---|---|---|---|
| N/A | N/A | 6.01 | Slightly turbid |
| N/A | N/A | 6.63 | Filtered initially clear, slightly turbid for pH measurement |
| N/A | N/A | 6.71 | Clear, filtered |
| HCl | 10 | 3.85 | Clear |
| NaOH | 5 | 4.21 | Clear |
| NaOH | 5 | 5.07 | Slightly turbid |
| HCl | 5 | 4.83 | Clear |
| N/A | N/A | 5.51 | Clear, 1 h at ambient temperature |
| N/A | N/A | 6.36 | Clear, 1 week at ambient temperature |

TABLE 20

Water pH titration results for HCl salt (5 g batch)

| Acid/Base Added | Volume Added (μL) | pH | Observations |
|---|---|---|---|
| N/A | N/A | 6.17 | Slightly turbid |
| N/A | N/A | 6.31 | Initially clear, slightly turbid for pH measurement |
| N/A | N/A | 6.74 | Clear, filtered |
| HCl | 10 | 3.76 | Clear |
| NaOH | 5 | 4.37 | Clear |
| NaOH | 5 | 5.05 | Slightly turbid |
| HCl | 5 | 4.81 | Clear |
| N/A | N/A | 5.58 | Clear, 1 h at ambient temperature |
| N/A | N/A | 5.62 | Clear, 1 week at ambient temperature |

Citrate Buffer Formulation. The attempt to solubilize the HCl salt in pH 4.75 citrate buffer at a concentration of ~1.7 mg/mL (Nintedanib) was unsuccessful. When aliquots of salt were added to the buffer (with stirring), full dissolution was not observed after stirring at ambient temperature for 30 min The attempt to solubilize the HBr and HCl salts in pH 4.8 buffer at ca. 0.5 mg/mL (Nintedanib) was also unsuccessful. pH measurements are shown in Table 21.

TABLE 21 pH measurements for 0.5 mg/mL citrate buffer experiments

| Salt | Initial pH | pH 1 h |
|---|---|---|
| HBr | 4.83 | 4.82 |
| HCl | 4.84 | 4.80 |

0.5 mg/mL Solubility Assessment. Table 22 shows the results for the filtered and unfiltered experiments. The HBr salt gave 94% concentration for filtered sample compared to unfiltered and 99% for HCl salt. The results show that the insoluble component is likely unreacted freebase, which appears to have lower aqueous solubility than the salts.

TABLE 22

0.5 mg/mL experiment results

| | Filtered | | Unfiltered | |
| Salt | pH | Concentration (mg/mL) | pH | Concentration (mg/mL) |
|---|---|---|---|---|
| HBr | 5.31 | 0.4644 | 5.12 | 0.4965 |
| HCl | 5.36 | 0.4797 | 5.28 | 0.4850 |

The received Nintedanib freebase was found to be crystalline, with melt ca. 253° C. and to be slightly hygroscopic with 99.9% purity by HPLC. Solubility of the Nintedanib freebase was found to be ≥17 mg/mL for 2 of the 24 solvent systems, with the majority of solvent systems tested showing low solubility.

Salt formation was successful with 15 of the 17 counterions tested in the primary screen. From the successful salts produced in the primary screen, Pattern 1 HCl salt was scaled-up on a 500 mg scale in acetone. However, it became apparent as additional data was collected that Pattern 1 was possibly a mixture of two forms. The first of the two forms were produced in the initial scale-up of the HCl salt and was found to be a mono-hydrate. The second of the two forms were produced when the material was scaled-up to produce 5 g of HCl salt. This material was found to be a potentially anhydrous form based on the thermal data. Pattern 2 of the phosphate salt was not able to be prepared, however Pattern 3 bis-phosphate salt was produced instead and characterized. Pattern 1 of the HBr salt was successfully reproduced on a 500 mg scale. The mono-hydrated form of the HCl salt was found to be a more developable than the phosphate salt, due to more favorable thermal properties, significantly less hygroscopicity than the phosphate salt and remaining unchanged under stability testing. In general, the HBr salt Pattern 1 was found to be more developable compared to the phosphate salt mainly due to lower hygroscopicity, but the mono-hydrated form of the HCl salt was found to be more developable than the HBr salt due to better stability. An attempt to produce Pattern 1 HCl salt was also prepared on 5 g scale, however this resulted in a potentially anhydrous material. Along with a polymorphism study of the HCl salt, recommended further work would include full characterization on more potentially suitable salts in order to locate other suitable salts with the desired aqueous solubility and citrate buffer stability. Potential salts that could be considered for further analysis are fumarate Pattern 1, tartrate Pattern 1 and citrate Pattern 1. A summary of three nintedanib salt forms is described in Table 23 below.

TABLE 23

Initially Selected Nintedanib Salt Summary

| Salt | HCl | Phosphate | HBr |
|---|---|---|---|
| XRPD Pattern | Mono-hydrated form present in 1 | 3 (2 not produced) | 1 |
| Solvent Used In Production | Acetone | Acetone | Acetone |
| Equiv. of Acid Added | 1.05 | 1.05 | 1.05 |
| Melt Onset from TG/DTA (° C.) | 273 (possible degradation from 183° C. onwards) | ~210 (steady loss in mass from the outset) | 263 (possible degradation from 220° C. onwards) |
| Hygroscopicity | Contained 5.4% and a further 2.2% uptake up to 90% RH Hygroscopic | Contained 4.1% and a further 10.6% uptake up to 90% RH Hygroscopic | Contained 1.0% and further 4.5% uptake up to 90% RH Hygroscopic |
| Post-DVS | Pattern unchanged | Pattern 3 produced with decreased crystallinity and additional peaks | Pattern 1 remained, no evidence of form change |
| Stability: Ambient temperature & light, humidity 40° C./75% RH and 80° C. sealed vial (1 week) | Pattern retained under all conditions | Pattern 3 remained under ambient conditions and 80° C. Pattern 4 produced at 40° C./75% RH | Pattern 1 remained under ambient light and 80° C., 40° C./75% RH observed to be mixture of pattern 1 and 4 |
| Salt Stoichiometry | Mono | Bis | Mono |
| Hydration | Solution obtained, presence of hydrated material not able to be determined at low, medium and high water activity due to high solubility | Insufficient material for XRPD analysis, presence of hydrated material not able to be determined at low, medium and high water activity due to high solubility | Pattern 1 observed at 0.3 $a_w$, pattern 4 at 0.6 $a_w$, and a new pattern at 0.9 $a_w$. No hydration observed at low water activity. Pattern 4 (likely hydrated) at medium water activity. New likely hydrated form (Pattern 6) at high water activity. |

Solid state and chemical stability of nintedanib HBr and nintedanib HCl salts at 25 C/60% RH and 40 C/75% RH has been tested through 6 months. Pattern 1 of the HCl salt and pattern 1 of the HBr salt were tested. Table 24 and Table 25 summarize the total impurities (by HPLC), polymorphic form (by X-ray powder diffraction) and, where applicable, weight loss (by TGA/DSC) for both the HCl and HBr salt forms. Both salt forms showed negligible change in total impurities through 6 months at both storage conditions. While the HCl salt form remained as pattern 1 through 6 months at both storage condition, the HBr salt stored at 40 C/75% RH condition slowly converted to pattern 4. There were no changes in polymorphic form for both salt forms stored at 25 C/60% RH condition.

TABLE 24

Stability of nintedanib HBr and nintedanib HCl salt forms at 25° C./60% RH

| Test Attribute | Initial | 1 week | 4 weeks | 2 months | 6 months |
|---|---|---|---|---|---|
| Nintedanib HBr salt | | | | | |
| Total impurities | 0.29% | 0.40% | 0.33% | 0.42% | 0.47% |
| Polymorphic form | Pattern 1 | Pattern 1 | Pattern 1 | Pattern 1 | Pattern 1 |
| Weight loss[a] | 0.23% | Not required | Not required | Not required | Not required |
| Nintedanib HCl salt | | | | | |
| Total impurities | 0.29% | 0.41% | 0.36% | 0.36% | 0.46% |
| Polymorphic form | Pattern 1 | Pattern 1 | Pattern 1 | Pattern 1 | Pattern 1 |
| Weight loss[a] | 0.82% | Not required | Not required | Not required | Not required |

[a]Except for the initial time point, testing is conducted only when there is a polymorphic change

TABLE 25

Stability of nintedanib HBr and nintedanib HCl salt forms at 40° C./75% RH

| Test Attribute | Initial | 1 week | 4 weeks | 2 months | 6 months |
|---|---|---|---|---|---|
| Nintedanib HBr salt | | | | | |
| Total impurities | 0.29% | 0.43% | 0.34% | 0.41% | 0.44% |
| Polymorphic form | Pattern 1 | Pattern 1 | Pattern 1 & Pattern 4 | Pattern 4 | Pattern 4 |
| Weight loss[a] | 0.23% | Not required | 1.33% | 4.12% | 3.72% |
| Nintedanib HCl salt | | | | | |
| Total impurities | 0.29% | 0.39% | 0.34% | 0.37% | 0.52% |
| Polymorphic form | Pattern 1 | Pattern 1 | Pattern 1 | Pattern 1 | Pattern 1 |
| Weight loss[a] | 0.82% | Not required | Not required | Not required | Not required |

[a]Except for the initial time point, testing is conducted only when there is a polymorphic change Process development of the nintedanib HBr salt was conducted at laboratory scales (~25 g) under various conditions to evaluate process reproducibility and to optimize the process. Table 26 shows the nintedanib HBr polymorphic forms obtained and the apparent solubility of each. During this process, a new polymorphic form was identified (pattern X)

TABLE 26

Polymorphic Forms of Various Nintedanib HBr Laboratory Scale Batches

| Batch Number | Polymorph | Apparent Solubility (mg/mL) |
|---|---|---|
| AP036 | Pattern 1 | 0.97 |
| AP069 | Pattern 4 | 1.02 |
| AP143 | Pattern 4 | 0.96 |
| AP018 | Pattern X | 2.04 |
| AP064 | Pattern X | 1.96 |
| AP152 | Pattern X | 1.95 |
| AP177w | Pattern 3 | 1.03 |
| AP177d | Pattern X | 2.05 |
| AP178w | Pattern 3 | 1.01 |
| AP178d | Pattern X | 1.94 |

Table 27 provides the characteristic peaks (2θ and relative peak intensity) of patterns 1, 3, 4 and X of nintedanib HBr Salt and pattern 1 of nintedanib HCl salt.

TABLE 27

Nintedanib salt 2θ and relative peak intensity

| Nintedanib HBr | | | | | | | | | Nintedanib HCl | |
|---|---|---|---|---|---|---|---|---|---|---|
| Pattern 1 | | Pattern 3 | | Pattern 4 | | Pattern X | | Pattern 1 | |
| 2θ | Relative Intensity (%) | 2θ | Relative Intensity (%) | 2θ | Relative Intensity (%) | 2θ | Relative Intensity (%) | 2θ | Relative Intensity (%) |
| 6.0 | 8.9 | 9.0 | 3.6 | 8.7 | 35.9 | 6.1 | 9.5 | 3.4 | 7.5 |
| 8.9 | 21.4 | 9.5 | 6.9 | 9.3 | 0.7 | 7.5 | 3.0 | 6.0 | 87.3 |
| 9.2 | 5.3 | 9.9 | 26.8 | 10.6 | 1.9 | 9.5 | 12.7 | 8.8 | 10.0 |
| 11.1 | 15.6 | 14.2 | 24.7 | 11.4 | 7.1 | 9.8 | 14.4 | 9.1 | 7.1 |
| 11.3 | 4.3 | 14.3 | 27.3 | 12.0 | 6.4 | 12.0 | 2.9 | 10.9 | 12.9 |
| 12.0 | 28.4 | 14.4 | 27.2 | 13.0 | 8.6 | 12.3 | 9.5 | 11.3 | 8.3 |
| 13.7 | 13.6 | 14.6 | 7.5 | 13.4 | 4.5 | 14.2 | 25.5 | 12.1 | 93.9 |
| 14.3 | 2.4 | 15.7 | 6.4 | 14.4 | 2.7 | 14.6 | 24.0 | 12.6 | 6.5 |
| 15.3 | 21.4 | 15.8 | 5.2 | 15.2 | 2.0 | 15.3 | 2.8 | 13.8 | 25.0 |
| 17.0 | 55.5 | 16.5 | 6.9 | 15.7 | 16.0 | 16.0 | 15.0 | 15.2 | 10.4 |
| 17.3 | 12.8 | 18.7 | 5.1 | 16.6 | 2.7 | 16.4 | 7.1 | 16.6 | 19.6 |
| 17.6 | 48.9 | 19.0 | 10.4 | 16.8 | 6.1 | 16.6 | 8.4 | 16.9 | 79.0 |
| 18.0 | 26.3 | 19.7 | 16.1 | 17.4 | 100.0 | 18.4 | 37.9 | 17.5 | 54.5 |
| 18.4 | 22.4 | 19.8 | 38.3 | 18.2 | 4.0 | 19.2 | 8.9 | 17.6 | 44.0 |
| 18.8 | 50.9 | 20.2 | 8.6 | 18.6 | 2.9 | 19.7 | 100.0 | 17.9 | 17.2 |
| 19.1 | 28.4 | 20.6 | 17.3 | 18.9 | 5.1 | 20.1 | 4.2 | 18.3 | 52.9 |
| 20.0 | 6.2 | 20.8 | 20.8 | 19.2 | 3.0 | 20.6 | 27.3 | 18.5 | 60.9 |
| 20.3 | 59.4 | 21.5 | 16.2 | 19.6 | 6.4 | 21.1 | 12.4 | 18.6 | 59.0 |
| 20.8 | 12.8 | 21.8 | 12.9 | 20.3 | 12.7 | 21.4 | 22.1 | 19.1 | 39.7 |
| 21.2 | 32.1 | 21.9 | 10.7 | 21.4 | 22.3 | 21.7 | 17.9 | 19.8 | 6.7 |
| 21.6 | 100.0 | 22.4 | 15.3 | 21.8 | 73.2 | 22.3 | 37.7 | 20.4 | 50.1 |

TABLE 27-continued

Nintedanib salt 2θ and relative peak intensity

| Nintedanib HBr | | | | | | | | Nintedanib HCl | |
|---|---|---|---|---|---|---|---|---|---|
| Pattern 1 | | Pattern 3 | | Pattern 4 | | Pattern X | | Pattern 1 | |
| 2θ | Relative Intensity (%) | 2θ | Relative Intensity (%) | 2θ | Relative Intensity (%) | 2θ | Relative Intensity (%) | 2θ | Relative Intensity (%) |
| 22.1 | 74.3 | 22.5 | 20.0 | 22.3 | 8.1 | 23.2 | 27.3 | 20.6 | 35.1 |
| 22.5 | 16.8 | 23.0 | 7.1 | 22.7 | 34.1 | 23.8 | 20.9 | 21.2 | 100.0 |
| 22.9 | 63.3 | 23.4 | 100.0 | 22.9 | 7.4 | 24.3 | 29.0 | 22.0 | 65.3 |
| 23.2 | 17.0 | 23.4 | 42.3 | 23.2 | 5.3 | 24.7 | 9.6 | 22.5 | 36.7 |
| 24.0 | 56.7 | 23.8 | 11.2 | 23.8 | 5.3 | 25.6 | 12.9 | 22.9 | 61.4 |
| 25.1 | 14.3 | 24.0 | 12.2 | 24.1 | 11.5 | 26.1 | 10.9 | 23.2 | 15.3 |
| 25.5 | 8.6 | 24.4 | 17.0 | 24.6 | 15.3 | 27.0 | 27.5 | 23.9 | 19.9 |
| 26.2 | 12.5 | 24.4 | 14.2 | 25.5 | 11.2 | 28.0 | 4.4 | 24.2 | 18.1 |
| 27.3 | 9.4 | 28.2 | 7.3 | 25.9 | 5.3 | 28.2 | 6.8 | 25.3 | 9.4 |
| 27.6 | 17.8 | 28.4 | 10.4 | 26.5 | 10.2 | 28.6 | 4.4 | 26.2 | 10.6 |
| 27.8 | 51.9 | 28.8 | 6.4 | 26.9 | 5.4 | 28.9 | 12.5 | 27.4 | 7.1 |
| 28.8 | 12.2 | 29.5 | 11.0 | 27.2 | 2.7 | 29.5 | 11.6 | 27.8 | 12.1 |
| 29.3 | 38.3 | 29.9 | 8.4 | 27.9 | 9.9 | 29.9 | 6.5 | 28.3 | 32.6 |
| 29.6 | 11.2 | 30.0 | 6.7 | 28.5 | 13.0 | | | 29.2 | 47.5 |
| | | 31.9 | 13.1 | 28.8 | 15.3 | | | 30.2 | 6.2 |
| | | 34.5 | 7.6 | | | | | 32.2 | 8.1 |
| | | | | | | | | 34.3 | 12.2 |

The solubility of Pattern 4 and Pattern X at various pH values were determined by UV/vis spectrophotometry. Excess Pattern 4 and Pattern X HBr salts were added to distilled water, vortexed at high speed and the pH was adjusted to the target value by adding 1N HCl or 1N NaOH. The test solutions were mixed on a magnetic stirrer for over 48 hours, then filtered through a 0.22 μm nylon membrane syringe filter and analyzed by uv/vis spectrophotometry at 390 nm. Table 28 shows the solubility of pattern 4 and pattern X as a function of pH. The solubility of both polymorphic forms decreases with increasing pH. Both polymorphic forms have similar solubility profile.

TABLE 28 pH-Solubility of Nintedanib HBr Salt Pattern 4 and Pattern X

| pH | Nintedanib HBr Pattern 4 | Nintedanib HBr Pattern X |
|---|---|---|
| 3.1 | 2.01 | 1.86 |
| 3.9 | 1.47 | 1.72 |
| 4.4 | Not measured | 1.49 |
| 4.7 | 1.38 | Not measured |
| 5.1 | Not measured | 1.40 |
| 5.3 | 1.07 | Not measured |

The temperature-solubility profiles of nintedanib HBr Pattern 4 and Pattern X were determined by adding excess nintedanib HBr to distilled water, vortexed at high speed and kept in a refrigerator at 5° C., ambient room temperature at 22° C., and in a stability chamber at 40° C. for over 48 hours. During this time period, the samples were periodically taken out of the storage, vortexed, and returned to storage condition. At the end of the incubation period, the test solutions were filtered through a 0.22 μm nylon membrane syringe filter and analyzed by uv/vis spectrophotometry (at 390 nm) for drug concentration. Table 29 summarizes the solubility of both salt forms as a function of temperature. The solubility of both polymorphic forms increases with increasing temperature. Both polymorphic forms have similar solubility profiles.

TABLE 29

Temperature-Solubility of Nintedanib HBr Pattern 4 and Pattern X

| | Nintedanib HBr Solubility (mg/mL) | |
|---|---|---|
| Storage Condition | Pattern 4 | Pattern X |
| 5° C. | 0.79 | 0.65 |
| 22° C. | 1.38 | 1.49 |
| 40° C. | 3.20 | 3.41 |

The process to salt nintedanib base into nintedanib hydrobromide, XRPD Pattern 4 is as follows. Listed volumes may be scaled proportionately. To a flask is charged methyl (Z)-3-(((4-(N-methyl-2-(4-methylpiperazin-1-yl)acetamido)phenyl)amino)(phenyl)methylene)-2-oxoindoline-6-carboxylate (10 g, 18.53 mmol). At 20 Celsius, acetone (90 ml, 9 vol) and water (40 ml, 4 vol) are charged in the flask and the mixture is stirred (200 rpm). The mixture is heated in a glycol bath to 50 Celsius. HBr (48% aq., 2.2 ml, 19.31 mmol) is charged in a single portion. The solution is filtered to a second flask and cooled at a rate of 1 Celsius/min to about 33 Celsius, over which time about 5% XRPD Pattern 4 seed was slowly added. At about 33 Celsius, the remainder of the seed is added and temperature maintained for 1 additional hour. The mixture is then cooled from about 33 Celsius to 0 Celsius over 3 hours with a linear cooling profile. The mixture is then stirred at 0 Celsius for 1 hour. The solids are isolated by filtration on a sintered funnel. The isolated solids are washed with acetone (2×20 ml, 2×2 vol), then vacuum dried for 5 minutes. The solid is dried in a vacuum oven overnight (40 Celsius, 16-18 hours) to obtain Nintedanib hydrobromide, XRPD Pattern 4.

The process to salt nintedanib base into nintedanib hydrobromide, XRPD Pattern X is as follows. Listed volumes may be scaled proportionately. To a flask is charged methyl (Z)-3-(((4-(N-methyl-2-(4-methylpiperazin-1-yl)acetamido)phenyl)amino)(phenyl) methylene)-2-oxoindoline-6-carboxylate (10 g, 18.53 mmol). At 20 Celsius, acetone (90 ml, 9 vol) and water (40 ml, 4 vol) are charged in the flask and the mixture is stirred (200 rpm). The mixture is heated in a glycol bath to 50 Celsius. HBr (48% aq., 2.2 ml, 19.31 mmol) is charged in a single portion. The solution is filtered to a second flask and cooled at a rate of 1 Celsius/min to about 33 Celsius, over which time about 5% XRPD Pattern X seed was slowly added. At about 33 Celsius, the remainder of the seed is added and temperature maintained for 1 additional hour. The mixture is then cooled from about 33 Celsius to 0 Celsius over 3 hours with a linear cooling profile. The mixture is then stirred at 0 Celsius for 1 hour. The solids are isolated by filtration on a sintered funnel. The isolated solids are washed with acetone (2×20 ml, 2×2 vol), then vacuum dried for 5 minutes. The solid is dried in a vacuum oven overnight (40 Celsius, 16-18 hours) to obtain Nintedanib hydrobromide, XRPD Pattern X.

Example 4: Formulations

TABLE 30

Exemplary Nintedanib Formulations

| Formulation | Nintedanib Salt, Nintedanib HCl or Nintedanib HBr (mg/mL)$^a$ | Propylene Glycol (%) | Sodium Chloride (mM) | Sodium Bromide (mM) | Sodium Saccharin (mM) | Lysinate/N-acetylcysteine Buffer (mM) |
|---|---|---|---|---|---|---|
| 1 | 1.875 | 1.875 | 0 | 0 | 0 | 0 |
| 2 | 0.625 | 1.875 | 0 | 0 | 0 | 0 |
| 3 | 0.1 | 1.875 | 0 | 0 | 0 | 0 |
| 4 | 0.01 | 1.875 | 0 | 0 | 0 | 0 |
| 5 | 1.875 | 1.875 | 0 | 0 | 0 | 1 |
| 6 | 0.625 | 1.875 | 0 | 0 | 0 | 1 |
| 7 | 0.1 | 1.875 | 0 | 0 | 0 | 1 |
| 8 | 0.01 | 1.875 | 0 | 0 | 0 | 1 |
| 9 | 1.875 | 1.875 | 0 | 0 | 0 | 0 |
| 10 | 0.625 | 1.875 | 0 | 0 | 0 | 0 |
| 11 | 0.1 | 1.875 | 0 | 0 | 0 | 0 |
| 12 | 0.01 | 1.875 | 0 | 0 | 0 | 0 |
| 13 | 1.875 | 1.875 | 0 | 0 | 0 | 0 |
| 14 | 0.625 | 1.875 | 0 | 0 | 0 | 0 |
| 15 | 0.1 | 1.875 | 0 | 0 | 0 | 0 |
| 16 | 0.01 | 1.875 | 0 | 0 | 0 | 0 |
| 17 | 1.875 | 1.875 | 0 | 0 | 0 | 10 |
| 18 | 0.625 | 1.875 | 0 | 0 | 0 | 10 |
| 19 | 0.1 | 1.875 | 0 | 0 | 0 | 10 |
| 20 | 0.01 | 1.875 | 0 | 0 | 0 | 10 |
| 21 | 1.875 | 1.875 | 0 | 0 | 0 | 0 |
| 22 | 0.625 | 1.875 | 0 | 0 | 0 | 0 |
| 23 | 0.1 | 1.875 | 0 | 0 | 0 | 0 |
| 24 | 0.01 | 1.875 | 0 | 0 | 0 | 0 |
| 25 | 1.875 | 1.875 | 0 | 0 | 0 | 0 |
| 26 | 0.625 | 1.875 | 0 | 0 | 0 | 0 |
| 27 | 0.1 | 1.875 | 0 | 0 | 0 | 0 |
| 28 | 0.01 | 1.875 | 0 | 0 | 0 | 0 |
| 29 | 1.875 | 1.875 | 0 | 0 | 0 | 100 |
| 30 | 0.625 | 1.875 | 0 | 0 | 0 | 100 |
| 31 | 0.1 | 1.875 | 0 | 0 | 0 | 100 |
| 32 | 0.01 | 1.875 | 0 | 0 | 0 | 100 |
| 33 | 1.875 | 1.875 | 0 | 0 | 0 | 0 |
| 34 | 0.625 | 1.875 | 0 | 0 | 0 | 0 |
| 35 | 0.1 | 1.875 | 0 | 0 | 0 | 0 |
| 36 | 0.01 | 1.875 | 0 | 0 | 0 | 0 |
| 37 | 1.875 | 1.875 | 0 | 0 | 0 | 0 |
| 38 | 0.625 | 1.875 | 0 | 0 | 0 | 0 |
| 39 | 0.1 | 1.875 | 0 | 0 | 0 | 0 |
| 40 | 0.01 | 1.875 | 0 | 0 | 0 | 0 |
| 41 | 0 | 1.5 | 150 | 0 | 0 | 0 |
| 42 | 0 | 1.5 | 0 | 150 | 0 | 0 |
| 43 | 0 | 1.5 | 150 | 0 | 0.1 | 0 |
| 44 | 0 | 1.5 | 150 | 0 | 2.0 | 0 |
| 45 | 0 | 1.5 | 0 | 150 | 0.1 | 0 |
| 46 | 0 | 1.5 | 0 | 150 | 2.0 | 0 |
| 47 | 0 | 1.5 | 150 | 0 | 0 | 10 |
| 48 | 0 | 1.5 | 0 | 150 | 0 | 10 |
| 49 | 0 | 1.5 | 150 | 0 | 0.1 | 0 |
| 50 | 0 | 1.5 | 150 | 0 | 2.0 | 0 |
| 51 | 0 | 1.5 | 0 | 150 | 0.1 | 0 |
| 52 | 0 | 1.5 | 0 | 150 | 2.0 | 0 |
| 53 | 0 | 1.5 | 150 | 0 | 0 | 100 |
| 54 | 0 | 1.5 | 0 | 150 | 0 | 100 |
| 55 | 0 | 1.5 | 150 | 0 | 0.1 | 0 |
| 56 | 0 | 1.5 | 150 | 0 | 2.0 | 0 |
| 57 | 0 | 1.5 | 0 | 150 | 0.1 | 0 |
| 58 | 0 | 1.5 | 0 | 150 | 2.0 | 0 |
| 59 | 1.5 | 1.5 | 30 | 0 | 0 | 0 |
| 60 | 1.5 | 1.5 | 30 | 0 | 0 | 1 |
| 61 | 1.5 | 1.5 | 30 | 0 | 0 | 0 |
| 62 | 1.5 | 1.5 | 30 | 0 | 0 | 0 |

TABLE 30-continued

Exemplary Nintedanib Formulations

| | | | | | | |
|---|---|---|---|---|---|---|
| 63 | 1.5 | 1.5 | 30 | 0 | 0 | 10 |
| 64 | 1.5 | 1.5 | 30 | 0 | 0 | 0 |
| 65 | 1.5 | 1.5 | 30 | 0 | 0 | 0 |
| 66 | 1.5 | 1.5 | 30 | 0 | 0 | 100 |
| 67 | 1.5 | 1.5 | 30 | 0 | 0 | 0 |
| 68 | 1.5 | 1.5 | 30 | 0 | 0 | 0 |
| 69 | 1.5 | 1.5 | 0 | 30 | 0 | 0 |
| 70 | 1.5 | 1.5 | 0 | 30 | 0 | 1 |
| 71 | 1.5 | 1.5 | 0 | 30 | 0 | 0 |
| 72 | 1.5 | 1.5 | 0 | 30 | 0 | 0 |
| 73 | 1.5 | 1.5 | 0 | 30 | 0 | 10 |
| 74 | 1.5 | 1.5 | 0 | 30 | 0 | 0 |
| 75 | 1.5 | 1.5 | 0 | 30 | 0 | 0 |
| 76 | 1.5 | 1.5 | 0 | 30 | 0 | 100 |
| 77 | 1.5 | 1.5 | 0 | 30 | 0 | 0 |
| 78 | 1.5 | 1.5 | 0 | 30 | 0 | 0 |
| 79 | 1.5 | 1.5 | 30 | 0 | 0.1 | 0 |
| 80 | 1.5 | 1.5 | 30 | 0 | 0.1 | 1 |
| 81 | 1.5 | 1.5 | 30 | 0 | 0.1 | 0 |
| 82 | 1.5 | 1.5 | 30 | 0 | 0.1 | 0 |
| 83 | 1.5 | 1.5 | 30 | 0 | 0.1 | 10 |
| 84 | 1.5 | 1.5 | 30 | 0 | 0.1 | 0 |
| 85 | 1.5 | 1.5 | 30 | 0 | 0.1 | 0 |
| 86 | 1.5 | 1.5 | 30 | 0 | 0.1 | 100 |
| 87 | 1.5 | 1.5 | 30 | 0 | 0.1 | 0 |
| 88 | 1.5 | 1.5 | 30 | 0 | 0.1 | 0 |
| 89 | 1.5 | 1.5 | 30 | 0 | 2 | 0 |
| 90 | 1.5 | 1.5 | 30 | 0 | 2 | 1 |
| 91 | 1.5 | 1.5 | 30 | 0 | 2 | 0 |
| 92 | 1.5 | 1.5 | 30 | 0 | 2 | 0 |
| 93 | 1.5 | 1.5 | 30 | 0 | 2 | 10 |
| 94 | 1.5 | 1.5 | 30 | 0 | 2 | 0 |
| 95 | 1.5 | 1.5 | 30 | 0 | 2 | 0 |
| 96 | 1.5 | 1.5 | 30 | 0 | 2 | 100 |
| 97 | 1.5 | 1.5 | 30 | 0 | 2 | 0 |
| 98 | 1.5 | 1.5 | 30 | 0 | 2 | 0 |
| 99 | 1.5 | 1.5 | 0 | 30 | 0 | 0 |
| 100 | 1.5 | 1.5 | 0 | 30 | 0 | 1 |
| 101 | 1.5 | 1.5 | 0 | 30 | 0 | 0 |
| 102 | 1.5 | 1.5 | 0 | 30 | 0 | 0 |
| 103 | 1.5 | 1.5 | 0 | 30 | 0 | 10 |
| 104 | 1.5 | 1.5 | 0 | 30 | 0 | 0 |
| 105 | 1.5 | 1.5 | 0 | 30 | 0 | 0 |
| 106 | 1.5 | 1.5 | 0 | 30 | 0 | 100 |
| 107 | 1.5 | 1.5 | 0 | 30 | 0 | 0 |
| 108 | 1.5 | 1.5 | 0 | 30 | 0 | 0 |
| 109 | 1.5 | 1.5 | 0 | 30 | 0.1 | 0 |
| 110 | 1.5 | 1.5 | 0 | 30 | 0.1 | 1 |
| 111 | 1.5 | 1.5 | 0 | 30 | 0.1 | 0 |
| 112 | 1.5 | 1.5 | 0 | 30 | 0.1 | 0 |
| 113 | 1.5 | 1.5 | 0 | 30 | 0.1 | 10 |
| 114 | 1.5 | 1.5 | 0 | 30 | 0.1 | 0 |
| 115 | 1.5 | 1.5 | 0 | 30 | 0.1 | 0 |
| 116 | 1.5 | 1.5 | 0 | 30 | 0.1 | 100 |
| 117 | 1.5 | 1.5 | 0 | 30 | 0.1 | 0 |
| 118 | 1.5 | 1.5 | 0 | 30 | 0.1 | 0 |
| 119 | 1.5 | 1.5 | 0 | 30 | 2 | 0 |
| 120 | 1.5 | 1.5 | 0 | 30 | 2 | 1 |
| 121 | 1.5 | 1.5 | 0 | 30 | 2 | 0 |
| 122 | 1.5 | 1.5 | 0 | 30 | 2 | 0 |
| 123 | 1.5 | 1.5 | 0 | 30 | 2 | 10 |
| 124 | 1.5 | 1.5 | 0 | 30 | 2 | 0 |
| 125 | 1.5 | 1.5 | 0 | 30 | 2 | 0 |
| 126 | 1.5 | 1.5 | 0 | 30 | 2 | 100 |
| 127 | 1.5 | 1.5 | 0 | 30 | 2 | 0 |
| 128 | 1.5 | 1.5 | 0 | 30 | 2 | 0 |
| 129 | 0.5 | 1.5 | 30 | 0 | 0 | 0 |
| 130 | 0.5 | 1.5 | 30 | 0 | 0 | 1 |
| 131 | 0.5 | 1.5 | 30 | 0 | 0 | 0 |
| 132 | 0.5 | 1.5 | 30 | 0 | 0 | 0 |
| 133 | 0.5 | 1.5 | 30 | 0 | 0 | 10 |
| 134 | 0.5 | 1.5 | 30 | 0 | 0 | 0 |
| 135 | 0.5 | 1.5 | 30 | 0 | 0 | 0 |
| 136 | 0.5 | 1.5 | 30 | 0 | 0 | 100 |
| 137 | 0.5 | 1.5 | 30 | 0 | 0 | 0 |
| 138 | 0.5 | 1.5 | 30 | 0 | 0 | 0 |
| 139 | 0.5 | 1.5 | 0 | 30 | 0 | 0 |
| 140 | 0.5 | 1.5 | 0 | 30 | 0 | 1 |

TABLE 30-continued

Exemplary Nintedanib Formulations

| | | | | | | |
|---|---|---|---|---|---|---|
| 141 | 0.5 | 1.5 | 0 | 30 | 0 | 0 |
| 142 | 0.5 | 1.5 | 0 | 30 | 0 | 0 |
| 142 | 0.5 | 1.5 | 0 | 30 | 0 | 10 |
| 144 | 0.5 | 1.5 | 0 | 30 | 0 | 0 |
| 145 | 0.5 | 1.5 | 0 | 30 | 0 | 0 |
| 146 | 0.5 | 1.5 | 0 | 30 | 0 | 100 |
| 147 | 0.5 | 1.5 | 0 | 30 | 0 | 0 |
| 148 | 0.5 | 1.5 | 0 | 30 | 0 | 0 |
| 149 | 0.5 | 1.5 | 30 | 0 | 0.1 | 0 |
| 150 | 0.5 | 1.5 | 30 | 0 | 0.1 | 1 |
| 151 | 0.5 | 1.5 | 30 | 0 | 0.1 | 0 |
| 152 | 0.5 | 1.5 | 30 | 0 | 0.1 | 0 |
| 153 | 0.5 | 1.5 | 30 | 0 | 0.1 | 10 |
| 154 | 0.5 | 1.5 | 30 | 0 | 0.1 | 0 |
| 155 | 0.5 | 1.5 | 30 | 0 | 0.1 | 0 |
| 156 | 0.5 | 1.5 | 30 | 0 | 0.1 | 100 |
| 157 | 0.5 | 1.5 | 30 | 0 | 0.1 | 0 |
| 158 | 0.5 | 1.5 | 30 | 0 | 0.1 | 0 |
| 159 | 0.5 | 1.5 | 30 | 0 | 2 | 0 |
| 160 | 0.5 | 1.5 | 30 | 0 | 2 | 1 |
| 161 | 0.5 | 1.5 | 30 | 0 | 2 | 0 |
| 162 | 0.5 | 1.5 | 30 | 0 | 2 | 0 |
| 163 | 0.5 | 1.5 | 30 | 0 | 2 | 10 |
| 164 | 0.5 | 1.5 | 30 | 0 | 2 | 0 |
| 165 | 0.5 | 1.5 | 30 | 0 | 2 | 0 |
| 166 | 0.5 | 1.5 | 30 | 0 | 2 | 100 |
| 167 | 0.5 | 1.5 | 30 | 0 | 2 | 0 |
| 168 | 0.5 | 1.5 | 30 | 0 | 2 | 0 |
| 169 | 0.5 | 1.5 | 0 | 30 | 0 | 0 |
| 170 | 0.5 | 1.5 | 0 | 30 | 0 | 1 |
| 171 | 0.5 | 1.5 | 0 | 30 | 0 | 0 |
| 172 | 0.5 | 1.5 | 0 | 30 | 0 | 0 |
| 173 | 0.5 | 1.5 | 0 | 30 | 0 | 10 |
| 174 | 0.5 | 1.5 | 0 | 30 | 0 | 0 |
| 175 | 0.5 | 1.5 | 0 | 30 | 0 | 0 |
| 176 | 0.5 | 1.5 | 0 | 30 | 0 | 100 |
| 177 | 0.5 | 1.5 | 0 | 30 | 0 | 0 |
| 178 | 0.5 | 1.5 | 0 | 30 | 0 | 0 |
| 179 | 0.5 | 1.5 | 0 | 30 | 0.1 | 0 |
| 180 | 0.5 | 1.5 | 0 | 30 | 0.1 | 1 |
| 181 | 0.5 | 1.5 | 0 | 30 | 0.1 | 0 |
| 182 | 0.5 | 1.5 | 0 | 30 | 0.1 | 0 |
| 183 | 0.5 | 1.5 | 0 | 30 | 0.1 | 10 |
| 184 | 0.5 | 1.5 | 0 | 30 | 0.1 | 0 |
| 185 | 0.5 | 1.5 | 0 | 30 | 0.1 | 0 |
| 186 | 0.5 | 1.5 | 0 | 30 | 0.1 | 100 |
| 187 | 0.5 | 1.5 | 0 | 30 | 0.1 | 0 |
| 188 | 0.5 | 1.5 | 0 | 30 | 0.1 | 0 |
| 189 | 0.5 | 1.5 | 0 | 30 | 2 | 0 |
| 190 | 0.5 | 1.5 | 0 | 30 | 2 | 1 |
| 191 | 0.5 | 1.5 | 0 | 30 | 2 | 0 |
| 192 | 0.5 | 1.5 | 0 | 30 | 2 | 0 |
| 193 | 0.5 | 1.5 | 0 | 30 | 2 | 10 |
| 194 | 0.5 | 1.5 | 0 | 30 | 2 | 0 |
| 195 | 0.5 | 1.5 | 0 | 30 | 2 | 0 |
| 196 | 0.5 | 1.5 | 0 | 30 | 2 | 100 |
| 197 | 0.5 | 1.5 | 0 | 30 | 2 | 0 |
| 198 | 0.5 | 1.5 | 0 | 30 | 2 | 0 |
| 199 | 4.0 | 1.5 | 30 | 0 | 0 | 0 |
| 200 | 4.0 | 1.5 | 30 | 0 | 0 | 1 |
| 201 | 4.0 | 1.5 | 30 | 0 | 0 | 0 |
| 202 | 4.0 | 1.5 | 30 | 0 | 0 | 0 |
| 203 | 4.0 | 1.5 | 30 | 0 | 0 | 10 |
| 204 | 4.0 | 1.5 | 30 | 0 | 0 | 0 |
| 205 | 4.0 | 1.5 | 30 | 0 | 0 | 0 |
| 206 | 4.0 | 1.5 | 30 | 0 | 0 | 100 |
| 207 | 4.0 | 1.5 | 30 | 0 | 0 | 0 |
| 208 | 4.0 | 1.5 | 30 | 0 | 0 | 0 |
| 209 | 4.0 | 1.5 | 0 | 30 | 0 | 0 |
| 210 | 4.0 | 1.5 | 0 | 30 | 0 | 1 |
| 211 | 4.0 | 1.5 | 0 | 30 | 0 | 0 |
| 212 | 4.0 | 1.5 | 0 | 30 | 0 | 0 |
| 213 | 4.0 | 1.5 | 0 | 30 | 0 | 10 |
| 214 | 4.0 | 1.5 | 0 | 30 | 0 | 0 |
| 215 | 4.0 | 1.5 | 0 | 30 | 0 | 0 |
| 216 | 4.0 | 1.5 | 0 | 30 | 0 | 100 |
| 217 | 4.0 | 1.5 | 0 | 30 | 0 | 0 |
| 218 | 4.0 | 1.5 | 0 | 30 | 0 | 0 |

TABLE 30-continued

Exemplary Nintedanib Formulations

| | | | | | | |
|---|---|---|---|---|---|---|
| 219 | 4.0 | 1.5 | 30 | 0 | 0.1 | 0 |
| 220 | 4.0 | 1.5 | 30 | 0 | 0.1 | 1 |
| 221 | 4.0 | 1.5 | 30 | 0 | 0.1 | 0 |
| 222 | 4.0 | 1.5 | 30 | 0 | 0.1 | 0 |
| 223 | 4.0 | 1.5 | 30 | 0 | 0.1 | 10 |
| 224 | 4.0 | 1.5 | 30 | 0 | 0.1 | 0 |
| 225 | 4.0 | 1.5 | 30 | 0 | 0.1 | 0 |
| 226 | 4.0 | 1.5 | 30 | 0 | 0.1 | 100 |
| 227 | 4.0 | 1.5 | 30 | 0 | 0.1 | 0 |
| 228 | 4.0 | 1.5 | 30 | 0 | 0.1 | 0 |
| 229 | 4.0 | 1.5 | 30 | 0 | 2 | 0 |
| 230 | 4.0 | 1.5 | 30 | 0 | 2 | 1 |
| 231 | 4.0 | 1.5 | 30 | 0 | 2 | 0 |
| 232 | 4.0 | 1.5 | 30 | 0 | 2 | 0 |
| 233 | 4.0 | 1.5 | 30 | 0 | 2 | 10 |
| 234 | 4.0 | 1.5 | 30 | 0 | 2 | 0 |
| 235 | 4.0 | 1.5 | 30 | 0 | 2 | 0 |
| 236 | 4.0 | 1.5 | 30 | 0 | 2 | 100 |
| 237 | 4.0 | 1.5 | 30 | 0 | 2 | 0 |
| 238 | 4.0 | 1.5 | 30 | 0 | 2 | 0 |
| 239 | 4.0 | 1.5 | 0 | 30 | 0 | 0 |
| 240 | 4.0 | 1.5 | 0 | 30 | 0 | 1 |
| 241 | 4.0 | 1.5 | 0 | 30 | 0 | 0 |
| 242 | 4.0 | 1.5 | 0 | 30 | 0 | 0 |
| 243 | 4.0 | 1.5 | 0 | 30 | 0 | 10 |
| 244 | 4.0 | 1.5 | 0 | 30 | 0 | 0 |
| 245 | 4.0 | 1.5 | 0 | 30 | 0 | 0 |
| 246 | 4.0 | 1.5 | 0 | 30 | 0 | 100 |
| 247 | 4.0 | 1.5 | 0 | 30 | 0 | 0 |
| 248 | 4.0 | 1.5 | 0 | 30 | 0 | 0 |
| 249 | 4.0 | 1.5 | 0 | 30 | 0.1 | 0 |
| 250 | 4.0 | 1.5 | 0 | 30 | 0.1 | 1 |
| 251 | 4.0 | 1.5 | 0 | 30 | 0.1 | 0 |
| 252 | 4.0 | 1.5 | 0 | 30 | 0.1 | 0 |
| 253 | 4.0 | 1.5 | 0 | 30 | 0.1 | 10 |
| 254 | 4.0 | 1.5 | 0 | 30 | 0.1 | 0 |
| 255 | 4.0 | 1.5 | 0 | 30 | 0.1 | 0 |
| 256 | 4.0 | 1.5 | 0 | 30 | 0.1 | 100 |
| 257 | 4.0 | 1.5 | 0 | 30 | 0.1 | 0 |
| 258 | 4.0 | 1.5 | 0 | 30 | 0.1 | 0 |
| 259 | 4.0 | 1.5 | 0 | 30 | 2 | 0 |
| 260 | 4.0 | 1.5 | 0 | 30 | 2 | 1 |
| 261 | 4.0 | 1.5 | 0 | 30 | 2 | 0 |
| 262 | 4.0 | 1.5 | 0 | 30 | 2 | 0 |
| 263 | 4.0 | 1.5 | 0 | 30 | 2 | 10 |
| 264 | 4.0 | 1.5 | 0 | 30 | 2 | 0 |
| 265 | 4.0 | 1.5 | 0 | 30 | 2 | 0 |
| 266 | 4.0 | 1.5 | 0 | 30 | 2 | 100 |
| 267 | 4.0 | 1.5 | 0 | 30 | 2 | 0 |
| 268 | 4.0 | 1.5 | 0 | 30 | 2 | 0 |
| 269 | 1.0 | 0 | 150 | 0.0 | 0.0 | 0.0 |
| 270 | 11.0 | 0 | 150 | 0.0 | 0.0 | 0.0 |
| 271 | 2.0 | 0 | 150 | 0.0 | 0.0 | 0.0 |
| 272 | 0.1 | 0 | 25 | 0.0 | 0.0 | 0.0 |
| 273 | 0.1 | 0 | 200 | 0.0 | 0.0 | 0.0 |
| 274 | 11.0 | 0 | 25 | 0.0 | 0.0 | 0.0 |
| 275 | 11.0 | 0 | 200 | 0.0 | 0.0 | 0.0 |
| 276 | 0.1 | 0 | 25 | 0.0 | 2.0 | 0.0 |
| 277 | 0.1 | 0 | 25 | 0.0 | 0.1 | 0.0 |
| 278 | 11.0 | 0 | 200 | 0.0 | 2.0 | 0.0 |
| 279 | 11.0 | 0 | 200 | 0.0 | 0.1 | 0.0 |
| 280 | 0.1 | 0 | 0.0 | 25 | 0.0 | 0.0 |
| 281 | 0.1 | 0 | 0.0 | 200 | 0.0 | 0.0 |
| 282 | 11.0 | 0 | 0.0 | 25 | 0.0 | 0.0 |
| 283 | 11.0 | 0 | 0.0 | 200 | 0.0 | 0.0 |
| 284 | 0.1 | 0 | 0.0 | 25 | 2.0 | 0.0 |
| 285 | 0.1 | 0 | 0.0 | 25 | 0.1 | 0.0 |
| 286 | 11.0 | 0 | 0.0 | 200 | 2.0 | 0.0 |
| 287 | 11.0 | 0 | 0.0 | 200 | 0.1 | 0.0 |
| 288 | 0.1 | 0 | 25 | 0.0 | 0.0 | 0.1 |
| 289 | 0.1 | 0 | 200 | 0.0 | 0.0 | 0.1 |
| 290 | 11.0 | 0 | 25 | 0.0 | 0.0 | 0.1 |
| 291 | 11.0 | 0 | 200 | 0.0 | 0.0 | 0.1 |
| 292 | 0.1 | 0 | 25 | 0.0 | 2.0 | 0.1 |
| 293 | 0.1 | 0 | 25 | 0.0 | 0.1 | 0.1 |
| 294 | 11.0 | 0 | 200 | 0.0 | 2.0 | 0.1 |
| 295 | 11.0 | 0 | 200 | 0.0 | 0.1 | 0.1 |
| 296 | 0.1 | 0 | 0.0 | 25 | 0.0 | 0.1 |

TABLE 30-continued

Exemplary Nintedanib Formulations

| | | | | | | |
|---|---|---|---|---|---|---|
| 297 | 0.1 | 0 | 0.0 | 200 | 0.0 | 0.1 |
| 298 | 11.0 | 0 | 0.0 | 25 | 0.0 | 0.1 |
| 299 | 11.0 | 0 | 0.0 | 200 | 0.0 | 0.1 |
| 300 | 0.1 | 0 | 0.0 | 25 | 2.0 | 0.1 |
| 301 | 0.1 | 0 | 0.0 | 25 | 0.1 | 0.1 |
| 302 | 11.0 | 0 | 0.0 | 200 | 2.0 | 0.1 |
| 303 | 11.0 | 0 | 0.0 | 200 | 0.1 | 0.1 |
| 304 | 0.1 | 0 | 25 | 0.0 | 0.0 | 200 |
| 305 | 0.1 | 0 | 200 | 0.0 | 0.0 | 200 |
| 306 | 11.0 | 0 | 25 | 0.0 | 0.0 | 200 |
| 307 | 11.0 | 0 | 200 | 0.0 | 0.0 | 200 |
| 308 | 0.1 | 0 | 25 | 0.0 | 2.0 | 200 |
| 309 | 0.1 | 0 | 25 | 0.0 | 0.1 | 200 |
| 310 | 11.0 | 0 | 200 | 0.0 | 2.0 | 200 |
| 311 | 11.0 | 0 | 200 | 0.0 | 0.1 | 200 |
| 312 | 0.1 | 0 | 0.0 | 25 | 0.0 | 200 |
| 313 | 0.1 | 0 | 0.0 | 200 | 0.0 | 200 |
| 314 | 11.0 | 0 | 0.0 | 25 | 0.0 | 200 |
| 315 | 11.0 | 0 | 0.0 | 200 | 0.0 | 200 |
| 316 | 0.1 | 0 | 0.0 | 25 | 2.0 | 200 |
| 317 | 0.1 | 0 | 0.0 | 25 | 0.1 | 200 |
| 318 | 11.0 | 0 | 0.0 | 200 | 2.0 | 200 |
| 319 | 11.0 | 0 | 0.0 | 200 | 0.1 | 200 |
| 320 | 0.1 | 0 | 25 | 0.0 | 0.0 | 0.0 |
| 321 | 0.1 | 0 | 200 | 0.0 | 0.0 | 0.0 |
| 322 | 11.0 | 0 | 25 | 0.0 | 0.0 | 0.0 |
| 323 | 11.0 | 0 | 200 | 0.0 | 0.0 | 0.0 |
| 324 | 0.1 | 0 | 25 | 0.0 | 2.0 | 0.0 |
| 325 | 0.1 | 0 | 25 | 0.0 | 0.1 | 0.0 |
| 326 | 11.0 | 0 | 200 | 0.0 | 2.0 | 0.0 |
| 327 | 11.0 | 0 | 200 | 0.0 | 0.1 | 0.0 |
| 328 | 0.1 | 0 | 0.0 | 25 | 0.0 | 0.0 |
| 329 | 0.1 | 0 | 0.0 | 200 | 0.0 | 0.0 |
| 330 | 11.0 | 0 | 0.0 | 25 | 0.0 | 0.0 |
| 331 | 11.0 | 0 | 0.0 | 200 | 0.0 | 0.0 |
| 332 | 0.1 | 0 | 0.0 | 25 | 2.0 | 0.0 |
| 333 | 0.1 | 0 | 0.0 | 25 | 0.1 | 0.0 |
| 334 | 11.0 | 0 | 0.0 | 200 | 2.0 | 0.0 |
| 335 | 11.0 | 0 | 0.0 | 200 | 0.1 | 0.0 |
| 336 | 0.1 | 0 | 25 | 0.0 | 0.0 | 0.0 |
| 337 | 0.1 | 0 | 200 | 0.0 | 0.0 | 0.0 |
| 338 | 11.0 | 0 | 25 | 0.0 | 0.0 | 0.0 |
| 339 | 11.0 | 0 | 200 | 0.0 | 0.0 | 0.0 |
| 340 | 0.1 | 0 | 25 | 0.0 | 2.0 | 0.0 |
| 341 | 0.1 | 0 | 25 | 0.0 | 0.1 | 0.0 |
| 342 | 11.0 | 0 | 200 | 0.0 | 52.0 | 0.0 |
| 343 | 11.0 | 0 | 200 | 0.0 | 0.1 | 0.0 |
| 344 | 0.1 | 0 | 0.0 | 25 | 0.0 | 0.0 |
| 345 | 0.1 | 0 | 0.0 | 200 | 0.0 | 0.0 |
| 346 | 11.0 | 0 | 0.0 | 25 | 0.0 | 0.0 |
| 347 | 11.0 | 0 | 0.0 | 200 | 0.0 | 0.0 |
| 348 | 0.1 | 0 | 0.0 | 25 | 2.0 | 0.0 |
| 349 | 0.1 | 0 | 0.0 | 25 | 0.1 | 0.0 |
| 350 | 11.0 | 0 | 0.0 | 200 | 2.0 | 0.0 |
| 351 | 11.0 | 0 | 0.0 | 200 | 0.1 | 0.0 |
| 352 | 0.1 | 0 | 25 | 0.0 | 0.0 | 0.0 |
| 353 | 0.1 | 0 | 200 | 0.0 | 0.0 | 0.0 |
| 354 | 11.0 | 0 | 25 | 0.0 | 0.0 | 0.0 |
| 355 | 11.0 | 0 | 200 | 0.0 | 0.0 | 0.0 |
| 356 | 0.1 | 0 | 25 | 0.0 | 2.0 | 0.0 |
| 357 | 0.1 | 0 | 25 | 0.0 | 0.1 | 0.0 |
| 358 | 11.0 | 0 | 200 | 0.0 | 2.0 | 0.0 |
| 359 | 11.0 | 0 | 200 | 0.0 | 0.1 | 0.0 |
| 360 | 0.1 | 0 | 0.0 | 25 | 0.0 | 0.0 |
| 361 | 0.1 | 0 | 0.0 | 200 | 0.0 | 0.0 |
| 362 | 11.0 | 0 | 0.0 | 25 | 0.0 | 0.0 |
| 363 | 11.0 | 0 | 0.0 | 200 | 0.0 | 0.0 |
| 364 | 0.1 | 0 | 0.0 | 25 | 2.0 | 0.0 |
| 365 | 0.1 | 0 | 0.0 | 25 | 0.1 | 0.0 |
| 366 | 11.0 | 0 | 0.0 | 200 | 2.0 | 0.0 |
| 367 | 11.0 | 0 | 0.0 | 200 | 0.1 | 0.0 |
| 368 | 0.1 | 0 | 25 | 0.0 | 0.0 | 0.0 |
| 369 | 0.1 | 0 | 200 | 0.0 | 0.0 | 0.0 |
| 370 | 11.0 | 0 | 25 | 0.0 | 0.0 | 0.0 |
| 371 | 11.0 | 0 | 200 | 0.0 | 0.0 | 0.0 |
| 372 | 0.1 | 0 | 25 | 0.0 | 2.0 | 0.0 |
| 373 | 0.1 | 0 | 25 | 0.0 | 0.1 | 0.0 |
| 374 | 11.0 | 0 | 200 | 0.0 | 2.0 | 0.0 |

TABLE 30-continued

Exemplary Nintedanib Formulations

| | | | | | | |
|---|---|---|---|---|---|---|
| 375 | 11.0 | 0 | 200 | 0.0 | 0.1 | 0.0 |
| 376 | 0.1 | 0 | 0 | 25 | 2.0 | 0.0 |
| 377 | 0.1 | 0 | 0 | 25 | 0.1 | 0.0 |
| 378 | 11.0 | 0 | 0 | 200 | 2.0 | 0.0 |
| 379 | 11.0 | 0 | 0 | 200 | 0.1 | 0.0 |
| 380 | 1.5 | 2.0 | 0 | 0 | 0 | 0 |
| 381 | 1.5[b] | 2.0 | 0 | 0 | 0 | 0 |

| Formulation | Glycine Buffer (mM) | Tris Buffer (mM) | Water | Osmolality (mOsmo/kg; +/−200) | pH (+/−3.0) |
|---|---|---|---|---|---|
| 1 | 0 | 0 | q.s. | 300 | 5.0 |
| 2 | 0 | 0 | q.s. | 300 | 5.0 |
| 3 | 0 | 0 | q.s. | 300 | 5.0 |
| 4 | 0 | 0 | q.s. | 300 | 5.0 |
| 5 | 0 | 0 | q.s. | 300 | 5.0 |
| 6 | 0 | 0 | q.s. | 300 | 5.0 |
| 7 | 0 | 0 | q.s. | 300 | 5.0 |
| 8 | 0 | 0 | q.s. | 300 | 5.0 |
| 9 | 1 | 0 | q.s. | 300 | 5.0 |
| 10 | 1 | 0 | q.s. | 300 | 5.0 |
| 11 | 1 | 0 | q.s. | 300 | 5.0 |
| 12 | 1 | 0 | q.s. | 300 | 5.0 |
| 13 | 0 | 1 | q.s. | 300 | 5.0 |
| 14 | 0 | 1 | q.s. | 300 | 5.0 |
| 15 | 0 | 1 | q.s. | 300 | 5.0 |
| 16 | 0 | 1 | q.s. | 300 | 5.0 |
| 17 | 0 | 0 | q.s. | 300 | 5.0 |
| 18 | 0 | 0 | q.s. | 300 | 5.0 |
| 19 | 0 | 0 | q.s. | 300 | 5.0 |
| 20 | 0 | 0 | q.s. | 300 | 5.0 |
| 21 | 10 | 0 | q.s. | 300 | 5.0 |
| 22 | 10 | 0 | q.s. | 300 | 5.0 |
| 23 | 10 | 0 | q.s. | 300 | 5.0 |
| 24 | 10 | 0 | q.s. | 300 | 5.0 |
| 25 | 0 | 10 | q.s. | 300 | 5.0 |
| 26 | 0 | 10 | q.s. | 300 | 5.0 |
| 27 | 0 | 10 | q.s. | 300 | 5.0 |
| 28 | 0 | 10 | q.s. | 300 | 5.0 |
| 29 | 0 | 0 | q.s. | 300 | 5.0 |
| 30 | 0 | 0 | q.s. | 300 | 5.0 |
| 31 | 0 | 0 | q.s. | 300 | 5.0 |
| 32 | 0 | 0 | q.s. | 300 | 5.0 |
| 33 | 100 | 0 | q.s. | 300 | 5.0 |
| 34 | 100 | 0 | q.s. | 300 | 5.0 |
| 35 | 100 | 0 | q.s. | 300 | 5.0 |
| 36 | 100 | 0 | q.s. | 300 | 5.0 |
| 37 | 0 | 100 | q.s. | 300 | 5.0 |
| 38 | 0 | 100 | q.s. | 300 | 5.0 |
| 39 | 0 | 100 | q.s. | 300 | 5.0 |
| 40 | 0 | 100 | q.s. | 300 | 5.0 |
| 41 | 0 | 0 | q.s. | 300 | 5.0 |
| 42 | 0 | 0 | q.s. | 300 | 5.0 |
| 43 | 0 | 0 | q.s. | 300 | 5.0 |
| 44 | 0 | 0 | q.s. | 300 | 5.0 |
| 45 | 0 | 0 | q.s. | 300 | 5.0 |
| 46 | 0 | 0 | q.s. | 300 | 5.0 |
| 47 | 0 | 0 | q.s. | 300 | 5.0 |
| 48 | 0 | 0 | q.s. | 300 | 5.0 |
| 49 | 10 | 0 | q.s. | 300 | 5.0 |
| 50 | 10 | 0 | q.s. | 300 | 5.0 |
| 51 | 0 | 10 | q.s. | 300 | 5.0 |
| 52 | 0 | 10 | q.s. | 300 | 5.0 |
| 53 | 0 | 0 | q.s. | 300 | 5.0 |
| 54 | 0 | 0 | q.s. | 300 | 5.0 |
| 55 | 100 | 0 | q.s. | 300 | 5.0 |
| 56 | 100 | 0 | q.s. | 300 | 5.0 |
| 57 | 0 | 100 | q.s. | 300 | 5.0 |
| 58 | 0 | 100 | q.s. | 300 | 5.0 |
| 59 | 0 | 0 | q.s. | 300 | 5.0 |
| 60 | 0 | 0 | q.s. | 300 | 5.0 |
| 61 | 1 | 0 | q.s. | 300 | 5.0 |
| 62 | 0 | 1 | q.s. | 300 | 5.0 |
| 63 | 0 | 0 | q.s. | 300 | 5.0 |
| 64 | 10 | 0 | q.s. | 300 | 5.0 |
| 65 | 0 | 10 | q.s. | 300 | 5.0 |
| 66 | 0 | 0 | q.s. | 300 | 5.0 |
| 67 | 100 | 0 | q.s. | 300 | 5.0 |

TABLE 30-continued

Exemplary Nintedanib Formulations

| | | | | | |
|---|---|---|---|---|---|
| 68 | 0 | 100 | q.s. | 300 | 5.0 |
| 69 | 0 | 0 | q.s. | 300 | 5.0 |
| 70 | 0 | 0 | q.s. | 300 | 5.0 |
| 71 | 1 | 0 | q.s. | 300 | 5.0 |
| 72 | 0 | 1 | q.s. | 300 | 5.0 |
| 73 | 0 | 0 | q.s. | 300 | 5.0 |
| 74 | 10 | 0 | q.s. | 300 | 5.0 |
| 75 | 0 | 10 | q.s. | 300 | 5.0 |
| 76 | 0 | 0 | q.s. | 300 | 5.0 |
| 77 | 100 | 0 | q.s. | 300 | 5.0 |
| 78 | 0 | 100 | q.s. | 300 | 5.0 |
| 79 | 0 | 0 | q.s. | 300 | 5.0 |
| 80 | 0 | 0 | q.s. | 300 | 5.0 |
| 81 | 1 | 0 | q.s. | 300 | 5.0 |
| 82 | 0 | 1 | q.s. | 300 | 5.0 |
| 83 | 0 | 0 | q.s. | 300 | 5.0 |
| 84 | 10 | 0 | q.s. | 300 | 5.0 |
| 85 | 0 | 10 | q.s. | 300 | 5.0 |
| 86 | 0 | 0 | q.s. | 300 | 5.0 |
| 87 | 100 | 0 | q.s. | 300 | 5.0 |
| 88 | 0 | 100 | q.s. | 300 | 5.0 |
| 89 | 0 | 0 | q.s. | 300 | 5.0 |
| 90 | 0 | 0 | q.s. | 300 | 5.0 |
| 91 | 1 | 0 | q.s. | 300 | 5.0 |
| 92 | 0 | 1 | q.s. | 300 | 5.0 |
| 93 | 0 | 0 | q.s. | 300 | 5.0 |
| 94 | 10 | 0 | q.s. | 300 | 5.0 |
| 95 | 0 | 10 | q.s. | 300 | 5.0 |
| 96 | 0 | 0 | q.s. | 300 | 5.0 |
| 97 | 100 | 0 | q.s. | 300 | 5.0 |
| 98 | 0 | 100 | q.s. | 300 | 5.0 |
| 99 | 0 | 0 | q.s. | 300 | 5.0 |
| 100 | 0 | 0 | q.s. | 300 | 5.0 |
| 101 | 1 | 0 | q.s. | 300 | 5.0 |
| 102 | 0 | 1 | q.s. | 300 | 5.0 |
| 103 | 0 | 0 | q.s. | 300 | 5.0 |
| 104 | 10 | 0 | q.s. | 300 | 5.0 |
| 105 | 0 | 10 | q.s. | 300 | 5.0 |
| 106 | 0 | 0 | q.s. | 300 | 5.0 |
| 107 | 100 | 0 | q.s. | 300 | 5.0 |
| 108 | 0 | 100 | q.s. | 300 | 5.0 |
| 109 | 0 | 0 | q.s. | 300 | 5.0 |
| 110 | 0 | 0 | q.s. | 300 | 5.0 |
| 111 | 1 | 0 | q.s. | 300 | 5.0 |
| 112 | 0 | 1 | q.s. | 300 | 5.0 |
| 113 | 0 | 0 | q.s. | 300 | 5.0 |
| 114 | 10 | 0 | q.s. | 300 | 5.0 |
| 115 | 0 | 10 | q.s. | 300 | 5.0 |
| 116 | 0 | 0 | q.s. | 300 | 5.0 |
| 117 | 100 | 0 | q.s. | 300 | 5.0 |
| 118 | 0 | 100 | q.s. | 300 | 5.0 |
| 119 | 0 | 0 | q.s. | 300 | 5.0 |
| 120 | 0 | 0 | q.s. | 300 | 5.0 |
| 121 | 1 | 0 | q.s. | 300 | 5.0 |
| 122 | 0 | 1 | q.s. | 300 | 5.0 |
| 123 | 0 | 0 | q.s. | 300 | 5.0 |
| 124 | 10 | 0 | q.s. | 300 | 5.0 |
| 125 | 0 | 10 | q.s. | 300 | 5.0 |
| 126 | 0 | 0 | q.s. | 300 | 5.0 |
| 127 | 100 | 0 | q.s. | 300 | 5.0 |
| 128 | 0 | 100 | q.s. | 300 | 5.0 |
| 129 | 0 | 0 | q.s. | 300 | 5.0 |
| 130 | 0 | 0 | q.s. | 300 | 5.0 |
| 131 | 1 | 0 | q.s. | 300 | 5.0 |
| 132 | 0 | 1 | q.s. | 300 | 5.0 |
| 133 | 0 | 0 | q.s. | 300 | 5.0 |
| 134 | 10 | 0 | q.s. | 300 | 5.0 |
| 135 | 0 | 10 | q.s. | 300 | 5.0 |
| 136 | 0 | 0 | q.s. | 300 | 5.0 |
| 137 | 100 | 0 | q.s. | 300 | 5.0 |
| 138 | 0 | 100 | q.s. | 300 | 5.0 |
| 139 | 0 | 0 | q.s. | 300 | 5.0 |
| 140 | 0 | 0 | q.s. | 300 | 5.0 |
| 141 | 1 | 0 | q.s. | 300 | 5.0 |
| 142 | 0 | 1 | q.s. | 300 | 5.0 |
| 142 | 0 | 0 | q.s. | 300 | 5.0 |
| 144 | 10 | 0 | q.s. | 300 | 5.0 |
| 145 | 0 | 10 | q.s. | 300 | 5.0 |

TABLE 30-continued

Exemplary Nintedanib Formulations

| | | | | | |
|---|---|---|---|---|---|
| 146 | 0 | 0 | q.s. | 300 | 5.0 |
| 147 | 100 | 0 | q.s. | 300 | 5.0 |
| 148 | 0 | 100 | q.s. | 300 | 5.0 |
| 149 | 0 | 0 | q.s. | 300 | 5.0 |
| 150 | 0 | 0 | q.s. | 300 | 5.0 |
| 151 | 1 | 0 | q.s. | 300 | 5.0 |
| 152 | 0 | 1 | q.s. | 300 | 5.0 |
| 153 | 0 | 0 | q.s. | 300 | 5.0 |
| 154 | 10 | 0 | q.s. | 300 | 5.0 |
| 155 | 0 | 10 | q.s. | 300 | 5.0 |
| 156 | 0 | 0 | q.s. | 300 | 5.0 |
| 157 | 100 | 0 | q.s. | 300 | 5.0 |
| 158 | 0 | 100 | q.s. | 300 | 5.0 |
| 159 | 0 | 0 | q.s. | 300 | 5.0 |
| 160 | 0 | 0 | q.s. | 300 | 5.0 |
| 161 | 1 | 0 | q.s. | 300 | 5.0 |
| 162 | 0 | 1 | q.s. | 300 | 5.0 |
| 163 | 0 | 0 | q.s. | 300 | 5.0 |
| 164 | 10 | 0 | q.s. | 300 | 5.0 |
| 165 | 0 | 10 | q.s. | 300 | 5.0 |
| 166 | 0 | 0 | q.s. | 300 | 5.0 |
| 167 | 100 | 0 | q.s. | 300 | 5.0 |
| 168 | 0 | 100 | q.s. | 300 | 5.0 |
| 169 | 0 | 0 | q.s. | 300 | 5.0 |
| 170 | 0 | 0 | q.s. | 300 | 5.0 |
| 171 | 1 | 0 | q.s. | 300 | 5.0 |
| 172 | 0 | 1 | q.s. | 300 | 5.0 |
| 173 | 0 | 0 | q.s. | 300 | 5.0 |
| 174 | 10 | 0 | q.s. | 300 | 5.0 |
| 175 | 0 | 10 | q.s. | 300 | 5.0 |
| 176 | 0 | 0 | q.s. | 300 | 5.0 |
| 177 | 100 | 0 | q.s. | 300 | 5.0 |
| 178 | 0 | 100 | q.s. | 300 | 5.0 |
| 179 | 0 | 0 | q.s. | 300 | 5.0 |
| 180 | 0 | 0 | q.s. | 300 | 5.0 |
| 181 | 1 | 0 | q.s. | 300 | 5.0 |
| 182 | 0 | 1 | q.s. | 300 | 5.0 |
| 183 | 0 | 0 | q.s. | 300 | 5.0 |
| 184 | 10 | 0 | q.s. | 300 | 5.0 |
| 185 | 0 | 10 | q.s. | 300 | 5.0 |
| 186 | 0 | 0 | q.s. | 300 | 5.0 |
| 187 | 100 | 0 | q.s. | 300 | 5.0 |
| 188 | 0 | 100 | q.s. | 300 | 5.0 |
| 189 | 0 | 0 | q.s. | 300 | 5.0 |
| 190 | 0 | 0 | q.s. | 300 | 5.0 |
| 191 | 1 | 0 | q.s. | 300 | 5.0 |
| 192 | 0 | 1 | q.s. | 300 | 5.0 |
| 193 | 0 | 0 | q.s. | 300 | 5.0 |
| 194 | 10 | 0 | q.s. | 300 | 5.0 |
| 195 | 0 | 10 | q.s. | 300 | 5.0 |
| 196 | 0 | 0 | q.s. | 300 | 5.0 |
| 197 | 100 | 0 | q.s. | 300 | 5.0 |
| 198 | 0 | 100 | q.s. | 300 | 5.0 |
| 199 | 0 | 0 | q.s. | 300 | 5.0 |
| 200 | 0 | 0 | q.s. | 300 | 5.0 |
| 201 | 1 | 0 | q.s. | 300 | 5.0 |
| 202 | 0 | 1 | q.s. | 300 | 5.0 |
| 203 | 0 | 0 | q.s. | 300 | 5.0 |
| 204 | 10 | 0 | q.s. | 300 | 5.0 |
| 205 | 0 | 10 | q.s. | 300 | 5.0 |
| 206 | 0 | 0 | q.s. | 300 | 5.0 |
| 207 | 100 | 0 | q.s. | 300 | 5.0 |
| 208 | 0 | 100 | q.s. | 300 | 5.0 |
| 209 | 0 | 0 | q.s. | 300 | 5.0 |
| 210 | 0 | 0 | q.s. | 300 | 5.0 |
| 211 | 1 | 0 | q.s. | 300 | 5.0 |
| 212 | 0 | 1 | q.s. | 300 | 5.0 |
| 213 | 0 | 0 | q.s. | 300 | 5.0 |
| 214 | 10 | 0 | q.s. | 300 | 5.0 |
| 215 | 0 | 10 | q.s. | 300 | 5.0 |
| 216 | 0 | 0 | q.s. | 300 | 5.0 |
| 217 | 100 | 0 | q.s. | 300 | 5.0 |
| 218 | 0 | 100 | q.s. | 300 | 5.0 |
| 219 | 0 | 0 | q.s. | 300 | 5.0 |
| 220 | 0 | 0 | q.s. | 300 | 5.0 |
| 221 | 1 | 0 | q.s. | 300 | 5.0 |
| 222 | 0 | 1 | q.s. | 300 | 5.0 |
| 223 | 0 | 0 | q.s. | 300 | 5.0 |

TABLE 30-continued

| Exemplary Nintedanib Formulations | | | | | |
|---|---|---|---|---|---|
| 224 | 10 | 0 | q.s. | 300 | 5.0 |
| 225 | 0 | 10 | q.s. | 300 | 5.0 |
| 226 | 0 | 0 | q.s. | 300 | 5.0 |
| 227 | 100 | 0 | q.s. | 300 | 5.0 |
| 228 | 0 | 100 | q.s. | 300 | 5.0 |
| 229 | 0 | 0 | q.s. | 300 | 5.0 |
| 230 | 0 | 0 | q.s. | 300 | 5.0 |
| 231 | 1 | 0 | q.s. | 300 | 5.0 |
| 232 | 0 | 1 | q.s. | 300 | 5.0 |
| 233 | 0 | 0 | q.s. | 300 | 5.0 |
| 234 | 10 | 0 | q.s. | 300 | 5.0 |
| 235 | 0 | 10 | q.s. | 300 | 5.0 |
| 236 | 0 | 0 | q.s. | 300 | 5.0 |
| 237 | 100 | 0 | q.s. | 300 | 5.0 |
| 238 | 0 | 100 | q.s. | 300 | 5.0 |
| 239 | 0 | 0 | q.s. | 300 | 5.0 |
| 240 | 0 | 0 | q.s. | 300 | 5.0 |
| 241 | 1 | 0 | q.s. | 300 | 5.0 |
| 242 | 0 | 1 | q.s. | 300 | 5.0 |
| 243 | 0 | 0 | q.s. | 300 | 5.0 |
| 244 | 10 | 0 | q.s. | 300 | 5.0 |
| 245 | 0 | 10 | q.s. | 300 | 5.0 |
| 246 | 0 | 0 | q.s. | 300 | 5.0 |
| 247 | 100 | 0 | q.s. | 300 | 5.0 |
| 248 | 0 | 100 | q.s. | 300 | 5.0 |
| 249 | 0 | 0 | q.s. | 300 | 5.0 |
| 250 | 0 | 0 | q.s. | 300 | 5.0 |
| 251 | 1 | 0 | q.s. | 300 | 5.0 |
| 252 | 0 | 1 | q.s. | 300 | 5.0 |
| 253 | 0 | 0 | q.s. | 300 | 5.0 |
| 254 | 10 | 0 | q.s. | 300 | 5.0 |
| 255 | 0 | 10 | q.s. | 300 | 5.0 |
| 256 | 0 | 0 | q.s. | 300 | 5.0 |
| 257 | 100 | 0 | q.s. | 300 | 5.0 |
| 258 | 0 | 100 | q.s. | 300 | 5.0 |
| 259 | 0 | 0 | q.s. | 300 | 5.0 |
| 260 | 0 | 0 | q.s. | 300 | 5.0 |
| 261 | 1 | 0 | q.s. | 300 | 5.0 |
| 262 | 0 | 1 | q.s. | 300 | 5.0 |
| 263 | 0 | 0 | q.s. | 300 | 5.0 |
| 264 | 10 | 0 | q.s. | 300 | 5.0 |
| 265 | 0 | 10 | q.s. | 300 | 5.0 |
| 266 | 0 | 0 | q.s. | 300 | 5.0 |
| 267 | 100 | 0 | q.s. | 300 | 5.0 |
| 268 | 0 | 100 | q.s. | 300 | 5.0 |
| 269 | 0.0 | 0.0 | q.s. | 300 | 5.0 |
| 270 | 0.0 | 0.0 | q.s. | 300 | 5.0 |
| 271 | 0.0 | 0.0 | q.s. | 300 | 5.0 |
| 272 | 0.0 | 0.0 | q.s. | 300 | 5.0 |
| 273 | 0.0 | 0.0 | q.s. | 300 | 5.0 |
| 274 | 0.0 | 0.0 | q.s. | 300 | 5.0 |
| 275 | 0.0 | 0.0 | q.s. | 300 | 5.0 |
| 276 | 0.0 | 0.0 | q.s. | 300 | 5.0 |
| 277 | 0.0 | 0.0 | q.s. | 300 | 5.0 |
| 278 | 0.0 | 0.0 | q.s. | 300 | 5.0 |
| 279 | 0.0 | 0.0 | q.s. | 300 | 5.0 |
| 280 | 0.0 | 0.0 | q.s. | 300 | 5.0 |
| 281 | 0.0 | 0.0 | q.s. | 300 | 5.0 |
| 282 | 0.0 | 0.0 | q.s. | 300 | 5.0 |
| 283 | 0.0 | 0.0 | q.s. | 300 | 5.0 |
| 284 | 0.0 | 0.0 | q.s. | 300 | 5.0 |
| 285 | 0.0 | 0.0 | q.s. | 300 | 5.0 |
| 286 | 0.0 | 0.0 | q.s. | 300 | 5.0 |
| 287 | 0.0 | 0.0 | q.s. | 300 | 5.0 |
| 288 | 0.0 | 0.0 | q.s. | 300 | 5.0 |
| 289 | 0.0 | 0.0 | q.s. | 300 | 5.0 |
| 290 | 0.0 | 0.0 | q.s. | 300 | 5.0 |
| 291 | 0.0 | 0.0 | q.s. | 300 | 5.0 |
| 292 | 0.0 | 0.0 | q.s. | 300 | 5.0 |
| 293 | 0.0 | 0.0 | q.s. | 300 | 5.0 |
| 294 | 0.0 | 0.0 | q.s. | 300 | 5.0 |
| 295 | 0.0 | 0.0 | q.s. | 300 | 5.0 |
| 296 | 0.0 | 0.0 | q.s. | 300 | 5.0 |
| 297 | 0.0 | 0.0 | q.s. | 300 | 5.0 |
| 298 | 0.0 | 0.0 | q.s. | 300 | 5.0 |
| 299 | 0.0 | 0.0 | q.s. | 300 | 5.0 |
| 300 | 0.0 | 0.0 | q.s. | 300 | 5.0 |
| 301 | 0.0 | 0.0 | q.s. | 300 | 5.0 |

TABLE 30-continued

Exemplary Nintedanib Formulations

| | | | | | |
|---|---|---|---|---|---|
| 302 | 0.0 | 0.0 | q.s. | 300 | 5.0 |
| 303 | 0.0 | 0.0 | q.s. | 300 | 5.0 |
| 304 | 0.0 | 0.0 | q.s. | 300 | 5.0 |
| 305 | 0.0 | 0.0 | q.s. | 500 | 5.0 |
| 306 | 0.0 | 0.0 | q.s. | 300 | 5.0 |
| 307 | 0.0 | 0.0 | q.s. | 500 | 5.0 |
| 308 | 0.0 | 0.0 | q.s. | 300 | 5.0 |
| 309 | 0.0 | 0.0 | q.s. | 300 | 5.0 |
| 310 | 0.0 | 0.0 | q.s. | 500 | 5.0 |
| 311 | 0.0 | 0.0 | q.s. | 500 | 5.0 |
| 312 | 0.0 | 0.0 | q.s. | 300 | 5.0 |
| 313 | 0.0 | 0.0 | q.s. | 500 | 5.0 |
| 314 | 0.0 | 0.0 | q.s. | 300 | 5.0 |
| 315 | 0.0 | 0.0 | q.s. | 500 | 5.0 |
| 316 | 0.0 | 0.0 | q.s. | 300 | 5.0 |
| 317 | 0.0 | 0.0 | q.s. | 300 | 5.0 |
| 318 | 0.0 | 0.0 | q.s. | 500 | 5.0 |
| 319 | 0.0 | 0.0 | q.s. | 500 | 5.0 |
| 320 | 0.1 | 0.0 | q.s. | 300 | 6.5 |
| 321 | 0.1 | 0.0 | q.s. | 300 | 6.5 |
| 322 | 0.1 | 0.0 | q.s. | 300 | 6.5 |
| 323 | 0.1 | 0.0 | q.s. | 300 | 6.5 |
| 324 | 0.1 | 0.0 | q.s. | 300 | 6.5 |
| 325 | 0.1 | 0.0 | q.s. | 300 | 6.5 |
| 326 | 0.1 | 0.0 | q.s. | 300 | 6.5 |
| 327 | 0.1 | 0.0 | q.s. | 300 | 6.5 |
| 328 | 0.1 | 0.0 | q.s. | 300 | 6.5 |
| 329 | 0.1 | 0.0 | q.s. | 300 | 6.5 |
| 330 | 0.1 | 0.0 | q.s. | 300 | 6.5 |
| 331 | 0.1 | 0.0 | q.s. | 300 | 6.5 |
| 332 | 0.1 | 0.0 | q.s. | 300 | 6.5 |
| 333 | 0.1 | 0.0 | q.s. | 300 | 6.5 |
| 334 | 0.1 | 0.0 | q.s. | 300 | 6.5 |
| 335 | 0.1 | 0.0 | q.s. | 300 | 6.5 |
| 336 | 200 | 0.0 | q.s. | 300 | 6.5 |
| 337 | 200 | 0.0 | q.s. | 500 | 6.5 |
| 338 | 200 | 0.0 | q.s. | 300 | 6.5 |
| 339 | 200 | 0.0 | q.s. | 500 | 6.5 |
| 340 | 200 | 0.0 | q.s. | 300 | 6.5 |
| 341 | 200 | 0.0 | q.s. | 300 | 6.5 |
| 342 | 200 | 0.0 | q.s. | 500 | 6.5 |
| 343 | 200 | 0.0 | q.s. | 500 | 6.5 |
| 344 | 200 | 0.0 | q.s. | 300 | 6.5 |
| 345 | 200 | 0.0 | q.s. | 500 | 6.5 |
| 346 | 200 | 0.0 | q.s. | 300 | 6.5 |
| 347 | 200 | 0.0 | q.s. | 500 | 6.5 |
| 348 | 200 | 0.0 | q.s. | 300 | 6.5 |
| 349 | 200 | 0.0 | q.s. | 300 | 6.5 |
| 350 | 200 | 0.0 | q.s. | 500 | 6.5 |
| 351 | 200 | 0.0 | q.s. | 500 | 6.5 |
| 352 | 0.0 | 0.1 | q.s. | 300 | 5.0 |
| 353 | 0.0 | 0.1 | q.s. | 300 | 5.0 |
| 354 | 0.0 | 0.1 | q.s. | 300 | 5.0 |
| 355 | 0.0 | 0.1 | q.s. | 300 | 5.0 |
| 356 | 0.0 | 0.1 | q.s. | 300 | 5.0 |
| 357 | 0.0 | 0.1 | q.s. | 300 | 5.0 |
| 358 | 0.0 | 0.1 | q.s. | 300 | 5.0 |
| 359 | 0.0 | 0.1 | q.s. | 300 | 5.0 |
| 360 | 0.0 | 0.1 | q.s. | 300 | 5.0 |
| 361 | 0.0 | 0.1 | q.s. | 300 | 5.0 |
| 362 | 0.0 | 0.1 | q.s. | 300 | 5.0 |
| 363 | 0.0 | 0.1 | q.s. | 300 | 5.0 |
| 364 | 0.0 | 0.1 | q.s. | 300 | 5.0 |
| 365 | 0.0 | 0.1 | q.s. | 300 | 5.0 |
| 366 | 0.0 | 0.1 | q.s. | 300 | 5.0 |
| 367 | 0.0 | 0.1 | q.s. | 300 | 5.0 |
| 368 | 0.0 | 200 | q.s. | 300 | 5.0 |
| 369 | 0.0 | 200 | q.s. | 500 | 5.0 |
| 370 | 0.0 | 200 | q.s. | 300 | 5.0 |
| 371 | 0.0 | 200 | q.s. | 500 | 5.0 |
| 372 | 0.0 | 200 | q.s. | 300 | 5.0 |
| 373 | 0.0 | 200 | q.s. | 300 | 5.0 |
| 374 | 0.0 | 200 | q.s. | 500 | 5.0 |
| 375 | 0.0 | 200 | q.s. | 500 | 5.0 |
| 376 | 0.0 | 200 | q.s. | 300 | 5.0 |
| 377 | 0.0 | 200 | q.s. | 300 | 5.0 |
| 378 | 0.0 | 200 | q.s. | 500 | 5.0 |
| 379 | 0.0 | 200 | q.s. | 500 | 5.0 |

TABLE 30-continued

| Exemplary Nintedanib Formulations | | | | | |
|---|---|---|---|---|---|
| 380 | 0 | 0 | q.s. | 300 | 5.0 |
| 381 | 0 | 0 | q.s. | 300 | 5.0 |

[a]Nintedanib salt is any salt form described herein. Values in milligram/milliliter nintedanib
[b]Also contains 12.5 mg/mL pirfenidone

Example 5. Nintedanib Liquid Formulations

The objective of these studies was to determine the feasibility of formulating a standalone nintedanib esylate formulation and a fixed dose nintedanib esylate/pirfenidone combination formulation for nebulization with the following requirements:

Adequate long-term stability and shelf life (≥2 years at room temperature
Suitable for oral inhalation:
Acceptable taste Comprised of at least 30 mM of permeant ion (chloride or bromide ions)
Formulated to an osmolality in the range of 50 mOsm/kg-600 mOsm/kg
pH 3-7.0

Formulation screening of stand alone nintedanib esylate and in combination with pirfenidone were conducted. Commonly used ionic osmolality adjusting agents include sodium chloride, sodium citrate, magnesium chloride were evaluated as excipients. In addition, mannitol and propylene glycol, which are ionic osmolality adjusting agents, were also tested.

Nintedanib esylate was dissolved in water to either 1.5 mg/mL or 3.0 mg/mL concentration, to which other excipients were added. The resulting solutions, if not immediately precipitated, were filled into clear Type I glass vials and sealed with a Teflon lined rubber stopper and aluminum crimp cap. The test solutions were stored at ambient room condition in the dark. Visual appearance was periodically assessed within 24 hours and periodically thereafter. Table 31 summarizes the initial formulation screening results.

TABLE 31

Compatibility Assessment of Nintedanib Esylate with Pirfenidone and Various Osmolality Adjusting Agents

| Solution ID | Nintedanib Esylate (mg/mL) | Pirfenidone (mg/mL) | NaCl (mM) | Sodium Citrate (mM) | MgCl$_2$ (mM) | Nonionic osmol adjusting agent % w/w | Osmolality (mOsm/kg) | pH | Observation |
|---|---|---|---|---|---|---|---|---|---|
| 101-01-10-01 | 1.5 | 0 | 60 | 0 | 0 | 0 | 120 | NT | Light precip after dissolution |
| 101-01-10-02 | 1.5 | 12.5 | 60 | 0 | 0 | 0 | 182 | NT | Precip after dissolution |
| 101-01-11-03 | 1.5 | 0 | 30 | 0 | 0 | 1 (mannitol) | 125 | 4.75 | Viscous, precip w/in24 hrs |
| 101-01-11-04 | 3.0 | 0 | 30 | 0 | 0 | 1 (mannitol) | 127 | 4.58 | Viscous, precip w/in 24 hrs |
| 101-01-12-01 | 3.0 | 12.5 | 30 | 0 | 0 | 1 (mannitol) | 186 | 4.56 | NO precip thru 4 months RT[b] |
| 101-01-07-03 | 3.0 | 12.5 | 0 | 4.5 | 0 | 0 | NT[a] | NT | Precip upon NaCit addition |
| 101-01-08-03 | 3.0 | 12.5 | 30 | 0 | 0 | 0 | 125 | 4.51 | Precip w/in24 hrs |
| 101-01-08-04 | 3.0 | 12.5 | 60 | N/A | N/A | N/A | NT | NT | Precip upon addition NaCl |
| 101-01-12-02 | 3.0 | N/A | N/A | N/A | 50 | N/A | 144 | NT | Viscous, precip w/in 24 hrs |
| 101-01-12-03 | 3.0 | N/A | N/A | N/A | 100 | N/A | 271 | 4.75 | Viscous, precip w/in 24 hrs |
| 101-01-13-01 | 3.0 | 12.5 | N/A | N/A | 50 | N/A | NT | NT | Precip upon addition MgCl$_2$ |
| 101-01-13-02 | 1.5 | 12.5 | N/A | N/A | 25 | N/A | 133 | NT | Viscous, precip w/in 24 hrs |
| 101-01-13-03 | 1.5 | 12.5 | N/A | N/A | 37.5 | N/A | 166 | 4.90 | Viscous, precip w/in 24 hrs |

TABLE 31-continued

Compatibility Assessment of Nintedanib Esylate with Pirfenidone and Various Osmolality Adjusting Agents

| Solution ID | Nintedanib Esylate (mg/mL) | Pirfenidone (mg/mL) | NaCl (mM) | Sodium Citrate (mM) | $MgCl_2$ (mM) | Nonionic osmol adjusting agent % w/w | Osmolality (mOsm/kg) | pH | Observation |
|---|---|---|---|---|---|---|---|---|---|
| 101-01-13-04 | 1.5 | 12.5 | N/A | N/A | 50 | N/A | 200 | NT | Viscous, precip w/in 24 hrs |
| 101-01-13-05 | 1.5 | N/A | 30 | N/A | 50 | 1.5 (propylene glycol) | 268 | 4.87 | Viscous, precip w/in 24 hrs |
| 101-01-14-01 | 1.5 | 12.5 | 30 | N/A | N/A | 1.5 (propylene glycol) | 328 | 4.93 | NO precip thru 4 months RT |

NT: not tested;
[b]RT: Room temperature

Key findings from formulation screening study: Nintedanib esylate is incompatible with sodium citrate because nintedanib esylate precipitated immediately after the addition of sodium citrate (Formulation 101-01-07-03). Nintedanib esylate is incompatible with sodium chloride at 60 mM or higher as nintedanib esylate precipitated shortly after adding sodium chloride (Formulations 10-01, 10-02 and 08-04). Nintedanib esylate may be compatible with sodium chloride at 30 mM as two formulations containing NaCl at this concentration did not precipitate (even after 4 months) and those precipitated did not occur immediately after the addition of NaCl. Formulations 101-01-12-01 and 101-01-14-01, both of which are nintedanib esylate/pirfenidone combination formulations that contain a nonionic excipient, remained clear yellow solution did not precipitate (remained in solution for at least 4 months).

Out of the 16 formulations screened, only two formulations both of which contain nintedanib esylate and pirfenidone are physically stable. At the time this study was carried out, it was not initially clear why: (1) the standalone nintedanib esylate formulation (101-01-11-04 and 101-01-13-05) precipitated while the combination nintedanib esylate/pirfenidone formulation 101-01-12-01 and 101-01-14-01 (which have similar composition as the respective standalone nintedanib esylate formulations) remained stable, and (2) why not all nintedanib esylate/pirfenidone combination formulations are stable (e.g. 101-01-08-03).

Therefore, a three-tier drug-excipient compatibility study was conducted to gain insights into the compatibility of nintedanib esylate with various excipients: Tier 1: compatibility of nintedanib esylate with one excipient (nintedanib esylate+excipient). Tier 2: compatibility of nintedanib esylate and pirfenidone with one excipient (nintedanib esylate+pirfenidone+excipient). Tier 3: compatibility of standalone nintedanib esylate or in combination with pirfenidone in 30 mM NaCl with one other osmolality adjusting agent (nintedanib esylate+30 mM NaCl+excipient or nintedanib esylate+pirfenidone+30 mM NaCl+excipient)

Tier 1: Nintedanib Esylate-Excipient Compatibility Study. Except where noted, all test solutions were formulated with 1.5 mg/mL nintedanib esylate. The concentrations of excipients are shown in Table 32. Test solution 101-01-16-00 was filtered through a 0.22 micron PVDF filter, all other formulations were not filtered. The test solutions were filled into 10 mL clear Type I glass vials and sealed with Teflon-lined rubber stopper and aluminum crimp cap.

TABLE 32

Compatibility of Nintedanib Esylate with NaCl, $MgCl_2$, mannitol, Propylene Glycol, Ethanol, sodium citrate and pirfenidone

| Solution Composition | Solution ID | Initial Appearance | Stability |
|---|---|---|---|
| Nintedanib esylate Control | 101-01-15-00 (control) | Clear yellow solution | Precipitated w/in 2 hours, precipitation initiated on the wall of glass vial |
| Filtered nintedanib esylate Control (via 0.22 μm pvdf filter) | 101-01-16-00 | Precip formed after filtration | Precipitated immediately after filtration |
| Nintedanib esylate + 30 mM NaCl | 101-01-15-01 | Clear yellow viscous | Precipitated overnight |
| Nintedanib esylate + 45 mM NaCl | 101-01-15-02 | Clear yellow viscous | Precipitated overnight |
| Nintedanib esylate + 25 mM $MgCl_2$ | 101-01-15-03 | Clear yellow viscous | Precipitated overnight |
| Nintedanib esylate + 1% Mannitol | 101-01-15-04 | Clear yellow solution | No precipitation thru 4 months |
| Nintedanib esylate + 1.5% propylene glycol | 101-01-15-05 | Clear yellow solution | Light precip overnight |

TABLE 32-continued

Compatibility of Nintedanib Esylate with NaCl, MgCl$_2$, mannitol, Propylene Glycol, Ethanol, sodium citrate and pirfenidone

| Solution Composition | Solution ID | Initial Appearance | Stability |
|---|---|---|---|
| Nintedanib esylate + 1% EtOH | 101-01-15-06 | Clear yellow solution | Light precip overnight |
| Nintedanib esylate + 4.5 mM sodium citrate | 101-01-15-07 | Precipitation formed immediately | Heavy precipitation formed immediately |
| Nintedanib esylate + 12.5 mg/mL pirfenidone | 101-01-15-08 | Clear yellow solution | No precipitation thru 4 months |
| 3 mg/mL nintedanib esylate + 12.5 mg/mL pirfenidone | 101-01-15-09 | Clear yellow solution | No precipitation thru 4 months |

Key findings: Nintedanib esylate control solution 101-01-05-01 precipitated in clear borosilicate glass vials. Precipitation was first observed on the wall of the glass vial, indicating nintedanib esylate is not compatible with clear borosilicate glass vial. Nintedanib esylate control solution 101-01-05-01 filtered through 0.22 μm pvdf filter precipitated immediately filtration, forming a milky yellowish green suspension. This shows that nintedanib esylate is not compatible with PVDF membrane filter. Nintedanib esylate solutions containing pirfenidone (101-01-15-08 and -09) remains in solution form through 4 months at room temperature, reconfirming pirfenidone has a stabilizing effect on nintedanib esylate. Mannitol and to some extent, propylene glycol and ethanol also have a stabilizing effect on nintedanib esylate.

Tier 2: Nintedanib-Pirfenidone-Excipient Compatibility Study. Except where noted, all formulations were formulated with 1.5 mg/mL nintedanib esylate and 12.5 mg/mL pirfenidone. The concentrations of the excipients used are shown in Table 33. Except formulation 101-01-16-02 where it was filtered through a 0.22 micron PVDF filter, all other formulations were not filtered. All formulations were stored in a 10 mL clear Type I glass vial sealed with Teflon-lined rubber stopper and aluminum crimp cap.

TABLE 33

Compatibility of nintedanib esylate, pirfenidone and an excipient in a three-component solution

| Formulation ID | Composition | Formulation Appearance | Stability |
|---|---|---|---|
| 101-01-16-01 | Nintedanib esylate + pirfenidone control | Clear yellow solution | No precipitation thru 4 months |
| 101-01-16-02 | Filtered Nintedanib esylate + pirfenidone control (via 0.22 μm pvdf filter) | Light precip observed within 2 hours | Precipitated within 2 hours after preparation |
| 101-01-16-03 | Nintedanib esylate + pirfenidone control + 30 mM NaCl | Clear yellow solution | Crystals observed on glass vial wall after 1 month |
| 101-01-16-04 | Nintedanib esylate + pirfenidone control + 45 mM NaCl | Clear yellow solution | Precipitated within 2 days |
| 101-01-16-05 | Nintedanib esylate + pirfenidone control + 25 mM MgCl$_2$ | Clear yellow solution | Crystals observed on glass wall after one month |
| 101-01-16-06 | Nintedanib esylate + pirfenidone control + 1% mannitol | Clear yellow solution | No precipitation thru 4 months |
| 101-01-16-07 | Nintedanib esylate + pirfenidone control + 1.5% propylene glycol | Clear yellow solution | No precipitation thru 4 months |
| 101-01-16-08 | Nintedanib esylate + pirfenidone control + 1% ethanol | Clear yellow solution | No precipitation thru 4 months |

Key findings: The nintedanib esylate plus pirfenidone control solution 101-01-16-01 is free of precipitates through 4 months, confirming that pirfenidone has a stabilizing effect on nintedanib esylate in solution. Nintedanib esylate is incompatible with PVDF filter (101-01-16-02), even in the presence of pirfenidone, confirming observation made in Tier 1 testing. Mannitol, propylene glycol and ethanol do not adversely effect nintedanib stability (101-01-16-06 through -08)

Tier 3: Compatibility of nintedanib esylate and nintedanib esylate plus pirfenidone control with sodium chloride and a second excipient was assessed. Specifically, the compatibility of nintedanib esylate and nintedanib esylate plus pirfenidone with sodium chloride at 30 mM and with another excipient was evaluated at the minimum concentration of 30 mM (to provide adequate permeant ion concentration to the airway to attain acceptable tolerability). A second excipient (mannitol, propylene glycol, ethanol) was used to adjust the osmolality to an acceptable range (200-400 mOsm/kg). nintedanib esylate was tested 1.5 mg/mL, and pirfenidone, where applicable, was at 12.5 mg/mL. The test solutions were filled into 10 mL clear Type I glass vials with Teflon lined rubber stopper and aluminum crimp caps and stored at ambient room condition away from light. Results are shown in Table 34.

fenidone, can stabilize nintedanib esylate formulated in 30 mM sodium chloride solution (101-01-17-07 and -08).

Compatibility of Nintedanib Esylate with Container System and Type of Membrane Filter: The objective of this study is to determine the suitability of low density polyethylene (LDPE) vials and nylon filters for use with nintedanib esylate standalone and nintedanib esylate plus pirfenidone combination formulations. The compositions of the test solutions, filtration process and type of container used are

TABLE 34

Combability of nintedanib esylate (1.5 mg/mL) and nintedanib esylate (1.5 mg/mL) plus pirfenidone (12.5 mg/mL) in 30 mM NaCl with a second excipient

| Composition | Form ID | Initial Appearance | Stability |
|---|---|---|---|
| Nintedanib esylate + 30 mM NaCl + 1% mannitol | 101-01-17-02 | Clear yellow viscous | Precipitation within 24 hours |
| Nintedanib esylate + 30 mM NaCl + 1.5% propylene glycol | 101-01-17-03 | Clear yellow viscous | Precipitation within 24 hours |
| Nintedanib esylate + 30 mM NaCl + 1% ethanol | 101-01-17-04 | Clear yellow viscous | Precipitation within 24 hours |
| Nintedanib esylate + pirfenidone + 30 mM NaCl + 1% mannitol | 101-01-17-06 | Clear yellow solution | Crystals observed on wall of glass vial after one month |
| Nintedanib esylate + pirfenidone + 30 mM NaCl + 1.5% propylene glycol | 101-01-17-07 | Clear yellow solution | No precipitation thru 4 months |
| Nintedanib esylate + pirfenidone + 30 mM NaCl + 1% ethanol | 101-01-17-08 | Clear yellow solution | No precipitation thru 4 months |

Key findings: Nintedanib esylate by itself is not stable in 30 mM NaCl (101-01-17-02 through -06). Pirfenidone, in combination with either propylene glycol or ethanol, pirfenidone, can stabilize nintedanib esylate formulated in 30 mM sodium chloride solution (101-01-17-07 and -08).

listed in Table 35. The test samples were stored at ambient room condition and periodically check for precipitation or crystallization.

TABLE 35

Compatibility assessment of nintedanib esylate solutions with nylon filter and LDPE vials

| Composition | Form ID | Container Type | Filtration | Stability |
|---|---|---|---|---|
| Nintedanib esylate 0.5 mg/mL | 101-01-23-03 | Clear glass vial | Not filtered | Precipitated after 5 minutes |
| | 101-01-23-04 | Clear glass vial | Nylon filtered | Precipitated after 5 minutes |
| | 101-01-24-01 | LDPE vial | Not filtered | No precipitation through 4 months |
| | 101-01-24-02 | Amber Type I glass vial | Not filtered | No precipitation through 4 months |
| Nintedanib esylate 1.5 mg/mL | 101-01-24-05 | LDPE vial | Not filtered | No precipitation through 4 months |
| | 101-01-24-06 | LDPE vial | Nylon filter | No precipitation through 4 months |
| Nintedanib esylate 1.5 mg/mL + 1.5% propylene glycol | 101-01-27-02 | LDPE vial | Not filtered | No precipitation through 4 months |
| | 101-01-27-03 | LDPE vial | Nylon filter | No precipitation through 4 months |
| Nintedanib esylate + 30 mM NaCl | 101-01-21-01 | Clear glass vial | Not filtered | Precipitated overnight |
| | 101-01-21-02 | LDPE vial | Not filtered | Precipitated overnight |
| | 101-01-21-03 | Clear glass vial | Nylon filtered | Precipitated overnight |
| | 101-01-21-04 | LDPE vial | Nylon filtered | Precipitated overnight |

TABLE 35-continued

Compatibility assessment of nintedanib esylate solutions with nylon filter and LDPE vials

| Composition | Form ID | Container Type | Filtration | Stability |
|---|---|---|---|---|
| Nintedanib esylate + 30 mM NaBr | 101-01-23-01 | LDPE vial | Not filtered | Precipitated overnight |
| Nintedanib esylate + 30 mM + 1.5% propylene glycol | 101-01-21-05 | Glass vial | Not filtered | Precipitated overnight |
| | 101-01-21-06 | LDPE vial | Not filtered | Precipitated overnight |
| | 101-01-27-03 | | | |
| Nintedanib esylate + pirfenidone + 30 mM NaCl + 1.5% propylene glycol | 101-01-22-01 | Glass vial | Not filtered | No precipitation through 3 months |
| | 101-01-22-02 | LDPE vial | Not filtered | No precipitation through 3 months |
| | 101-01-22-03 | Glass vial | Nylon filtered | No precipitation through 3 months |
| | 101-01-22-04 | LDPE vial | Nylon filtered | No precipitation through 3 months |

Key findings: Clear borosilicate glass vial is not suitable for use with nintedanib esylate, even at low nintedanib esylate concentration of 0.5 mg/mL (101-01-23-03 and -04). LDPE vial is suitable for use with nintedanib esylate and with nintedanib esylate in 1.5% propylene glycol solutions (101-01-24-05 and -05, 101-01-27-02 and -03). Nintedanib esylate, in absence of pirfenidone, is incompatible with NaCl (at 30 mM), irrespective of container type and filtration material used (101-01-21-01 through -04, 101-21-05 and -06, 101-01-27-03). Pirfenidone, in combination with propylene glycol, stabilized nintedanib esylate in 30 mM NaCl solution. This formulation can be filled in both glass and plastic vials (101-01-22-01 through -04).

HBr and HCl salts-filter compatibility study: this study was conducted to assess the compatibility of the HBr and the HCl salts with various membrane filters. The Nintedanib salts were dissolved in 3% PG solution then filtered through 0.22 μm membrane filters of either nylon, polyester, polytetrafluoroethylene (PTFE) or polyvinylidene fluoride (PVDF) into a clear borosilicate glass vials. The glass vials were stored at ambient room condition and visual appearance was periodically inspected. Table 36 shows the visual appearance of the test samples at various time points. The HCl sample filtered through the nylon filter and nintedanib HBr filtered through both nylon and PTFE filters exhibited no change in appearance through 1 month. The HCl and HBr samples filtered through the PES showed light precipitation after 2 weeks at ambient room condition. Samples of both salts filtered through the PVDF filters precipitated shortly after filtration, with the HCl salt precipitated more heavily.

TABLE 36

HCl and HBr Salts - Filter Compatibility at Ambient Room Condition

| Filter | Initial | 1 week | 2 weeks | 1 month |
|---|---|---|---|---|
| Nintedanib HBr salt | | | | |
| Nylon | Clear yellow solution | Clear yellow solution | Clear yellow solution | Clear yellow solution |
| Polyester | Clear yellow solution | Clear yellow solution | Light precipitation | Light precipitation |
| PTFE | Clear yellow solution | Clear yellow solution | Clear yellow solution | Clear yellow solution |
| PVFD | Light precipitation | Light precipitation | Light precipitation | Light precipitation |

TABLE 36-continued

HCl and HBr Salts - Filter Compatibility at Ambient Room Condition

| Filter | Initial | 1 week | 2 weeks | 1 month |
|---|---|---|---|---|
| Nintedanib HCl Salt | | | | |
| Nylon | Clear yellow solution | Clear yellow solution | Clear yellow solution | Clear yellow solution |
| Polyester | Clear yellow solution | Light precipitation | Light precipitation | Light precipitation |
| PTFE | Clear yellow solution | Precipitation | Precipitation | Precipitation |
| PVFD | Precipitation | Precipitation | Precipitation | Precipitation |

Key findings: Both HBr and HCl salts are compatible with nylon filter, HBr salt is also compatible with PTFE, filters. All other filters tested have limited compatibility (PES) or no compatibility with the HBr and HCl salt solutions when stored in glass vials.

Formulation Screening and Compatibility Studies Summary: Nintedanib esylate cannot be formulated with NaCl (or MgCl2 or NaBr) as a stand-alone, ready to use formulation. Admixing nintedanib esylate in 1.5% propylene glycol (for osmolality adjustment) with normal saline (to obtain the required concentration of permeant ion) at the point of use is be necessary to achieve tolerability while maintaining physical stability of the nintedanib esylate solution through its shelf life. PVDF filter and clear borosilicate glass vials are incompatible with stand-alone nintedanib esylate formulation (i.e. without pirfenidone) while nylon filter and LDPE vials are compatible with both stand-alone nintedanib esylate formulations and nintedanib esylate plus pirfenidone combination formulations. Pirfenidone and to some extent, propylene glycol, mannitol and ethanol have a stabilizing effect on nintedanib esylate, enabling a ready-to-use combination formulation nintedanib esylate plus pirfenidone with acceptable osmolality and pH possible.

Nintedanib esylate stand-alone formulation: For stand-alone nintedanib esylate formulation for inhalation, a solution of 1.875 mg/mL nintedanib esylate, 1.875% propylene glycol solution is formulated and packaged in LDPE vials for long term storage. At the point of use, this formulation may be mixed with normal saline solution at a 4:1 ratio. In other applications, this mixture may range from about 1:10 to about 10:1. The admixed formulation has 1.5 mg/mL nintedanib esylate, 1.5% propylene glycol and 30 mM NaCl. The osmolality of this admixed formulation ranges from 200-350 mOsm/kg and pH in the range of 3-7. This formulation approach is taken to ensure that at the point of use that (1) the nintedanib esylate solution has adequate storage shelf life, and (2) upon mixing with normal saline solution, the admixed formulation has adequate tolerability (from acceptable pH and osmolality perspective) and can be used within one to two hours timeframe.

The composition of the proposed nintedanib esylate-premixed solution and admixed solution are listed in Table 37.

TABLE 37

Composition of premix nintedanib esylate solution and admixed nintedanib esylate formulation and characteristics

| Formulation | Composition/container | pH | Osmolality | Target Shelf Life/Use Life |
|---|---|---|---|---|
| Nintedanib esylate solution | 1.875 mg/mL nintedanib esylate, 1.875% propylene glycol in LDPE vials | 3-7 | 150-500 | ≥2 years (shelf life) |
| Saline solution | 150 mM NaCl | 3-7 | 150-500 | ≥2 years (shelf life) |
| Admix 4 parts nintedanib esylate solution with 1 part saline solution, mix by inversion | | | | |
| Admixed solution | 1.5 mg/mL nintedanib esylate, 1.5% propylene glycol, 30 mM NaCl | 3-7 (4.87 for formulation 101-01-13-05) | 150-500 mOsm/kg (268 for formulation 101-01-13-05) | 0-120 min (use life) (No precipitation within 60 minutes after mixing and during nebulization for formulation 101-01-13-05) |

Alternatively, nintedanib salt may be formulated in a ready-use formulation wherein propylene glycol provides sufficient osmolality in the absence of an additional permeant ion. However, tolerability is limited in the absence of permeant ion addition. Such formulations are described in Table 38 and have been used in animal experimentation.

TABLE 38

Composition of ready-to-use nintedanib salt formulation

| Composition | pH | Osmolality | Stability |
|---|---|---|---|
| 0.5 mg/mL nintedanib HCl, 2.0% propylene glycol | 4.97 | 283 | Stable through at least 2 months at room temperature |
| 0.5 mg/mL nintedanib HBr, 2.0% propylene glycol | 4.33 | 274 | Stable through at least 2 months at room temperature |
| 0.5 mg/mL nintedanib esylate, 2.0% propylene glycol | 4.86 | 279 | Stable through at least 2 months at room temperature |
| 0.0625 mg/mL nintedanib HCl, 2.0% propylene glycol | 4.88 | 273 | Stable through at least 2 months at room temperature |
| 0.25 mg/mL nintedanib HCl, 2.0% propylene glycol | 4.86 | 278 | Stable through at least 2 months at room temperature |
| 1.0 mg/mL nintedanib HCl, 2.0% propylene glycol | 4.77 | 292 | Stable through at least 2 months at room temperature |

Nintedanib salt plus pirfenidone combination formulation: Based on the results of formulation screening and nintedanib esylate compatibility studies summarized above, a ready-to-use nintedanib esylate plus pirfenidone combination formulation with an acceptable shelf life can be formulated. This ready to use combination formulation is tolerable for inhalation based on its formulation composition and the expected pH and osmolality. The composition and critical attributes of the proposed ready-to-use combination formulation of nintedanib esylate plus pirfenidone are shown in Table 39.

TABLE 39

Composition of ready-to-use nintedanib esylate combination formulation

| Composition | pH | Osmolality | Stability |
|---|---|---|---|
| 1.5 mg/mL nintedanib esylate, 12.5 mg/mL pirfenidone, 30 mM NaCl in LDPE or glass vials | 4.93 | 328 mOsm/kg | Stable through at least 4 months at room temperature |
| 1.5 mg/mL nintedanib HCl, 12.5 mg/mL pirfenidone in LDPE | 3-8 | 150-500 mOsm/kg | Stable through at least 4 months at room temperature |

Table 39 describes two ready-to-use formulations. The combination formation contains permeant ion (in this case chloride, provided from NaCl), while the single agent nintedanib formulation does not. Permeant ion is required for tolerability. Thus, while the single-agent nintedanib formulation is stable in the absence of permeant ion, it is not well tolerated.

The feasibility of formulating nintedanib esylate formulation for admixing with saline solution at point of use has been assessed. The pre-mix nintedanib formulations are stable for at least three months at ambient room temperature and accelerated storage conditions (40° C./75% RH). The admixed solution of nintedanib esylate formulation with saline is stable for use for at least four hours.

The ready-to-use combination formulation and pirfenidone (without admixing) is stable at ambient room temperature and accelerated storage conditions for at least three months.

Example 6. Stability of Nintedanib Esylate Formulations

TABLE 40

Stability of Premix Nintedanib Esylate Formulation and Ready-to-Use Nintedanib Esylate/Pirfenidone Combination Formulation

| Formulation (Formulation Number) | | % Nintedanib Esylate Remaining (pH) | | | | | |
|---|---|---|---|---|---|---|---|
| | | 1 month | | 2 month | | 3 month | |
| | T0 | 25° C. | 40° C. | 25° C. | 40° C. | 25° C. | 40° C. |
| 1.875 mg/mL Nintedanib esylate, 1.875% PG (GP-101-02-30-01) | 100.0% (5.26) | 01.1% (4.88) | 100.6% (4.78) | 101.7% (4.87) | 101.7% (4.48) | 101.7% (4.72) | 101.7% (4.66) |
| 1.5 mg/mL Nintedanib esylate, 12.5 mg/mL pirfenidone, 1.5% PG, 30 mM NaCl (GP-101-02-31-01) | 100.0% (5.45) | 102.0% (5.30) | 100.7% (5.25) | 102.0% (5.37) | 101.3% (5.09) | 99.3% (5.38) | 100.7% (5.16) |

TABLE 41

Stability of Admixed Nintedanib Esylate Formulations with Saline Solution

| Formulation | Diluent | Admixed formulation | Admixed stability | | | | |
|---|---|---|---|---|---|---|---|
| | | | Initial | 2 hrs | 4 hrs | 8 hrs | 24 hrs |
| 1.875 mg/mL Nintedanib esylate, 1.875% PG, water | 0.9% NaCl | 4 parts formulation: 1 part diluent | % Nintedanib esylate remained post mixing | | | | |
| | | | 100% | 100.1% | 100.2% | 95.0% | 93.7% |
| | | | Visual appearance | | | | |
| | | | Clear viscous yellow solution free of particles | Clear viscous yellow solution free of particles | Clear viscous yellow solution free of particles | Yellow solution with visible particles | Yellow solution with more visible particles |

The above results demonstrated that nintedanib esylate is suitable to be formulated as inhalation solution in either ready-to-use form or for admixing with saline solution at the point of use.

Example 7. Formulation Development and Stability of Nintedanib Salt Formulations

TABLE 42

Feasibility Assessment of Ready-to-Use Nintedanib HBr, Nintedanib HCl and Nintedanib Esylate Formulations

| Formulation (date prepared) | Formulation Characteristics | Stability/Compatibility |
|---|---|---|
| 0.5 mg/mL Nintedanib HBr, 2% PG | Clear yellow solution, pH = 4.27, osmolality = 291 mOsm/kg | Nintedanib HBr dissolved slowly, dissolution can be facilitated by heating in water bath at 40° C.; formed precipitate on glass wall when stored in clear borosilicate glass, does not form precipitates in LDPE vials |
| 0.5 mg/mL Nintedanib HCl, 2% PG | Clear yellow solution, pH = 5.38, osmolality = 365 mOsm/kg | Formed precipitates when stored in clear glass container, does not form precipitate in LDPE vial |
| 0.5 mg/mL Nintedanib HCl, 1.5% PG, 30 mM NaCl | Clear yellow, slightly viscous solution, pH = 5.40, osmolality = 278 mOsm/kg | Changed to pale greenish yellow with white precipitates after 30 minutes, no longer viscous |
| 0.5 mg/mL Nintedanib HBr, 1.5% PG, 30 mM NaCl | Clear yellow, slightly viscous solution, pH = 4.22, osmolality = 267 mOsm/kg | Changed to pale greenish yellow with white precipitates after 2 days, no longer viscous |
| 0.5 mg/mL Nintedanib HBr, 2% PG | Clear yellow solution, pH = 4.33, osmolality = 274 mOsm/kg | Stability not monitored |
| 0.5 mg/mL Nintedanib HCl, 2% PG | Clear yellow solution, pH = 4.97, osmolality = 283 mOsm/kg | Stability not monitored |
| 0.5 mg/mL Nintedanib esylate, 2% PG | Clear yellow solution, pH = 4.97, osmolality = 283 mOsm/kg | Stability not monitored |
| 1.5 mg/mL Nintedanib HBr, 2% PG, 10 mM Tris, HCl (to adjust pH to 5.5) | Clear yellow solution, pH = 5.5 | Remained clear bright yellow with no precipitation after 1 month; several needle-like crystals found after 6 months although the solution remained clear bright yellow |
| 1.5 mg/mL Nintedanib HCl, 2% PG 10 mM Tris, HCl (to adjust pH to 5.5) | Clear yellow solution, pH 5.5 | Remained clear bright yellow with no precipitation after 1 month; several needle-like crystals found after 6 months although the solution remained clear bright yellow |
| 1.5 mg/mL NE, 2% PG, 10 mM Tris, HCl (to adjust pH to 5.5) | Clear yellow solution | Remained clear bright yellow with no precipitation after 1 month; several needle-like crystals found after 6 months although the solution remained clear bright yellow |
| 1.5 mg/mL NinBr, 2% PG, 10 mM lysine | Clear yellow solution, pH = 5.5 | Remained clear bright yellow with no precipitation after 1 month; several needle-like crystals found after 6 months although the solution remained clear bright yellow |
| 1.5 mg/mL Nintedanib HCl, 2% PG, 10 mM lysine, HCl (to adjust pH to 5.5) | Hazy yellow solution, pH = 5.5 | Remained hazy yellow with light precipitates formed overnight |
| 1.5 mg/mL NinEs, 2% PG, 10 mM lysine, HCl (to adjust pH to 5.5) | Clear yellow solution, pH = 5.5 | Remained yellow with light precipitates formed overnight |
| 0.5 mg/mL Nintedanib HBr, 1.5% PG, 30 mM NaCl | Clear yellow solution | Changed to pale greenish yellow with white precipitates after 1 month |
| 1 mg/mL Nintedanib HCl, 10 mM HCl | Clear yellow solution | Solution remained clear yellow after 8 months with transparent material coated LDPE container wall |
| 1 mg/mL Nintedanib HCl, 100 mM HCl, water | Clear yellow solution | Solution changed to turbid suspension within 30 minutes with transparent granular material coated LDPE container wall |
| 1 mg/mL Nintedanib HCl, 10 mM HCl, glycine (to adjust pH to 3.5) | Clear yellow viscous solution, pH 3.5 | Clear viscous yellow solution free of precipitates through 6 months |
| 1 mg/mL Nintedanib HCl, 10 mM HCl Glycine (to adjust pH to 4.0) | Clear yellow solution, pH = 4.0 | Clear bright yellow solution, with exception of a long strand of fiber, free of precipitates through 6 months |

TABLE 42-continued

Feasibility Assessment of Ready-to-Use Nintedanib HBr, Nintedanib HCl and Nintedanib Esylate Formulations

| Formulation (date prepared) | Formulation Characteristics | Stability/Compatibility |
|---|---|---|
| 1 mg/mL Nintedanib HCl, 10 mM HCl, lysine (to adjust pH to 4.0) | Clear yellow solution, pH = 4.5 | Clear yellow solution after 6 months with several needle-like crystals formed at bottom of vials |
| 1 mg/mL Nintedanib HCl, 10 mM HCl, lysine (sufficient quantity to adjust pH to 6.0) | Clear yellow solution, pH initial = 6.24, pH final = 5.12 | Solution precipitated as pH overshot to 6.24, pH slowly drifted to 5.12 |
| 1 mg/mL Nintedanib HCl, 10 mM HCl, 15 mM N-acetylcysteine, lysine (quantity sufficient to adjust pH to 4.0) | Viscous clear yellow solution, pH = 4.04 | Solution remained clear yellow with no precipitation after 8 months (Jun. 23, 2019) at RT |
| 1 mg/mL Nintedanib HCl, 33 mM HCl, 6.1 mg/mL glycine 0.735 mg/mL lysine | Clear yellow, slightly viscous solution, pH = 3.51 | Solution changed to pale greenish yellow with white precipitates after 3 hours |
| 1 mg/mL Nintedanib HCl, 33 mM HCl, 6.1 mg/mL glycine, 1.5 mg/mL lysine | Clear yellow, slightly viscous solution, pH = 4.21, osmolality = 144 mOsm/kg | Solution changed to pale greenish yellow with white precipitates after 3 hours |
| 1 mg/mL NHBr, 33 mM HCl 6 mg/mL glycine, 4 mg/mL tromethamine | Clear yellow, slight viscous solution, pH = 3.99, osmolality = 146 mOsm/kg | Solution changed to pale greenish yellow with white precipitates within 8 months |
| 0.5 mg/mL Nintedanib HCl 3% PG, 33 mM NaCl, 1.25% mannitol | Clear yellow, slightly viscous solution | Solution changed to pale greenish yellow with white precipitates after 2 hours |
| 0.5 mg/mL Nintedanib HCl 6% PG, 33 mM NaCl, 1.25% mannitol | Clear yellow solution | Solution changed to pale greenish yellow with white precipitates after 2 hours |
| 0.5 mg/mL Nintedanib HCl 9% PG, 33 mM NaCl, 1.25% mannitol | Clear yellow solution | Solution changed to pale greenish yellow with white precipitates after 2 hours |
| 0.5 mg/mL Nintedanib HCl 12% PG, 33 mM NaCl, 1.25% mannitol (Oct. 23, 2018) | Clear yellow solution | Solution changed to pale greenish yellow with white precipitates overnight |
| 0.5 mg/mL Nintedanib HCl 15% PG, 33 mM NaCl, 1.25% mannitol | Clear yellow solution | Solution changed to pale greenish yellow with white precipitates overnight |
| 0.5 mg/mL Nintedanib HCl 2% PG, 67 mM NaCl | Clear yellow solution | Solution changed to pale greenish yellow with white precipitates within 2 hours |
| 0.5 mg/mL Nintedanib HCl, 1.25% PG, 67 mM NaCl | Clear yellow solution | Solution changed to pale greenish yellow with white precipitates within 2 hours |
| 0.25 mg Nintedanib HCl, 150 mM NaCl | Pale greenish yellow solution | Precipitation formed immediately when saline solution is added to dissolved Nintedanib HCl solution |
| 2.75 mg/mL Nintedanib HCl, 33 mM NaCl, 12% PG | Clear viscous yellow solution | Precipitation appeared after 45 minutes of preparation |
| 1.5 mg/mL Nintedanib HCl, 3% PG, 33 mN NaCl, 1.25% mannitol | Clear yellow solution | Solution changed to pale greenish yellow with white precipitates overnight |

Neither Nintedanib HBr nor Nintedanib HCl is compatible with NaCl at 30 mM or higher concentrations. Nintedanib HCl by itself is not compatible with NaCl at 10 mM, but when formulated with glycine or lysine/N-acetylcysteine buffers became compatible Glycine and lysine/N-acetylcysteine may act as a stabilizer to stabilize Nintedanib HCl in the presence of NaCl. All formulations containing 1.5 mg/mL Nintedanib HBr and Nintedanib HCl that did not form white precipitates initially had clear crystals formed within 6 months, indicating Nintedanib HBr and Nintedanib HCl are saturated at 1.5 mg/mL concentration.

Based on the findings above, further studies were conducted to optimize the Nintedanib HBr and Nintedanib HCl for long term stability. Excipients considered are PG as osmolality adjusting agent and fumaric acid, glycine, Tris, maleic acid, malic acid, HCl, and NaOH as pH buffering agents. NaCl was not included due to its effect on the stability of Nintedanib HBr and Nintedanib HCl. These formulations can be admixed with saline solution at the point of use to achieve optimal tolerability.

As noted above, Osmolality adjusting agents are comprised of consists of one or more classes of excipients from the following groups: sugars, alcohols, inorganic salts, amino acids, and acids/bases and combinations thereof. Individually, sugars can be selected from, but not limited to: glucose, fructose, lactose, sucrose, maltose, mannose, trehalose and xylose. Alcohols include but not limited to: erythritol, glycerol, inositol, maltitol, mannitol, menthol, propylene glycol, sorbitol, xylitol, threitol, propylene glycol. Inorganic salts may include but not limited to: sodium acetate, sodium bromide, sodium chloride, sodium sulfate, sodium phosphate, sodium carbonate, sodium bicarbonate, potassium carbonate, potassium iodide, potassium chloride, potassium bromide, magnesium chloride, calcium chloride Amino acids include, but not limited to: arginine, asparagine, aspartic acid, glutamic acid, glutamine, glycine, histidine, lysine and proline. Finally, acids and bases may include, but not limited to: boric acid, acetic acid, hydrogen bromide, hydrogen chloride, sulfuric acid, nitric acid, phosphoric acid, sodium hydroxide, sodium hydroxide, potassium hydroxide and calcium hydroxide

TABLE 43

Formulation Development/Optimization of Nintedanib HBr and Nintedanib HCl and Long-Term Stability Assessment

| Formulation (Formulation Number) | Formulation Characteristics | Stability Summary |
| --- | --- | --- |
| 2.88 mg/mL Nintedanib HBr, 4% PG (GP-101-02-55-02) | Clear yellow solution | Solution remained as clear yellow solution with needle-like crystals after 1 month; crystalline needles re-dissolved when heated to 50° C. (suggesting crystals formed due to physical change, e.g. precipitation due to supersaturation, rather than chemical change, e.g., complexation) |
| 1.44 mg/mL, Nintedanib HBr, 4.0% PG (GP-101-02-55-03) | Clear yellow solution | Remained as clear yellow solution through 7 months |
| 2.88 mg/mL Nintedanib HBr, 2.5 mg/mL pirfenidone, 4% PG (GP-101-02-55-04) | Clear yellow solution | Solution remained as clear yellow solution with needle-like crystals (to a lesser extent than GP-101-02-55-02) after one month; crystals re-dissolved when heated to 50° C. |
| 1.44 mg/mL Nintedanib HBr, 1.25 mg/mL pirfenidone, 4% PG (GP-101-02-55-05) | Clear yellow solution | Remained as clear yellow solution free of precipitates through 7 months |
| 0.58 mg/mL, Nintedanib HBr, 4% PG (GP-101-02-56-02) | Clear yellow solution | Remained as clear yellow solution free of precipitates through 7 months |
| 2.76 mg/mL, Nintedanib HBr, 4% PG (GP101-02-60-02) | Clear yellow solution | Solution remained as clear yellow solution with needle-like crystals after 1 month; crystals re-dissolved when heated to 50° C. |
| 1.38 mg/mL Nintedanib HBr, 4% PG (GP101-02-60-03) | Clear yellow solution | Solution remained clear yellow free of precipitate through 1 month |
| 2.76 mg/mL Nintedanib HBr, 2.4 mg/mL, pirfenidone, 4% PG (GP101-02-60-04) | Clear yellow solution | Solution remained as clear yellow solution with needle-like crystals through 1 month; crystals re-dissolved when heated to 50° C. |
| 1.38 mg/mL Nintedanib HBr, 1.2 mg/mL pirfenidone, 4% PG (GP101-02-61-01) | Clear yellow solution | Solution remained clear yellow with no precipitation through 1 month |
| 1.35 mg/mL Nintedanib HCl (GP-101-02-63-01) | Clear yellow solution | Solution remained clear yellow with no precipitation through 6 months |
| 1.35 mg/mL Nintedanib HCl, 3% PG (GP-101-02-63-02) | Clear yellow solution | Solution remained clear yellow with no precipitation through 6 months |
| 0.675 mg/mL Nintedanib HCl (GP-101-02-63-03) | Clear yellow solution | Solution remained clear yellow with no precipitation through 6 months |
| 0.675 mg/mL Nintedanib HCl, 3% PG (GP-101-02-63-04) | Clear yellow solution | Solution remained clear yellow with no precipitation through 6 months |
| 0.338 mg/mL Nintedanib HCl (GP-101-02-63-05) | Clear yellow solution | Solution remained clear yellow with no precipitation through 6 months |
| 0.338 mg/mL Nintedanib HCl, 3% PG (GP-101-02-63-06) | Clear yellow solution | Solution remained clear yellow with no precipitation through 6 months |
| 1.44 mg/mL Nintedanib HBr (GP-101-02-65-01) | Clear yellow solution | Crystalline needles formed with 83.8% nintedanib HBr remained after 6 months |
| 1.44 mg/mL Nintedanib HBr, 3.0% PG (GP-101-02-65-02) | Clear yellow solution | Clear yellow solution with no precipitation; 103.1% remained after 6 months |

TABLE 43-continued

Formulation Development/Optimization of Nintedanib HBr and Nintedanib HCl and Long-Term Stability Assessment

| Formulation (Formulation Number) | Formulation Characteristics | Stability Summary |
|---|---|---|
| 0.72 mg/mL Nintedanib HBr (GP-101-02-65-03) | Clear yellow solution | Clear yellow solution with no precipitation, 108.6% remained after 6 months |
| 0.36 mg/mL Nintedanib HBr, 3.0% PG (GP-101-02-65-04) | Clear yellow solution | Clear yellow solution with no precipitation; 111.1% remained after 6 months |
| 0.36 mg/mL Nintedanib HBr (GP-101-02-65-05) | Clear yellow solution | Clear yellow solution with no precipitation; 101.4% remained after 6 months |
| 0.3125 mg/mL Nintedanib HBr, 3.0% PG (GP-101-02-65-06) | Clear yellow solution | Clear yellow solution with no precipitation; 102.7% remained after 6 months |
| 0.36 mg/mL Nintedanib HBr, 3% PG (GP-101-02-70-04) | Clear yellow solution | Clear yellow solution with no precipitation; 100.8% remained after 5 months |
| 0.72 mg/mL Nintedanib HBr, 3% PG (GP-101-02-70-03) | Clear yellow solution | Clear yellow solution with no precipitation; 102.6% remained after 5 months |
| 1.45 mg/mL Nintedanib HBr, 3% PG (GP-101-02-70-02) | Clear yellow solution | Clear yellow solution with no precipitation; 101.3% remained after 5 months |
| 1.60 mg/mL Nintedanib HBr, 1.67% PG (GP-101-02-71-02) | Clear yellow solution | Clear yellow solution with no precipitation; 99.0% remained after 5 months at RT |
| 1.53 mg/mL Nintedanib HBr, 1.67% PG (GP-101-02-72-02) | Clear yellow solution | Clear yellow solution with no precipitation after 5 months at RT |
| 0.153 mg/mL Nintedanib HBr, 1.67% PG (GP-101-02-72-03) | Clear greenish yellow solution | Clear yellow solution with no precipitation after 5 months at RT |
| 0.0153 mg/mL Nintedanib HBr, 1.67% PG (GP-101-02-73-01) | Clear slight greenish yellow solution | Clear yellow solution with no precipitation after 5 months at RT |
| 0.8 mg/mL Nintedanib HBr, 1.67% PG (GP-101-01-63-02) | Clear yellow solution | Clear yellow solution with no precipitation; 106.3% remained after 4 months |
| 0.16 mg/mL Nintedanib HBr, 1.67% PG (GP-101-01-63-03) | Clear yellow solution | Clear yellow solution with no precipitation; 108.7% remained after 4 months |
| 1.2 mg/mL Nintedanib HBr, 1.67% PG (GP-101-01-64-01) | Clear yellow solution | Clear yellow solution with no visible particles; 98.4% remained after 4 months |
| 0.2 mg/mL Nintedanib HBr, 15 mM glycine, 2% PG, HCl (to adjust to pH 4.0) (GP-101-02-81-01) | Clear yellow solution, pH = 3.96 | Stable through 2 months at room temperature and 5 C., and 1 month at 50 C.; see stability table 37 |
| 1 mg/mL Nintedanib HBr 15 mM glycine, 2% PG, HCl (to adjust to pH 4.0) (GP-101-02-81-02) | Clear yellow solution, pH = 4.02 | Stable through 2 months at room temperature and 5 C., and 1 month at 50 C.; see stability table 37 |
| 1.25 mg/mL Nintedanib HBr, 15 mM glycine, 2% PG, HCl (to adjust to pH 4.0) (GP-101-02-81-03) | Clear yellow solution, pH = 3.98 | Stable through 2 months at room temperature and 5 C., and 1 month at 50° C.; see stability table 37 |
| 1 mg/mL Nintedanib HBr, 15 mM glycine, HCl (to adjust pH to 4.25), 2% PG (GP-101-02-85-03) | Clear yellow solution, pH = 4.19 | Stable through 5 weeks at room temperature and 5 C., and 3 weeks at 50° C.; see stability table 37 |
| 1 mg/mL Nintedanib HCl, 15 mM glycine, HCl (to adjust pH to 4.25), 2% PG (GP-101-02-85-04) | Clear yellow solution | See stability table 44 |
| 1 mg/mL Nintedanib HBr, 15 mM glycine, HCl (to adjust pH to 4.0), 2% PG (GP-101-02-85-05) | Clear yellow solution, pH = 4.02 | Stable through 5 weeks at room temperature and 5 C., and 3 weeks at 50° C.; see stability table 44 |
| 1 mg/mL Nintedanib HBr, 15 mM maleic acid, sodium hydroxide (to adjust pH to 4.5), 2% PG (GP-101-02-90-02) | Clear yellow solution, pH = 4.63 | See stability table 44 |
| 1 mg/mL Nintedanib HBr, 15 mM glycine, HCl (to adjust pH to 4.25), 2% PG (GP-101-02-92-01) | Clear yellow solution, pH = 4.35 | See stability table 44 |

TABLE 43-continued

Formulation Development/Optimization of Nintedanib HBr and Nintedanib HCl and Long-Term Stability Assessment

| Formulation (Formulation Number) | Formulation Characteristics | Stability Summary |
|---|---|---|
| 1 mg/mL Nintedanib HBr, 15 mM glycine, HCl (to adjust pH to 4.25) (GP-101-02-92-04) | Clear yellow solution, pH = 4.47 | See stability table 44 |
| 0.2 mg/mL Nintedanib HBr, 15 mM glycine HCl (to adjust pH to 4.25), 2% PG (GP-101-02-92-05) | Clear yellow solution, pH = 4.44 | See stability table 44 |
| 1 mg/mL Nintedanib HBr, 15 mM fumaric acid, Tris (to adjust pH to 4.0) (GP-101-02-98-01) | Turbid yellow suspension | Nintedanib HBr did not dissolve in fumarate-Tris buffer solution, heating resulting suspension at 50° C. overnight did not dissolve Nintedanib HBr |
| 1 mg/mL Nintedanib HBr, 15 mM fumaric acid, NaOH (to adjust pH to 4.0) (GP-101-02-98-02) | Turbid yellow suspension | Nintedanib HBr did not dissolve in fumarate buffer solution, heating resulting suspension at 50° C. overnight did not dissolve Nintedanib HBr |
| 1.15 mg/mL Nintedanib HBr, 3% PG (GP-101-01-69-1) | Clear yellow solution | See stability table 44 |
| 1.15 mg/mL Nintedanib HBr, 15 mM malic acid, Tris (to adjust pH to 4.0) (GP-101-01-70-02) | Clear yellow, slightly viscous solution, pH 3.89 | Changed to pale greenish yellow with white precipitates formed overnight |
| 0.58 mg/mL Nintedanib HBr, 15 mM malic acid (pH not adjusted), 1.5% PG (GP-101-01-70-03) | Clear yellow solution | Formulation is not viscous (compared to GP-101-01-70-02), remained clear yellow without precipitates through 1 week; see stability table 44 |
| 1 mg/mL Nintedanib HBr, 15 mM malic acid (pH not adjusted) (GP-101-01-72-01) | Clear yellow solution, pH 2.73, 106.3% nominal | See stability table 44 |
| 1 mg/mL Nintedanib HBr, 15 mM malic acid, NaOH (to adjust pH to 3.5) (GP-101-01-72-02) | Clear yellow solution, pH 3.5, 103.3% nominal | Remained clear yellow without precipitates through 1 week; see stability table44 |
| 1 mg/mL Nintedanib HBr, 15 mM malic acid, NaOH (to adjust pH to 4.0) (GP-101-01-72-03) | Clear yellow solution, pH 4.0, 102.8% nominal | Changed to pale greenish yellow with white precipitates formed after four days at RT |
| 1 mg/mL Nintedanib HBr, 15 mM malic acid, NaOH (to adjust pH to 4.5) (GP-101-01-73-01) | Clear yellow solution, pH 4.5, 11.0% nominal | Changed to pale greenish yellow with white precipitates formed overnight |

Note:
while 15 mM gly-HCl buffer solution showed formed white suspending flocculates after 1 week at RT, test samples containing Nintedanib HBr and 15 mM glycine-HCl buffer have not form any white suspending flocculates through 2 months at RT

TABLE 44

Stability of Selected Nintedanib HBr and Nintedanib HCl Formulations

| Formulation (Formulation Number) | 5° C. Storage Condition | Ambient Room Temperature Condition | 40° C. Storage Condition | 50° C. Storage Condition |
|---|---|---|---|---|
| 0.2 mg/mL Nintedanib HBr, 15 mM glycine, 2% PG, pH 4.0 (GP-101-02-81-01) | 1.5 month: 93.8% | 3 months: 99.6% | 3 months: 98.7% | 1 month: 103.9% |
| 1 mg/mL Nintedanib HBr, 15 mM glycine, 2% PG, pH 4.0 (GP-101-02-81-02) | 3 months: 100.2% | 3 months: 98.3% (pH 4.06) | 3 months: 96.1% | 1 month: 95.6% |

TABLE 44-continued

Stability of Selected Nintedanib HBr and Nintedanib HCl Formulations

| Formulation (Formulation Number) | 5° C. Storage Condition | Ambient Room Temperature Condition | 40° C. Storage Condition | 50° C. Storage Condition |
|---|---|---|---|---|
| (1.25 mg/mL Nintedanib HBr, 15 mM glycine, 2% PG, pH 4.0 (GP-101-02-81-03) | 3 months: 105.1% | 3 months: 100.4% (pH 4.06) | 3 months: 95.8% | 1 month: 96.0% |
| 1 mg/mL Nintedanib HBr, 15 mM glycine, 2% PG, pH 4.25 (GP-101-02-85-03) | 2 months: 106.6% | 2 months: 98.7% | 2 months: 101.3% | 3 weeks: 100.4% |
| 1.25 mg/mL Nintedanib HCl, 15 mM glycine, 2% PG, pH 4.25 (GP-101-02-85-04) | 2 months: 100.1% | 2 months: 99.2% | 2 months: 102.2% | Not tested |
| 1.25 mg/mL Nintedanib HBr, 15 mM glycine, 2% PG, pH 4.0 (GP-101-02-85-05) | 2 months: 100.7% | 2 months: 100.5% | 2 months: 100.4% | 3 weeks: 97.0% |
| 1 mg/mL Nintedanib HBr, 15 mM maleic acid, 2% PG, pH 4.6 (GP-101-02-90-02) | Precipitated within 1 month, stability study terminated | | | |
| 1 mg/mL Nintedanib HBr, 15 mM glycine, 2% PG, pH 4.35 (GP-101-02-92-01) | 1 months: 101.6% | 1 month: 100.4% (pH 4.38) | 1 month: 100.7% (pH 4.33) | Not tested |
| 1 mg/mL Nintedanib HBr, 15 mM glycine, pH 4.47 (GP-101-02-92-04) | 1 month: 99.0% | 1 month: 101.6% (pH 4.60) | 1 month: 101.4% (pH 4.51) | Not tested |
| 0.2 mg/mL Nintedanib HBr, 15 mM glycine, 2% PG, pH 4.44 (GP-101-02-92-05) | 1 month: 100.9% | 1 month: 102.3% (pH 4.46) | 1 month: 101.8% (pH 4.33) | Not tested |
| 1.15 mg/mL Nintedanib HBr, 3% PG, water, pH 4.0 (GP-101-01-69-01) | 1 month: 102.0% | 1 month: 103.0% | 1 month: 102.3% | Not tested |
| 1.15 mg/mL Nintedanib HBr, 15 mM malic acid, Tris, pH 4.0 (GP-101-01-70-01) | Precipitated within 1 month, stability study terminated | | | |

TABLE 44-continued

Stability of Selected Nintedanib HBr and Nintedanib HCl Formulations

| Formulation (Formulation Number) | 5° C. Storage Condition | Ambient Room Temperature Condition | 40° C. Storage Condition | 50° C. Storage Condition |
|---|---|---|---|---|
| 0.58 mg/mL Nintedanib HBr, 7.5 mM malic acid, 1.5% PG, (GP-101-01-70-02) | | Precipitated within 1 month, stability study terminated | | |
| 1 mg/mL Nintedanib HBr, 15 mM malic acid (GP-101-01-72-01) | | Precipitated within 1 month, stability study terminated | | |
| 1 mg/mL Nintedanib HBr, 15 mM malic acid, pH adjusted to 3.5 (GP-101-01-72-02) | | Precipitated within 1 month, stability study terminated | | |
| 1 mg/mL Nintedanib HBr, 15 mM maleic acid, pH adjusted to 4.0 (GP-101-01-72-03) | | Precipitated within 1 month, stability study terminated | | |
| 1 mg/mL Nintedanib HBr, 15 mM maleic acid, pH adjusted to 4.5 (GP-101-01-72-04) | | Initial: 11.0% Stability terminated due to precipitation | | |

Nintedanib HBr and HCl concentrations at or above 1.44 mg/mL formed needle-like crystals over time. Heating the precipitated samples at 50° C. re-dissolved the crystals, indicating that precipitation is due to over-saturation and re-crystallization of Nintedanib HBr or Nintedanib HCl. Formulations prepared with Nintedanib HBr or Nintedanib HCl concentrations at or below 1.38 mg/mL showed no re-crystallization, suggesting 1.38 mg/mL as the upper concentration limit.

Nintedanib HBr and Nintedanib HCl, like Nintedanib esylate, are compatible with PG, glycine, pirfenidone and water. Furthermore, Nintedanib HBr and Nintedanib HCl are also compatible with glycine, lysine/N-acetylcysteine, maleate, mannitol, and Tris. Nintedanib HBr and Nintedanib HCl are incompatible with citric acid, fumaric acid, and have limited compatibility with malic acid (pH dependent). Glycine, on the other hand, by itself forms white flocculates at ambient room temperature within 2 weeks, is stabilized by Nintedanib HBr and Nintedanib HCl. In formulations containing Nintedanib HBr and Nintedanib HCl tested through approximately 2 months, glycine does not form flocculations.

While most of the formulations listed above are suitable for direct nebulization (pH 3-8, osmolality 150-500), due to the absence or low concentrations of permeant ions (Cl— or Br—), airway irritation is found in certain patients. To achieve optimal airway tolerability while still maintaining acceptable in-use stability (≥2 hours post mixing), as in the case of nintedanib esylate, Nintedanib HBr and Nintedanib HCl can be admixed with saline solution to produce chloride concentration in the admixed solution at 10 mM, more preferably 30 mM and most preferably 40 mM. Tables 45 and 46 shows the characteristics and in-use stability of various admixed Nintedanib HBr and Nintedanib HCl formulations with saline solution.

TABLE 45

Characteristics of Admixed Nintedanib HBr Formulations with Saline Solution

| Formulation (Formulation Number) | Diluent | Admixed formulation | Characteristics of Admixed Formulation | |
|---|---|---|---|---|
| | | | pH | Osmolality |
| 2.89 mg/mL Nintedanib HBr, 4% PG (GP-101-02-55-02) | 0.8% NaCl | 1 part formulation: 1 part diluent | 4.04 | 417 mOsm/kg |
| 1.44 mg/mL Nintedanib HBr, 4.0% PG (GP-101-02-55-03) | 0.8% NaCl | 1 part formulation: 1 part diluent | 4.36 | 411 mOsm/kg |

TABLE 45-continued

Characteristics of Admixed Nintedanib HBr Formulations with Saline Solution

| Formulation (Formulation Number) | Diluent | Admixed formulation | pH | Osmolality |
|---|---|---|---|---|
| 2.89 mg/mL Nintedanib HBr, 2.5 mg/mL pirfenidone, 4% PG (GP-101-02-55-04) | 0.8% NaCl | 1 part formulation: 1 part diluent | 4.12 | 411 mOsm/kg |
| 1.44 mg/mL Nintedanib HBr, 1.25 mg/mL pirfenidone, 4% PG (GP-101-02-55-05) | 0.8% NaCl | 1 part formulation: 1 part diluent | 4.46 | 419 mOsm/kg |
| 0.578 mg/mL Nintedanib HBr, 4% PG (GP-101-02-56-02) | 0.8% NaCl | 1 part formulation: 1 part diluent | 4.61 | 412 mOsm/kg |

TABLE 46

Stability of Nintedanib HBr admixed solutions with saline solution at Various Mixing Ratios

| Formulation (Formulation Number) | Diluent | Mixing Ratio | Composition of Admixed Solution | Visual Stability |
|---|---|---|---|---|
| 1.25 mg/mL Nintedanib HCl 1.56% mannitol 1.875% PG (10-10-18) | 1.8% NaCl | 4 parts formulation: 1 part diluent | 1 mg/mL Nintedanib HCl 1.25% mannitol 1.5% PG, 0.36% NaCl | Clear viscous yellow solution free of particles that remained unchanged after 4 hours of admixing |
| 0.16 mg/mL Nintedanib HBr, 1.67% PG (GP-101-01-63-03) | 4% NaCl | 9 parts formulation: 1 part diluent | 0.144 mg/mL Nintedanib HBr, 1.5% PG, 0.4% NaCl | No visual change in admixed solution through 3 hours |
| 0.8 mg/mL Nintedanib HBr, 1.67% PG (GP-101-02-63-02) | 4% NaCl | 9 parts formulation: 1 part diluent | 0.72 mg/mL Nintedanib HBr, 1.5% PG, 0.4% NaCl | No visual change in admixed solution through 3 hours |
| 1.2 mg/mL Nintedanib HBr, 1.67% PG (GP-101-02-64-01) | 4% NaCl | 9 parts formulation: 1 part diluent | 1.08 mg/mL Nintedanib HBr, 1.5% PG, 0.4% NaCl | No visual change in admixed solution through 3 hours |
| 1.44 mg/mL Nintedanib HBr, 3% PG (GP-101-02-70-02) | 0.9% NaCl | 5 parts formulation: 4 parts diluent | 0.8 mg/mL Nintedanib HBr, 1.67% PG, 0.4% NaCl | A thin strand of light precipitates appear after 2 hours of admixing, admixed solution remained slight viscous and clear bright yellow |
| | 0.675% NaCl | 5 parts formulation: 4 parts diluent | 0.8 mg/mL Nintedanib HBr, 1.67% PG, 0.3% NaCl | No visual change within 2 hours after admixing, faint precipitation observed at 3 hours |
| | 0.45% NaCl | 5 parts formulation: 4 parts diluent | 0.8 mg/mL Nintedanib HBr, 1.67% PG, 0.2% NaCl | No visual change in admixed solution after 2 hours, faint appearance of fine crystals when viewed under bright light after 3 hours |
| 1.04 mg/mL Nintedanib HBr, 2.7% PG (GP-101-02-75-02) | 0.9% NaCl | 5 parts formulation: 4 parts diluent | 0.58 mg/mL Nintedanib HBr, 1.5% PG, 0.4% NaCl | No visual change in admixed solution after 2 hours, faint appearance of fine crystals when viewed under bright light after 3 hours |
| | 0.675% NaCl | 5 parts formulation: 4 parts diluent | 0.58 mg/mL Nintedanib HBr, 1.5% PG, 0.3% NaCl | No visual change in admixed solution after 2 hours, faint appearance of fine crystals when viewed under bright light after 3 hours |
| | 0.45% NaCl | 5 parts formulation: 4 parts diluent | 0.58 mg/mL Nintedanib HBr, 1.5% PG, | No visual change in admixed solution after 2 hours, faint appearance of fine crystals |

TABLE 46-continued

Stability of Nintedanib HBr admixed solutions with saline solution at Various Mixing Ratios

| Formulation (Formulation Number) | Diluent | Mixing Ratio | Composition of Admixed Solution | Visual Stability |
|---|---|---|---|---|
| | | | 0.2% NaCl | when viewed under bright light after 3 hours |
| 0.26 mg/mL Nintedanib HBr, 2.7% PG (GP-101-02-75-04) | 0.9% NaCl | 5 parts formulation: 4 parts diluent | 0.14 mg/mL Nintedanib HBr, 1.5% PG, 0.4% NaCl | No visual change within 75 minutes of admixing, faint precipitation observed at 90 minutes, more apparent after 2 hours |
| | 0.675% NaCl | 5 parts formulation: 4 parts diluent | 0.14 mg/mL Nintedanib HBr, 1.5% PG, 0.3% NaCl | No visual change within 2.5 hours after admixing, faint precipitation observed at 3 hours |
| | 0.45% NaCl | 5 parts formulation: 4 parts diluent | 0.14 mg/mL Nintedanib HBr, 1.5% PG, 0.2% NaCl | No visual change after 3 hours |
| 0.2 mg/mL Nintedanib HBr, 15 mM glycine, 2% PG, pH 4.0 (GP-101-02-81-01) | 1.6% NaCl | 3-parts formulation: 1 part diluent | 0.15 mg/mL Nintedanib HBr 11.25 mM glycine, HCl | Clear viscous yellow solution through 2 hours post admixing; precipitates first became visible 2 hours after admixing Initial pH = 4.01; after 2 hours pH = 4.09; Placing precipitated admixed solution from above in a 50° C. water bath returned solution to clear bright yellow precipitate free; Freshly prepared admixed solution kept in 50° C. water bath also remained precipitate free through 12 hours |
| 1 mg/mL Nintedanib HBr, 2% PG, 15 mM glycine, pH 4.0 (GP-101-02-81-02) | 1.6% NaCl | 3 parts formulation: 1part diluent | 0.75 mg/mL Nintedanib HBr, 1.5% PG, 11.3 mM glycine | T0 post mixing: pH = 3.99, no precipitate; 15 min: pH = 4.07, no precipitate; 1 hr: pH = 4.08, no precipitate; 2 hrs: pH = 4.08 no precipitate; 3 hrs: pH = 4.09, precipitates first visible; 8 hrs: pH = 4.08, solution changed to pale greenish yellow solution with white precipitates; Freshly prepared admixed solution kept in 50° C. water bath remained precipitate free through 12 hours |
| 1.5 mg/mL Nintedanib HBr, 2% PG, 15 mM glycine, pH 4.0 (GP-101-02-81-03) | 1.6% NaCl | 3 parts formulation: 1 part diluent | 0.94 mg/mL Nintedanib HBr, 1.5% PG, 11.3 mM glycine | T0 post mixing: pH = 4.00, no precipitate; 15 min: pH = 4.06, no precipitate; 1 hr: pH = 4.08, no precipitate; 2 hrs: pH = 4.07 precipitates first observed; 3 hrs: pH = 4.07, precipitates more visible; Placing the admixed solution from above into 50° C. water bath returned the solution to clear bright yellow with no precipitations; Freshly prepared admixed solution kept in 50° C. water bath remained precipitate free through 12 hours |

The above admixed formulations of Nintedanib HBr and Nintedanib HCl with saline solution have acceptable pH (3-8), osmolality (150-500 mOsm/kg) to be delivered as aerosol for oral inhalation. These admixed formulations are shown to have adequate in-use stability (at least 2 hours and can be up to 3-4 hours). The admixed formulation can be kept even longer if maintained in a 50° C. condition for at least 12 hours.

With adequate controls using appropriate type of containers, type of filters, type of buffering agents and amount of permeant ions, nintedanib salts can be formulated as ready-to-use or for admixing with saline solution with acceptable shelf life and in-use stability.

Nintedanib esylate with sodium chloride admixed solutions and nintedanib hydrobromide with sodium chloride admixed solutions at different sodium chloride concentrations were assessed for post admixing stability. Nintedanib esylate and nintedanib hydrobromide at 0.5 mg/mL (calculated as freebase) were formulated in 15 mM glycinate buffer at pH 4.0 containing 3% propylene glycol. These solutions were admixed with sodium chloride solution at different concentrations at 1:1 ratio to form 0.25 mg/mL nintedanib solution (expressed as freebase), 7.5 mM glycinate buffer, 1.5% propylene glycol, and either 0.2%, 0.3% or 0.4% NaCl. The admixed solutions were visually inspected for visual appearance and presence of precipitates, an indicator for physical instability. The stability results are summarized in Table 47 below.

TABLE 47

Stability of nintedanib esylate/sodium chloride and nintedanib hydrobromide/sodium chloride admixtures

| Time after admixing | Nintedanib esylate/ NaCl admixture | | | Nintedanib hydrobromide/ NaCl admixture | | |
|---|---|---|---|---|---|---|
| (hours) | 0.2% NaCl | 0.3% NaCl | 0.4% NaCl | 0.2% NaCl | 0.3% NaCl | 0.4% NaCl |
| 1 | Clear yellow | Clear yellow | Clear yellow | Clear yellow | Clear yellow | Clear yellow |
| 1.5 | Clear yellow | Faint precipitation | Faint precipitation | Clear yellow | Clear yellow | Clear yellow |
| 2 | Clear yellow | Precipitated | Precipitated | Clear yellow | Clear yellow | Faint precipitation |
| 2.5 | Clear yellow | Precipitated | Precipitated | Clear yellow | Clear yellow | Precipitated |
| 4 | Clear yellow | Precipitated | Precipitated | Clear yellow | Clear yellow | Precipitated |
| 6 | Faint precipitation | Precipitated | Precipitated | Clear yellow | Faint precipitation | Precipitated |

The data shows that solution stability of both nintedanib esylate and nintedanib hydrobromide admixtures decrease with increasing NaCl concentration. At a given NaCl concentration, nintedanib hydrobromide admixture is more stable in solution than the nintedanib esylate admixture. Greater than 1 hour admixture stability is clinically important to allow sufficient time for the patient to perform the admixture and administer the given dosage. Nebulized dosing solutions containing at least 0.3% NaCl are most well-tolerated. The nintedanib hydrobromide admixture meets both of these requirements.

Example 8: Pharmacokinetics and Lung-Tissue Distribution

To characterize and compare nintedanib plasma and lung pharmacokinetics following oral and inhaled administration, six-week-old female C57BL/6 mice (18-20 gram) were administered nintedanib esylate by oral (gavage; PO) or direct-lung aerosol delivery (intratracheal; Penn Century MicroSprayer® nebulizing catheter; IT). For oral administration, 100 mg/kg nintedanib esylate (120 mg/kg esylate salt form) was dissolved in 1% methylcellulose and delivered by gavage. Plasma and lung tissue samples were taken at 2, 5, 10, 20, 40 min and 1, 2, and 4 hours post dose. Nintedanib was extracted and quantitated as µg/mL plasma and µg/gram lung tissue. For IT aerosol administration, 2.5 and 10 mg/kg nintedanib esylate (3.0 and 12 mg/kg esylate salt form) was formulated in 0.050 mL 2% propylene glycol and delivered directly to the lung by nebulizing catheter. Plasma and lung tissue samples were taken 2, 5, 10, 20, 40 min and 1, 2, and 4 hours post dose. Nintedanib was extracted and quantitated as µg/mL plasma and µg/gram lung tissue. Results from these studies are shown in Table 48.

TABLE 48

Pharmacokinetics of nintedanib esylate oral and intratracheal formulations

| Drug | Dose (mg/kg) | Route[a] | Matrix[b] | Cmax[c] | Half-life[d] | AUC[e] |
|---|---|---|---|---|---|---|
| Nintedanib esylate | 100.0 | PO | Plasma | 0.6 | 112 | 1.8 |
| | | | Lung | 12.1 | ND | 24.1 |
| | 2.5 | IT | Plasma | 0.7 | 2.3 | 0.2 |
| | | | Lung | 57.5 | 3.8 | 67.8 |

TABLE 48-continued

Pharmacokinetics of nintedanib esylate oral and intratracheal formulations

| Drug | Dose (mg/kg) | Route[a] | Matrix[b] | Cmax[c] | Half-life[d] | AUC[e] |
|---|---|---|---|---|---|---|
| | 10.0 | | Plasma | 2.7 | 2.3 | 0.6 |
| | | | Lung | 250.0 | 5.6 | 167.8 |

[a]IT: Intratracheal;
[b]Lung: Whole lung homogenate;
[c]plasma: mcg/mL; lung: mcg/gram;
[d]Elimination half-life (alpha-phase in minutes);
[e]AUC: Area under the curve 0-last (plasma: mg · hour/L; lung: mg · hour/kg)

Results indicate that 2.5 and 10 mg/kg direct lung administered nintedanib doses result in about 5-fold and about 20-fold greater lung Cmax than 100 mg/kg delivered orally. Results also show that 2.5 and 10 mg/kg direct lung administered nintedanib doses result in about 3-fold and about 7-fold greater lung AUC than 100 mg/kg delivered orally. Hence, much small inhaled nintedanib doses deliver superior critical lung pharmacokinetic parameters compared to much larger oral doses. More specifically, it can be calculated that about 200-fold less IT nintedanib will achieve the same lung Cmax was achieved following oral delivery (12.1 mcg/gram oral lung Cmax divided by 57.5 mcg/gram 2.5 mg/kg IT Cmax=0.21. 0.21 times 2.5 mg/kg IT dose=0.5 mg/kg IT compared to 100 mg/kg oral). As these lung-delivered Cmax levels are relatively short-lived, important for inhaled product success was the Example 2 demonstration that only short-duration nintedanib peak levels are required for maximum nintedanib activity. An oral-equivalent inhaled nintedanib lung Cmax will result in oral-equivalent efficacy such that much less inhaled drug is required for equivalent efficacy; small inhaled nintedanib dose levels enable improved safety and tolerability. Improving the safety and tolerability of nintedanib by inhalation administration effectively broadens the nintedanib therapeutic index (TI).

For systemic exposure, results indicate that 2.5 mg/kg and 10 mg/kg inhaled nintedanib results in plasma Cmax levels that are equivalent and about 5-fold that of the 100 mg/kg oral dose, respectively, and plasma AUCs that are about ⅛th and ⅓rd that of the 100 mg/kg oral dose, respectively. Taken together, these results show promise for inhalation to improve lung dose with reduced systemic exposure. Because nintedanib side effects are largely due to gastrointestinal exposure and drug-blood levels, achieving high lung levels in the absence of high blood levels offers potential for improved pulmonary efficacy with fewer side effects. In this study 10 mg/kg nintedanib esylate salt caused dyspnea in the IT-delivered animals. This adverse effect was not observed at 2.5 mg/kg.

To characterize and compare the plasma and lung pharmacokinetic profiles of inhaled nintedanib and inhaled pirfenidone when administered in fixed-combination, six-week-old female C57BL/6 mice (18-20 gram) were administered a combined nintedanib esylate and pirfenidone formulation by direct-lung aerosol delivery (intratracheal; Penn Century MicroSprayer® nebulizing catheter; IT). For IT aerosol administration, 10 mg/kg nintedanib esylate (12 mg/kg esylate salt form) was co-formulated with 10 mg/kg pirfenidone in 0.050 mL 2% propylene glycol and delivered directly to the lung by nebulizing catheter. Plasma and lung tissue samples were taken 2, 5, 10, 20, 40 min and 1, 2, and 4 hours post dose. Nintedanib was extracted and quantitated as µg/mL plasma and µg/gram lung tissue. Results from these studies are shown in Table 49.

TABLE 49

Inhaled pharmacokinetics of fixed combination nintedanib esylate and pirfenidone formulation

| Drug | Dose (mg/kg) | Route[a] | Matrix[b] | Cmax[c] | Half-life[d] | AUC[e] |
|---|---|---|---|---|---|---|
| Nintedanib esylate | 10.0 | IT | Plasma | 2.8 | 7.7 | 1.0 |
|  |  |  | Lung | 171.1 | 1.8 | 68.4 |
| Pirfenidone | 10.0 |  | Plasma | 7.9 | 8.9 | 3.8 |
|  |  |  | Lung | 279.0 | 0.7 | 5.2 |

[a]IT: Intratracheal;
[b]Lung: Whole lung homogenate;
[c]mcg/mL;
[d]Elimination half-life (alpha-phase in minutes);
[e]AUC: Area under the curve 0-last (plasma: mg · hour/L; lung: mg · hour/kg)

Results indicate that a fixed combination of nintedanib and pirfenidone can be co-formulated and co-administered directly to the lung of an animal Results indicate that administration results in pirfenidone having a higher lung and plasma Cmax than nintedanib, with nintedanib having a lower elimination half-life resulting in a much larger lung AUC.

To characterize and compare the pharmacokinetic profiles of various inhaled nintedanib salt forms, six-week-old female C57BL/6 mice (18-20 gram) were administered either nintedanib esylate, nintedanib hydrochloride or nintedanib hydrobromide by direct-lung aerosol delivery (intratracheal; Penn Century MicroSprayer® nebulizing catheter; IT). For IT aerosol administration and calculated on a base equivalent, 1 mg/kg of each salt was formulated in 0.050 mL 2% propylene glycol and delivered directly to the lung by nebulizing catheter. Plasma and lung tissue samples were taken 2, 5, 10, 20, 40 min and 1, 2, 3 and 4 hours post dose. Nintedanib was extracted and quantitated as µg/mL plasma and µg/gram lung tissue. Results from these studies are shown in Table 50.

TABLE 50

Inhaled pharmacokinetics of various nintedanib salt forms

| Salt | Dose (mg/kg) | Route[a] | Matrix[b] | Cmax[c] | Half-life[d] | AUC[e] |
|---|---|---|---|---|---|---|
| Nintedanib esylate | 1.0 | IT | Plasma | 0.4 | 2.0 | 0.2 |
|  |  |  | Lung | 34.5 | 2.9 | 21.7 |
| Nintedanib chloride |  |  | Plasma | 0.4 | 1.7 | 0.2 |
|  |  |  | Lung | 34.4 | 3.9 | 60.1 |
| Nintedanib bromide |  |  | Plasma | 0.2 | 2.4 | 0.2 |
|  |  |  | Lung | 30.6 | 4.1 | 51.2 |

[a]IT: Intratracheal;
[b]Lung: Whole lung homogenate;
[c]mcg/mL;
[d]Elimination half-life (alpha-phase in minutes);
[e]AUC: Area under the curve 0-last (plasma: mg · hour/L; lung: mg · hour/kg)

a. IT: Intratracheal; b. Lung: Whole lung homogenate; c. mcg/mL; d. Elimination half-life (alpha-phase in minutes); e. AUC: Area under the curve 0-last (plasma: mg·hour/L; lung: mg·hour/kg)

Results indicate that each salt is efficiently delivered to the lung and achieve a similar lung and plasma Cmax. While plasma half-life and AUCs were also similar between the salts, lung half-life varied (half-lifes of about 4 minutes for nintedanib hydrochloride and hydrobromide, but about 3 minutes for nintedanib esylate). This variance also contributes to lung AUC where the hydrochloride and hydrobromide salt forms were between about 50 and 60 mg·hr/kg, whereas the esylate salt was about 20 mg·hr/kg. While nintedanib efficacy appears to be concentration dependent, such prolonged lung half-lives for the hydrochloride and hydrobromide salts also contributes to therapeutic effect (longer lung exposure) compared to the esylate salt form. All salts were well-tolerated at these dose levels.

TABLE 51

Human inhaled dose projection

|  | Plasma | Lung |
|---|---|---|
| Ofev (150 mg oral) |  |  |
| Cmax (µg/mL or µg/g) | 0.029 | 0.014 |
| AUC (mg · hr/L or mg · hr/kg) | 0.174 | 0.087 |
| Inhaled nintedanib (0.42 mg device loaded dose[a]) |  |  |
| Cmax (µg/mL or µg/g) | 0.024 | 0.364 |
| AUC (mg · hr/L or mg · hr/kg) | 0.174 | 0.911 |
| % Pharmacokinetics (inhaled compared to oral) |  |  |
| Cmax | 83 | 2600 |
| AUC | 100 | 1047 |

[a]Assumes 67% loaded drug is inhaled (inhaled mass) and that 78% of aerosol particles in the inhaled mass are less than 5 µm in diameter.

a. Assumes 67% loaded drug is inhaled (inhaled mass) and that 78% of aerosol particles in the inhaled mass are less than 5 µm in diameter.

Table 51 results indicate that a 0.42 mg device loaded nintedanib dose will delivers an inhaled dose resulting in the same plasma AUC as a 150 mg oral dose, with a 2600% (26-fold) greater nintedanib lung Cmax than a 150 mg oral dose, and a 1047% (10.47-fold) greater nintedanib lung AUC. Under the assumption that plasma AUC drives oral nintedanib side effects, this 0.42 mg device loaded nintedanib dose will deliver the same side effects as the 150 mg oral dose. Under this scenario, this may be assumed as the highest dose. This projected highest dose may then be dose de-escalated to a more-well-tolerated dose level while maintaining superior lung levels. By example, with lung Cmax as the target, this oral-equivalent plasma AUC dose delivers 26-fold more lung Cmax. This may then be dose de-escalated up to 26-fold while maintaining a lung-equivalent or superior Cmax. Similarly, with lung AUC as the target, this dose may be dose de-escalated about 10- to 11-fold while maintaining a lung-equivalent or superior AUC. Clinical dose escalation will confirm or modify these dose and pharmacokinetic predictions.

Example 9: Nebulization Device Performance

To evaluate aerosol performance, several nintedanib salt formulations (Table 30, formulations 380 and 381) were tested in the eFlow device. In addition, a formulation combining pirfenidone and nintedanib HCl was also tested. For these studies the standard eFlow 35L head was used. Particle size distribution was determined using a Malvern Spraytec laser particle sizer. Results are shown in Table 52. Each result is an average of duplicate trials in each of three devices.

TABLE 52

Nebulized aerosol particle sizing

| Formulation (Table 24): | | Formulation | | | |
|---|---|---|---|---|---|
| Nintedanib | Salt form | HCl | HBr | Esylate | HCl |
| Nintedanib | mg/mL | 1.5 | 1.5 | 1.5 | 1.5 |
| Pirfenidone | mg/mL | 0.0 | 0.0 | 0.0 | 12.5 |
| Fill volume | mL | 1.0 | 1.0 | 1.0 | 1.0 |
| Duration | min | 2.7 | 2.5 | 2.3 | 2.1 |
| ≤1 μm | % | 0.0 | 0.0 | 0.0 | 0.0 |
| ≤3 μm | | 15.4 | 13.8 | 12.5 | 14.4 |
| ≤5 μm[a] | | 61.5 | 58.1 | 54.9 | 61.4 |
| GSD | | 1.4 | 1.4 | 1.4 | 1.4 |
| Dv(50)[b] | % <5 μm | 4.5 | 4.6 | 4.8 | 4.5 |
| Nebulized dose[c] | mg | 811.7 | 794.7 | 752.3 | 751.2 |
| TOR[d] | mg/min | 324.7 | 327.5 | 337.5 | 377.0 |
| FPD[e] | mg | 499.2 | 461.7 | 413.0 | 461.2 |
| FPD output rate | mg/min | 195.8 | 188.5 | 185.6 | 231.4 |
| Residual delivered dose | mg | 139.8 | 177.0 | 231.2 | 207.8 |

[a]Percent nebulized particles <5 μm (also known as respirable fraction; RF);
[b]Maximum particle diameter below which 50% of the sample volume exists;
[c]mg aerosol emitted from device;
[d]Total output rate or nebulized dose per min;
[e]Fine particle dose or mg nebulized dose particles <5 μm Table 52 results show that 1.0 mL of a 1.5 mg/mL nintedanib formulation will be administered in about 2.5 minutes and produced a fine particle dose (mg dose present within inhaled aerosol particles less than 5 microns (μm) in diameter; FPD) of about 0.46 mg; a nebulization efficiency of about 31%. Manipulation of the nintedanib concentration and device fill volume will permit optimization of dose delivery time and lung/plasma exposure ratio. By example, a high nintedanib concentration formulation will be administered in only a few breaths over a short time. The result will be a higher lung Cmax with the same plasma exposure as the same amount of nintedanib delivered in a larger volume over more breaths and longer time. Similarly, if the resulting plasma Cmax is determined to be of concern, this is addressed by either less administered nintedanib or a lower concentration nintedanib formulation. Both will reduce lung Cmax, but permit balancing the two critical parameters.

Example 10: Inhaled Nintedanib Salt In Vivo Pharmacology—Therapeutic Bleomycin Model To evaluate the in vivo activity of inhaled nintedanib, the therapeutic bleomycin pulmonary fibrosis model was performed. Briefly, acclimated Sprague Dawley male rats (c.a. 253 grams at first dosing) were administered bleomycin on days 1, 2, 3 and 6 by the oropharyngeal (OP) route. On the eighth day, treatment was initiated with either saline or nintedanib. Inhaled nintedanib formulations were delivered by OP administration. Preliminary experiments showed good lung delivery and distribution by this method. On days 8 through 27, OP animals were anesthetized with isoflurane and dosed once a day (QD) with either 0.05, 0.25 or 0.375 mg/kg nintedanib HBr formulation (Table 53). Oral gavage-treated (PO) animals were dosed twice a day (BID) with 60 mg/kg nintedanib esylate in water Sham and bleomycin control groups received saline either OP or PO. Ten animals were enrolled into each dosing group. For OP nintedanib administration, doses were selected to deliver PO-inferior, -equivalent and -superior lung Cmax and AUC (Table 54). All animals were euthanized on day 28d. Body weights were collected throughout the study, with lung weights at termination (Table 55). Left lungs were extracted and measured for hydroxyproline content, while left lungs were subjected to histology for Ashcroft fibrosis score determination (Table 56).

TABLE 53

Oropharyngeal formulations and admixed dosing solution compositions

| | | Solution Compositions | | |
|---|---|---|---|---|
| Route | Dose Level | Solution 1 | Solution 2 | Admixed Dosing Solution (9:1)[a] |
| Oropharyngeal (OP) | Vehicle | ~1.67% propylene glycol | 4.0% NaCl | ~1.5% propylene glycol<br>~0.4% NaCl |

TABLE 53-continued

Oropharyngeal formulations and admixed dosing solution compositions

| | | Solution Compositions | | |
|---|---|---|---|---|
| Route | Dose Level | Solution 1 | Solution 2 | Admixed Dosing Solution (9:1)[a] |
| | 0.05 mg/kg nintedanib | ~0.14 mg/mL nintedanib ~1.67% propylene glycol | 4.0% NaCl | ~0.125 mg/mL nintedanib ~1.5% propylene glycol ~0.4% NaCl |
| | 0.25 mg/kg nintedanib | ~0.69 mg/mL nintedanib ~1.67% propylene glycol | 4.0% NaCl | ~0.625 mg/mL nintedanib ~1.5% propylene glycol ~0.4% NaCl |
| | 0.375 mg/kg nintedanib | ~1.04 mg/mL nintedanib ~1.67% propylene glycol | 4.0% NaCl | ~0.938 mg/mL nintedanib ~1.5% propylene glycol ~0.4% NaCl |

[a]Expressed as nintedanib free base

TABLE 54

Bleomycin dose levels and pharmacokinetic comparison

| Route | Dose (mg/kg) | Lung Cmax (µg/g) | Lung AUC (mg · hr/kg) |
|---|---|---|---|
| Oropharyngeal (OP) | 0.05 | 1.4 | 1.6 |
| | 0.25 | 7.0 | 7.8 |
| | 0.375 | 10.5 | 11.6 |
| Oral Gavage (PO) | 60.0 | 4.4 | 29.3 |

Oropharyngeal (OP) dose levels were selected by comparing lung pharmacokinetics following OP dosing to lung pharmacokinetics determined following 60 mg/kg oral gavage (PO). By this comparison, 0.05 was selected to deliver lung Cmax and AUC lower than that delivered by 60 mg/kg PO, 0.25 mg/kg was selected to deliver an equivalent Cmax as 60 mg/kg PO, and 0.375 mg/kg was selected to deliver a lung Cmax greater than 60 mg/kg PO. It should be noted that preliminary assessment showed that 0.5 mg/kg OP was not well tolerated by bleomycin-exposed animals, hence the well-tolerated 0.375 mg/kg was selected as the highest OP dose.

TABLE 55

Animal weight gain and lung weight-body-weight ratios

| | | Body Weight | | Lung weight-to-body weight | |
|---|---|---|---|---|---|
| Route | Dose Group | Gain (g) (SD) | Delta to Sham (%) | Ratio (SD) | Delta to Sham (%) |
| Oropharyngeal (OP) | Sham | 132.0 (37.7) | 0.0 | 0.392 (0.031) | 0.0 |
| | Vehicle | 107.6 (25.6) | −18.5 | 0.493 (0.055) | 25.8 |
| | 0.05 mg/kg | 107.7 (28.5) | −18.4 | 0.526 (0.063) | 34.2 |
| | 0.25 mg/kg | 96.8 (18.9) | −26.7 | 0.476 (0.036) | 21.4 |
| | 0.375 mg/kg | 127.0 (34.0) | −4.8 | 0.466 (0.022) | 18.9 |
| Oral Gavage (PO) | Sham | 126.8 (22.3) | 0.0 | 0.399 (0.027) | 0.0 |
| | Vehicle | 128.7 (33.8) | 1.9 | 0.483 (0.038) | 21.1 |
| | 60 mg/kg | 67.4 (28.8) | −46.9 | 0.455 (0.032) | 14.0 |

Animal body weight results indicate the following: 1. Inhaled (OP) dose group animals exposed to both bleomycin and isoflurane exhibited less weight gain than sham animals receiving isofluorane without bleomycin; 2. High dose OP resulted in weight gain equivalent to sham animals; 3. Oral (PO) nintedanib dosed animals gained about half the weight of control animals; and 4. Bleomycin exposure (vehicle control group animals) resulted in an ~20% increase in lung-to-body weight ratio over sham animals. Both OP showed a dose responsive reduction in lung-to-body weight ratio. PO administration also reduced lung-to-body weight ratio.

TABLE 56

Animal lung fibrosis scores (Ashcroft)

| Route | Dose Group | Fibrosis Score (SD) | Delta to Vehicle (%) |
|---|---|---|---|
| Oropharyngeal (OP) | Sham | 0.1 (0.11) | 100.0 |
| | Vehicle | 2.4 (1.04) | 0.0 |
| | 0.05 mg/kg | 2.7 (0.94) | −12.5 |
| | 0.25 mg/kg | 2.1 (0.97) | 12.5 |
| | 0.375 mg/kg | 1.9 (0.48) | 20.8 |
| Oral Gavage (PO) | Sham | 0.0 (0.00) | 100.0 |
| | Vehicle | 2.6 (0.70) | 0.0 |
| | 60 mg/kg | 2.3 (0.45) | 11.5 |

Lung fibrosis score results indicate the following: 1. Inhaled (OP) dose group animals showed a dose responsive reduction in fibrosis score; 2. The inhaled low dose (less lung-delivered nintedanib Cmax and AUC than oral) resulted in less anti-fibrotic activity than oral, the inhaled mid-dose (similar lung-delivered nintedanib Cmax and lower AUC than oral) resulted in an equivalent amount of anti-fibrotic activity as oral, and the inhaled high dose (more lung-delivered nintedanib Cmax and lower AUC than oral) resulted in more anti-fibrotic activity as oral; 3. High dose OP resulted in weight gain equivalent to sham animals; 3. Oral (PO) nintedanib dosed animals gained about half the weight of control animals; and 4. Bleomycin exposure (vehicle control group animals) resulted in an ~20% increase in lung-to-body weight ratio over sham animals. Both OP showed a dose responsive reduction in lung-to-body weight ratio. PO administration also reduced lung-to-body weight ratio.

Compared to oral, inhalation was superior to equivalent in all key fibrosis measurements. At oral-equivalent lung exposures, inhalation showed similar results (at 1/240 the dose) in key fibrosis measures. At higher lung exposure, treatment was more effective (at 1/160 the dose).

Example 11: Inhaled Nintedanib Salt In Vivo Pharmacology—Therapeutic Silica Model To evaluate the in vivo activity of inhaled nintedanib, the therapeutic silica pulmonary fibrosis model was performed. Briefly, acclimated 20-22 g female C57BL/6 mice were administered silica on day 1 by the intratracheal route. On the tenth day, treatment was initiated with either saline or nintedanib. Inhaled nintedanib formulations (35 μL per dose) were delivered by intranasal (IN) administration. Preliminary experiments showed good lung delivery and distribution by this method. On days 10 through 29, IN animals were anesthetized with isoflurane and dosed once a day (QD) with either 0.021, 0.21 or 2.1 mg/kg nintedanib HBr formulation (Table 57). Oral gavage-treated (PO) animals were dosed twice a day (BID) with 30 mg/kg nintedanib HBr in water. Sham and silica control groups received saline either IN or PO. Five animals were enrolled into sham groups, 10 animals enrolled into each PO dose groups, and 13 animals were enrolled into each IN dosing group. For IN nintedanib administration, doses were selected to deliver PO-inferior, equivalent and superior lung Cmax and AUC (Table 58). All animals were euthanized on day 30d. Body weights were collected throughout the study, with lung weights at termination. Flexivent was performed to determine elastance (lung function; Table 59). Left lungs were extracted, stained as assessed for parenchymal collagen (Table 60) and α-smooth muscle actin (αSMA; Table 61), while right lungs were assessed for interleukin-1β (IL-1β; Table 62).

TABLE 57

Intranasal formulations and admixed dosing solution compositions

| | | Solution Compositions | | |
|---|---|---|---|---|
| Route | Dose Level | Solution 1 | Solution 2 | Admixed Dosing Solution (9:1)[b] |
| Intranasal (IN) | Vehicle | ~1.67% propylene glycol | 4.0% NaCl | ~1.5% propylene glycol<br>~0.4% NaCl |
| | 0.021 mg/kg nintedanib | ~0.013 mg/mL nintedanib<br>~1.67% propylene glycol | 4.0% NaCl | ~0.012 mg/mL nintedanib<br>~1.5% propylene glycol<br>~0.4% NaCl |
| | 0.21 mg/kg nintedanib | ~0.13 mg/mL nintedanib<br>~1.67% propylene glycol | 4.0% NaCl | ~0.12 mg/mL nintedanib<br>~1.5% propylene glycol<br>~0.4% NaCl |
| | 2.1 mg/kg nintedanib | ~1.33 mg/mL nintedanib<br>~1.67% propylene glycol | Distilled water[a] | ~1.2 mg/mL nintedanib<br>~1.5% propylene glycol |

[a]To avoid high viscosity (impairing delivery and causing animal breathing problems), NaCl was excluded from the highest nintedanib dose formulation
[b]Expressed as nintedanib free base

TABLE 58

Silica dose levels and pharmacokinetic comparison

| Route | Dose (mg/kg) | Lung Cmax (μg/g) | Lung AUC (mg · hr/kg) |
|---|---|---|---|
| Intranasal (IN) | 0.021 | 0.29 | 0.4 |
| | 0.21 | 2.9 | 4.0 |
| | 2.1 | 29.0 | 40.0 |
| Oral Gavage (PO) | 30.0 | 1.1 | 7.4 |

Intranasal (IN) dose levels were selected by comparing lung pharmacokinetics following IN dosing to lung pharmacokinetics determined following 30 mg/kg oral gavage (PO). By this comparison, 0.021 was selected to deliver lung Cmax and AUC lower than that delivered by 30 mg/kg PO, 0.21 mg/kg was selected to deliver an equivalent Cmax as 30 mg/kg PO, and 2.1 mg/kg was selected to deliver a lung Cmax greater than 30 mg/kg PO.

As expected, all mice administered silica lost weight from days 0 to 4. All silica administered mice began to recover from weight loss at around day 6 and continued recovery reaching their initial weight by day 10 (first therapeutic intervention). Weight remained stable until study endpoint at day 30. Neither oral or inhaled (IN) treatment or vehicles altered these characteristics. Delivering the nintedanib via the inhaled route did not affect eating habits. Administration of silica significantly increased right lung weights compared to naïve mice. Neither oral nor inhaled (IN) nintedanib significantly affected lung weights when compared to control mice.

TABLE 59

Lung function (lung elastance)

| Route | Dose Group | Elastance (cmH$_2$0/mL) | Sham Subtracted | SEM | Delta to Vehicle (%) |
|---|---|---|---|---|---|
| Intranasal (IN) | Sham | 14.37 | 0.0 | NA | 100.0 |
| | Vehicle | 15.31 | 0.9 | 0.9 | 0.0 |
| | 0.021 mg/kg | 15.90 | 1.5 | 0.8 | 66.7 |
| | 0.21 mg/kg | 14.90 | 0.5 | 0.6 | −44.4 |
| | 2.1 mg/kg | 12.53 | −1.9 | 0.5 | −311.1[a] |
| Oral Gavage (PO) | Sham | 14.64 | 0.0 | NA | 100.0 |
| | Vehicle | 15.54 | 0.9 | 0.6 | 0.0 |
| | 30 mg/kg | 14.41 | −0.2 | 0.6 | −122.2 |

[a] $p < 0.005$

The lung function of each mouse in the study was assessed at 30 days post silica exposure using a rodent mechanical ventilator. The ventilator determined the elastance of each lung as a measure of lung stiffness/fibrosis by inflating the lungs and assessing changes in flow and pressure. Table 59 results indicate an inhaled dose response to improving lung function (reduced elasticity), with the high dose achieving significance. Oral was also significant in improving lung function.

TABLE 60

Parenchymal collagen

| Route | Dose Group | Parenchymal Collagen | SEM | Delta to Vehicle (%) |
|---|---|---|---|---|
| Intranasal (IN) | Sham | 0.28 | 0.04 | 100.0 |
| | Vehicle | 0.45 | 0.04 | 0.0 |
| | 0.021 mg/kg | 0.51 | 0.07 | 13.3 |
| | 0.21 mg/kg | 0.64 | 0.10 | 20.0 |
| | 2.1 mg/kg | 0.64 | 0.11 | 20.0 |
| Oral Gavage (PO) | Sham | 0.25 | 0.03 | 100.0 |
| | Vehicle | 0.64 | 0.12 | 0.0 |
| | 30 mg/kg | 0.74 | 0.15 | 15.6 |

Parencymal collagen was measured by Picrosirius Red (PSR) histopathological analysis. Results indicate that parenchymal collagen was increased by silica exposure but was not reversed by either inhalation or oral nintedanib treatment (Table 60). Due to the positive impact on other key fibrosis modulators (αSMA, IL-1α; Tables 61 and 62) and that silica-induced fibrosis was well-established prior to start of dosing, it is possible that extending the treatment time would ultimately impact parenchymal collagen.

TABLE 61

Lung α-smooth muscle actin (αSMA)

| Route | Dose Group | αSMA (%) | SEM | Delta to Vehicle (%) |
|---|---|---|---|---|
| Intranasal (IN) | Sham | 12.7 | 0.05 | 100.0 |
| | Vehicle | 27.0 | 5.90 | 0.0 |
| | 0.021 mg/kg | 16.1 | 1.52 | −42.5[a] |
| | 0.21 mg/kg | 19.1 | 1.74 | −31.8 |
| | 2.1 mg/kg | 18.3 | 1.81 | −34.6 |
| Oral Gavage (PO) | Sham | 14.0 | 0.90 | 100.0 |
| | Vehicle | 43.6 | 4.99 | 0.0 |
| | 30 mg/kg | 22.8 | 3.34 | −47.7[b] |

[a] $p < 0.05$;
[b] $p < 0.005$

TABLE 62

Lung interleukin-1β (IL-1β)

| Route | Dose Group | IL-1β (pg/mL) | SEM | Delta to Vehicle (%) |
|---|---|---|---|---|
| Intranasal (IN) | Sham | 189.2 | 43.8 | 100.0 |
| | Vehicle | 1257.0 | 112.0 | 0.0 |
| | 0.021 mg/kg | 1037.0 | 178.1 | −17.4 |
| | 0.21 mg/kg | 992.0 | 130.1 | −21.1 |
| | 2.1 mg/kg | 834.7 | 130.2 | −33.6[a] |
| Oral Gavage (PO) | Sham | 96.4 | 40.3 | 100.0 |
| | Vehicle | 1016.0 | 181.1 | 0.0 |
| | 30 mg/kg | 1001.0 | 148.6 | −1.5 |

[a] $p < 0.05$

Alpha-smooth muscle actin (αSMA) is a marker of myofibroblast, a key cell type present in fibrotic diseases, including IPF, and is required for production and deposition of collagen. Silica-induced lung αSMA results indicate both oral and inhaled routes have a substantial impact reducing αSMA lung levels, with the inhaled low and oral doses showing significance (Table 61). Interleukin 1β (IL-1β) is a cytokine important for the initiation and progression of fibrotic diseases, including IPF. Silica-induced lung IL-1β results indicated Inhaled (IN) dose group animals showed a dose responsive reduction, with the high dose achieving significance (Table 62). Oral dosing did not reduce IL-1β levels.

Silica fibrosis model results indicate that inhaled nintedanib is effective at reducing formation of myofibroblasts (reduced αSMA) and is dose responsive at reducing IL-1β (a key cytokine in fibrosis initiation and progression) and improving lung function (reduced elastance). Together, inhalation works for fibrosis outcomes. Compared to oral, inhalation was superior to equivalent in all key fibrosis measurements (αSMA, IL-1β and lung function). Parenchymal collagen was not affected by either oral or inhalation. Due to the positive impact upon the other key fibrosis modulators and that fibrosis was well-established prior to start of dosing, it is possible that extending the treatment time would ultimately impact parenchymal collagen. At oral-equivalent lung exposures, inhalation showed similar results (at 1/143 the oral dose) in key fibrosis measures. At higher lung exposure, treatment was more effective (at 1/14 the oral dose).

Taken together, inhaled doses were well-tolerated in both the bleomycin and silica treatment models. The bleomycin study showed that oral is less-well-tolerated than inhaled, and high dose inhaled showed improved growth and lung weights compared to controls and that following oral administration. Bleomycin pathology showed an inhaled dose response reducing fibrosis. Data supported by observation that at equivalent lung doses, inhaled and oral exhibit a similar response. Moreover, at higher lung dose, inhaled was superior, and at lower lung exposure, inhaled was inferior. In both studies, anti-fibrotic responses are achieved with substantially lower inhaled dose levels than oral.

Allometric scaling doses from mouse to human (divide mouse mg/kg dose by 12.3) and rat to human (divide rate mg/kg dose by 6.2) are shown in Table 63.

TABLE 63

Allometric dose scaling

| Species | Route | Animal dose (mg/kg) | Animal lung half-life (alpha) (min) | Scaling factor | Predicted human dose (60 kg) | Predicted human ELF half-life (alpha) (min) |
|---|---|---|---|---|---|---|
| Mouse | Inhaled | 2.1 | 4 | 12.3 | 10.2[b] | 84[c] |
|  |  | 0.21 | 4 | 12.3 | 1.0[b] | 84[c] |
|  |  | 0.021 | 4 | 12.3 | 0.1[b] | 84[c] |
|  | Oral | 30.0 | 112[a] | 12.3 | 146.3 | 13.6 hr |
| Rat | Inhaled | 0.375 | 14 | 6.2 | 3.6[b] | 294[c] |
|  |  | 0.25 | 14 | 6.2 | 2.4[b] | 294[c] |
|  |  | 0.05 | 14 | 6.2 | 0.5[b] | 294[c] |
|  | Oral | 60.0 | 160[a] | 6.2 | 580.7 | 13.6 hr |

[a]Terminal half-life;
[b]device-loaded dose;
[c]Based upon previous observations that inhaled drugs ELF half-life is 21-fold longer than mouse or rat-measured lung half-life In the mouse silica model, 2.1 and 0.21 mg/kg inhaled (IN) were more effective than 30 mg/kg oral. Taking from Table 63, 2.1 mg/kg in mice is a 10.2 mg inhalation device-loaded human dose. Similarly, 0.21 and 0.021 mg/kg are 1.0 and 0.1 mg in humans, respectively. In the rat bleomycin model, the 0.25 mg/kg inhaled (OP) dose exhibited a similar effect as the 60 mg/kg oral dose. Taking from Table 63, 0.25 mg/kg in rats is a 2.4 mg inhalation device-loaded human dose. Similarly, 0.375 mg/kg (exhibited more efficacy than the 60 mg/kg oral dose) and 0.05 mg/kg (exhibited less efficacy than the 60 mg/kg oral dose) are 3.6 mg and 0.5 mg in humans, respectively. Assuming the 0.21 mg/kg inhaled mouse dose had equivalent efficacy as the 30 mg/kg oral dose, and given the 30 mg/kg oral mouse dose scales to approximately the approved nintedanib oral dose (Ofev, 150 mg), then a 1.0 mg inhalation device loaded human dose is as effective in treating a pulmonary fibrotic disease as a 150 mg oral dose. Making a similar argument for the rat data, with the 0.25 mg/kg inhaled dose having similar efficacy as the 60 mg/kg oral dose, and given the 60 mg/kg oral rat dose scales to approximately 3.9-fold the approved Ofev dose (~581 mg vs. 150 mg), then 2.4 mg divided by 3.9, or 0.64 mg inhalation device loaded human dose is as effective in treating pulmonary fibrotic disease as a 150 mg oral dose. Taken together, comparing allometrically scaled animal oral doses to their similar efficacy, inhaled dose levels suggests a 0.64 to 1.0 mg inhalation device loaded nintedanib dose is as effective in treating a pulmonary fibrotic disease as a 150 mg oral nintedanib dose. These and below dose levels are scaled to a 70 or 75 kg human by multiplying by 70/60 or 75/60, respectively. Comparatively, when taking the allometrically-scaled animal inhaled doses which exhibited similar efficacy as their respective oral doses, the mouse data suggests a 1.0 mg inhalation device loaded human dose is as effective in treating a pulmonary fibrotic disease as a 150 mg oral dose. Similarly, the rat data suggests a 2.4 mg inhalation device loaded human dose is as effective in treating a pulmonary fibrotic disease as a 150 mg oral dose.

Comparing to the human modeled results presented in Table 51 (which include a longer lung elimination half-life than considered in the animal discussion above), results indicate that a 0.42 mg device loaded nintedanib dose delivers a human inhaled dose resulting in the same plasma AUC as a 150 mg oral dose, with a 26-fold greater nintedanib lung Cmax than a 150 mg oral dose, and a 10.5-fold greater nintedanib lung AUC. Thus, a longer lung elimination half-life allows a much lower device-loaded dose to produce higher lung AUC and Cmax levels. Moreover, a 0.04 mg device loaded nintedanib dose is predicted to deliver an inhaled dose resulting in the same lung AUC as the 150 mg oral dose, with substantially lower blood levels. By non-limiting example, one possible therapeutic range could be 0.04 mg nintedanib (delivering equivalent efficacy as 150 mg oral nintedanib) to 0.42 mg (or greater) nintedanib (delivering equivalent blood levels as 150 mg oral nintedanib). From the above animal results, it appears achieving a higher lung Cmax and/or AUC is beneficial; which follows that greater target exposure will result in greater efficacy. Thus, projecting this observation to humans, this smaller device loaded dose, using these superior lung levels, is predicted to result in equivalent or greater human efficacy than the 150 mg approved oral nintedanib dose. Clinical dose escalation will confirm or modify these dose and pharmacokinetic predictions.

Taken together, scaling the animal inhaled doses suggests a 1.0 to 2.4 mg inhalation device loaded human dose is as effective in treating a pulmonary fibrotic disease as a 150 mg oral dose. Human modeling using a predicted longer lung elimination half-life allows a much smaller 0.04 mg to 0.42 mg inhalation device loaded dose to provide the same or additional efficacy benefit in humans. Putting these animal and human approaches together, the animal data suggests a 0.64 to 2.4 mg inhalation device loaded human dose is as effective in treating a pulmonary fibrotic disease as a 150 mg oral dose. However, including the expected longer human lung half-life will reduce this dose (to at or below 0.42 mg) while maintaining superior pharmacokinetic lung efficacy parameters.

Modeling the above data suggests this possible oral dose-equivalent inhalation device loaded dose may deliver the same blood levels as the 150 mg approved oral dose, but with substantially greater lung levels. This creates three interesting scenarios: 1. If inhalation of these Ofev-equivalent inhalation device loaded doses results in oral-like side effects, the inhaled drug may be dose de-escalated to reduce or eliminate side effects while maintaining superior lung levels; 2. If inhalation of these Ofev-equivalent inhalation device loaded doses does not result in oral-like side effects, the inhaled drug may be maintained at these dose levels, whereby the superior lung dose is further benefited by Ofev-equivalent blood levels; or 3. Further dose-escalated to achieve further additional efficacy while remaining under the oral side effect limit. Given the bleomycin study results showing an inhaled dose (0.375 mg/kg OP) was more effective and more-well tolerated than the 60 mg/kg oral dose, while delivering both greater lung and plasma levels, it appears possible that Blood levels may not drive oral side effects, rather it is the high gastrointestinal and liver exposure of 150 mg nintedanib taken orally to these issues. As additional support of this possibility, oral nintedanib is only 5% bioavailable (mostly due to rapid and extensive first-pass metabolism) and the primary side effects are diarrhea and liver. Thus, gastrointestinal and liver exposure, rather than blood levels/CNS involvement appear to be the driving factors to oral side effects. Something small inhaled doses delivery high lung levels in the presence of absence of Ofev-like blood levels may largely or completely avoid.

The invention claimed is:

1. A method to administer an aerosol formulation of nintedanib comprising:
   1) combining at the point of use: a) a sealed, sterile first solution of a dissolved nintedanib salt at a nintedanib concentration less than 1.5 mg/mL in a non-glass container, wherein the salt counterion is selected from the group consisting of esylate, chloride, and bromide and combinations thereof, and a buffer selected from the group consisting of lysinate, acetylcysteine, glycine, glutamate, borate, succinate, tartrate, phosphate or Tris and combinations thereof, with b) a separate sealed, sterile second solution comprised of permeant ions to adjust the permeant ion concentration of an admixture of the first and second solution to between 30 mM and 150 mM and wherein either or both of the first or the second solution is further comprised of a non-ionic osmolality adjusting agent that increases the osmolality of the admixture and avoids precipitation of the nintedanib salt;

2) containing the admixture in the reservoir of a nebulizer;
3) activating the nebulizer within 2 hours of forming the admixture to deliver by inhalation an aerosol dose of the nintedanib salt to the lungs of a patient to reduce a progression of a decline in Forced Vital Capacity (FVC) or Forced Expiratory Volume ($FEV_1$).

2. The method of claim 1, wherein the buffer is glycine or glutamate or combinations thereof.

3. The method of claim 1, wherein the first solution contains between 0.005 mg/mL and less than 1.5 mg/ml of the dissolved nintedanib salt.

4. The method of claim 1, wherein the permeant ions in the second solution are provided by compounds selected from group consisting of hydrogen chloride, hydrogen bromide, sodium chloride, magnesium chloride, calcium chloride, potassium chloride, sodium bromide, potassium bromide, magnesium bromide and calcium bromide and combinations thereof.

5. The method of claim 1, wherein the osmolality adjusting agent is selected from the group consisting of propylene glycol, ethanol, lactose, sucrose, glucose, mannitol and glycerin and combinations thereof.

6. The method of claim 5, wherein the permeant ion concentration is between 30 mM to 1500 mM in the second solution and between 30 mM and to 150 mM in the admixture.

7. The method of claim 1, wherein the first solution has an added salt concentration less than 30 mM.

8. The method of claim 1, wherein the permeant ions contained in the second solution are selected from the group consisting of chloride and bromide and combinations thereof.

9. The method of claim 1, wherein the step of combining the first solution and the second solution is comprised of utilizing a first solution that is pre-filtered through a synthetic polymer filter substantially free of PVDF before being placed in the first container.

10. The method of claim 1, wherein the volume to volume ratio of the first solution to the second solution is between 10:1 and 1:10.

11. The method of claim 10, wherein the volume ratio of the first solution to the second solution is between 1:1 and 9:1.

12. The method of claim 11, wherein the buffer concentration is between 0.01 mM and 1000 mM in the admixture and is substantially free of fumarate, malate, and maleate buffers.

13. The method of claim 1, wherein the step of activating the nebulizer delivers the admixture having a pH between 3.5 and 4.6.

14. The method of claim 1, wherein the step of activating the nebulizer generates the aerosol of the resulting admixture having a mass median aerodynamic diameter (MMAD) of about 1 μm to about 5 μm, a geometric standard deviation (GSD) of emitted droplet size distribution of the resulting admixture of about 1.0 to about 2.5, a fine particle fraction (FPF) having a particle diameter less than 5 microns, wherein the FPF of droplets emitted from the liquid nebulizer is at least about 30%, and the nebulizer has an output rate of at least 0.1 mL/min and delivers the aerosol dose of nintedanib within 1 hour of combining the first solution and the second solution.

15. The method of claim 1, wherein the step of containing the admixture in the reservoir of a nebulizer is comprised of adding the admixture to an in-line nebulizer that is a component of a mechanical ventilator system such that the aerosolized resulting admixture is administered to the patient through a forced air circuit of the mechanical ventilator.

16. The method of claim 1, wherein the step of combining the first and second solutions is comprised of separately adding the first solution and the second solution to contain the admixture in the reservoir of the nebulizer.

* * * * *